(12) United States Patent
Mempel et al.

(10) Patent No.: US 11,571,427 B2
(45) Date of Patent: Feb. 7, 2023

(54) TARGETING THE CBM SIGNALOSOME COMPLEX INDUCES REGULATORY T CELLS TO INFLAME THE TUMOR MICROENVIRONMENT

(71) Applicant: THE GENERAL HOSPITAL CORPORATION, Boston, MA (US)

(72) Inventors: Thorsten R. Mempel, Chestnut Hill, MA (US); Mauro Di Pilato, Wakefield, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 38 days.

(21) Appl. No.: 16/958,536

(22) PCT Filed: Dec. 28, 2018

(86) PCT No.: PCT/US2018/067856
§ 371 (c)(1),
(2) Date: Jun. 26, 2020

(87) PCT Pub. No.: WO2019/133809
PCT Pub. Date: Jul. 4, 2019

(65) Prior Publication Data
US 2021/0052596 A1    Feb. 25, 2021

Related U.S. Application Data

(60) Provisional application No. 62/611,186, filed on Dec. 28, 2017.

(51) Int. Cl.
| A61K 31/5415 | (2006.01) |
| A61K 35/17 | (2015.01) |
| A61K 39/395 | (2006.01) |
| C12Q 1/6886 | (2018.01) |

(52) U.S. Cl.
CPC .......... *A61K 31/5415* (2013.01); *A61K 35/17* (2013.01); *A61K 39/3955* (2013.01); *A61K 39/39558* (2013.01); *C12Q 1/6886* (2013.01); *C12Q 2600/106* (2013.01); *C12Q 2600/156* (2013.01)

(58) Field of Classification Search
CPC combination set(s) only.
See application file for complete search history.

(56) References Cited

U.S. PATENT DOCUMENTS

| 9,718,811 B2 * | 8/2017 | Krappmann .......... C07D 211/22 |
| 2018/0153870 A1 | 6/2018 | El Gammal et al. |
| 2019/0389904 A2 * | 12/2019 | Gray ..................... A61K 38/07 |

FOREIGN PATENT DOCUMENTS

| WO | 2014074815 A1 | 5/2014 |
| WO | 2016193339 A1 | 12/2016 |
| WO | 2017008046 A1 | 1/2017 |
| WO | 2017040304 A1 | 3/2017 |
| WO | 2018141749 A1 | 8/2018 |
| WO | WO-2018141749 A1 * | 8/2018 ............. A61K 31/50 |

OTHER PUBLICATIONS

Inhibition of MALT1 protease with biperiden or mepazine: A new therapeutic treatment approach in pancreatic cancer. Developmental Therapeutics—Clinical Pharmacology and experimental therapeutics. El Gammal et al (May 20, 2016 (Year: 2016).*
Saba et al (2017) (MALT1 Inhibition is Efficacious in Both Naïve and Ibrutinib-Resistant Chronic Lymphocytic Leukemia, Cancer Research, Oct. 2017) (Year: 2017).*
Wang et al (Oncogenesis, Jul. 31, 2017; 6:e365) (Year: 2017).*
Weber et al (Lancet Oncology, 2015, 16:375-384). (Year: 2015).*
Gao et al. "VISTA is an inhibitory immune checkpoint that is increased after ipilimumab therapy in patients with prostate cancer." Nature Medicine 23(5): 551-555 (2017).
Brustle et al., "MALT1 is an intrinsic regulator of regulatory T cells." Cell Death and Differentiation 24(7):1214-1223 (Sep. 25, 2015).
Fontan et al., "MALT1 small molecule inhibitors specifically suppress ABC-DLBCL in vitro and in vivo." Cancer Cell 22(6):812-824 (2012).
Nagel et al. "Pharmacologic inhibition of MALT1 protease by phenothiazines as a therapeutic approach for the treatment of aggressive ABC-DLBCL." Cancer Cell 22(6):825-837 (2012).
Xin et al. "Development of new Malt1 inhibitors and probes." Bioorganic & Medicinal Chemistry 24(15):3312-3329 (2016).
Pan et al. "MALT1 is required for EGFR-induced NF-κB activation and contributes to EGFR-driven lung cancer progression." Oncogene 35(7): 919-928 (2016).
Pubchem: "SID 377483935—PubChem", Aug. 1, 2021, Retrieved from the Internet: URL: http://pubchem.ncbi.nlm.nih.gov/substance/377483935#section=External-ID [retrieved on Aug. 3, 2021].
El Gammal et al. "Inhibition of MALT1 protease with biperiden or mepazine: A new therapeutic treatment approach in pancreatic cancer." Journal of Clinical Oncology 34(15): e14075 (2016).

* cited by examiner

*Primary Examiner* — Laura B Goddard
*Assistant Examiner* — Sarah A Alsomairy
(74) *Attorney, Agent, or Firm* — Nixon Peabody LLP; David S. Resnick; Jeanne Jodoin

(57) ABSTRACT

Described herein are methods and compositions for the treatment of cancer. Aspects include administering (1) an agent that inhibits activity of a CBM signalosome complex, or (2) a cell engineered to have reduced CBM signalosome complex levels to a subject having cancer. In various embodiment, the methods further comprise administering second therapeutic, for example, a checkpoint inhibitor or anti-cancer therapy, to the subject.

9 Claims, 76 Drawing Sheets
Specification includes a Sequence Listing.

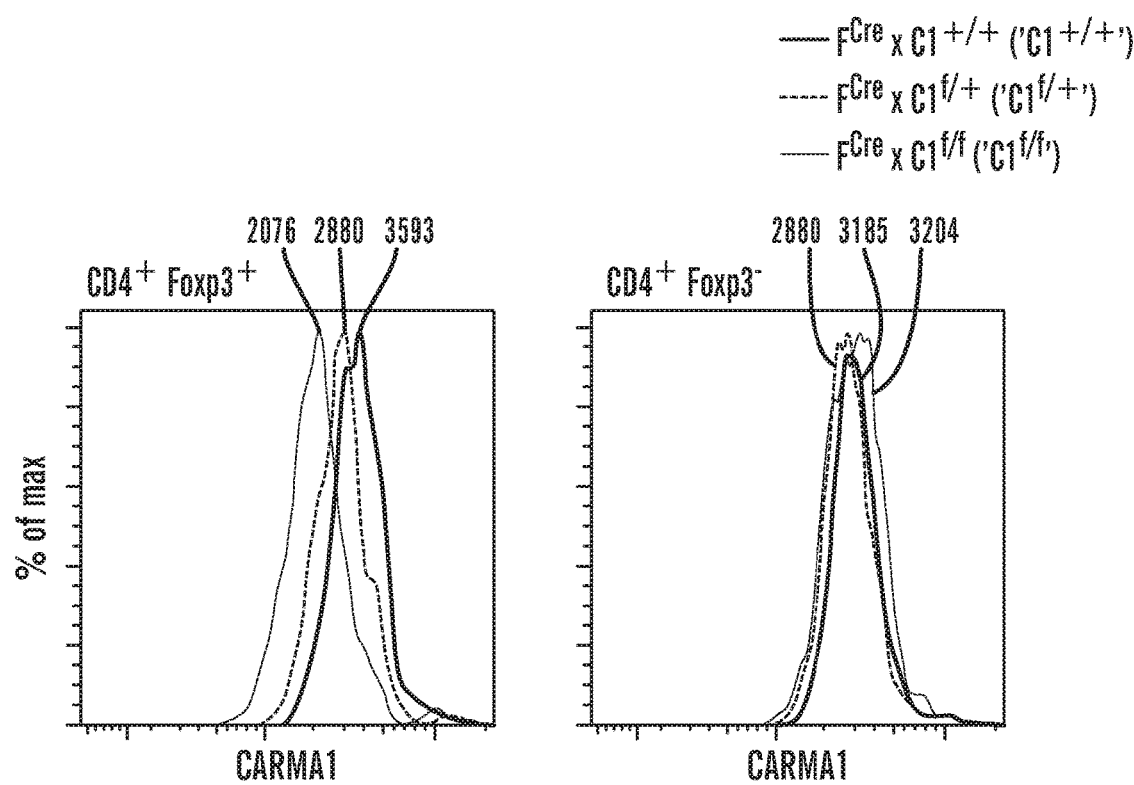
FIG. 1A
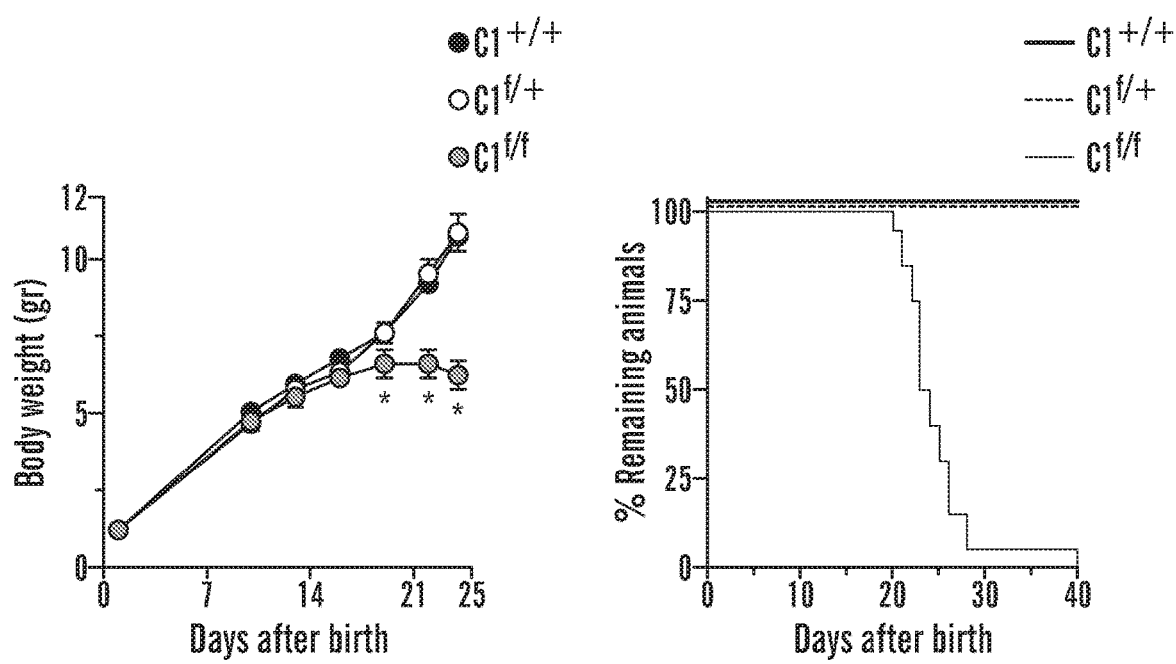
FIG. 1B
FIG. 1C

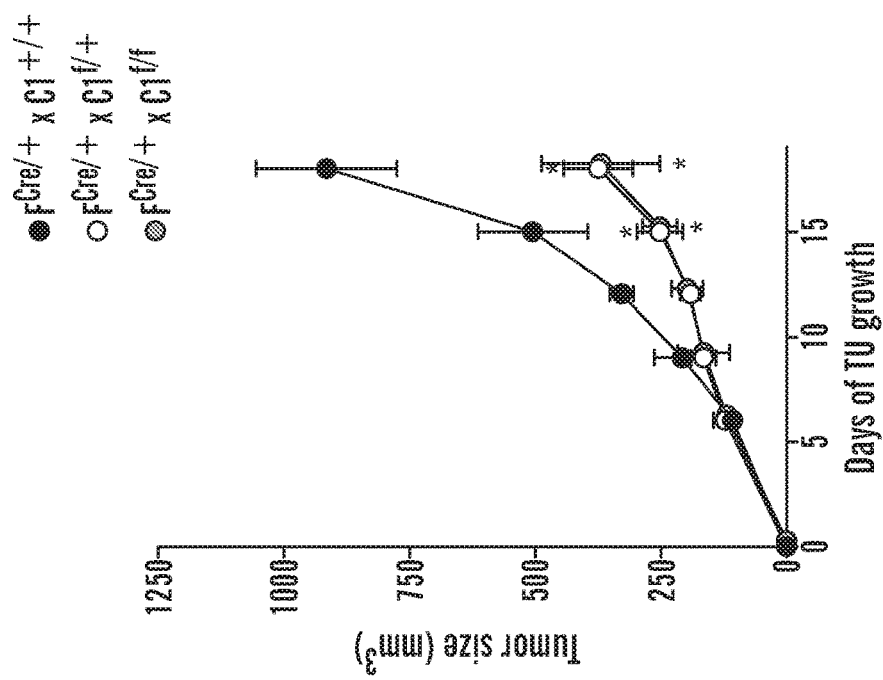
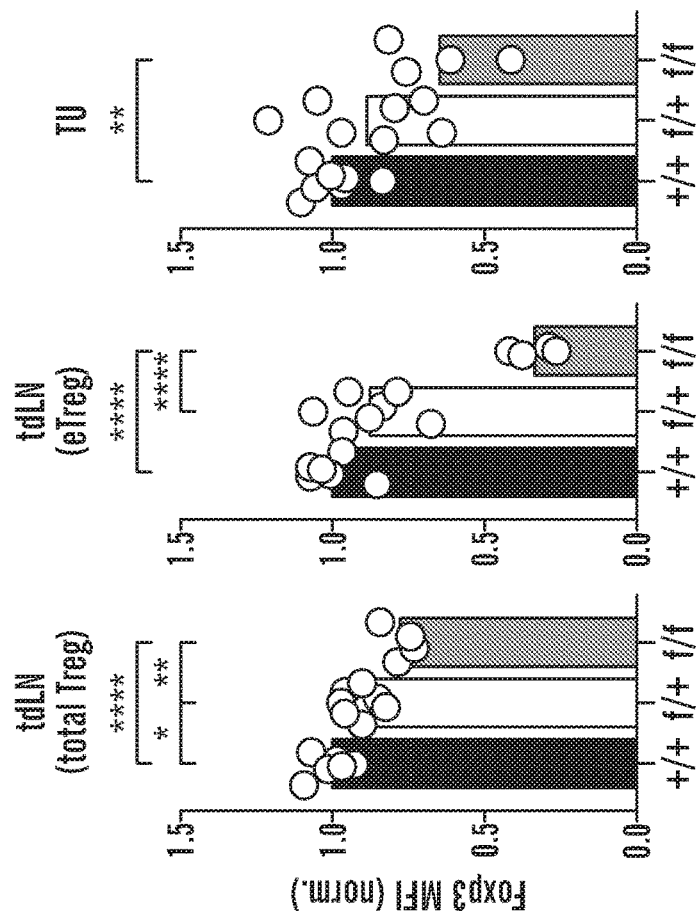
FIG. 2B
FIG. 2C

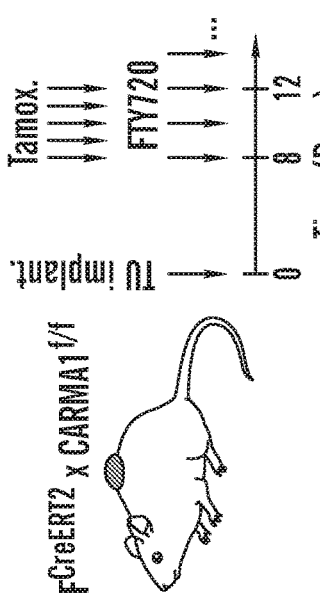
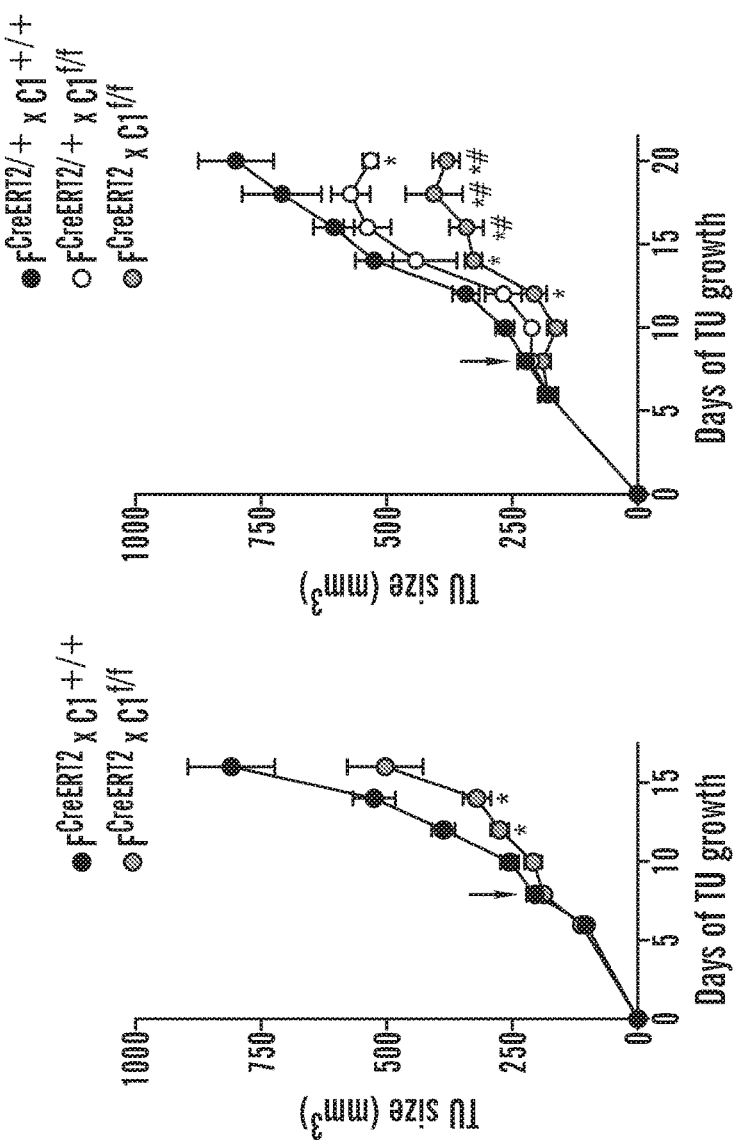
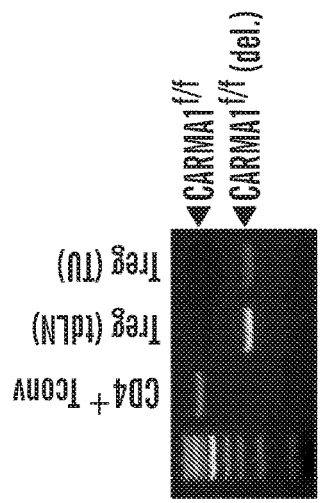
FIG. 3A  FIG. 3B  FIG. 3C  FIG. 3D

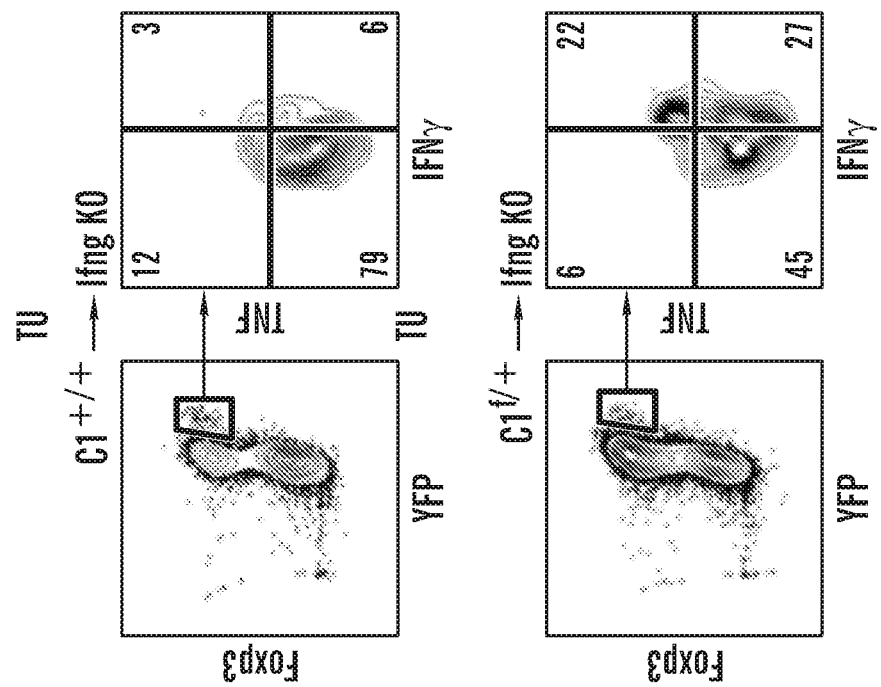
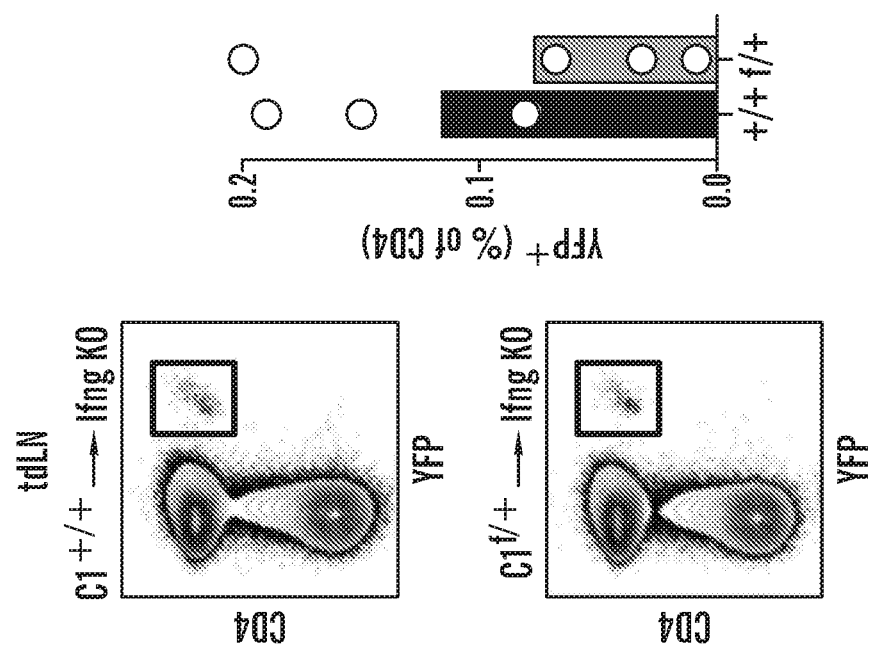
FIG. 11A
FIG. 11B

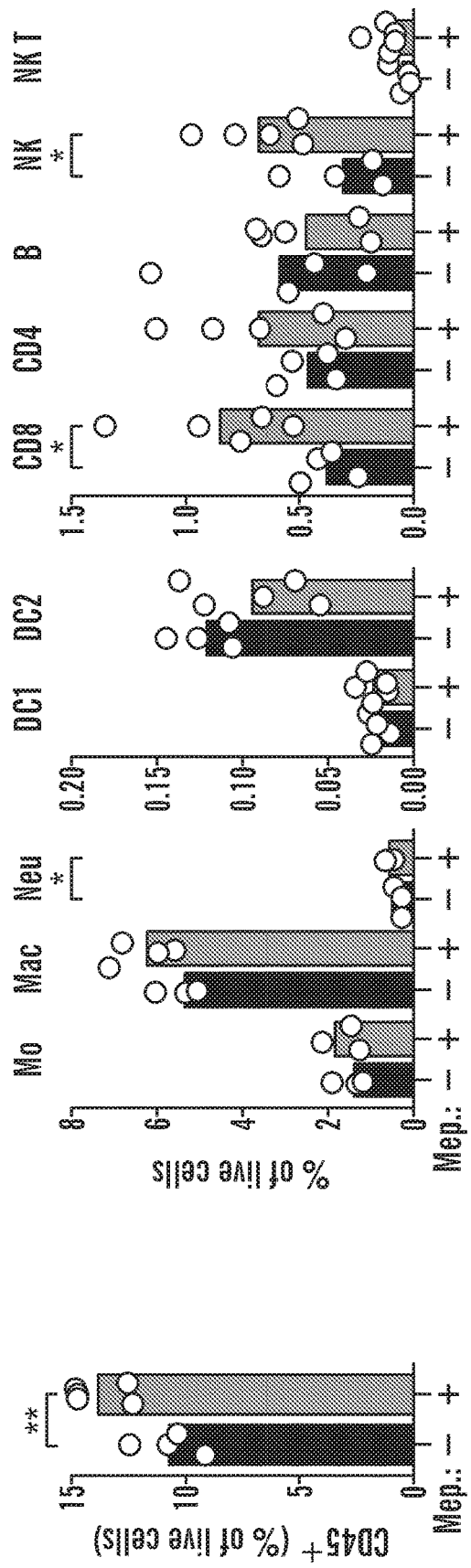
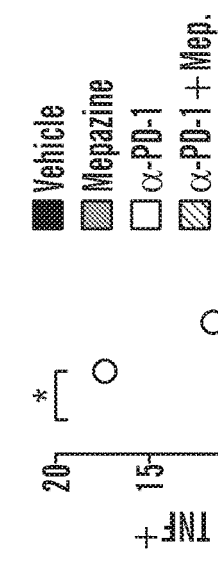
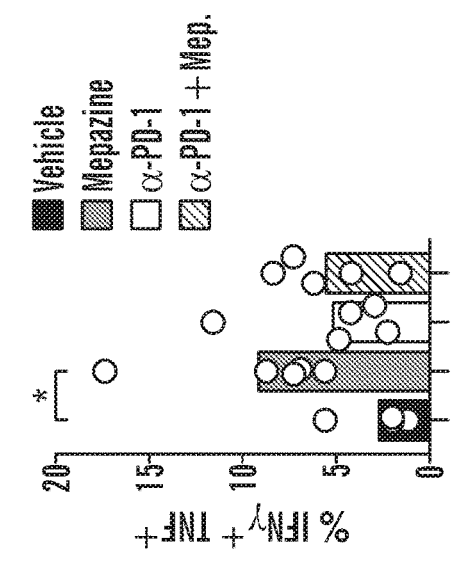
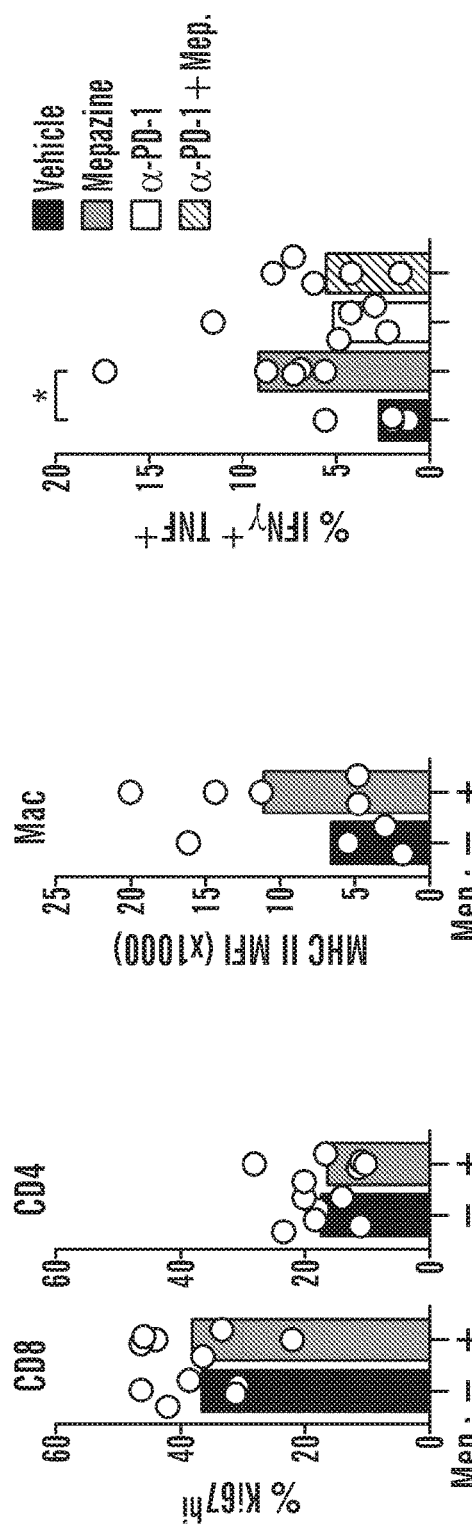
FIG. 13G  FIG. 13H  FIG. 13I  FIG. 13J  FIG. 13K

SEQUENCE LISTING

```
<160> NUMBER OF SEQ ID NOS: 49

<210> SEQ ID NO 1
<211> LENGTH: 3465
<212> TYPE: DNA
```

<213> ORGANISM: Homo sapiens

<400> SEQUENCE: 1

| | | | | | | |
|---|---|---|---|---|---|---|
| atgccaggag | gagggccaga | gatggatgac | tacatggaga | cgctgaagga | tgaagaggac | 60 |
| gccttgtggg | agaatgtgga | gtgtaaccgg | cacatgctca | gccgctatat | caaccctgcc | 120 |
| aagctcacgc | cctacctgcg | tcagtgtaag | gtcattgatg | agcaggatga | agatgaagtg | 180 |
| cttaatgccc | ctatgctgcc | atccaagatc | aaccgagcag | gccggctgtt | ggacattcta | 240 |
| cataccaagg | ggcaaagggg | ctatgtggtc | ttcttggaga | gcctagaatt | ttattaccca | 300 |
| gaactgtaca | aactggtgac | tgggaaagag | cccactcgga | gattctccac | cattgtggtg | 360 |
| gaggaaggcc | acgagggcct | cacgcacttc | ctgatgaacg | aggtcatcaa | gctgcagcag | 420 |
| cagatgaagg | ccaaggacct | gcaacgctgc | gagctgctgg | ccaggttgcg | gcagctggag | 480 |
| gatgagaaga | agcagatgac | gctgacgcgc | gtggagctgc | taaccttcca | ggagcggtac | 540 |
| tacaagatga | aggaagagcg | ggacagctac | aatgacgagc | tggtcaaggt | gaaggacgac | 600 |
| aactacaact | tagccatgcg | ctacgcacag | ctcagtgagg | agaagaacat | ggcggtcatg | 660 |
| aggagccgag | acctccaact | cgagatcgat | cagctaaagc | accggttgaa | taagatggag | 720 |
| gaggaatgta | agctggagag | aaatcagtct | ctaaaactga | agaatgacat | tgaaaatcgg | 780 |
| cccaagaagg | agcaggttct | ggaactggag | cgggagaatg | aaatgctgaa | gaccaaaaac | 840 |
| caggagctgc | agtccatcat | ccaggccggg | aagcgcagcc | tgccagactc | agacaaggcc | 900 |
| atcctggaca | tcttggaaca | cgaccgcaag | gaggccctgg | aggacaggca | ggagctggtc | 960 |
| aacaggatct | acaacctgca | ggaggaggcc | cgccaggcag | aggagctgcg | agacaagtac | 1020 |
| ctggaggaga | aggaggacct | ggagctcaag | tgctcgaccc | tgggaaagga | ctgtgaaatg | 1080 |
| tacaagcacc | gcatgaacac | ggtcatgctg | cagctggagg | aggtggagcg | ggagcgggac | 1140 |
| caggccttcc | actcccgaga | tgaagctcag | acacagtact | cgcagtgctt | aatcgaaaag | 1200 |
| gacaagtaca | ggaagcagat | ccgcgagctg | gaggagaaga | cgacgagat | gaggatcgag | 1260 |
| atggtgcggc | gggaggcctg | catcgtcaac | ctggagagca | agctgcggcg | cctctccaag | 1320 |
| gacagcaaca | acctggacca | gagtctgccc | aggaacctgc | cagtaaccat | catctctcag | 1380 |
| gactttgggg | atgccagccc | caggaccaat | ggtcaagaag | ctgacgattc | ttccacctcg | 1440 |
| gaggagtcac | tgaagacag | caagtacttc | ctgccctacc | atccgcccca | gcgcaggatg | 1500 |
| aacctgaagg | gcatccagct | gcagagagcc | aaatcccca | tcagcctgaa | gcgaacatca | 1560 |
| gattttcaag | ccaaggggca | cgaggaagaa | ggcacggacg | ccagccctag | ctcctgcgga | 1620 |
| tctctgccca | tcaccaactc | cttcaccaag | atgcagcccc | ccggagccg | cagcagcatc | 1680 |
| atgtcaatca | ccgccgagcc | cccgggaaac | gactccatcg | tcagacgcta | caaggaggac | 1740 |
| gcgcccatc | gcagcacagt | cgaagaagac | aatgacagcg | gcgggtttga | cgccttagat | 1800 |
| ctggatgatg | acagtcacga | acgctactcc | ttcggaccct | cctccatcca | ctcctcctcc | 1860 |
| tcctcccacc | aatccgaggg | cctggatgcc | tacgacctgg | agcaggtcaa | cctcatgttc | 1920 |
| aggaagttct | ctctggaaag | acccttccgg | ccttcggtca | cctctgtggg | gcacgtgcgg | 1980 |
| ggcccagggc | cctcggtgca | gcacacgacg | ctgaatggcg | acagcctcac | ctcccagctc | 2040 |
| accctgctgg | ggggcaacgc | gcgagggagc | ttcgtgcact | cggtcaagcc | tggctctctg | 2100 |
| gccgagaaag | ccggcctccg | tgagggccac | cagctgctgc | tgctagaagg | ctgcatccga | 2160 |
| ggcgagaggc | agagtgtccc | gttggacaca | tgcaccaaag | aggaagccca | ctggaccatc | 2220 |
| cagaggtgca | gcggccccgt | cacgctgcac | tacaaggtca | ccacgaagg | gtaccggaag | 2280 |

-continued

```
ctggtgaagg acatggagga cggcctgatc acatcggggg actcgttcta catccggctg    2340
aacctgaaca tctccagcca gctggacgcc tgcaccatgt ccctgaagtg tgacgatgtt    2400
gtgcacgtcc gtgacaccat gtaccaggac aggcacgagt ggctgtgcgc gcgggtcgac    2460
cctttcacag accatgacct ggatatgggc accataccca gctacagccg agcccagcag    2520
ctcctcctgg tgaaactgca gcgcctgatg caccgaggca gccgggagga ggtagacggc    2580
acccaccaca ccctgcgggc actccggaac accctgcagc cagaagaagc gctttcaaca    2640
agcgaccccc gggtcagccc ccgtctctcg cgagcaagct tccttttgg ccagctcctt    2700 cagttcgtca gcaggtccga gaacaagtat aagcggatga acagcaacga gcgggtccgc    2760
atcatctcgg ggagtccgct agggagcctg gcccggtcct cgctggacgc caccaagctc    2820
ttgactgaga agcaggaaga gctggaccct gagagcgagc tgggcaagaa cctcagcctc    2880
atcccctaca gcctggtacg cgccttctac tgcgagcgcc gccggcccgt gctcttcaca    2940
cccaccgtgc tggccaagac gctggtgcag aggctgctca actcgggagg tgccatggag    3000
ttcaccatct gcaagtcaga tatcgtcaca agagatgagt tcctcagaag gcagaagacg    3060
gagaccatca tctactcccg agagaagaac cccaacgcgt tcgaatgcat cgcccctgcc    3120
aacattgaag ctgtggccgc caagaacaag cactgcctgc tggaggctgg gatcggctgc    3180
acaagagact tgatcaagtc caacatctac cccatcgtgc tcttcatccg ggtgtgtgag    3240
aagaacatca agaggttcag aaagctgctg ccccgacctg agacggagga ggagttcctg    3300
cgcgtgtgcc ggctgaagga aaggagctg gaggccctgc cgtgcctgta cgccacggtg    3360
gaacctgaca tgtggggcag cgtagaggag ctgctccgcg ttgtcaagga caagatcggc    3420
gaggagcagc gcaagaccat ctgggtggac gaggaccagc tgtga              3465
```

<210> SEQ ID NO 2
<211> LENGTH: 669
<212> TYPE: DNA
<213> ORGANISM: Homo sapiens
<400> SEQUENCE: 2

```
atggagccca ccgcaccgtc cctcaccgag gaggacctca ctgaagtgaa gaaggacgcc      60
ttagaaaatt tacgtgtata cctgtgtgag aaaatcatag ctgagagaca ttttgatcat     120
ctacgtgcaa aaaaaatact cagtagagaa gacactgaag aaatttcttg tcgaacatca     180
agtagaaaaa gggctggaaa attgttagac tacttacagg aaaacccaaa aggtctggac     240
acccttgttg aatctattcg gcgagaaaaa acacagaact tcctgataca gaagattaca     300
gatgaagtgc tgaaacttag aaatataaaa ctagaacatc tgaaagatgg agccacgaac     360
aacctctcca gatcaaattc agatgagagt aatttctctg aaaaactgag gcatccact     420 gtcatgtacc atccagaagg agaatccagc acgacgccct tttttctac taattcttct     480 ctgaatttgc ctgttctaga agtaggcaga actgaaaata ccatcttctc ttcaactaca     540
cttcccagac ctggggaccc aggggctcct cctttgccac cagatctaca gttagaagaa     600
gaaggaactt gtgcaaactc tagtgagatg tttcttccct taagatcacg tactgtttca     660
cgacaatga                                                             669
```

<210> SEQ ID NO 3
<211> LENGTH: 2475
<212> TYPE: DNA
<213> ORGANISM: Homo sapiens

```
<400> SEQUENCE: 3
atgtcgctgt tgggggaccc gctacaggcc ctgccgccct cggccgcccc cacggggccg      60
ctgctcgccc ctccggccgg cgcgaccctc aaccgcctgc gggagccgct gctgcggagg     120
ctcagcgagc tcctggatca ggcgcccgag ggcgggggct ggaggagact ggcggagctg     180
gcggggagtc gcgggcgcct ccgcctcagt tgcctagacc tggagcagtg ttctcttaag     240
gtactggagc tgaaggaag cccagcctg tgtctgctga gttaatggg tgaaaaaggt        300 tgcacagtca cagaattgag tgatttcctg caggctatgg aacacactga agttcttcag     360
cttctcagcc ccccaggaat aaagattact gtaaacccag agtcaaaggc agtcttggct     420
ggacagtttg tgaaactgtg ttgccgggca actggacatc cttttgttca atatcagtgg     480
ttcaaaatga ataaagagat tccaaatgga aatacatcag agcttatttt taatgcagtg     540
catgtaaaag atgcaggctt ttatgtctgt cgagttaata acaatttcac ctttgaattc     600
agccagtggt cacagctgga tgtttgcgac atcccagaga gcttccagag aagtgttgat     660
ggcgtctctg aatccaagtt gcaaatctgt gttgaaccaa cttcccaaaa gctgatgcca     720
ggcagcacat tggttttaca gtgtgttgct gttggaagcc ctattcctca ctaccagtgg     780
ttcaaaaatg aattaccatt aacacatgag accaaaaagc tatacatggt gccttatgtg     840
gatttggaac accaaggaac ctactggtgt catgtatata atgatcgaga cagtcaagat     900
agcaagaagg tagaaatcat cataggaaga acagatgagg cagtggagtg cactgaagat     960
gaattaaata atcttggtca tcctgataat aaagagcaaa caactgacca gcctttggcg    1020
aaggacaagg ttgccctttt gataggaaat atgaattacc gggagcaccc caagctcaaa    1080
gctcctttgg tggatgtgta cgaattgact aacttactga dacagctgga cttcaaagtg    1140
gtttcactgt tggatcttac tgaatatgag atgcgtaatg ctgtggatga gtttttactc    1200
cttttagaca agggagtata tgggttatta tattatgcag acatggtta tgaaaatttt    1260 gggaacagct tcatggtccc cgttgatgct ccaaatccat ataggtctga aaattgtctg    1320
tgtgtacaaa atatactgaa attgatgcaa gaaaagaaa ctggacttaa tgtgttctta    1380
ttggatatgt gtaggaaaag aaatgactac gatgatacca ttccaatctt ggatgcacta    1440
aaagtcaccg ccaatattgt gtttggatat gccacgtgtc aaggagcaga agcttttgaa    1500
atccagcatt ctggattggc aaatggaatc tttatgaaat ttttaaaaga cagattatta    1560
gaagataaga aaatcactgt gttactggat gaagttgcag aagatatggg taagtgtcac    1620
cttaccaaag gcaaacaggc tctagagatt cgaagtagtt tatctgagaa gagagcactt    1680
actgatccaa tacagggaac agaatattct gctgaatctc ttgtgcggaa tctacagtgg    1740
gccaaggctc atgaacttcc agaaagtatg tgtcttaagt ttgactgtgg tgttcagatt    1800
caattaggat ttgcagctga gttttccaat gtcatgatca tctatacaag tatagtttac    1860
aaaccaccgg agataataat gtgtgatgcc tacgttactg atttcccact tgatctagat    1920
attgatccaa aagatgcaaa taaaggcaca cctgaagaaa ctggcagcta cttggtatca    1980
aaggatcttc ccaagcattg cctctatacc agactcagtt cactgcaaaa attaaggaa    2040 catctagtct tcagatatg tttatcatat cagtactcag gattgaaga tactgtagag     2100 gacaagcagg aagtgaatgt tgggaaacct ctcattgcta aattagacat gcatcgaggt    2160
ttgggaagga agacttgctt tcaaacttgt cttatgtcta atggtcctta ccagagttct    2220
gcagccacct caggaggagc agggcattat cactcattgc aagacccatt ccatggtgtt    2280
taccattcac atcctggtaa tccaagtaat gttacaccag cagatagctg tcattgcagc    2340
```

-continued

```
cggactccag atgcatttat ttcaagtttc gctcaccatg cttcatgtca ttttagtaga    2400
agtaatgtgc cagtagagac aactgatgaa ataccattta gtttctctga caggctcaga    2460
atttctgaaa aatga                                                     2475
```

<210> SEQ ID NO 4
<211> LENGTH: 1154
<212> TYPE: PRT
<213> ORGANISM: Homo sapiens

<400> SEQUENCE: 4

```
Met Pro Gly Gly Gly Pro Glu Met Asp Asp Tyr Met Glu Thr Leu Lys
1               5                   10                  15

Asp Glu Glu Asp Ala Leu Trp Glu Asn Val Glu Cys Asn Arg His Met
            20                  25                  30

Leu Ser Arg Tyr Ile Asn Pro Ala Lys Leu Thr Pro Tyr Leu Arg Gln
        35                  40                  45

Cys Lys Val Ile Asp Glu Gln Asp Glu Asp Val Leu Asn Ala Pro
    50                  55                  60

Met Leu Pro Ser Lys Ile Asn Arg Ala Gly Arg Leu Leu Asp Ile Leu
65                  70                  75                  80

His Thr Lys Gly Gln Arg Gly Tyr Val Val Phe Leu Glu Ser Leu Glu
                85                  90                  95

Phe Tyr Tyr Pro Glu Leu Tyr Lys Leu Val Thr Gly Lys Glu Pro Thr
            100                 105                 110

Arg Arg Phe Ser Thr Ile Val Val Glu Glu Gly His Glu Gly Leu Thr
        115                 120                 125

His Phe Leu Met Asn Glu Val Ile Lys Leu Gln Gln Gln Met Lys Ala
    130                 135                 140

Lys Asp Leu Gln Arg Cys Glu Leu Leu Ala Arg Leu Arg Gln Leu Glu
145                 150                 155                 160

Asp Glu Lys Lys Gln Met Thr Leu Thr Arg Val Glu Leu Leu Thr Phe
                165                 170                 175

Gln Glu Arg Tyr Tyr Lys Met Lys Glu Glu Arg Asp Ser Tyr Asn Asp
            180                 185                 190

Glu Leu Val Lys Val Lys Asp Asp Asn Tyr Asn Leu Ala Met Arg Tyr
        195                 200                 205

Ala Gln Leu Ser Glu Glu Lys Asn Met Ala Val Met Arg Ser Arg Asp
    210                 215                 220

Leu Gln Leu Glu Ile Asp Gln Leu Lys His Arg Leu Asn Lys Met Glu
225                 230                 235                 240

Glu Glu Cys Lys Leu Glu Arg Asn Gln Ser Leu Lys Leu Lys Asn Asp
                245                 250                 255

Ile Glu Asn Arg Pro Lys Lys Glu Gln Val Leu Glu Leu Glu Arg Glu
            260                 265                 270

Asn Glu Met Leu Lys Thr Lys Asn Gln Glu Leu Gln Ser Ile Ile Gln
        275                 280                 285

Ala Gly Lys Arg Ser Leu Pro Asp Ser Asp Lys Ala Ile Leu Asp Ile
    290                 295                 300

Leu Glu His Asp Arg Lys Glu Ala Leu Glu Asp Arg Gln Glu Leu Val
305                 310                 315                 320

Asn Arg Ile Tyr Asn Leu Gln Glu Glu Ala Arg Gln Ala Glu Glu Leu
                325                 330                 335

Arg Asp Lys Tyr Leu Glu Glu Lys Glu Asp Leu Glu Leu Lys Cys Ser
```

```
                340                 345                 350
Thr Leu Gly Lys Asp Cys Glu Met Tyr Lys His Arg Met Asn Thr Val
            355                 360                 365
Met Leu Gln Leu Glu Glu Val Glu Arg Glu Arg Asp Gln Ala Phe His
            370                 375                 380
Ser Arg Asp Glu Ala Gln Thr Gln Tyr Ser Gln Cys Leu Ile Glu Lys
385                 390                 395                 400
Asp Lys Tyr Arg Lys Gln Ile Arg Glu Leu Glu Glu Lys Asn Asp Glu
                405                 410                 415
Met Arg Ile Glu Met Val Arg Glu Ala Cys Ile Val Asn Leu Glu
            420                 425                 430
Ser Lys Leu Arg Arg Leu Ser Lys Asp Ser Asn Asn Leu Asp Gln Ser
            435                 440                 445
Leu Pro Arg Asn Leu Pro Val Thr Ile Ile Ser Gln Asp Phe Gly Asp
            450                 455                 460
Ala Ser Pro Arg Thr Asn Gly Gln Glu Ala Asp Asp Ser Ser Thr Ser
465                 470                 475                 480
Glu Glu Ser Pro Glu Asp Ser Lys Tyr Phe Leu Pro Tyr His Pro Pro
                485                 490                 495
Gln Arg Arg Met Asn Leu Lys Gly Ile Gln Leu Gln Arg Ala Lys Ser
                500                 505                 510
Pro Ile Ser Leu Lys Arg Thr Ser Asp Phe Gln Ala Lys Gly His Glu
            515                 520                 525
Glu Glu Gly Thr Asp Ala Ser Pro Ser Ser Cys Gly Ser Leu Pro Ile
            530                 535                 540
Thr Asn Ser Phe Thr Lys Met Gln Pro Pro Arg Ser Arg Ser Ser Ile
545                 550                 555                 560
Met Ser Ile Thr Ala Glu Pro Pro Gly Asn Asp Ser Ile Val Arg Arg
                565                 570                 575
Tyr Lys Glu Asp Ala Pro His Arg Ser Thr Val Glu Glu Asp Asn Asp
            580                 585                 590
Ser Gly Gly Phe Asp Ala Leu Asp Leu Asp Asp Ser His Glu Arg
            595                 600                 605
Tyr Ser Phe Gly Pro Ser Ser Ile His Ser Ser Ser Ser His Gln
            610                 615                 620
Ser Glu Gly Leu Asp Ala Tyr Asp Leu Glu Gln Val Asn Leu Met Phe
625                 630                 635                 640
Arg Lys Phe Ser Leu Glu Arg Pro Phe Arg Pro Ser Val Thr Ser Val
                645                 650                 655
Gly His Val Arg Gly Pro Gly Pro Ser Val Gln His Thr Thr Leu Asn
                660                 665                 670
Gly Asp Ser Leu Thr Ser Gln Leu Thr Leu Leu Gly Gly Asn Ala Arg
            675                 680                 685
Gly Ser Phe Val His Ser Val Lys Pro Gly Ser Leu Ala Glu Lys Ala
            690                 695                 700
Gly Leu Arg Glu Gly His Gln Leu Leu Leu Leu Glu Gly Cys Ile Arg
705                 710                 715                 720
Gly Glu Arg Gln Ser Val Pro Leu Asp Thr Cys Thr Lys Glu Glu Ala
                725                 730                 735
His Trp Thr Ile Gln Arg Cys Ser Gly Pro Val Thr Leu His Tyr Lys
            740                 745                 750
Val Asn His Glu Gly Tyr Arg Lys Leu Val Lys Asp Met Glu Asp Gly
            755                 760                 765
```

```
Leu Ile Thr Ser Gly Asp Ser Phe Tyr Ile Arg Leu Asn Leu Asn Ile
            770                 775                 780

Ser Ser Gln Leu Asp Ala Cys Thr Met Ser Leu Lys Cys Asp Asp Val
785                 790                 795                 800

Val His Val Arg Asp Thr Met Tyr Gln Asp Arg His Glu Trp Leu Cys
            805                 810                 815

Ala Arg Val Asp Pro Phe Thr Asp His Asp Leu Asp Met Gly Thr Ile
            820                 825                 830

Pro Ser Tyr Ser Arg Ala Gln Gln Leu Leu Val Lys Leu Gln Arg
            835                 840                 845

Leu Met His Arg Gly Ser Arg Glu Glu Val Asp Gly Thr His His Thr
            850                 855                 860

Leu Arg Ala Leu Arg Asn Thr Leu Gln Pro Glu Glu Ala Leu Ser Thr
865                 870                 875                 880

Ser Asp Pro Arg Val Ser Pro Arg Leu Ser Arg Ala Ser Phe Leu Phe
            885                 890                 895

Gly Gln Leu Leu Gln Phe Val Ser Arg Ser Glu Asn Lys Tyr Lys Arg
            900                 905                 910

Met Asn Ser Asn Glu Arg Val Arg Ile Ile Ser Gly Ser Pro Leu Gly
            915                 920                 925

Ser Leu Ala Arg Ser Ser Leu Asp Ala Thr Lys Leu Leu Thr Glu Lys
930                 935                 940

Gln Glu Glu Leu Asp Pro Glu Ser Glu Leu Gly Lys Asn Leu Ser Leu
945                 950                 955                 960

Ile Pro Tyr Ser Leu Val Arg Ala Phe Tyr Cys Glu Arg Arg Pro
            965                 970                 975

Val Leu Phe Thr Pro Thr Val Leu Ala Lys Thr Leu Val Gln Arg Leu
            980                 985                 990

Leu Asn Ser Gly Gly Ala Met Glu Phe Thr Ile Cys Lys Ser Asp Ile
            995                 1000                1005

Val Thr Arg Asp Glu Phe Leu Arg Arg Gln Lys Thr Glu Thr Ile
            1010                1015                1020

Ile Tyr Ser Arg Glu Lys Asn Pro Asn Ala Phe Glu Cys Ile Ala
            1025                1030                1035

Pro Ala Asn Ile Glu Ala Val Ala Ala Lys Asn Lys His Cys Leu
            1040                1045                1050

Leu Glu Ala Gly Ile Gly Cys Thr Arg Asp Leu Ile Lys Ser Asn
            1055                1060                1065

Ile Tyr Pro Ile Val Leu Phe Ile Arg Val Cys Glu Lys Asn Ile
            1070                1075                1080

Lys Arg Phe Arg Lys Leu Leu Pro Arg Pro Glu Thr Glu Glu Glu
            1085                1090                1095

Phe Leu Arg Val Cys Arg Leu Lys Glu Lys Glu Leu Glu Ala Leu
            1100                1105                1110

Pro Cys Leu Tyr Ala Thr Val Glu Pro Asp Met Trp Gly Ser Val
            1115                1120                1125

Glu Glu Leu Leu Arg Val Val Lys Asp Lys Ile Gly Glu Glu Gln
            1130                1135                1140

Arg Lys Thr Ile Trp Val Asp Glu Asp Gln Leu
            1145                1150

<210> SEQ ID NO 5
<211> LENGTH: 222
```

```
<212> TYPE: PRT
<213> ORGANISM: Homo sapiens

<400> SEQUENCE: 5

Met Glu Pro Thr Ala Pro Ser Leu Thr Glu Glu Asp Leu Thr Glu Val
1               5                   10                  15

Lys Lys Asp Ala Leu Glu Asn Leu Arg Val Tyr Leu Cys Glu Lys Ile
                20                  25                  30

Ile Ala Glu Arg His Phe Asp His Leu Arg Ala Lys Lys Ile Leu Ser
            35                  40                  45

Arg Glu Asp Thr Glu Glu Ile Ser Cys Arg Thr Ser Ser Arg Lys Arg
        50                  55                  60

Ala Gly Lys Leu Leu Asp Tyr Leu Gln Glu Asn Pro Lys Gly Leu Asp
65                  70                  75                  80

Thr Leu Val Glu Ser Ile Arg Arg Glu Lys Thr Gln Asn Phe Leu Ile
                85                  90                  95

Gln Lys Ile Thr Asp Glu Val Leu Lys Leu Arg Asn Ile Lys Leu Glu
                100                 105                 110

His Leu Lys Asp Gly Ala Thr Asn Asn Leu Ser Arg Ser Asn Ser Asp
            115                 120                 125

Glu Ser Asn Phe Ser Glu Lys Leu Arg Ala Ser Thr Val Met Tyr His
130                 135                 140

Pro Glu Gly Glu Ser Ser Thr Thr Pro Phe Phe Ser Thr Asn Ser Ser
145                 150                 155                 160

Leu Asn Leu Pro Val Leu Glu Val Gly Arg Thr Glu Asn Thr Ile Phe
                165                 170                 175

Ser Ser Thr Thr Leu Pro Arg Pro Gly Asp Pro Gly Ala Pro Pro Leu
            180                 185                 190

Pro Pro Asp Leu Gln Leu Glu Glu Gly Thr Cys Ala Asn Ser Ser
        195                 200                 205

Glu Met Phe Leu Pro Leu Arg Ser Arg Thr Val Ser Arg Gln
210                 215                 220

<210> SEQ ID NO 6
<211> LENGTH: 824
<212> TYPE: PRT
<213> ORGANISM: Homo sapiens

<400> SEQUENCE: 6

Met Ser Leu Leu Gly Asp Pro Leu Gln Ala Leu Pro Pro Ser Ala Ala
1               5                   10                  15

Pro Thr Gly Pro Leu Leu Ala Pro Ala Gly Ala Thr Leu Asn Arg
                20                  25                  30

Leu Arg Glu Pro Leu Leu Arg Arg Leu Ser Glu Leu Leu Asp Gln Ala
            35                  40                  45

Pro Glu Gly Arg Gly Trp Arg Arg Leu Ala Glu Leu Ala Gly Ser Arg
        50                  55                  60

Gly Arg Leu Arg Leu Ser Cys Leu Asp Leu Glu Gln Cys Ser Leu Lys
65                  70                  75                  80

Val Leu Glu Pro Glu Gly Ser Pro Ser Leu Cys Leu Leu Lys Leu Met
                85                  90                  95

Gly Glu Lys Gly Cys Thr Val Thr Glu Leu Ser Asp Phe Leu Gln Ala
                100                 105                 110

Met Glu His Thr Glu Val Leu Gln Leu Leu Ser Pro Pro Gly Ile Lys
            115                 120                 125
```

-continued

```
Ile Thr Val Asn Pro Glu Ser Lys Ala Val Leu Ala Gly Gln Phe Val
    130                 135                 140

Lys Leu Cys Cys Arg Ala Thr Gly His Pro Phe Val Gln Tyr Gln Trp
145                 150                 155                 160

Phe Lys Met Asn Lys Glu Ile Pro Asn Gly Asn Thr Ser Glu Leu Ile
                165                 170                 175

Phe Asn Ala Val His Val Lys Asp Ala Gly Phe Tyr Val Cys Arg Val
                180                 185                 190

Asn Asn Asn Phe Thr Phe Glu Phe Ser Gln Trp Ser Gln Leu Asp Val
            195                 200                 205

Cys Asp Ile Pro Glu Ser Phe Gln Arg Ser Val Asp Gly Val Ser Glu
    210                 215                 220

Ser Lys Leu Gln Ile Cys Val Glu Pro Thr Ser Gln Lys Leu Met Pro
225                 230                 235                 240

Gly Ser Thr Leu Val Leu Gln Cys Val Ala Val Gly Ser Pro Ile Pro
                245                 250                 255

His Tyr Gln Trp Phe Lys Asn Glu Leu Pro Leu Thr His Glu Thr Lys
                260                 265                 270

Lys Leu Tyr Met Val Pro Tyr Val Asp Leu Glu His Gln Gly Thr Tyr
            275                 280                 285

Trp Cys His Val Tyr Asn Asp Arg Asp Ser Gln Asp Ser Lys Lys Val
    290                 295                 300

Glu Ile Ile Ile Gly Arg Thr Asp Glu Ala Val Glu Cys Thr Glu Asp
305                 310                 315                 320

Glu Leu Asn Asn Leu Gly His Pro Asp Asn Lys Glu Gln Thr Thr Asp
                325                 330                 335

Gln Pro Leu Ala Lys Asp Lys Val Ala Leu Leu Ile Gly Asn Met Asn
                340                 345                 350

Tyr Arg Glu His Pro Lys Leu Lys Ala Pro Leu Val Asp Val Tyr Glu
            355                 360                 365

Leu Thr Asn Leu Leu Arg Gln Leu Asp Phe Lys Val Val Ser Leu Leu
    370                 375                 380

Asp Leu Thr Glu Tyr Glu Met Arg Asn Ala Val Asp Glu Phe Leu Leu
385                 390                 395                 400

Leu Leu Asp Lys Gly Val Tyr Gly Leu Leu Tyr Tyr Ala Gly His Gly
                405                 410                 415

Tyr Glu Asn Phe Gly Asn Ser Phe Met Val Pro Val Asp Ala Pro Asn
                420                 425                 430

Pro Tyr Arg Ser Glu Asn Cys Leu Cys Val Gln Asn Ile Leu Lys Leu
            435                 440                 445

Met Gln Glu Lys Glu Thr Gly Leu Asn Val Phe Leu Leu Asp Met Cys
    450                 455                 460

Arg Lys Arg Asn Asp Tyr Asp Asp Thr Ile Pro Ile Leu Asp Ala Leu
465                 470                 475                 480

Lys Val Thr Ala Asn Ile Val Phe Gly Tyr Ala Thr Cys Gln Gly Ala
                485                 490                 495

Glu Ala Phe Glu Ile Gln His Ser Gly Leu Ala Asn Gly Ile Phe Met
                500                 505                 510

Lys Phe Leu Lys Asp Arg Leu Leu Glu Asp Lys Lys Ile Thr Val Leu
            515                 520                 525

Leu Asp Glu Val Ala Glu Asp Met Gly Lys Cys His Leu Thr Lys Gly
    530                 535                 540

Lys Gln Ala Leu Glu Ile Arg Ser Ser Leu Ser Glu Lys Arg Ala Leu
```

```
           545                 550                 555                 560
Thr Asp Pro Ile Gln Gly Thr Glu Tyr Ser Ala Glu Ser Leu Val Arg
                565                 570                 575

Asn Leu Gln Trp Ala Lys Ala His Glu Leu Pro Glu Ser Met Cys Leu
                580                 585                 590

Lys Phe Asp Cys Gly Val Gln Ile Gln Leu Gly Phe Ala Ala Glu Phe
                595                 600                 605

Ser Asn Val Met Ile Ile Tyr Thr Ser Ile Val Tyr Lys Pro Pro Glu
            610                 615                 620

Ile Ile Met Cys Asp Ala Tyr Val Thr Asp Phe Pro Leu Asp Leu Asp
625                 630                 635                 640

Ile Asp Pro Lys Asp Ala Asn Lys Gly Thr Pro Glu Thr Gly Ser
                645                 650                 655

Tyr Leu Val Ser Lys Asp Leu Pro Lys His Cys Leu Tyr Thr Arg Leu
                660                 665                 670

Ser Ser Leu Gln Lys Leu Lys Glu His Leu Val Phe Thr Val Cys Leu
                675                 680                 685

Ser Tyr Gln Tyr Ser Gly Leu Glu Asp Thr Val Glu Asp Lys Gln Glu
            690                 695                 700

Val Asn Val Gly Lys Pro Leu Ile Ala Lys Leu Asp Met His Arg Gly
705                 710                 715                 720

Leu Gly Arg Lys Thr Cys Phe Gln Thr Cys Leu Met Ser Asn Gly Pro
                725                 730                 735

Tyr Gln Ser Ser Ala Ala Thr Ser Gly Gly Ala Gly His Tyr His Ser
            740                 745                 750

Leu Gln Asp Pro Phe His Gly Val Tyr His Ser His Pro Gly Asn Pro
                755                 760                 765

Ser Asn Val Thr Pro Ala Asp Ser Cys His Cys Ser Arg Thr Pro Asp
            770                 775                 780

Ala Phe Ile Ser Ser Phe Ala His His Ala Ser Cys His Phe Ser Arg
785                 790                 795                 800

Ser Asn Val Pro Val Glu Thr Thr Asp Glu Ile Pro Phe Ser Phe Ser
                805                 810                 815

Asp Arg Leu Arg Ile Ser Glu Lys
            820

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Arg Pro Arg
1

<210> SEQ ID NO 8
<211> LENGTH: 8
<212> TYPE: PRT
<213> ORGANISM: Gallus gallus

<400> SEQUENCE: 8

Ser Ile Ile Asn Phe Glu Lys Leu
1               5
```

```
<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Ser Ser Arg
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Ser Ser Arg
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ala Ser Arg
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ala Ser Arg
1

<210> SEQ ID NO 13
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (57)..(57)
<223> OTHER INFORMATION: a, c, t, g, unknown or other

<400> SEQUENCE: 13
aagcagtggt atcaacgcag agtactttt tttttttttt tttttttttt tttttvn        57

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide

<400> SEQUENCE: 14
aagcagtggt atcaacgcag agtacatggg                                      30

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aagcagtggt atcaacgcag agt                                             23

<210> SEQ ID NO 16
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (30)..(37)
<223> OTHER INFORMATION: This region may encompass one of the following
      sequences: "AAGTAGAG" or "ACACGATC" or "TGTTCCGA"
<220> FEATURE:
<223> OTHER INFORMATION: See specification as filed for detailed
      description of substitutions and preferred embodiments

<400> SEQUENCE: 16
aatgatacgg cgaccaccga gatctacacn nnnnnnntcg tcggcagcgt c               51

<210> SEQ ID NO 17
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(32)
<223> OTHER INFORMATION: This region may encompass one of the following
      sequences: "AGCAATTC" or "AACTTGAC" or "TGTCGGAT" or "TCGCCTTG" or
      "AAGACACT" or "TCTCGGTC"
<220> FEATURE:
<223> OTHER INFORMATION: See specification as filed for detailed
      description of substitutions and preferred embodiments

<400> SEQUENCE: 17
caagcagaag acggcatacg agatnnnnnn nngtgactgg agttcagacg tgtgctcttc      60
cgatctggg                                                             69

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acatgctgag ccgttacatc a                                               21
```

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccacatagcc cctttgtccc                                                     20

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cggcacagtc attgaaagcc ta                                                  22

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gttgctgatg gcctgattgt c                                                   21

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcttcctaga ttacccttc tgc                                                  23

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cgggcatggt tctggatca                                                      19

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccacattcaa agccctctcc ta                                                  22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gttttcccac acttcatctt gc                                            22

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ttggccagcg ccatctt                                                  17

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgcctcctcc agagagaagt g                                             21

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aaggttcaga acggaagtg                                                19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gggtctccac agtggtact                                                19

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
caaatcccac acaaccactg                                               20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
tgctcacttg gtcacaggac                                               20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
catgtagggt cgagagtggg                                               20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
cctcctgcta ctgctgacct                                               20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
tgctgcataa tcagctacgg                                               20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
gctggtcaca ttgagaagca                                               20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
acaagctgct acaaccaggg                                               20

<210> SEQ ID NO 37

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
acttctggct ggagacctca                                                 20

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtggccgcag tgggacaaga g                                               21

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agggcactgg tggcatcatc                                                 20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tggtgaaatt gcaagagctg                                                 20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cagacttccg ttggtggatt                                                 20

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cagaggaaag agagaaagtc c                                               21

<210> SEQ ID NO 43
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cacacggtga cagtgctgg                                                    19

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
catcctgctg ggtctgagtg                                                   20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
attctcactg gcccgtcatc                                                   20

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
caagagagtg ctgttccagg t                                                 21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gagcacgctg agtacctcat t                                                 21

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tggtgaaggt cggtgaac                                                     18

<210> SEQ ID NO 49
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 49
ccatgtagtt gaggtcaatg aagg                                           24
```

TARGETING THE CBM SIGNALOSOME COMPLEX INDUCES REGULATORY T CELLS TO INFLAME THE TUMOR MICROENVIRONMENT

CROSS-REFERENCE TO RELATED APPLICATION

This application is a U.S.C. § 371 National Entry Application of International Application No. PCT/US2018/067856 filed Dec. 28, 2018, which claims benefit under 35 U.S.C. § 119(e) of U.S. Provisional Application No. 62/611,186 filed Dec. 28, 2017, the contents of each of which are incorporated herein by reference in their entireties.

INCORPORATION BY REFERENCE

Incorporated by reference in its entirety is a computer-readable nucleotide/amino acid sequence listing submitted concurrently herewith and identified as follows: ASCII text file named 030258-090990WOPT_SL.txt created on Dec. 28, 2018 and is 38,540 bytes in size.

TECHNICAL FIELD

The technology described herein relates to the treatment of cancer.

BACKGROUND

Solid tumors are infiltrated by effector T cells (Teff) with the potential to control or reject them, as well as by regulatory T cells (Treg) that restrict the function of Teff and thereby promote tumor growth[1]. The anti-tumor activity of Teff can be therapeutically unleashed and is now being exploited for the treatment of some select forms of human cancer. However, weak tumor-associated inflammatory responses and low interferon (IFN)-γ secretion as well as the immune-suppressive function of Treg remain major hurdles to broader effectiveness of tumor immunotherapy[2].

SUMMARY

Presented herein in part is experimental data showing that upon disruption of the CARMA1-Bcl10-MALT1 (CBM) signalosome complex, the majority of tumor-infiltrating Treg produce IFN-γ and tumor growth is inhibited. Genetic deletion of both, or even just one allele, of CARMA1 as a means to disrupt activity of a CBM signalosome complex in only a fraction of Treg, which avoided systemic autoimmunity, was sufficient to produce this anti-tumor effect, indicating that gain of effector activity by Treg dominantly initiates tumor control. Treg production of IFN-γ was accompanied by macrophage activation and up-regulation of MHC-I on tumor cells, reflecting enhanced tumor immune-reactivity. Tumor cells also up-regulated expression of PD-L1, indicating activation of adaptive immune resistance[3]. Consequently, a PD-1 blockade concomitant with disruption of the CBM signalosome complex caused rejection of tumors that otherwise do not respond to anti-PD-1 monotherapy. Experimental findings described herein demonstrate, in part, that partial disruption of the CBM signalosome complex and induction of IFN-γ-secretion in the self-reactive Treg pool does not cause systemic autoimmunity but is sufficient to prime the tumor environment for successful immune checkpoint therapy.

Accordingly, one aspect of the invention described herein provides a method for treating cancer comprising administering an agent that inhibits the activity of a CARMA1-Bcl10-MALT1 signalosome complex to a subject in need thereof.

In one embodiment of any aspect described herein, the cancer is a carcinoma, a melanoma, a sarcoma, a myeloma, a leukemia, or a lymphoma. In another embodiment, the cancer is a solid tumor. Exemplary solid tumors include an Adrenocortical Tumor, an Alveolar Soft Part Sarcoma, a Chondrosarcoma, a Colorectal Carcinoma, a Desmoid Tumors, a Desmoplastic Small Round Cell Tumor, an Endocrine Tumors, an Endodermal Sinus Tumor, an Epithelioid Hemangioendothelioma, a Ewing Sarcoma, a Germ Cell Tumors (Solid Tumor), a Giant Cell Tumor of Bone and Soft Tissue, a Hepatoblastoma, a Hepatocellular Carcinoma, a Melanoma, a Nephroma, a Neuroblastoma, a Non-Rhabdomyosarcoma Soft Tissue Sarcoma (NRSTS), an Osteosarcoma, a Paraspinal Sarcoma, a Renal Cell Carcinoma, a Retinoblastoma, a Rhabdomyosarcoma, a Synovial Sarcoma, and a Wilms Tumor. In one embodiment of any aspect, the cancer is metastatic.

In one embodiment of any aspect described herein, the cancer is a melanoma or colon cancer.

In one embodiment of any aspect described herein, the method further comprises, prior to administering, diagnosing a subject as having cancer.

In one embodiment of any aspect described herein, the method further comprises, prior to administering, receiving the results of an assay that diagnoses a subject as having cancer.

In one embodiment of any aspect described herein, the method further comprises administering an immune checkpoint inhibitor to the subject. The checkpoint inhibitor can be a small molecule, an inhibitory nucleic acid, an inhibitory polypeptide, an antibody or antigen-binding domain thereof, or antibody reagent. In one embodiment of any aspect described herein, the antibody or antigen-binding domain thereof, or antibody reagent binds an immune checkpoint polypeptide and inhibits its activity. Exemplary immune checkpoint polypeptides include PD-L1, PD-L2, PD-1, CTLA-4, TIM-3, LAG-3, VISTA, or TIGIT. In one embodiment of any aspect, the immune checkpoint polypeptide is PD-1, PD-L1, or PD-L2.

In one embodiment of any aspect described herein, the checkpoint inhibitor inhibits PD-1, PD-L1, or PD-L2. Exemplary checkpoint inhibitors that inhibit PD-1 include Pembrolizumab (Keytruda), Nivolumab, AUNP-12, and Pidilizumab. Exemplary checkpoint inhibitors that inhibit PD-L1 include Atezolizumab, MPDL3280A, Avelumab, or Durvalumab.

In one embodiment of any aspect described herein, the activity of a CARMA1-Bcl10-MALT1 signalosome complex is inhibited in a regulatory T cell. In one embodiment of any aspect, the regulatory T cell is a tumor-infiltrating regulatory T cell.

In one embodiment of any aspect described herein, the activity inhibited by the agent is the CARMA1-Bcl10-MALT1 signalosome complex function. In one embodiment of any aspect, the activity inhibited by the agent is the formation of the CARMA1-Bcl10-MALT1 signalosome complex. In one embodiment of any aspect described herein, the activity inhibited by the agent is the function of at least one component of the CARMA1-Bcl10-MALT1 signalosome complex. In one embodiment of any aspect described herein, the activity inhibited by the agent is the expression level of at least one component of the CARMA1-Bcl10-MALT1 signalosome complex.

In one embodiment of any aspect described herein, the agent is a small molecule, an inhibitory nucleic acid, an antibody or antigen-binding fragment thereof or antibody reagent, or an inhibitory polypeptide. In one embodiment of any aspect described herein, the small molecule is a small molecule inhibitor of MALT1 paracaspase activity. Exemplary inhibitors of MALT1 paracaspase activity include, but are not limited to, MI-2 or analogs thereof, a pyrazolo pyrimidine derivative, a phenothiazine derivative, and tetrapeptide Z-VRPR-FMK (SEQ ID NO: 7). In one embodiment of any aspect, the phenothiazine is mepazine, thioridazine, or promazine. In other embodiments, the MALT1 inhibitor comprises one or more compounds or derivatives described in WO2018020474, WO2018119036, WO2018141749, or US20180251489, the contents of each of which are incorporated herein by reference in their entirety. In one embodiment, the MALT1 inhibitor is a peptide derivative of tetrapeptide Z-VRPR-FMK (SEQ ID NO: 7) as described in e.g., US20180251489, the contents of which are incorporated by reference in its entirety. In another embodiment, the MALT1 inhibitor is (S)-1-(6-(4-(aminomethyl)-1H-pyrazol-1-yl)-5-chloropyridin-3-yl)-3-(2-chloro-7-(1-methoxyethyl)pyrazolo[1,5-a]pyrimidin-6-yl)ureal as described in e.g., WO2018141749, the contents of which are incorporated herein by reference in its entirety. In another embodiment, the MALT1 inhibitor comprises a pyrazolo derivative as described in e.g., WO2018119036, the contents of which is incorporated herein by reference in its entirety. In another embodiment, the MALT1 inhibitor comprises one or more substituted thiazolo-pyridine compounds, for example, the substituted thiazolo-pyridine compounds described in WO2018020474, the contents of which are incorporated herein by reference in its entirety.

In another embodiment of various aspects described herein, the method further comprises administering an anti-cancer therapy to the subject. Exemplary anti-cancer therapies include chemotherapy, radiation therapy, chemo-radiation therapy, immunotherapy, hormone therapy, and stem cell therapy. In one embodiment of any aspect described herein, the immunotherapy is a tumor vaccine, a chimeric antigen receptor T cell (CAR T cell), an adoptive T cell therapy (e.g., adoptive $CD4^+$ or $CD8^+$ effector T cell therapy), an adoptive natural killer (NK) cell therapy, or an adoptive NK T cell therapy.

Another aspect of the invention described herein provides a method of treating cancer comprising administering an MI-2 inhibitor and an inhibitor of PD-1 to a subject in need thereof.

Yet another aspect of the invention described herein provides a method of treating cancer comprising administering Mepazine and an inhibitor of PD-1 to a subject in need thereof.

In one embodiment of any aspect described herein, the administration is systemic. In one embodiment of any aspect, the administration is local.

Another aspect of the invention described herein provides a cell engineered to have reduced CARMA1-Bcl10-MALT1 signalosome activity. In one embodiment, the cell has been engineered to inhibit the function of at least one gene selected from the group consisting of CARMA1, Bcl10, or MALT1. In another embodiment, the cell has been engineered to inhibit the function of at least one gene product selected from the group consisting of CARMA1, Bcl10, or MALT1. In another embodiment, the cell has been engineered to reduce the expression level of at least one gene selected from the group consisting of CARMA1, Bcl10, or MALT1. In yet another embodiment, the cell has been engineered to reduce the expression level of at least one gene product selected from the group consisting of CARMA1, Bcl10, or MALT1.

In one embodiment of any aspect described herein, the cell is an immune cell. In one embodiment of any aspect, the cell is a T cell. In another embodiment of any aspect, the cell is a T regulatory cell.

Another aspect of the invention described herein provides a method of treating cancer comprising administering any of the engineered cells described herein to a subject in need thereof. In one embodiment, the method further comprises administering a checkpoint inhibitor to the subject. In another embodiment, the method further comprises administering an anti-cancer therapy to the subject.

Another aspect of the invention described herein provides a method of treating cancer that is resistant to a checkpoint inhibitor therapy comprising: (a) administering an agent that inhibits activity of a CARMA1-Bcl10-MALT1 signalosome complex, or any of the cells described herein; and (b) a second therapeutic to a subject in need thereof.

In one embodiment of any aspect described herein, the method further comprises, prior to administering, diagnosing a subject as having cancer that is resistant to a checkpoint inhibitor therapy.

In one embodiment of any aspect described herein, the method further comprises, prior to administering, receiving the results of an assay that diagnoses a subject as having cancer that is resistant to a checkpoint inhibitor therapy.

In one embodiment of any aspect described herein, the second therapeutic is a checkpoint inhibitor or an anti-cancer therapy.

Exemplary checkpoint inhibitor therapies include an anti-PD-L1 therapy, an anti-PD-L2 therapy, an anti-PD-1 therapy, an anti-CTLA-4 therapy, an anti-TIM-3 therapy, an anti-LAG-3 therapy, an anti-VISTA therapy, and an anti-TIGIT therapy. In one embodiment of any aspect described herein, the checkpoint inhibitor therapy is an anti-PD-1 therapy.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

Definitions of common terms in molecular biology and medicine can be found, for example, in *The Merck Manual of Diagnosis and Therapy,* 19th Edition, published by Merck Sharp & Dohme Corp., 2011 (ISBN 978-0-911910-19-3); Robert S. Porter et al. (eds.), *The Encyclopedia of Molecular Cell Biology and Molecular Medicine,* published by Blackwell Science Ltd., 1999-2012 (ISBN 9783527600908); and Robert A. Meyers (ed.), *Molecular Biology and Biotechnology: a Comprehensive Desk Reference,* published by VCH Publishers, Inc., 1995 (ISBN 1-56081-569-8); *Lewin's*

*Genes XI*, published by Jones & Bartlett Publishers, 2014 (ISBN-1449659055); Michael Richard Green and Joseph Sambrook, *Molecular Cloning: A Laboratory Manual*, 4$^{th}$ ed., Cold Spring Harbor Laboratory Press, Cold Spring Harbor, N.Y., USA (2012) (ISBN 1936113414); Davis et al., *Basic Methods in Molecular Biology*, Elsevier Science Publishing, Inc., New York, USA (2012) (ISBN 044460149X); *Laboratory Methods in Enzymology: DNA*, Jon Lorsch (ed.) Elsevier, 2013 (ISBN 0124199542); *Current Protocols in Molecular Biology* (*CPMB*), Frederick M. Ausubel (ed.), John Wiley and Sons, 2014 (ISBN 047150338X, 9780471503385), *Current Protocols in Protein Science* (*CPPS*), John E. Coligan (ed.), John Wiley and Sons, Inc., 2005; and *Current Protocols in Immunology* (*CPI*) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. Where applicable, a decrease can be preferably down to a level accepted as within the range of normal for an individual without a given disease (e.g., melanoma or colon cancer.)

The terms "increased", increase", or "enhance" are all used herein to mean an increase by a statically significant amount. In some embodiments, the terms "increased", "increase", or "enhance" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker (e.g., expression of PD-1 on the cell surface) or symptom, an "increase" is a statistically significant increase in such level.

As used herein, a "subject" means a human or animal. Usually the animal is a vertebrate such as a primate, rodent, domestic animal or game animal. Primates include, for example, chimpanzees, cynomologous monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of disease e.g., cancer. A subject can be male or female. A subject can be of any developmental age, for example, a fetus, a neonate, a toddler, a child, a juvenile, an adolescent, a young adult, an adult, or a geriatric subject.

A subject can be one who has been previously diagnosed with or identified as suffering from or having a condition in need of treatment (e.g. melanoma, colon cancer, or another type of cancer, among others) or one or more complications related to such a condition, and optionally, have already undergone treatment for the condition or the one or more complications related to the condition. Alternatively, a subject can also be one who has not been previously diagnosed as having such condition or related complications. For example, a subject can be one who exhibits one or more risk factors for the condition or one or more complications related to the condition or a subject who does not exhibit risk factors. A subject can be one who has previously received a treatment or therapy for the condition (e.g., an anti-cancer therapy).

A "subject in need" of treatment for a particular condition can be a subject having that condition, diagnosed as having that condition, or at risk of developing that condition.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. melanoma, colon cancer, or other cancer, including cancer resistant to particular therapies, e.g., checkpoint inhibitor therapy. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality.

As used herein, "cancer" refers to a hyperproliferation of cells that have lost normal cellular control, resulting in unregulated growth, lack of differentiation, local tissue invasion, and metastasis. Cancers are classified based on the histological type (e.g., the tissue in which they originate) and their primary site (e.g., the location of the body the cancer first develops), and can be a carcinoma, a melanoma, a sarcoma, a myeloma, a leukemia, or a lymphoma. "Cancer" can also refer to a solid tumor. As used herein, the term "tumor" refers to an abnormal growth of cells or tissues, e.g., of malignant type or benign type. "Cancer" can be metastatic, meaning the cancer cells have disseminated from its primary site of origin and migrated to a secondary site.

In one embodiment, the term "engineered" and its grammatical equivalents as used herein can refer to one or more human-designed alterations of a nucleic acid, e.g., the nucleic acid within an organism's genome. In another embodiment, engineered can refer to alterations, additions, and/or deletion of genes. An "engineered cell" can refer to a cell with an added, deleted and/or altered gene. The term "cell" or "engineered cell" and their grammatical equivalents as used herein can refer to a cell of human or non-human animal origin.

The term "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a non-polypeptide moiety covalently or non-covalently associated therewith is still considered a "polypeptide." Exemplary modifications include glycosylation and palmitoylation. Polypeptides can be purified from natural sources, produced using recombinant DNA technology or synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

In some embodiments, a nucleic acid encoding a polypeptide as described herein (e.g. an inhibitory polypeptide) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "pharmaceutical composition" refers to an active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be an artificial or engineered carrier, e.g., a carrier in which the active ingredient would not be found to occur in nature.

As used herein, the term "administering," refers to the placement of a therapeutic (e.g., an agent) or pharmaceutical composition as disclosed herein into a subject by a method or route which results in at least partial delivery of the agent at a desired site. Pharmaceutical compositions comprising agents as disclosed herein can be administered by any appropriate route which results in an effective treatment in the subject. In one embodiment, administration is systemic administration. As used herein, "systemic administration" refers to a route of administration of the agent into the circulatory system of the subject. In one embodiment, administration is local administration. As used herein, "local administration" refers to administration of an agent to the site of action (e.g., a tumor). Local administration can be desirable to avoid adverse side effects caused by systemic administration of therapeutic or pharmaceutical composition.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the technology.

The singular terms "a," "an," and "the" include plural referents unless context clearly indicates otherwise. Similarly, the word "or" is intended to include "and" unless context clearly indicates otherwise. Although methods and materials similar or equivalent to those described herein can be used in the practice or testing of this disclosure, suitable

BRIEF DESCRIPTION OF THE DRAWINGS

(FIG. 1A) Intracellular CARMA1-protein expression in Treg and CD4$^+$ T$_{conv}$ from LNs of Foxp3$^{YFP-Cre}$× CARMA1$^{+/+}$, ×CARMA1$^{fl/+}$, and ×CARMA1$^{fl/fl}$ mice ('F$^{Cre}$×C1$^{+/+, fl/+, fl/fl}$') (FIGS. 1B and 1C) Weight gain (n=5/group) (FIG. 1B) and survival (n=8, 10, and 20 for +/+, +/f, and f/f, resp.) (FIG. 1C) of young mice. (FIG. 1O) YFP$^{bright}$ CD4 T cells from LNs of 1 year-old Foxp3$^{YFP-Ce/+}$×R26$^{YFP}$×CARMA1$^{fl/fl}$, ×CARMA1$^{fl/+}$, and ×CARMA1$^{fl/fl}$ mice were sorted and analyzed for the frequency of Foxp3$^{neg}$ exTreg. All graphs show means and either individual replicates or ±SEM. *=any p<0.05 in b, c. *=p<0.05, =p<0.01, *=p<0.001, and ****=p<0.0001 in other panels.

FIGS. 2A-2H present exemplary experimental data showing that reduced expression of CARMA1 converts tumor-infiltrating Treg into IFNγ-secreting effector cells that dominantly control tumor growth. (FIGS. 2A and 2B) Heterozygous female Foxp3$^{YFP-Cre/+}$×CARMA1$^{+/+}$, CARMA1$^{fl/+}$, and ×CARMA1$^{fl/fl}$ mice ('F$^{Cre/+}$×C1$^{+/+, fl/+, fl/f}$') were implanted with D4M.3A melanoma, and YFP$^+$ Treg from tdLN and tumor tissue analyzed on day 18 for their frequency among total CD4$^+$ T cells (FIG. 2A) and Foxp3 expression (FIG. 2B). (FIG. 2C) D4M.3A tumor growth in indicated mice, where either one or both alleles of CARMA1 were deleted in half of Treg. (FIGS. 2C-2F) In situ expression of effector cytokines in YFP$^+$ Treg lacking one or both alleles of CARMA1, in YFP$^{neg}$ Treg in the same tissue, as well as in CD4$^+$ and CD8$^+$ conventional T cells in tumor tissue (FIGS. 2D and 2E) or tdLNs (FIG. 2F) of indicated mice on day 18 after implantation of D4M.3A melanoma (Note: Cytokine expression by YFP$^+$ Treg of Foxp3$^{YFP-Cre}$ control mice results from low level cellular instability resulting from DNA damage through Cre recombinase activity on pseudo-LoxP sequences in the mouse genome; it was not observed in YFP$^{neg}$ Treg). (FIG. 2G) Tumor growth in indicated mice implanted with D4M.3A melanoma and treated with neutralizing α-IFNγ antibody or not. (FIG. 2H) 10$^6$ CD4$^+$ YFP$^+$ Treg from F$^{YFP-Cre/+}$×C1$^{f/+}$ or ×C1$^{+/+}$ mice were i.v. injected into either C57BL/6 or IFNγ-deficient hosts, which were implanted with D4M.3A melanoma the following day, and tumor growth was recorded. Data in FIG. 2A-F represent 2 independent replicates with similar results. All graphs show means and either individual replicates or ±SEM. *=any p<0.05 in FIG. 2C, G, H. *=p<0.05, =p<0.01, *=p<0.001, and ****=p<0.0001 in other panels.

FIGS. 3A-3F present exemplary experimental data showing that CARMA1-deleted Treg rapidly inflame tumor tissue but also induce adaptive immune resistance. (FIGS. 3A-3C) Foxp3$^{GFP-CreERT2}$×CARMA1$^{+/+}$ and ×CARMA1$^{fl/fl}$ mice ('F$^{CreERT2}$×C1$^{+/+, f/f}$') were implanted with D4M.3A melanoma and treated with 5 daily doses of tamoxifen starting on day 8 as well as with FTY720 daily starting the same day until the end of the experiment. (FIG. 3B) YFP$^+$ Treg and CD4$^+$ T$_{conv}$ were purified by FACS from tdLNs and tumor tissue 5 days after start of tamoxifen treatment and analyzed for deletion of floxed CARMA1 genes by PCR generating a product of decreased size. (FIG. 3D) Tumor growth in female mice in which CARMA1 was inducibly deleted in all Treg (FIG. 3C) or in female mice in which CARMA1 was deleted in all or half of Treg (FIG. 3D). Arrows indicate treatment start. (FIGS. 3E and 3F) MHC class II surface expression on F4/80+ tumor macrophages (FIG. 3E) and MHC class I as well as PD-L1 expression on D4M.3A tumor cells expressing a blue fluorescent H2B-Ceruelan-expressing fusion protein (FIG. 3F) 3 days after initiation of tamoxifen treatment of tumor-bearing FGFP-CreERT2× C1+/+ and ×C1f/f mice. Data in c-f represent 2 independent replicates with similar results. All graphs show means and either individual replicates or ±SEM. *=p<0.05 vs. FCre-ERT2×C1+/+, and #=p<0.05 vs. FCreERT2/+×C1f/f in FIGS. 3C and 3D. *=p<0.05 in FIGS. 3E and 3F.

(FIG. 4A) Female Foxp3$^{GFP-CreERT2}$× CARMA1$^{+/+}$ and ×CARMA1$^{fl/fl}$ mice were implanted with D4M.3A melanoma and starting on day 9 treated with tamoxifen until the end of the experiment as well as with three doses of 200 μg of the blocking α-PD-1 antibody 29F.1A12 or isotype control antibody, and tumor growth was recorded. (FIG. 4B) MALT1 protease inhibitors disrupt the mRNA-stabilizing and the NF-kB activity-optimizing functions of the CBM signalosome complex. (FIGS. 4C and 4D) D4M.3A tumor growth in C57BL/6 (FIG. 4C) or RAG1-deficient hosts (FIG. 4D) treated with MALT1 inhibitors mepazine or MI-2. (FIGS. 4E-4G) Mepazine effects within 3 days on MHC I and PD-L1 expression on tumor cells (FIG. 4E), expression of genes of adaptive immune resistance (Pdl1, Socs1), MHC I antigen presentation (Tap1), IFNγ-signaling (Stat1, Irf1), T cell recruitment (CXCL10), M1 macrophage activation (Nos2), and cytotoxicity (Gzmb) (FIG. 4F), as well as the frequency of CD4$^+$ and CD8$^+$ T cells (FIG. 4G). (FIGS. 4H-4J) Synergistic tumor control upon α-PD-1 and mepazine combination treatment of poorly immunogenic D4M.3A (FIG. 4H) and immunogenic D4M.3A-SIINFEKL ("SIINFEKL" disclosed as SEQ ID NO: 8) (FIG. 4I) tumors in male and of MC38 tumors (FIG. 4J) in female C57BL/6 hosts. Numbers in parentheses indicates fraction of tumors that did not relapse for at least 4 weeks following discontinuation of mepazine treatment. Data in 4A, 4C, 4D, 4H, and 4I represent 2 independent replicates with similar results. All graphs show means and either individual replicates or ±SEM. Arrows in graphs indicate treatment start. *=p<0.05 vs. $C1^{+/+}$, #=p<0.05 vs. $C1^{+/+}/\alpha$-PD-1, and &=p<0.05 vs. $C1^{f/f}$ in 4A; *=any p<0.05 vs. Vehicle, #=p<0.05 vs. $\alpha$-PD-1, and &=p<0.05 vs. Mepazine in 4C, 4H, 4I, and 4J; *=p<0.05 and ***=p<0.001 in 4E-4G.

(FIG. 5A) Data represent 5 mice per group, and were confirmed in an independent experiment. * indicates p<0.05. (FIG. 5B) Original histograms for data shown in FIG. 1N. Data represent 3-5 mice per group, and were confirmed in an independent experiment.

(FIG. 6A) Histological appearance of liver, skin, and lung at 21 days of age of indicated mice. Scale bars indicate 150 μm and 50 μm (insets), respectively. (FIG. 6B), Kidney, liver, and stomach tissue sections of healthy C57BL/6 Rag KO mice were reacted with serum from 21 days old mice of the indicated genotypes, and self tissue-reactive IgG revealed by α-mouse IgG staining. Nuclei were stained with DAPI (FIGS. 6C-6E), Size of the $CD11b^+$ splenic myeloid compartment and proportions of $Ly6G^+$ neutrophils, $CD11c^+$ MHC $II^{hi}$ DCs, $Ly6C^{hi}$ monocytes, $Lyc6G^{lo}$ $SSC^{hi}$ eosinophils, and $Ly6C^{lo}$ $SSC^{lo}$ macrophages in indicated mice. (FIG. 6F), Expression of MHC I, MHC II, and PD-L1 on splenic myeloid subsets. (FIG. 6G), Frequency of $CD4^+$ $Foxp3^{neg}$ and $CD8^+$ conventional T cells with a $CD44^{hi}$ $CD62L^{lo}$ effector memory phenotype in LNs of indicated mice at age 12 and 21 days. (FIG. 6H), Effector cytokine expression of Tconv from 21-day old mice upon 8-hour ex vivo stimulation on αCD3/CD28-coated plates. *=p<0.05, =p<0.01, *=p<0.001, and ****=p<0.0001.

(FIG. 7A) Survival of $F^{Cre}\times C1^{+/+\ or\ f/f}\times$ $Rosa26^{STOP\ f/f-IKK2ca}$ mice that express a constitutively active IKK2/β mutant upon expression of $Foxp3^{Cre}$. (FIG. 7B), Frequency of $CD4^+$ $Foxp3^{neg}$ and $CD8^+$ Tconv cells with a $CD44^{hi}$ $CD62L^{lo}$ effector memory phenotype in LNs of indicated mice at age 21 days. (FIGS. 7C-7D), Frequency of Treg among total $CD4^+$ T cells and of $CD44^{hi}$ $CD62L^{low}$ eTreg among total Treg in LNs of indicated mice (FIG. 7C) and effector cytokine expression by LN Treg upon 8-hour ex vivo stimulation on αCD3 and αCD28 antibody-coated plates (FIG. 7D). (FIG. 7E), Co-expression of indicated transcription factors by Treg from LNs of indicated mice. (FIG. 7F), Expression of CD44 and CD62L by $F^{Cre}\times$ $C1^{f/f}$Treg expressing T-bet, GATA-3, or RORγt, compared to total $C1^{f/f}$Treg (contour plots). *=p<0.05, *=p<0.001, and **=p<0.0001.

(FIG. 8A), Female heterozygous $Foxp^{YFP-Cre/+}$ ('$F^{Cre/+}$')$\times C1^{f/f}$ mice express YFP-Cre and delete $CARMA1^{f/f}$ in half of Treg due X-chromosomal location of the $Foxp3^{Cre}$ allele and random X chromosome inactivation, while the other half of Treg remains functional. (FIG. 8B), Frequency of $CD4^+$ $Foxp3^{neg}$ and $CD8^+$ Tconv with a $CD44^{hi}$ $CD62L^{lo}$ effector memory phenotype in peripheral blood of aging $F^{Cre/+}\times C1^{+/+,f/+,\ or\ fl/fl}$ mice (n=4/group). (FIG. 8C), Appearance of spleens and LNs of indicated mice at 1 year of age. (FIGS. 8D-8F), Expression of Foxp3, indicated markers of eTreg differentiation, as well as proliferation marker Ki67 and proapoptotic protein BIM by $YFP^+$ cTreg and eTreg from 9-week old $F^{Cre/+}\times$ $C1^{+/+,f/+,\ or\ f/f}$ mice. Note: Data on eTreg in e-f are the same as shown in FIG. 1k-1 and shown to facilitate comparison to cTreg and $YFP^-$ Treg in FIGS. 8G-8H. (FIGS. 8G-8H), Frequency of eTreg (g) and eTreg markers on $YFP^-$ cTreg and eTreg (h) from the same animals as shown in d and f. *=p<0.05, =p<0.01, *=p<0.001, and ****=p<0.0001.

(FIG. 9A), $CD4+CD45RB^{hi}$ YFP– Tconv and CD4+ $CD45RB^{lo}$ $YFP^{bright}$ Treg were double-sorted to >98% purity from LNs and spleens of $F^{Cre}\times C1^{+/+}\times$ $Rosa26^{STOP\ f/f-YFP}$ mice, which allow for clear differentiation of Cre-expressing Treg based on high expression of soluble EYFP in addition to the YFP-Cre fusion protein. (FIG. 9B), $YFP^{bright}$ Treg from $F^{Cre}\times C1^{+/+}$ or $F^{Cre/+}\times C1^{f/+}$ or $f/f$ mice and CellTrace Violet-labeled Tconv from $F^{Cre}\times$ $C1^{+/+}$ mice were co-cultured at indicated ratios for 3 days in the presence of αCD3 Abs and T-depleted splenocytes and suppression measured as reduction of Tconv proliferation. (FIG. 9C), Treg of various genotypes and Tconv were co-adoptively transferred into Rag-deficient hosts and their respective frequency in peripheral blood determined 8 weeks later. (FIG. 9D), $CD4^+$ $YFP^{bright}$ cells were sorted from LNs of 1-year old and $F^{Cre/+}\times C1^{+/+,\ f/+,\ or\ f/f}\times$ $Rosa26^{STOP\ f/f-YFP}$ mice and subsequently stained for expression of Foxp3 protein to determine the frequency of Foxp3-'exTreg'. *=p<0.05, =p<0.01, *=p<0.001, and ****=p<0.0001. 2-way ANOVA with Sidak post-test was used in FIG. 9A.

(FIG. 10A), Overlap between eTreg gene signatures generated by Grinberg-Bleyel et al and in this study (in each case, fold change >2, $p_{adj}$<0.01 between cTreg and eTreg was used). (FIG. 10B), Overlap between genes differentially expressed (fold change >2 and $p_{adj}$<0.05) between either cTreg (left) or eTreg (right) from female heterozygous $F^{Cre/+}\times C1^{f/f}$ and homozygous $F^{Cre}\times$c-$Rel^{f/f}$ and $F^{Cre}\times p65/RelA^{f/f}$ mice and to their respective 'WT' controls, following batch-correction of all, incl. publicly available NCBI GEO data sets.

FIGS. 11A-11E. (FIG. 11A), Frequency of adoptively transferred, YFP+ Treg of indicated genotypes in tdLNs of Ifng KO hosts at day 18 of tumor growth. FIGS. 11B-11D, Frequency (FIGS. 11B-11C)) and effector cytokine expression (FIG. 11D) of adoptively transferred, YFP+ Treg in tumors in Ifng KO hosts. (FIG. 11E), D4M.3A melanoma growth in Ifng KO hosts transferred with YFP+ Treg of indicated genotypes and treated with neutralizing αIFNγ Abs or isotype control as indicated. ****=p<0.0001 in d. *=any p<0.05 vs all other groups in FIG. 11E.

(FIG. 12C), Effector cytokine expression by tumor-infiltrating Treg. (FIG. 12D), Tumor growth. *=p<0.05, =p<0.01, *=p<0.001, and ****=p<0.0001 in a-c. *, &=any p<0.05 vs. $C1^{+/+}$ and $C1^{+/+}\times IKK2ca$, resp. in FIG. 12D.

FIGS. 13A-13K. (FIG. 13A), MHC II expression on tumor-associated macrophages in D4M.3A-implanted $F^{Cre/+}\times C1^{++,\ f/+\ or\ f/f}$ mice. (FIG. 13B), D4M.3A tumor growth in mice treated with depleting αCD8 Ab from day 8 and treated with mepazine or not from day 9. (FIG. 13C), D4M.3A tumor growth in $F^{Cre/+}\times C1^{+/+\ or\ f/f}$ mice treated with Mepazine or vehicle starting on day 9. (FIG. 13D), YFP$^+$ Treg were sorted from F$^{Cre}$×C1$^{+/+}$ mice and treated with 10 μM Mepazine of vehicle for 8 or 24 hours with or without concurrent αCD3/28 mAb TCR stimulation (8 h time-point only) and expression of Foxp3, markers of eTreg differentiation, cell viability, and frequency of eTreg were recorded. (FIG. 13E), RT-qPCR analysis of expression of Foxp3 and various Treg-associated genes in whole tumor tissue lysate following 3 days of Mepazine or vehicle treatment. (FIGS. 13F-13J), Composition of the tumor tissue immune infiltrate and frequencies of CD45$^+$ cells (FIG. 13G) and of various immune cell subsets (FIG. 13H) as well Ki67 expression by Tconv (FIG. 13I) and MHC II expression by macrophages (FIG. 13J) following 3 days of Mepazine or vehicle treatment. (FIG. 13K), Effector cytokine co-expression by tumor-infiltrating Treg following 12 days Mepazine and αPD-1 Ab treatment. *=p<0.05, =p<0.01, and *=p<0.001. *, #=any p<0.05 vs. C1$^{+/+}$ and C1$^{+/+}$+ Mepazine, resp. in FIG. 13C.

(FIG. 14A), Survival of F$^{Cre}$×C$^{f/f}$ mice treated with αIFNγ Abs from day 14 of life compared to F$^{Cre}$×C1$^{+/+}$ and to scurfy mice. (FIGS. 14M-14N), Synergistic tumor control upon αPD-1 and mepazine combination treatment of poorly immunogenic D4M.3A (FIG. 14M) and immunogenic D4M.3A-SIINFEKL ("SIINFEKL" disclosed as SEQ ID NO: 8) (FIG. 14N) tumors in male mice. Numbers in parentheses indicates fraction of tumors that did not relapse for at least 12 months following discontinuation of mepazine treatment. Data in FIGS. 14M and 14N represent 2 independent replicates with similar results. All graphs show means and either individual replicates or ±SEM. Arrows in graphs indicate treatment start. *=any p<0.05 vs. Vehicle; *=p<0.05 and ***=p<0.001 in FIG. 14M.

DETAILED DESCRIPTION

Figure 1D:
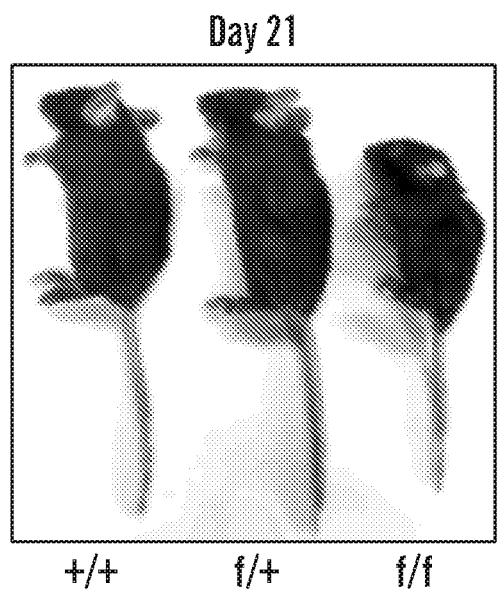
(FIGS. 1D-1F) Appearance of animals (FIG. 1D), of spleens and lymph nodes (FIG. 1E), and histological appearance of liver, lung, and skin (FIG. 1F) at 21 days of age of indicated mice. Scale bars in (FIG. 1F) indicate 150 μm and 50 μm (insets), respectively.
Figure 1E:
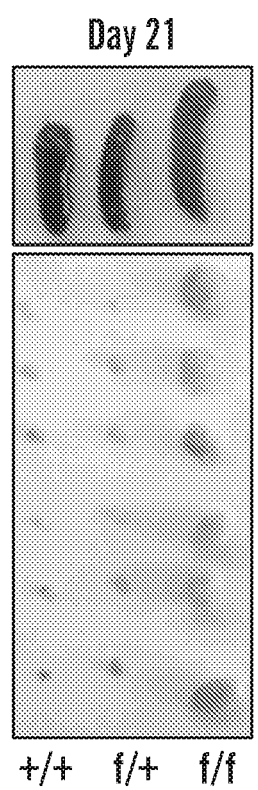
Figure 1F:
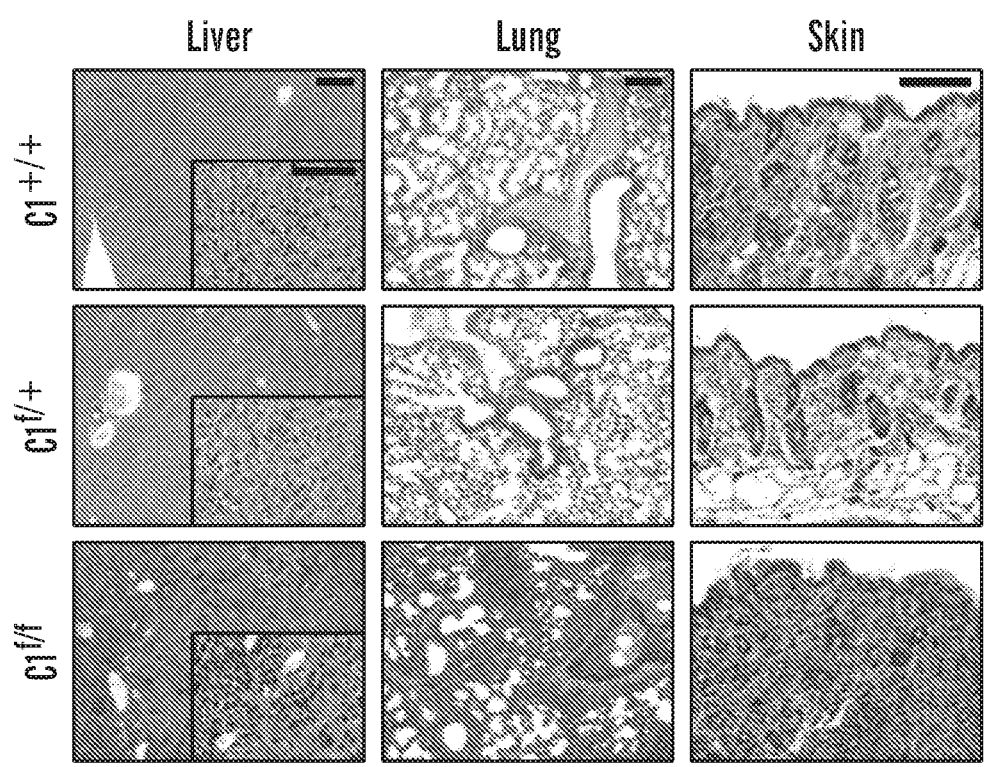

Exemplary experimental data provided herein demonstrates, in part, that the combined administration of an agent that inhibits activity of a CBM signalosome complex and a checkpoint inhibitor resulted in a rapid or pronounced reduction in tumor size, whereas a reduction in tumor size was not observed from a checkpoint inhibitor monotherapy. Thus, experimental data presented herein propose a therapeutic method for priming a tumor microenvironment to be more susceptible to a checkpoint inhibitor or an anti-cancer treatment.

CARMA1-Bcl10-MALT1 Signalosome Complex

The methods and compositions described herein are based, in part, on the finding that inhibition of the CARMA1-Bcl10-MALT1 (CBM) signalosome complex resulted in the secretion of IFN-γ by tumor-infiltrating regulatory T cells that was sufficient to arrest tumor growth. Regulatory T cells production of IFN-γ increased the immune-reactivity of the tumor cells and upregulated the expression of PD-L1 on the tumor cell surface. The combination of CBM signalosome complex inhibition and an anti-PD-1 therapy resulted in rejection of the tumor cells, whereas CBM signalosome complex inhibition or anti-PD-1 therapy alone did not.

As used herein, "CARM1-Bcl10-MALT1 (CBM) signalosome complex" refers to a trimolecular protein complex comprised of CARD- and membrane-associated guanylate kinase-like domain-containing protein 1 (CARMA1, also known as CARD11 and Bimp3), B-cell lymphoma/leukemia 10 (Bcl10), and mucosa-associated lymphoid tissue lymphoma translocation protein 1. The CBM signalosome complex is activated downstream of PKCθ/PKCβ and plays a critical role as molecular scaffold in mediating several downstream functions, e.g., NF-κB activation in B and T cells (e.g., translocation of NF-κB into the nucleus and activation of target genes), upon antigen-receptor stimulation. Assembly of the CBM signalosome complex in the cell additionally activates, e.g., the proteolytic activity of para-caspase MALT1, which, e.g., cleaves and inactivates the negative regulators of NF-κB and further enhances NF-κB activity. Enzymatic activity has only been identified for MALT1. As used herein "component of a/the CBM signalosome complex" refers to CARMA1, Bcl10, or MALT1.

Upon antigen-receptor ligation and signal cascade transduction, CARMA1/CARD11 is released from the auto-inhibition conformation and becomes accessible for the association with its downstream partners Bcl10 and MALT1 to assemble into a functional CBM signalosome complex. CARMA1 interacts with Bcl10 through CARD-CARD interaction and the C-terminus of Bcl10 directly interacts with the N-terminal Ig domains of MALT1. Electron Microscopy (EM), X-ray crystallography and Nuclear Magnetic Resonance (NMR) techniques revealed the assembly mechanism and structural architecture of the CBM signalosome complex. The CBM signalosome complex is a helical filamentous assembly where CARMA1 presents as a substoichiometric component in the complex and functions as the nucleator for the filament formation. Bcl10 CARD forms the core of the filament and MALT1 is brought to the periphery of the filament by interacting with the C-terminus of Bcl10 and thus becomes oligomerized and activated. The function of the CBM signalosome complex (e.g., its capacity to activate NF-κB signaling) requires the proper high order assembly described herein. Oligomers comprised of Bcl10 and MALT1 has been proposed to activate IKK complex via oligomerizing and activating TRAF6– the E3 ligase. Depletion of any of the components from the cell can inhibit the higher order assembly of the complex.

The CBM signalosome complex serves as the supramolecular hub where it integrates different receptor-induced signaling pathways that lead to NF-κB activation. Its aberrant activation has been associated with many NF-κB signaling dependent lymphocytic neoplasms.

The CBM signalosome complex is further reviewed in, e.g., Qiao, Q, et al. Molecular Cell. September 2013; 51 (6) 766-779, and Yang, C, et al. Cytokine Growth Factor Rev. 2014 April; 25(2): 175-183, which are incorporated by reference herein in their entireties.

Inhibition of CBM Signalosome Complex

In various aspects of the invention described herein, an agent that inhibits activity of a CBM signalosome complex is administered to a subject. In one embodiment, the agent can inhibit activity of a CBM signalosome complex by at least 10% compared to a reference level. In one embodiment, the agent can inhibit activity of a CBM signalosome complex by at least 20%, at least 30%, at least 40%, at least 50%, at least 60%, at least 70%, at least 80%, at least 90%, at least 99% or more compared to a reference level. A reference level can be, e.g., the activity of CBM signalosome complex prior to administration of an agent, or the activity of CBM signalosome complex in a cell not treated (e.g., contacted) with an agent. As used herein, "activity of a CBM signalosome complex" refers to formation, function, or expression level of the CBM signalosome complex.

In one embodiment, the agent inhibits activity of CBM signalosome complex in T cells. In one embodiment, the agent inhibits the activity of a CBM signalosome complex in a regulatory T cell. In one embodiment of any aspect, the regulatory T cell is a tumor-infiltrating regulatory T cell. As used herein "tumor-infiltrating regulatory T cell" refers to a regulatory T cell found in between tumor cells, for example, a regulatory T cell found in contact with a tumor cell on at least portion of its cell surface. One skilled in the art can identify tumor-infiltrating regulatory T cell by e.g., histological staining of a tumor sample obtained from a subject.

In one embodiment, the activity is the formation of the CBM signalosome complex. In one embodiment, the agent reduces the amount of intact CBM signalosome complex by at least 10% compared to a reference level, as measured by the amount of intact complexes in the cell. In one embodiment, the agent reduces the amount of intact CBM signalosome complex by at least 20%, at least 30%, at least 40%, at least 50%, at least 60%, at least 70%, at least 80%, at least 90%, at least 99% or more compared to a reference level. A reference level can be, e.g., the amount of intact prior to administration of an agent. As described above, the higher order assembly of the complex is required for its function. In one embodiment, the agent described herein inhibits the formation of the complex. The agent can inhibit the formation of the complex by binding to and inhibiting the binding sites comprised within the complex needed for the higher order assembly (e.g., the binding site for MALT1 on Bcl10). In one embodiment, the agent can inhibit the release of CARMA1 from its auto-inhibition confirmation. In one embodiment, an agent inhibits upstream factors required for CBM signalosome complex formation (e.g., (PKCθ or PKCβ phosphorylation). In one embodiment, the agent can decrease the expression level of at least one component of the CBM signalosome complex by at least 10% compared to a reference level. In one embodiment, the agent can decrease the expression level of at least one component of the CBM signalosome complex by at least 20%, at least 30%, at least 40%, at least 50%, at least 60%, at least 70%, at least 80%, at least 90%, at least 99% or more compared to a reference level. A reference level can be, e.g., the expression level of at least one component (e.g., CARMA1, Bcl10, or MALT1) prior to administration of an agent. One skilled in the art can determine if an agent is efficacious at inhibiting the formation of a CBM signalosome complex using, e.g., co-immunoprecipitation or sucrose gradient analysis to assess the intactness of the complex. To determine if the levels of at least one component of the complex have been decreased, a skilled person can perform PCR-based analysis or western blotting to assess the mRNA levels or protein levels, respectively, for a given component.

Various embodiments of the invention described herein require that the levels and/or activity of CARMA1 are inhibited. As used herein, caspase recruitment domain family member 11 (CARMA1), also known as CARD11, PPBL, BETA, BIMP3, IMD11, and IMD11A, refers to a scaffold protein part of the CARMA1/Bcl10/MALT1 (CBM) multiprotein complex. CARMA1 sequences are known for a number of species, e.g., human CARMA1 (NCBI Gene ID: 84433) polypeptide (e.g., NCBI Ref Seq NP_001311210.1) and mRNA (e.g., NCBI Ref Seq NM_001324281.1). CARMA1 can refer to human CARMA1, including naturally occurring variants, molecules, and alleles thereof. CARMA1 refers to the mammalian CARMA1 of, e.g., mouse, rat, rabbit, dog, cat, cow, horse, pig, and the like.

The nucleic sequence of SEQ ID NO: 1 comprises a nucleic sequence which encodes CARMA1.

Various embodiments of the invention described herein require that the levels and/or activity of Bcl10 are inhibited. As used herein, Bcl10, also known as CLAP, mE10, CIPER, IMD37, c-E10, and CARMEN, an immune signaling adaptor protein. Bcl10 is a component of the CARMA1/Bcl10/MALT1 (CBM) multiprotein complex. Bcl10 sequences are known for a number of species, e.g., human Bcl10 (NCBI Gene ID: 8915) polypeptide (e.g., NCBI Ref Seq NP_001320715.1) and mRNA (e.g., NCBI Ref Seq NM_001307644.1). Bcl10 can refer to human Bcl10, including naturally occurring variants, molecules, and alleles thereof. Bcl10 refers to the mammalian Bcl10 of, e.g., mouse, rat, rabbit, dog, cat, cow, horse, pig, and the like.

The nucleic sequence of SEQ ID NO: 2 comprises a nucleic sequence which encodes Bcl10.

Various embodiments of the invention described herein require that the levels and/or activity of MALT1 are inhibited. As used herein, MATL1 paracaspase (MALT1), also known as MET, MLT1, IMD12, and PCASP1, gene encodes a caspase-like protease that plays a role in BCL10-induced activation of NF-kappaB. The protein is a component of the CARMA1-BCL10-MALT1 (CBM) signalosome that triggers NF-kappaB signaling and lymphocyte activation following antigen-receptor stimulation. MALT1 sequences are known for a number of species, e.g., human MALT1 (NCBI Gene ID: 10892) polypeptide (e.g., NCBI Ref Seq NP_006776.1) and mRNA (e.g., NCBI Ref Seq NM_006785.4). MALT1 can refer to human MALT1, including naturally occurring variants, molecules, and alleles thereof. MALT1 refers to the mammalian MALT1 of, e.g., mouse, rat, rabbit, dog, cat, cow, horse, pig, and the like.

The nucleic sequence of SEQ ID NO: 3 comprises a nucleic sequence which encodes MALT1.

In another embodiment, the activity is the function of the CBM signalosome complex. In one embodiment, an agent inhibits the CBM signalosome complex from activating its downstream targets (e.g., NF-κB nuclear translocation and activation). In one embodiment, an agent reduces the paracaspase activity of MALT1 by at least 10% compared to a reference level. In one embodiment, an agent reduces the paracaspase activity of MALT1 by at least 20%, at least 30%, at least 40%, at least 50%, at least 60%, at least 70%, at least 80%, at least 90%, at least 99% or more compared to a reference level. A reference level can be, e.g., paracaspase activity of MALT1 prior to administration of an agent. In one embodiment, the agent inhibits the interaction with or activation of MALT1 substrates by at least 10%. In one embodiment, the agent inhibits the interaction with or activation of MALT1 substrates by at least 20%, at least 30%, at least 40%, at least 50%, at least 60%, at least 70%, at least 80%, at least 90%, at least 99% or more compared to a reference level. A reference level can be, e.g., interaction with or activation of MALT1 substrate prior to administration of an agent. In one embodiment, the agent reduces the cleavage of MALT1 substrates by at least 10%. In one embodiment, the agent reduces the cleavage of MALT1 substrates by at least 20%, at least 30%, at least 40%, at least 50%, at least 60%, at least 70%, at least 80%, at least 90%, at least 99% or more compared to a reference level. A reference level can be, e.g., cleavage of MALT1 substrates prior to administration of an agent. In lymphocytes, MALT1 has been shown to be controlled by its inducible mono-ubiquitination. In one embodiment, the agent reduces mono-ubiquitination of MALT1 by at least 10%. In one embodiment, the agent reduces mono-ubiquitination of MALT1 by at least 20%, at least 30%, at least 40%, at least 50%, at least 60%, at least 70%, at least 80%, at least 90%, at least 99% or more compared to a reference level. A reference level can be, e.g., mono-ubiquitination of MALT1 prior to administration of an agent. One skilled in the art will be able to determine if an agent is efficient at inhibiting activation of downstream targets using standard assays (e.g., using immunofluorescence to detect nuclear NF-κB). MALT1 paracaspase activity can be measured as described in, e.g., Halifinger, S, et al. Caspases, Paracaspases, and Metacaspases. Methods in Molecular Biology (Methods and Protocols), vol 1133. February 2014; 177-188. Mono-ubiquitination can be detected by a skilled person via western blotting using an anti-mono-ubiquitination antibody.

In another embodiment, the activity is the expression level of the CBM signalosome complex. In one embodiment, the agent reduces the expression level of the CBM signalosome complex by 10% compared to a reference level. In one embodiment, the agent reduces the expression level of the CBM signalosome complex by least 20%, at least 30%, at least 40%, at least 50%, at least 60%, at least 70%, at least 80%, at least 90%, at least 99% or more compared to a reference level. A reference level can be, e.g., the level of CBM signalosome complex prior to administration of an agent. In one embodiment, the agent reduces the expression level of at least one gene selected from: the CARMA1 gene, the Bcl10 gene, or the MALT1 gene by 10% compared to a reference level. In one embodiment, the agent reduces the expression level of at least one gene selected from: the CARMA1 gene, the Bcl10 gene, or the MALT1 gene by least 20%, at least 30%, at least 40%, at least 50%, at least 60%, at least 70%, at least 80%, at least 90%, at least 99% or more compared to a reference level. A reference level can be, e.g., the level of the CARMA1 gene, the Bcl10 gene, or the MALT1 gene expression prior to administration of an agent. In one embodiment, the agent reduces the expression level of at least one gene product selected from: the CARMA1 gene, the Bcl10gene, or the MALT1 gene by 10% compared to a reference level. In one embodiment, the agent reduces the expression level of at least one gene product selected from: the CARMA1 gene, the Bcl10 gene, or the MALT1 gene by least 20%, at least 30%, at least 40%, at least 50%, at least 60%, at least 70%, at least 80%, at least 90%, at least 99% or more compared to a reference level. A reference level can be, e.g., the level of the CARMA1 gene product, the Bcl10 gene product, or the MALT1 gene product prior to administration of an agent. Methods known in the art can be used to determine if an agent has reduced the expression level of a gene (e.g., via PCR-based assays), or a gene product (e.g., via western blotting).

In one embodiment, following administration of an agent, tumor-infiltrating regulatory T cells begin to secrete the cytokine IFNγ. One skilled in the art will be able to determine if the regulatory T cells in the tumor microenvironment are expressing IFNγ using, e.g., immunofluorescence to detect IFNγ by microscopy, or ELISA to detect IFNγ levels.

Agents

In one embodiment, an agent that inhibits activity of a CBM signalosome complex is administered as a treatment for cancer. An agent can be, for example, a small molecule, an inhibitory nucleic acid, an antibody or antigen-binding fragment thereof or antibody reagent, or an inhibitory polypeptide.

The agents used in the methods disclosed herein may be in salt form, e.g., with organic or inorganic acids. Examples of suitable acids for such acid addition salt formation include trifluoroacetic acid, hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethane sulfonic acid, nitrous acid, hydroxy ethane sulfonic acid, ethylene sulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known in the art. The salts are prepared by contacting the free base form with a sufficient amount of the desired acid to produce a salt in the conventional manner.

An agent can inhibit, e.g., at least one gene comprised in the CBM signalosome complex (e.g., CARMA1, Bcl10, or MALT1). An agent is considered effective for inhibiting activity of a CBM signalosome complex if said agent can, for example, upon contacting a CBM signalosome complex inhibit its activity, formation, and/or expression level.

In one embodiment, the agent that inhibits activity of a CBM signalosome complex is a small molecule. A small molecule can be defined as a low molecular weight (e.g., ranging from 500 to 900 daltons) organic compound that can regulate a biological process. It is desired that the small molecule can diffuse across membranes to reach its given target (e.g., a CBM signalosome complex). Small molecules can bind their given target with high affinity and act as an effector upon binding. Small molecules that bind a given target are known in the art and can be determined by a skilled person. Methods for screening small molecules are known in the art and can be used to identify a small molecule that is efficient at, for example, inhibiting activity of a CBM signalosome complex.

In one embodiment, the small molecule is a small molecule inhibitor of MALT1 paracaspase activity. In one embodiment, the inhibitor of MALT1 paracaspase activity is MALT1 Inhibitor-2 (MI-2, chemical name: 2-Chloro-A-[4-[5-(3,4-dichlorophenyl)-3-(2-methoxyethoxy)-1H-1,2,4-triazol-1-yl]phenylacetamide). MI-2 directly binds MALT1 and irreversibly suppresses the protease function of MALT1, and is commercially available from Tocris; Cat No. 4848; Minneapolis, Minn.

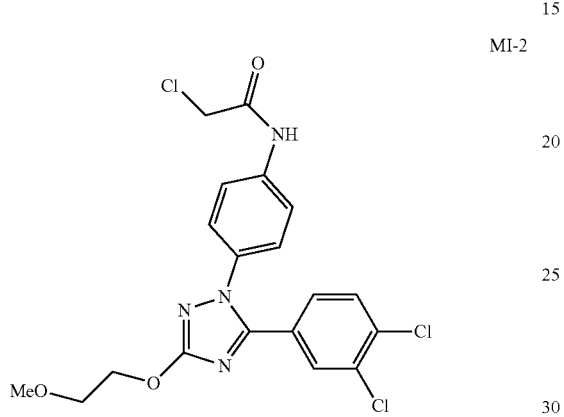

MI-2

In one embodiment, the inhibitor of MALT1 paracaspase activity is an analog of MI-2. Analogs of MI-2 (MI-2A1, MI-2A2, MI-2A3, MI-2A4, MI-2A5, MI-2A6, and MI-2A7) have been identified as having anti-MALT1 paracaspase activity, and are further described in e.g., Fontan, L, et al. Cancer Cell. 2012 Dec. 11; 22(6): 812-824, and Xin B T, et al. Bioorganic and Medicinal Chemistry 24, 2016: 3312-3329, which are incorporated herein by reference in their entireties.

In some cases, the analogs of MI-2 are disclosed in WO 2014/074815, the disclosure of which is incorporated herein by reference in its entirety. In some cases, the MALT1 inhibitor is a compound as disclosed in WO 2014/074815, the disclosure of which is incorporated herein by reference in its entirety. In some cases, the compound has a structure of

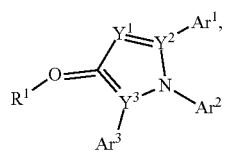

(I)

where a dashed bond indicates that a bond can be present or absent; when a double bond is present between $Y^1$ and $Y^2$, $Y^1$ is N or CR, $Y^2$ is C, and $Ar^1$ is present; when a single bond is present between $Y^1$ and $Y^2$, $Y^1$ is $CR_2$, $Y^2$ is O or S, and $Ar^1$ is absent, and each independently selected R is H or (C1-C6)alkyl; $R^1$ is alkyl, alkoxyalkyl, or arylalkyl, wherein any alkyl, alkoxyalkyl, or arylalkyl, can be mono- or independently multi-substituted with halo or (C1-C6)alkoxy, provided that when a double bond is present between the oxygen atom and the ring comprising $Y^3$, $R^1$ is absent and $Ar^3$ is present, and when a single bond is present between the oxygen atom and the ring, $R^1$ is present, a double bond between Y and the carbon atom bearing the oxygen atom is present, and $Ar^3$ is absent; $Ar^1$ is phenyl substituted with 1-3 $J^1$ groups; $J^1$ is halo or (C1-C6)alkoxy; $Ar^2$ is phenyl substituted with 1-3 $J^2$ groups; $J^2$ is a group of formula —N(R)C(0)-$R^2$ and $R^2$ is alkyl, aryl, or arylamino, wherein any alkyl, aryl, or arylamino is substituted with 0-2 halo, nitro, or (C1-C6)alkoxy groups; $Ar^3$ is phenyl substituted with 1-3 $J^3$ groups; and $J^3$ is halo or (C1-C6)alkoxy. In some cases, the compound is

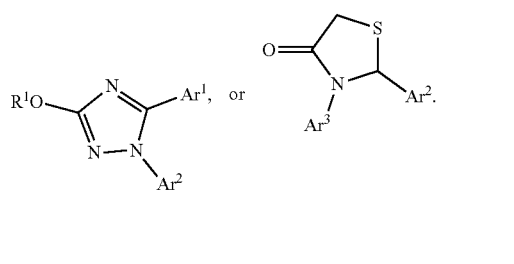

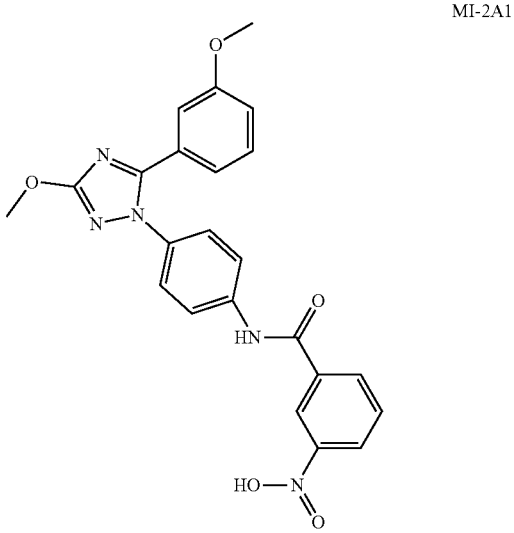

MI-2A1

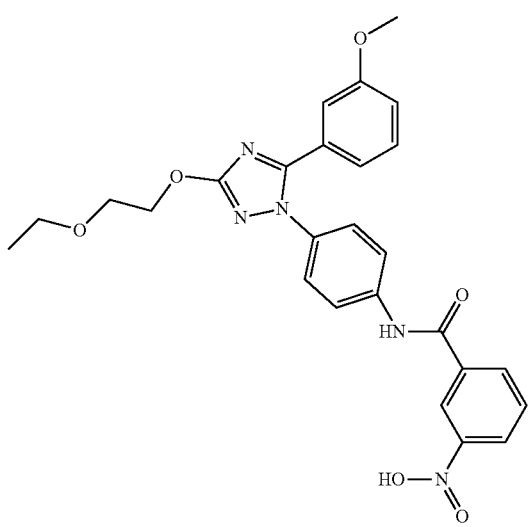

MI-2A2

MI-2A3

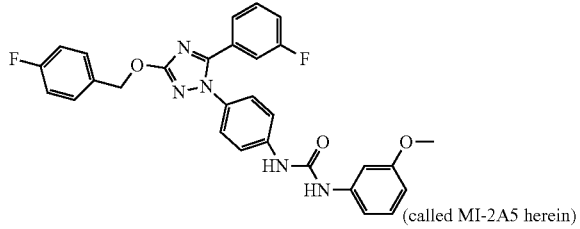

(called MI-2A5 herein)

MI-2A4

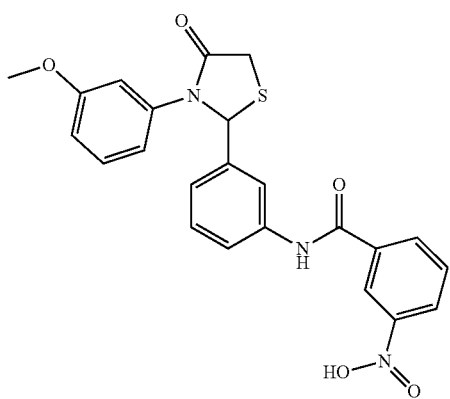

MI-2A3

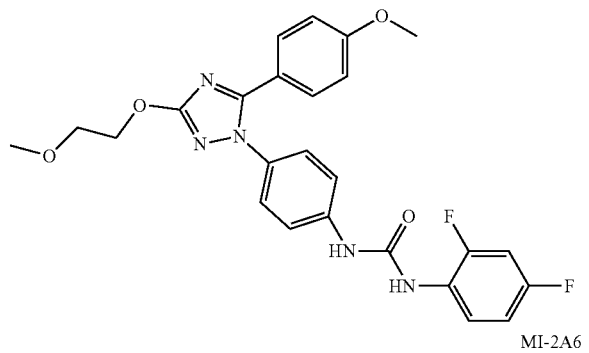

MI-2A6

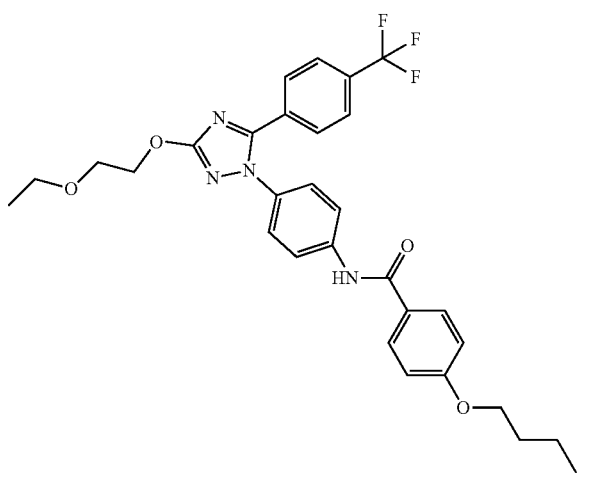

MI-2A7

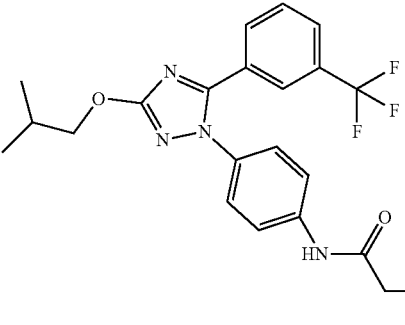

In another embodiment, the inhibitor of MALT1 paracaspase activity is a pyrazolo pyrimidine derivative. The inhibitory MALT1 action of the family of pyrazolo pyrimidine derivatives is further described in, e.g., U.S. patent application Ser. No. 15/312,321 or WO 2015/181747, the contents of each of which are incorporated herein by reference in their entirety. The pyrazolo pyrimidine derivative can have a structure of Formula (I) as disclosed in WO 2015/181747

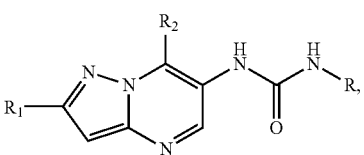

(I)

wherein $R_1$ is halogen, cyano, or $C_1$-$C_3$ alkyl optionally substituted by halogen;
$R_2$ is $C_1$-$C_6$ alkyl optionally substituted one or more times by $C_1$-$C_6$ alkyl, $C_3$-$C_6$ alkenyl, hydroxyl, N,N-di-$C_1$-$C_6$ alkylamino, N-mono-$C_1$-$C_6$ alkylamino, O-Rg, Rg, phenyl, or by $C_1$-$C_6$ alkoxy, wherein said alkoxy again may optionally be substituted by $C_1$-$C_6$ alkoxy, N,N-di-$C_1$-$C_6$ alkylamino, Rg or phenyl; $C_3$-$C_6$cycloalkyl optionally substituted by $C_1$-$C_6$ alkyl, N, N-di-$C_1$-$C_6$ alkylamino, or $C_1$-$C_6$ alkoxy-$C_1$-$C_6$ alkyl, and/or two of said optional substituents together with the atoms to which they are bound may form an annulated or spirocyclic 4-6 membered saturated heterocyclic ring comprising 1-20 atoms; phenyl optionally substituted by $C_1$-$C_6$ alkoxy; a 5-6 membered heteroaryl ring having 1 to 3 heteroatoms selected from N and O said ring being optionally substituted by $C_1$-$C_6$ alkyl, which may be optionally substituted by amino or hydroxy; Rg; or N,N-di-$C_1$-$C_6$ alkyl amino carbonyl; wherein
Rg is a 5-6 membered heterocyclic ring having 1-3 heteroatoms selected from N and O, said ring being optionally substituted by $C_1$-$C_6$ alkyl, $C_1$-$C_6$ alkoxy-$C_1$-$C_6$ alkyl, $C_1$-$C_6$ alkoxy-carbonyl;
R is phenyl independently substituted one or more times by Rd; wherein Ra independently from each other is halogen; cyano; —COO$C_1$-$C_6$ alkyl; $C_1$-$C_6$ alkoxy; $C_1$-$C_6$ alkyl optionally substituted by halogen or a 5-6 membered heterocyclyl ring having 1 to 2 heteroatoms selected from N and O which ring is optionally substituted by $C_1$-$C_6$ alkyl; a 5-6 membered heteroaryl ring having 1-3 heteroatoms selected from N and O said ring being optionally substituted by amino, $C_1$-$C_6$ alkyl optionally substituted by amino or hydroxyl, or by N-mono- or N,N-di-$C_1$-$C_6$ alkylamino carbonyl; and/or two Ra together with the ring atoms to which they are bound may form a 5 to 6 membered heterocyclic or heteroaromatic ring having 1 to 2 N atoms, any such ring being optionally substituted by $C_1$-$C_6$ alkyl or oxo;

Rb, Re, and Rd independently from each other are halogen; oxo; hydroxyl; cyano; $C_1$-$C_6$ alkoxy optionally substituted by halogen; $C_1$-$C_6$ alkoxy carbonyl; phenyl; N,N-di-$C_1$-$C_6$ alkyl amino; $C_1$-$C_6$ alkyl optionally substituted by halogen or phenyl; a 5-6 membered heteroaryl ring having 1 to 3 N atoms said ring being optionally substituted by amino or hydroxyl, or by mono- or di-N-d-Ce alkylamino carbonyl; O—Rh; or Rh; wherein Rh is a 5-6 membered heterocyclyl ring having 1 to 4 heteroatoms selected from N, O and S, said ring being optionally substituted by a $C_1$-$C_6$ alkyl, hydroxyl or oxo.

Pyrazolo pyrimidine derivatives include, but are not limited to, Zaleplon™, Indiplon™, Ocinaplon, Divaplon, and Lorediplon. Pyrazolo pyrimidine derivatives are a series of isomeric heterocyclic chemical compounds with the molecular formula $C_6H_5N_3$. They form the central core of various complex chemical compounds including, for example, some pharmaceuticals and pesticides. One isomer of pyrazolo pyrimidines, known as pyrazolo[1,5-a]pyrimidine, is the basis for a class of sedative and anxiolytic drugs related (in terms of their effect) to benzodiazepines. In one embodiment, the inhibitor of MALT1 paracaspase activity comprises a chemical structure comprising pyrazolo[1,5-a] pyrimidine.

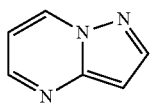

Pyrazolo[1,5-a]pyrimidine

In some cases, the MALT1 inhibitor is a pyrazolo pyrimidine derivative selected from (S)-1-(5-cyanopyridin-3-yl)-3-(7-(1-methoxyethyl)-2-methylpyrazolo[1,5-a]pyrimidin-6-yl)urea; (S)-1-(2-(difluoromethyl)pyridin-4-yl)-3-(2-fluoro-7-(1-methoxyethyl) pyrazolo[1,5-a]pyrimidin-6-yl) urea; (S)-1-(2-chloro-7-(1-methoxyethyl)pyrazolo[1,5-a] pyrimidin-6-yl)-3-(2-(trifluoromethyl)pyridin-4-yl)urea; 1-(5-chloro-6-(2H-1,2,3-triazol-2-yl)pyridin-3-yl)-3-(2-chloro-7-isopropylpyrazolo[1,5-a]pyrimidin-6-yl)urea; (S)-1-(5-chloro-6-(2H-1,2,3-triazol-2-yl)pyridin-3-yl)-3-(2-chloro-7-(1-methoxyethyl)pyrazolo[1,5-a]pyrimidin-6-yl) urea; (S)-1-(5-cyano-6-methoxypyridin-3-yl)-3-(2-fluoro-7-(1-methoxyethyl) pyrazolo[1,5-a]pyrimidin-6-yl)urea; (S)-1-(6-(2H-1,2,3-triazol-2-yl)-5-(trifluoromethyl)pyridin-3-yl)-3-(2-chloro-7-(1-(2-methoxyethoxy)ethyl)pyrazolo[1,5-a]pyrimidin-6-yl)urea; (S)-1-(6-(2H-1,2,3-triazol-2-yl)-5-(trifluoromethyl)pyridin-3-yl)-3-(2-chloro-7-(1-methoxy-2-methyl-propyl)pyrazolo[1,5-a]pyrimidin-6-yl)urea; 1-(2-chloro-7-(1-(methoxymethyl) cyclopropyl)pyrazolo[1,5-a] pyrimidin-6-yl)-3-(5-cyanopyridin-3-yl)urea; 1-(5-chloro-6-(2H-1,2,3-triazol-2-yl)pyridin-3-yl)-3-(2-chloro-7-((1 R,2S)-1,2-dimethoxypropyl) pyrazolo[1,5-a]pyrimidin-6-yl)urea; (S)-1-(2-chloro-7-(1-methoxyethyl)pyrazolo[1,5-a] pyrimidin-6-yl)-3-(5-cyano-6-(2H-1,2,3-triazol-2-yl)pyridin-3-yl)urea; (S)-1-(5-cyanopyridin-3-yl)-3-(2-fluoro-7-(1-methoxyethyl)pyrazolo[1,5-a]pyrimidin-6-yl) urea; 1-(7-((S)-1-(((R)-1-acetylpyrrolidin-3-yl)oxy)ethyl)-2-chloropyrazolo[1,5-a]pyrimidin-6-yl)-3-(5-chloro-6-(2H-1,2,3-triazol-2-yl)pyridin-3-yl)urea; (S)-1-(5-chloro-6-(2H-1,2,3-triazol-2-yl)pyridin-3-yl)-3-(2-fluoro-7-(1-methoxy-2-methylpropyl)-pyrazolo[1,5-a]pyrimidin-6-yl)urea; (S)-1-(5-cyano-6-(2H-1,2,3-triazol-2-yl)pyridin-3-yl)-3-(7-(1-methoxy-2-methylpropyl)-2-methylpyrazolo[1,5-a] pyrimidin-6-yl)urea; (S)-1-(2-chloro-7-(1-methoxyethyl) pyrazolo[1,5-a]pyrimidin-6-yl)-3-(5-cyano-6-methoxypyridin-3-yl)urea; 1-(2-fluoro-7-((S)-1-methoxyethyl)pyrazolo[1,5-a]pyrimidin-6-yl)-3-(2-(1-hydroxyethyl)-6-(trifluoromethyl)pyridin-4-yl)urea; (S)-1-(5-cyano-6-(2H-1,2,3-triazol-2-yl)pyridin-3-yl)-3-(2-fluoro-7-(1-methoxy ethyl)pyrazolo[1,5-a]pyrimidin-6-yl) urea; 1-(2-chloro-7-(1,2-dimethoxyethyl)pyrazolo[1,5-a] pyrimidin-6-yl)-3-(5-cyano-6-(2H-1,2,3-triazol-2-yl) pyridin-3-yl)urea; 1-(2-chloro-7-((S)-1-methoxyethyl) pyrazolo[1,5-a]pyrimidin-6-yl)-3-(2-(2,2,2-trifluoro-1-hydroxy-ethyl)pyridin-4-yl)urea; (S)-1-(5-chloro-2-(2-methoxyethoxy)pyridin-3-yl)-3-(2-chloro-7-(1-methoxyethyl)-pyrazolo[1,5-a]-pyrimidin-6-yl)urea; (S)-1-(5-cyano-6-methoxypyridin-3-yl)-3-(7-(1-methoxy-2-methylpropyl)-2-methylpyrazolo[1,5-a]-pyrimidin-6-yl) urea; (S)-1-(2-cyanopyridin-4-yl)-3-(2-fluoro-7-(1-methoxyethyl)pyrazolo[1,5-a]pyrimidin-6-yl)urea; (S)-1-(5-cyano-6-methoxypyridin-3-yl)-3-(7-(1-methoxyethyl)-2-methylpyrazolo[1,5-a]pyrimidin-6-yl)urea; 1-(2-chloro-7-((1 R,2S)-1,2-dimethoxypropyl)pyrazolo[1,5-a]pyrimidin-6-yl)-3-(5-cyano-6-(2H-1,2,3-triazol-2-yl)pyridin-3-yl) urea; 1-(7-((S)-1-(((S)-1-acetylpyrrolidin-3-yl)oxy)ethyl)-2-chloropyrazolo[1,5-a]pyrimidin-6-yl)-3-(5-cyano-6-methoxypyridin-3-yl)urea; (S)-1-(5-cyano-6-(2H-1,2,3-triazol-2-yl)pyridin-3-yl)-3-(7-(1-methoxyethyl)-2-methylpyrazolo[1,5-a]pyrimidin-6-yl)urea; (S)-6-chloro-4-(3-(2-chloro-7-(1-methoxyethyl)pyrazolo[1,5-a]pyrimidin-6-yl)ureido)-N,N-dimethylpicolinamide; (S)-1-(5-(difluoromethyl)pyridin-3-yl)-3-(2-fluoro-7-(1-methoxyethyl)-pyrazolo[1,5-a]pyrimidin-6-yl)urea; (S)-1-(2-fluoro-7-(1-methoxyethyl)pyrazolo[1,5-a]pyrimidin-6-yl)-3-(5-(trifluoro-methyl)pyridin-3-yl)urea; (S)-3-chloro-5-(3-(2-chloro-7-(1-methoxyethyl)pyrazolo[1,5-a]pyrimidin-6-yl) ureido)-N,N-dimethylpicolinamide; (S)-1-(5-chloro-pyridin-3-yl)-3-(2-fluoro-7-(1-methoxyethyl)pyrazolo[1,5-a]pyrimidin-6-yl)urea; (S)-1-(5-chloro-6-(pyrrolidine-1-carbonyl)pyridin-3-yl)-3-(2-chloro-7-(1-methoxyethyl) pyrazolo-[1,5-a]pyrimidin-6-yl)urea (S)-3-chloro-5-(3-(2-chloro-7-(1-methoxyethyl)pyrazolo[1,5-a]pyrimidin-6-yl) ureido)-N-methylpicolinamide; (S)-1-(2-chloro-7-(1-methoxyethyl)pyrazolo[1,5-a]pyrimidin-6-yl)-3-(5-chloropyridin-3-yl)urea; (S)-1-(7-(1-aminoethyl)-2-chloropyrazolo[1,5-a]pyrimidin-6-yl)-3-(5-chloro-6-(2H-1,2,3-triazol-2-yl)pyridin-3-yl)urea; (S)-1-(5-cyanopyridin-3-yl)-3-(7-(1-hydroxyethyl)-2-methylpyrazolo[1,5-a] pyrimidin-6-yl)urea; (S)-1-(2-(difluoromethyl)pyridin-4-yl)-3-(2-fluoro-7-(1-hydroxyethyl) pyrazolo[1,5-a] pyrimidin-6-yl)urea; 1-(2-((S)-2-aminopropoxy)-5-chloropyridin-3-yl)-3-(2-chloro-7-((S)-1-methoxyethyl) pyrazolo[1,5-a]pyrimidin-6-yl)urea; S)-2-(difluoromethyl)-4-(3-(2-fluoro-7-(1-methoxyethyl)pyrazolo[1,5-a] pyrimidin-6-yl)ureido)pyridine 1-oxide; 1-(2-chloro-7-((1 R,2S)-1,2-dimethoxypropyl)pyrazolo[1,5-a]pyrimidin-6-yl)-3-(5-cyano-6-methoxypyridin-3-yl)urea; 1-(2-chloro-7-(1-(methoxymethyl)cyclopropyl)pyrazolo[1,5-a]pyrimidin-6-yl)-3-(2-cyanopyridin-4-yl)urea; and (S)-3-chloro-5-(3-(2-fluoro-7-(1-methoxyethyl)pyrazolo[1,5-a]pyrimidin-6-yl)ureido)picolinamide.

In some cases, the pyrazolo pyrimidine MALT1 inhibitor compound is as disclosed in WO 2017/081641, the disclosure of which is incorporated by reference in its entirety. The compound can have a structure of

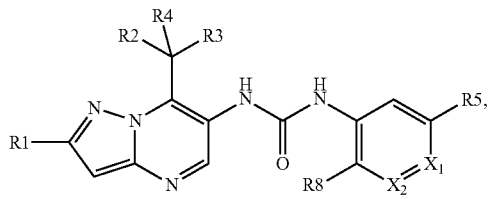

where R1 is fluoro, chloro, methyl or cyano; R2 and R 3 are independently from each other C₁-C₆ alkoxy optionally substituted by C₁-C₆ alkoxy; C₁-C₆ alkyl optionally substituted by halogen or C₁-C₆ alkoxy; amino optionally substituted by C₁-C₆ alkyl; phthalimido; or hydroxy optionally substituted by a 5 or 6 membered heterocyclic ring comprising a nitrogen or oxygen heteroatom wherein said ring is optionally substituted by C₁-C₃ alkyl carbonyl; or R2 and R3 together with carbon atom to which they are attached form a 3-5 membered carbocyclic ring or heterocyclic ring comprising 1 heteroatom selected from N and O; R4 is hydrogen; C C₆ alkyl optionally substituted by C G, alkoxy; X1 si N, N—O, or CR⁶; X₂ is N or CR7; R5 is chloro; cyano; or C C₆ alkyl optionally substituted by halogen and/or hydroxy; R6 is hydrogen; oxo; methoxy; 1,2,3-triazole-2-yl; or aminocarbonyl substituted at the nitrogen atom by R9 and R10; R7 is hydrogen; C₁-C₆ alkyl optionally substituted by halogen and/or hydroxy; or N,N-dimethylaminocarbonyl; R8 is hydrogen; C₁-C₆ alkoxy optionally substituted by methoxy or amino; R9 and 10 are independently of each other hydrogen; C₁-C₆ alkyl optionally substituted by C₁-C₆ alkoxy, N-mono-G-G, alkyl amino, or N,N-di-C₁-C₆ alkyl amino; or R9 and 10 together with the nitrogen atom to which they are attached form a 5-7 membered heterocyclic ring having one, two or three ring hetero atoms selected from the group consisting of oxygen, nitrogen and sulfur, that ring being optionally substituted by C₁-C₆ alkyl, hydroxy or oxo; with the proviso that X1 and X₂ must not be N at the same time, or X1 must not be N—O when X₂ is N. In some cases, the compound is selected from (S)-1-(2-(difluoromethyl)pyridin-4-yl)-3-(2-fluoro-7-(1-methoxyethyl) pyrazolo[1,5-a]pyrimidin-6-yl)urea; (S)-1-(2-chloro-7-(1-methoxyethyl)pyrazolo[1,5-a]pyrimidin-6-yl)-3-(2-(trifluoromethyl)pyridin-4-yl)urea; 1-(5-chloro-6-(2H-1,2,3-triazol-2-yl)pyridin-3-yl)-3-(2-chloro-7-isopropylpyrazolo[1,5-a]pyrimidin-6-yl)urea; (S)-1-(5-chloro-6-(2H-1,2,3-triazol-2-yl)pyridin-3-yl)-3-(2-chloro-7-(1-methoxyethyl)pyrazolo[1,5-a]pyrimidin-6-yl)urea; (S)-1-(5-cyano-6-methoxypyridin-3-yl)-3-(2-fluoro-7-(1-methoxyethyl) pyrazolo[1,5-a]pyrimidin-6-yl)urea; (S)-1-(6-(2H-1,2,3-triazol-2-yl)-5-(trifluoromethyl)pyridin-3-yl)-3-(2-chloro-7-(1-(2-methoxyethoxy) ethyl)pyrazolo[1,5-a] pyrimidin-6-yl)urea; (S)-1-(6-(2H-1,2,3-triazol-2-yl)-5-(trifluoromethyl)pyridin-3-yl)-3-(2-chloro-7-(1-methoxy-2-methyl-propyl)pyrazolo[1,5-a]pyrimidin-6-yl)urea; 1-(2-chloro-7-(1-(methoxymethyl)cyclopropyl)pyrazolo[1,5-a]pyrimidin-6-yl)-3-(5-cyanopyridin-3-yl)urea; 1-(5-chloro-6-(2H-1,2,3-triazol-2-yl)pyridin-3-yl)-3-(2-chloro-7-((1 R,2S)-1,2-dimethoxypropyl) pyrazolo[1,5-a]pyrimidin-6-yl)urea; (S)-1-(2-chloro-7-(1-methoxyethyl)pyrazolo[1,5-a] pyrimidin-6-yl)-3-(5-cyano-6-(2H-1,2,3-triazol-2-yl)pyridin-3-yl)urea; (S)-1-(5-cyanopyridin-3-yl)-3-(2-fluoro-7-(1-methoxyethyl)pyrazolo[1,5-a]pyrimidin-6-yl)urea; 1-(7-((S)-1-(((R)-1-acetylpyrrolidin-3-yl)oxy)ethyl)-2-chloropyrazolo[1,5-a]pyrimidin-6-yl)-3-(5-chloro-6-(2H-1,2,3-triazol-2-yl)pyridin-3-yl)urea; (S)-1-(5-chloro-6-(2H-1,2,3-triazol-2-yl)pyridin-3-yl)-3-(2-fluoro-7-(1-methoxy-2-methylpropyl)-pyrazolo[1,5-a]pyrimidin-6-yl)urea; (S)-1-(5-cyano-6-(2H-1,2,3-triazol-2-yl)pyridin-3-yl)-3-(7-(1-methoxy-2-methylpropyl)-2-methylpyrazolo[1,5-a] pyrimidin-6-yl)urea; (S)-1-(2-chloro-7-(1-methoxyethyl) pyrazolo[1,5-a]pyrimidin-6-yl)-3-(5-cyano-6-methoxypyridin-3-yl)urea; 1-(2-fluoro-7-((S)-1-methoxyethyl)pyrazolo[1,5-a]pyrimidin-6-yl)-3-(2-(1-hydroxyethyl)-6-(trifluoromethyl)pyridin-4-yl)urea; (S)-1-(5-cyano-6-(2H-1,2,3-triazol-2-yl)pyridin-3-yl)-3-(2-fluoro-7-(1-methoxyethyl)pyrazolo[1,5-a]pyrimidin-6-yl) urea; 1-(2-chloro-7-(1,2-dimethoxyethyl)pyrazolo[1,5-a] pyrimidin-6-yl)-3-(5-cyano-6-(2H-1/\triazol-2-yl)pyridin-3-yl)urea; 1-(2-chloro-7-((S)-1-methoxyethyl)pyrazolo[1,5-a]pyrimidin-6-yl)-3-(2-(2,2,2-trifluoro-1-hydroxy-ethyl) pyridin-4-yl)urea; (S)-1-(5-chloro-2-(2-methoxyethoxy) pyridin-3-yl)-3-(2-chloro-7-(1-methoxyethyl)-pyrazolo[1,5-a]-pyrimidin-6-yl)urea; (S)-1-(5-cyano-6-methoxypyridin-3-yl)-3-(7-(1-methoxy-2-methylpropyl)-2-methylpyrazolo [1,5-a]-pyrimidin-6-yl)urea; (S)-1-(2-cyanopyridin-4-yl)-3-(2-fluoro-7-(1-methoxyethyl)pyrazolo[1,5-a]pyrimidin-6-yl)urea; (S)-1-(5-cyano-6-methoxypyridin-3-yl)-3-(7-(1-methoxyethyl)-2-methylpyrazolo[1,5-a]pyrimidin-6-yl) urea; 1-(2-chloro-7-((1 R,2S)-1,2-dimethoxypropyl) pyrazolo[1,5-a]pyrimidin-6-yl)-3-(5-cyano-6-(2H-1,2,3-triazol-2-yl)pyridin-3-yl)urea; 1-(7-((S)-1-(((S)-1-acetylpyrrolidin-3-yl)oxy)ethyl)-2-chloropyrazolo[1,5-a] pyrimidin-6-yl)-3-(5-cyano-6-methoxypyridin-3-yl)urea; (S)-1-(5-cyano-6-(2H-1,2,3-triazol-2-yl)pyridin-3-yl)-3-(7-(1-methoxyethyl)-2-methylpyrazolo[1,5-a]pyrimidin-6-yl) urea; (S)-6-chloro-4-(3-(2-chloro-7-(1-methoxyethyl)pyrazolo[1,5-a]pyrimidin-6-yl)ureido)-N,N-dimethylpicolinamide; (S)-1-(5-(difluoro-methyl)pyridin-3-yl)-3-(2-fluoro-7-(1-methoxyethyl)-pyrazolo[1,5-a] pyrimidin-6-yl)urea; (S)-1-(2-fluoro-7-(1-methoxyethyl) pyrazolo[1,5-a]pyrimidin-6-yl)-3-(5-(trifluoro-methyl) pyridin-3-yl)urea; (S)-3-chloro-5-(3-(2-chloro-7-(1-methoxyethyl)pyrazolo[1,5-a]pyrimidin-6-yl)ureido)-N,N-dimethylpicolinamide; (S)-1-(5-chloro-pyridin-3-yl)-3-(2-fluoro-7-(1-methoxyethyl)pyrazolo[1,5-a]pyrimidin-6-yl) urea; (S)-1-(5-chloro-6-(pyrrolidine-1-carbonyl)pyridin-3-yl)-3-(2-chloro-7-(1-methoxyethyl)pyrazolo-[1,5-a] pyrimidin-6-yl)urea; (S)-3-chloro-5-(3-(2-chloro-7-(1-methoxyethyl)pyrazolo[1,5-a]pyrimidin-6-yl)ureido)-N-methylpicolinamide; (S)-1-(2-fluoro-7-(1-methoxyethyl) pyrazolo[1,5-a]pyrimidin-6-yl)-3-(5-chloropyridin-3-yl) urea; (S)-1-(7-(1-aminoethyl)-2-chloropyrazolo[1,5-a] pyrimidin-6-yl)-3-(5-chloro-6-(2H-1,2,3-triazol-2-yl) pyridin-3-yl)urea; (S)-1-(5-cyanopyridin-3-yl)-3-(7-(1-hydroxyethyl)-2-methylpyrazolo[1,5-a]pyrimidin-6-yl) urea; (S)-1-(2-(difluoromethyl)pyridin-4-yl)-3-(2-fluoro-7-(1-hydroxyethyl) pyrazolo[1,5-a]pyrimidin-6-yl)urea; 1-(2-((S)-2-aminopropoxy)-5-chloropyridin-3-yl)-3-(2-chloro-7-((S)-1-methoxyethyl)pyrazolo[1,5-a]pyrimidin-6-yl)urea; (S)-2-(difluoromethyl)-4-(3-(2-fluoro-7-(1-methoxyethyl) pyrazolo[1,5-a]pyrimidin-6-yl)ureido)pyridine 1-oxide; 1-(2-chloro-7-((1 R,2S)-1,2-dimethoxypropyl)pyrazolo[1,5-a]pyrimidin-6-yl)-3-(5-cyano-6-methoxypyridin-3-yl)urea; 1-(2-chloro-7-(1-(methoxymethyl)cyclopropyl)pyrazolo[1, 5-a]pyrimidin-6-yl)-3-(2-cyanopyridin-4-yl)urea; and (S)-3-chloro-5-(3-(2-fluoro-7-(1-methoxyethyl)pyrazolo[1,5-a]pyrimidin-6-yl)ureido)picolinamide.

In some cases, the MALT1 inhibitor is compound as disclosed in WO 2018/085247, the disclosure of which is incorporated by reference in its entirety. In some cases, the compound has a structure

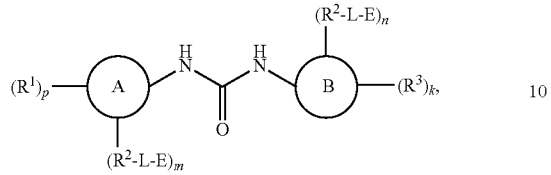

wherein A is a fused bicyclic heteroaryl ring; B is phenyl or pyridinyl; each occurrence of $R^1$ and $R^3$ is, independently, hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroalkyl, —$OR^A$, —$N(R^A)_2$, —$SR^A$, —CN, —SCN, —$C(=NR^A)R^A$, —$C(=NR^A)OR^A$, —$C(=NR^A)N(R^A)_2$, —$C(=O)R^A$, —$C(=O)OR^A$, —$C(=O)N(R^A)_2$, —$NO_2$, —$NR^AC(=O)R^A$, —$NR^AC(=O)OR^A$, —$NR^AC(=O)N(R^A)_2$, —$OC(=O)R^A$, —$OC(=O)OR^A$, —$OC(=O)N(R^A)_2$, or a nitrogen protecting group when attached to a nitrogen atom; R is substituted or unsubstituted alkylene, substituted or unsubstituted heterocyclylene, substituted or unsubstituted arylene, substituted or unsubstituted heteroarylene, substituted or unsubstituted heteroalkylene, substituted or unsubstituted alkylheteroarylene, substituted or unsubstituted heteroarylalkylene, —O—, —$N(R^A)$—, —S—, —C(=O)—, —C(=O)O—, —$C(=O)NR^A$—, —$NR^AC(=O)$—, —$NR^AC(=O)O$—, —$NR^AC(=O)N(R^A)$—, —OC(=O)—, —OC(=O)O—, or —$OC(=O)N(R^A)$—; each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^A$ groups are joined to form a substituted or unsubstituted heterocyclic ring; L is substituted or unsubstituted alkylene, substituted or unsubstituted alkenylene, substituted or unsubstituted alkynylene, substituted or unsubstituted carbocyclylene, substituted or unsubstituted heterocyclylene, substituted or unsubstituted arylene, substituted or unsubstituted heteroarylene, substituted or unsubstituted heteroalkylene, —O—, —$N(R^A)$—, —S—, —C(=O)—, —C(=O)O—, —$C(=O)NR^A$—, —$NR^AC(=O)$—, —$NR^AC(=O)R^A$, —$C(=O)R^A$—, —$NR^AC(=O)$ O—, —$NR^AC(=O)N(R^A)$—, —OC(=O)—, —OC(=O) O—, or —$OC(=O)N(R^A)$—, or a combination thereof; E is an E3 ubiquitin ligase binding moiety; m and n are each independently 0 or 1, provided that m+n=1; k is 0, 1, 2, 3, or 4; and p is 0, 1, 2, 3, or 4. In some cases,

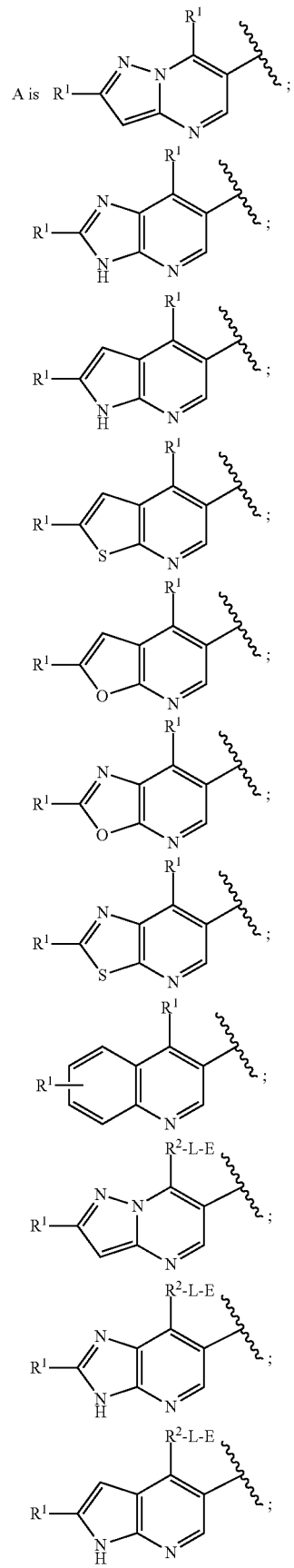

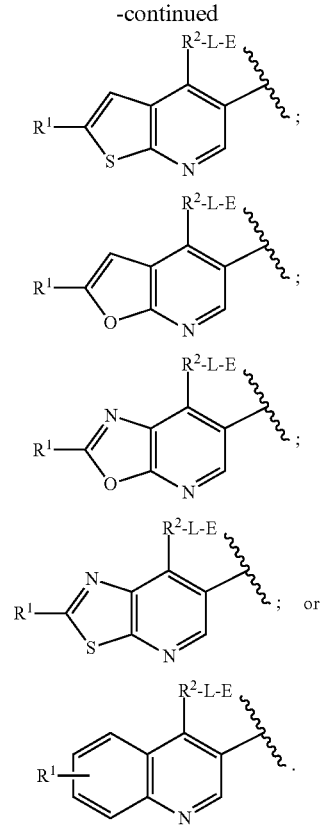
In some cases, R²-L- is
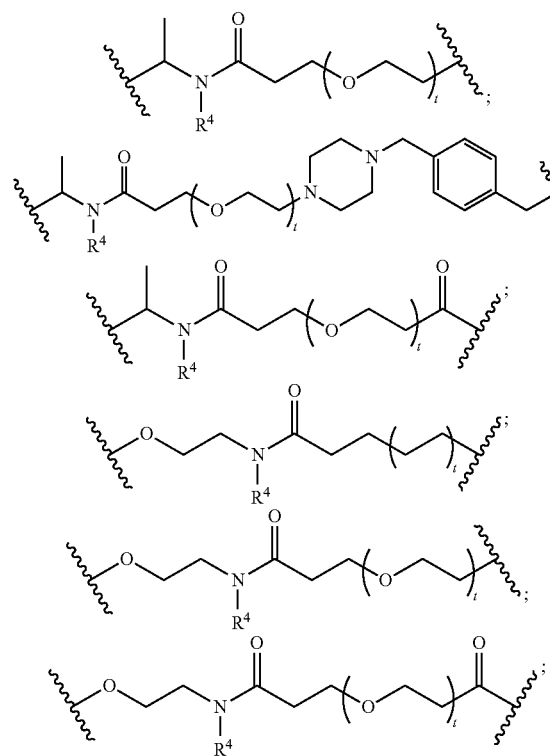
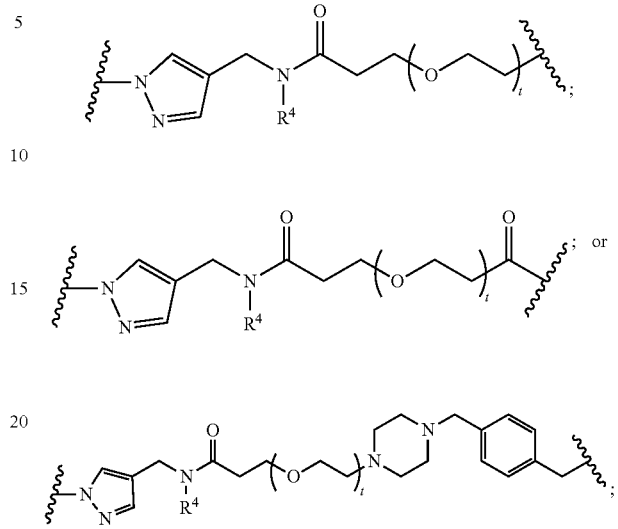
R⁴ is hydrogen or $C_{1-6}$ alkyl; and t is 0, 1, 2, 3, 4, 5, or 6. In some cases,
E is
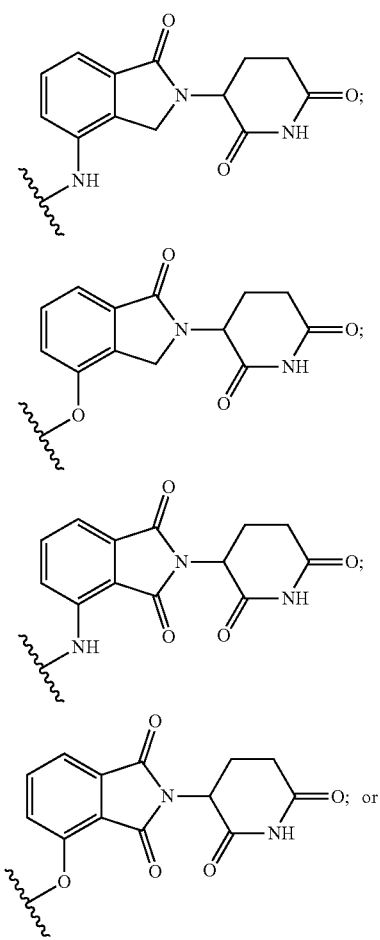

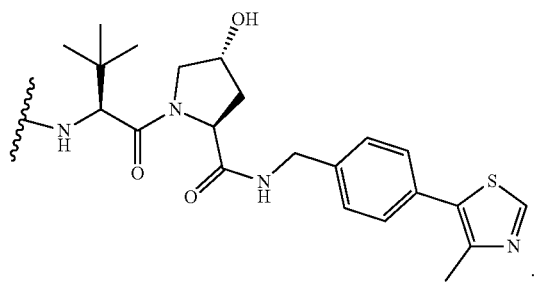
In various cases, the compound has a structure of
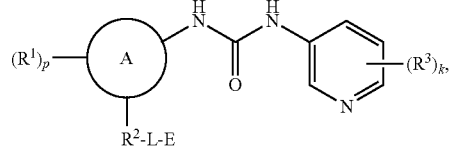
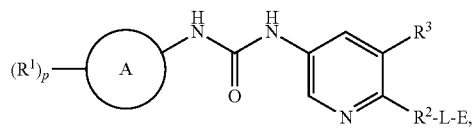
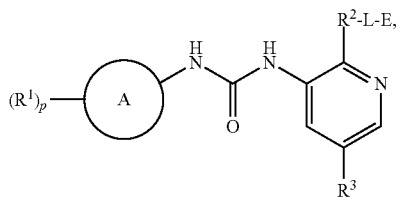
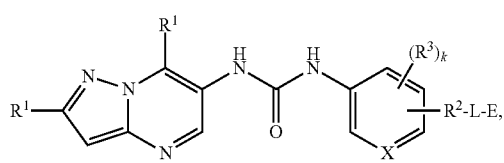
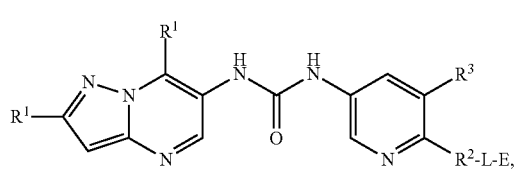
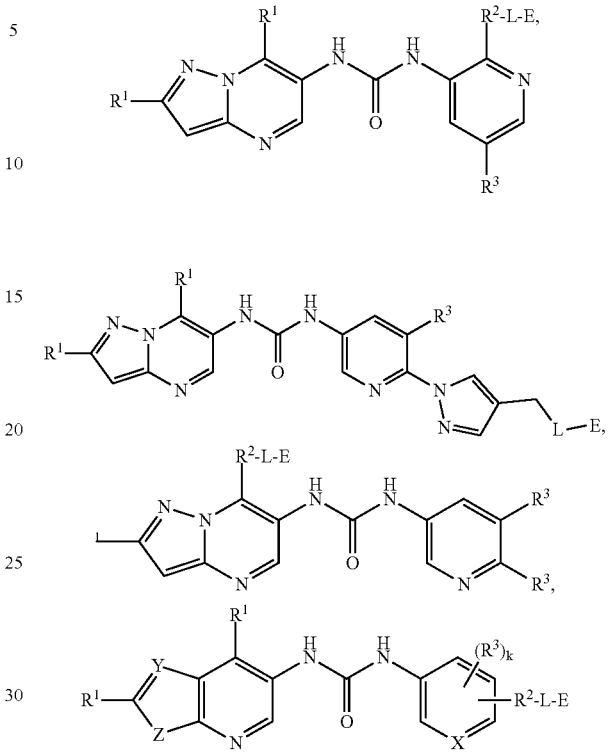
where X is N, CH, or CR³; Y is CH or N, and Z is NH, S, or O;
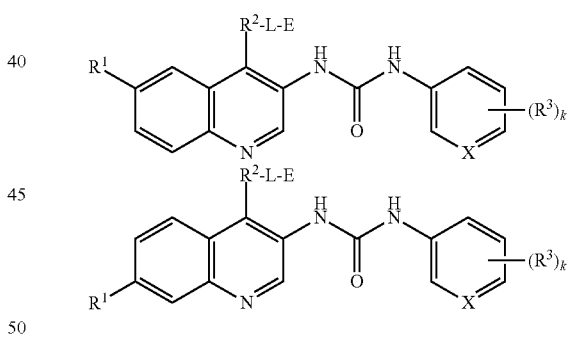
where X is N, CH, or CR³;
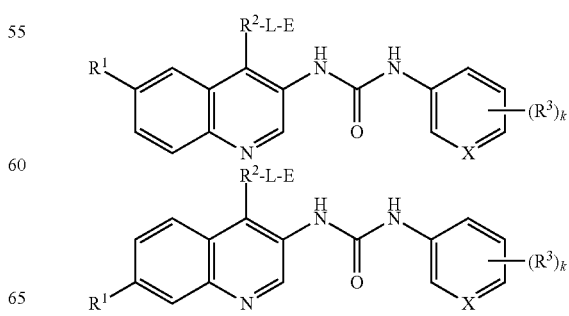

where X is N, CH, or CR³;
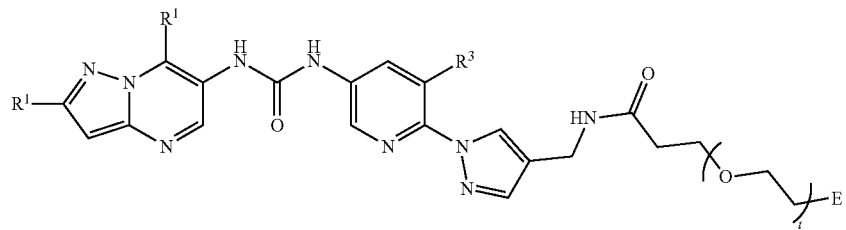
where t is 2 or 4;
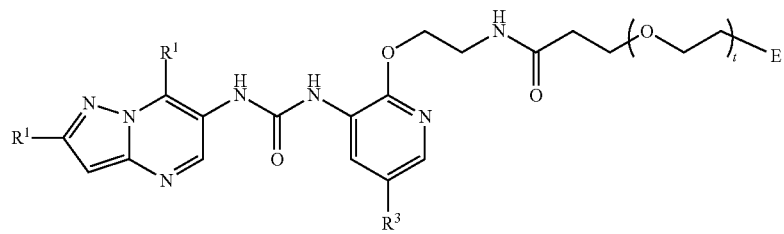
where t is 2 or 4;
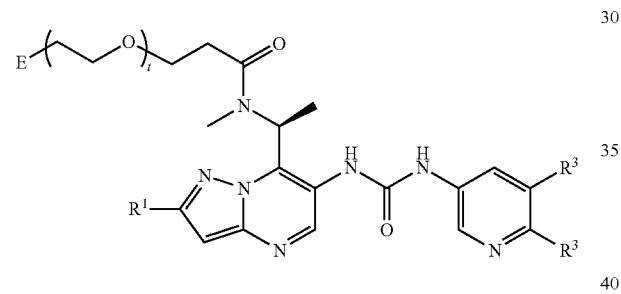
where t is 2 or 4;
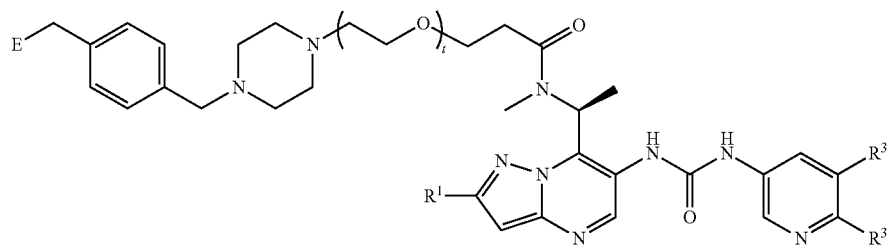
where t is 0, 1, 2, 3, 4, 5, or 6;
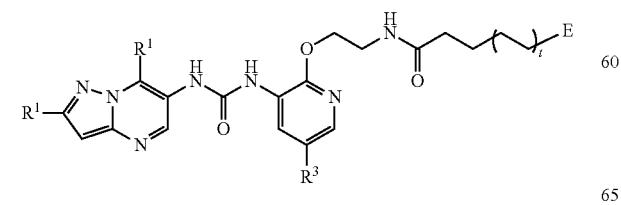
where t is 0, 1, 2, 3, 4, 5, or 6; or

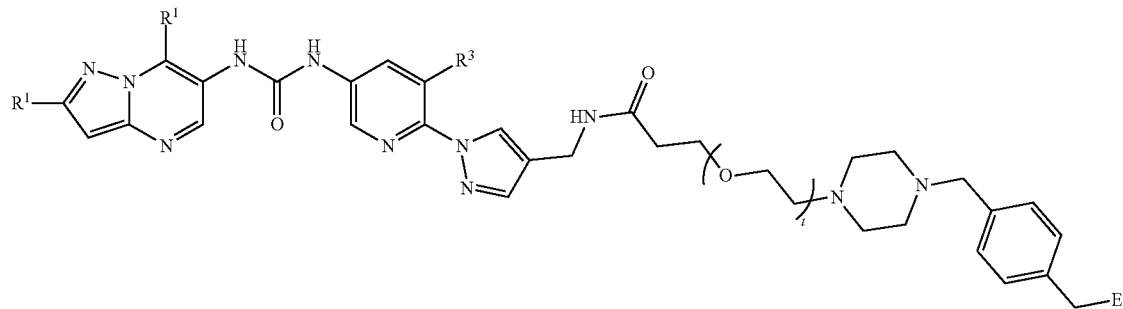

where t is 0, 1, 2, 3, 4, 5, or 6.

In another embodiment, the inhibitor of MALT1 paracaspase activity is a phenothiazine derivative. Phenothiazine is an organic compound that has the formula $S(C_6H_4)_2NH$ and is related to the thiazine-class of heterocyclic compounds. Phenothiazine has no medicinal use, it is a prototypical lead structure in medicinal chemistry and derivatives of Phenothiazine are widely used. Derivatives of Phenothiazine comprise the Phenothiazine core structure and include, but are not limited to mepazine, thioridazine, promazine, Chlorpromazine (Thorazine™, Aminazine™, Chlor-PZ™, Klorazine™, Promachlor™, Promapar™, Sonazine™, Chlorprom™, Chlor-Promanyl™, Largactil™), Promazine (Sparine™, Propazine™), Triflupromazine (Clinazine™, Novaflurazine™, Pentazine™, Terfluzine™, Triflurin™, Vesprin™), Mesoridazine (Serentil™), Thioridazine (Mellaril™, Novoridazine™, Thioril™, Sonapax™), Fluphenazine (Prolixin™, Permitil™, Modecate™, Moditen™), Perphenazine (Trilafon™, Etrafon™, Triavil™, Phenazine™, Etaperazin™), Prochlorperazine (Compazine™, Stemetil™), and Trifluoperazine (Stelazine™, Triphtazine™). In one embodiment, the inhibitor of MALT1 paracaspase activity comprises a chemical structure comprising Phenothiazine. In one embodiment, the inhibitor of MALT1 paracaspase activity is the Phenothiazine derivative, mepazine. Mepazine comprises MALT1 inhibitory action, and is further reviewed in, e.g., Nagel D. et al, *Cancer Cell,* 2012, which is incorporated herein by reference in its entirety.

In some cases, the mepazine is present as (S)-mepazine, or a pharmaceutically acceptable salt thereof. (S)-Mepazine is discussed in detail, e.g., in U.S. Pat. No. 9,718,811, the disclosure of which is incorporated by reference in its entirety.

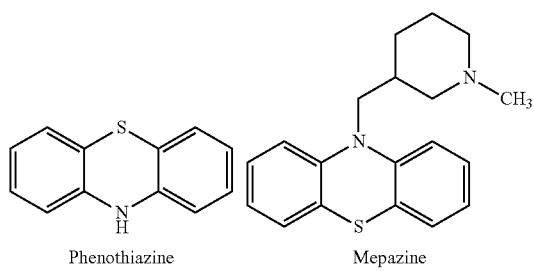

Phenothiazine      Mepazine

-continued

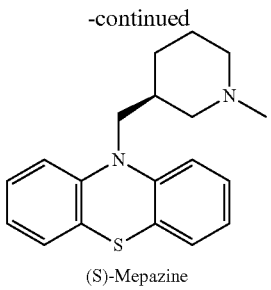

(S)-Mepazine

In some embodiments, the MALT1 inhibitor is a pyrazole derivative, e.g., as disclosed in WO 2018/119036, the disclosure of which is incorporated by reference in its entirety, e.g., having a structure of

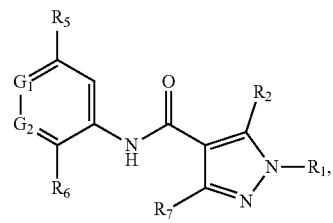

where R is selected from the group consisting of i) naphthalen-1-yl, optionally substituted with a fluoro or amino substituent; and ii) a heteroaryl of nine to ten members containing one to four heteroatoms selected from the group consisting of O, N, and S; such that no more than one heteroatom is O or S; wherein said heteroaryl of ii) is optionally independently substituted with one or two substituents selected from deuterium, methyl, ethyl, propyl, isopropyl, trifluoromethyl, cyclopropyl, methoxymethyl, difluoromethyl, 1,1-difluoroethyl, hydroxymethyl, 1-hydroxy ethyl, 1-ethoxy ethyl, hydroxy, methoxy, ethoxy, fluoro, chloro, bromo, methylthio, cyano, amino, methylamino, dimethylamino, 4-oxotetrahydrofuran-2-yl, 5-oxopyrrolidin-2-yl, 1,4-dioxanyl, aminocarbonyl, methylcarbonyl, methylaminocarbonyl, oxo, 1-(t-butoxycarbonyl) azetidin-2-yl, N-(methyl)formamidomethyl, tetrahydrofuran-2-yl, 3-hydroxy-pyrrolidin-1-yl, pyrrolidin-2-yl, 3-hydroxyazetidinyl, azetidin-3-yl, or azetidin-2-yl; $R_2$ is selected from the group consisting of C1-4alkyl, 1-methoxyethyl, difluoromethyl, fluoro, chloro, bromo, cyano, and trifluoromethyl; G1 is N or C(R4); G2 is N or C(R3); such that only one of G1 and G2 are N in any instance; $R_3$ is independently selected from the group consisting of trifluoromethyl, cyano, C1-4alkyl, fluoro, chloro, bromo, methylcarbonyl, methylthio, methyl sulfinyl, and methanesulfonyl; or, when Gi is N, R3 is further selected from C1-4alkoxycarbonyl; R4 is selected from the group consisting of i) hydrogen, when G2 is N; ii) Ci-4alkoxy; iii) cyano; iv) cyclopropyloxy; v) a heteroaryl selected from the group consisting of triazolyl, oxazolyl, isoxazolyl, pyrazolyl, pyrrolyl, thiazolyl, tetrazolyl, oxadiazolyl, imidazolyl, 2-amino-pyrimidin-4-yl, 2H-[1,2,3]triazolo[4,5-c]pyridin-2-yl, 2H-[1,2,3]triazolo[4,5-b]pyridin-2-yl, 3H-[1,2,3]triazolo[4,5-b]pyridin-3-yl, 1H-[1,2,3]triazolo[4,5-c]pyridin-1-yl, wherein the heteroaryl is optionally substituted with one or two substituents independently selected from oxo, C1-4alkyl, carboxy, methoxycarbonyl, aminocarbonyl, hydroxymethyl, aminomethyl, (dimethylamino)methyl, amino, methoxymethyl, trifluoromethyl, amino(C2-4alkyl) amino, or cyano; vi) 1-methyl-piperidin-4-yloxy; vii) 4-methyl-piperazin-1-ylcarbonyl; viii) (4-aminobutyl)aminocarbonyl; ix) (4-amino)butoxy; x) 4-(4-aminobutyl)-piperazin-1-ylcarbonyl; xi) methoxycarbonyl; xii) 5-chloro-6-(methoxycarbonyl)pyridin-3-ylaminocarbonyl; xiii) 1,1-dioxo-isothiazolidin-2-yl; xiv) 3-methyl-2-oxo-2,3-dihydro-1H-imidazol-1-yl; xv) 2-oxopyrrolidin-1-yl; xvi) (E)-(4-aminobut-1-en-1-yl-aminocarbonyl; xvii) difluoromethoxy; and xviii) morpholin-4-ylcarbonyl; $R_5$ is independently selected from the group consisting of hydrogen, chloro, fluoro, bromo, methoxy, methylsulfonyl, cyano, C1-4alkyl, ethynyl, morpholin-4-yl, trifluoromethyl, hydroxyethyl, methylcarbonyl, methylsulfinyl, 3-hydroxy-pyrrolidin-1-yl, pyrrolidin-2-yl, 3-hydroxyazetidinyl, azetidin-3-yl, azetidin-2-yl, methylthio, and 1,1-difluoroethyl; or R4 and $R_5$ may be taken together to form 8-chloro-4-methyl-3-oxo-3,4-dihydro-2H-benzo[b][1,4]oxazin-6-yl, 8-chloro-3-oxo-3,4-dihydro-2H-benzo[b][1,4]oxazin-6-yl, 2-methyl-1-oxo-1,2,3,4-tetrahydroisoquinolin-7-yl, 4-methyl-3-oxo-3,4-dihydro-2H-benzo[b][1,4]oxazin-6-yl, 3-oxo-3,4-dihydro-2H-benzo[b][1,4]oxazin-6-yl, 1-methyl-1H-pyrazolo[3,4-b]pyridin-5-yl, 1H-pyrazolo[3,4-b]pyridin-5-yl, 2,3-dihydro-[1,4]dioxino[2,3-b]pyridin-5-yl, 1,3-dioxolo[4,5]pyridine-5-yl, 1-oxo-1,3-dihydroisobenzofuran-5-yl, 2,2-dimethylbenzo[d][1,3]dioxol-5-yl, 2,3-dihydrobenzo[b][1,4]dioxin-6-yl, 1-oxoisoindobn-5-yl, or 2-methyl-1-oxoisoindolin-5-yl, 1H-indazol-5-yl; $R_6$ is hydrogen, C1-4alkyl, fluoro, 2-methoxy-ethoxy, chloro, cyano, or trifluoromethyl; $R_7$ is hydrogen or fluoro. In some cases, the MALT1 inhibitor is a compound as listed in Table 1 (compound 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, or 450) at pages 40-133 of WO 2018/119036.

In various cases, the MALT1 inhibitor is a compound as disclosed in WO 2018/021520, the disclosure of which is incorporated by reference in its entirety herein.

In another embodiment, the inhibitor of MALT1 paracaspase activity is tetrapeptide Z-VRPR-FMK (SEQ ID NO: 7) (Z-VRPR-FMK (SEQ ID NO: 7); $C_{31}H_{49}FN_{10}O_6$). Z-VRPR-FMK (SEQ ID NO: 7) is a selective MALT1 inhibitor MALT1's proteolytic activity of the paracaspase.

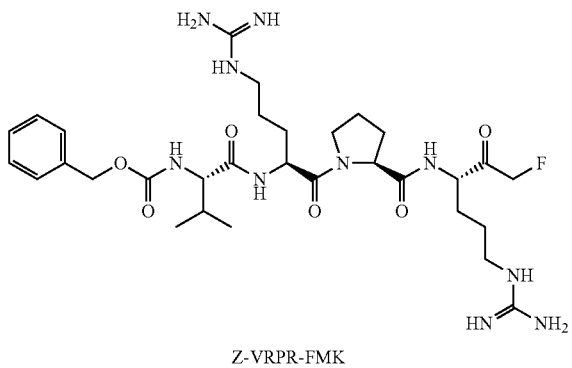

Z-VRPR-FMK

Derivatives of Z-VRPR-FMK (SEQ ID NO: 7) are specifically contemplated for use with the methods and compositions described herein. In some embodiments, the derivatives of Z-VRPR-FMK (SEQ ID NO: 7) can include those described in WO2009065897, the contents of which are incorporated herein by reference in its entirety. Non-limiting examples of Z-VRPR-FMK (SEQ ID NO: 7) derivatives include Z-LSSR-CHO (SEQ ID NO: 9), Z-LSSR-CMK (SEQ ID NO: 10), Z-GASR-CHO (SEQ ID NO: 11) and Z-GASR-CMK (SEQ ID NO: 12) (see e.g., WO2009065897).

Other MALT1 inhibitors contemplated for use in the disclosed methods include thiazolo-pyridines, e.g., those as disclosed in WO 2018/020474, the disclosure of which is incorporated by reference in its entirety. In some cases, the thiazolo-pyridine has a structure of

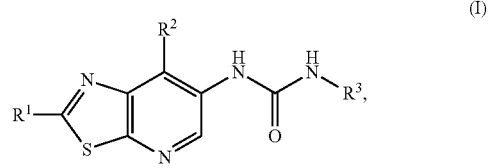

where $R^1$ is selected from hydrogen, halogen, cyano, substituted or unsubstituted alkyl, and cycloalkyl; $R^2$ is selected from—a) alkyl or alkyl substituted with 1 to 4 substituents independently selected from oxo (=O), halogen, cyano, cycloalkyl, substituted or unsubstituted aryl, heteroaryl, substituted or unsubstituted heterocyclyl, —OR$^4$, —C(=O)OH, —SO$_2$(alkyl), —C(=O)O(alkyl), —NR$^5$R$^{5A}$, —NR$^5$C(=O)R$^6$, C(=O)R$^6$, and C(=O)NR$^5$R$^{5A}$; b) cycloalkyl or cycloalkyl substituted with 1 to 4 substituents independently selected from halogen, cyano, substituted or unsubstituted alkyl, —OR$^4$, —C(=O)OH, —C(=O)O(alkyl), C(=O)R$^6$, and C(=O)NR$^5$R$^{5A}$; c) cycloalkenyl, d) cyano, e) substituted or unsubstituted aryl, f) substituted or unsubstituted heteroaryl, g) heterocyclyl or heterocyclyl substituted on either ring carbon atom or a ring nitrogen atom and when it is substituted on ring carbon atom it is substituted with 1 to 4 substituents independently selected from oxo (=O), halogen, cyano, substituted or unsubstituted alkyl, cycloalkyl, —OR$^4$, —C(=O)OH, —C(=O)O-alkyl, —C(=O)NR$^5$R$^{5A}$, —NHC(=O)(alkyl), —N(H)R$^5$, and —N(alkyl)$_2$, and when the heterocycle group is substituted on a ring nitrogen, it is substituted with substituents independently selected from alkyl, cycloalkyl, aryl, heteroaryl, SO$_2$(alkyl), 'C(=O)R$^6$, C(=O)O(alkyl), —C(=O)N(H)R$^5$, and —C(=O)N(alkyl)R$^5$, and h) —NR$^a$R$^b$, wherein, R$^a$ and R$^b$ are independently selected from hydrogen, cycloalkyl, and alkyl or alkyl substituted with 1 to 4 substituents independently selected from oxo (=O), halogen, cycloalkyl, —OR$^4$, and substituted or unsubstituted aryl; $R^3$ is selected from—a) heteroaryl or heteroaryl substituted with 1 to 4 substituents selected from halogen, cyano, —COOR$^{4b}$, —OR$^{4a}$, substituted or unsubstituted heteroaryl, substituted or unsubstituted alkyl, substituted or unsubstituted heterocyclyl, substituted or unsubstituted aryl, nitro, —SO$_2$alkyl, —SO$_2$NH(alkyl), —SO$_2$NH$_2$, —SO$_2$NH(CF$_3$), —SO$_2$N(alkyl)$_2$, —NHSO$_2$(alkyl), —COR$^6$, —CON(H)OH, —CONR$^5$R$^{5a}$, —N(R$^5$)COR$^{5a}$, and —NR$^5$R$^{5a}$, b) aryl or aryl substituted with 1 to 4 substituents selected from halogen, cyano, —COOR$^{4b}$, —OR$^{4a}$, substituted or unsubstituted alkyl, substituted or unsubstituted heterocyclyl, substituted or unsubstituted aryl, nitro, —SO$_2$alkyl, —SO$_2$NH(alkyl), —SO$_2$NH$_2$, —SO$_2$NH(CF$_3$), —SO$_2$N(alkyl)$_2$, —NHSO$_2$(alkyl), —COR$^6$, —CONR$^5$R$^{5a}$, —CO(NH)OH, —N(R$^5$)COR$^{5a}$, —NR$^5$R$^{5a}$, and heteroaryl or heteroaryl substituted with 1 to 4 substituents selected from substituted or unsubstituted alkyl, c) heterocyclyl or heterocyclyl substituted with 1 to 4 substituents selected from % oxo (=O) and substituted or unsubstituted alkyl, and d)

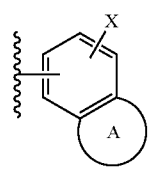

wherein, X is halogen and ring A is a heterocyclic ring containing heteroatom(s) selected from S, O, and N, which is optionally substituted with an oxo (=O) group; $R^4$ is selected from hydrogen, cycloalkyl, and substituted or unsubstituted alkyl; $R^{4A}$ is selected from a) hydrogen, alkyl, and cycloalkyl, and b) alkyl substituted with 1 to 4 substituents independently selected from halogen, —O-alkyl, —NR$^5$R$^{5A}$, and substituted or unsubstituted heterocyclyl; $R^{4b}$ is selected from hydrogen and alkyl; $R^5$ and $R^{5A}$ are each independently selected from a) hydrogen, alkyl, and cycloalkyl, b) alkyl substituted with O-alkyl, NH$_2$, and —CONH$_2$, c) heteroaryl, and d) heterocyclyl substituted with alkyl; and $R^6$ is selected from alkyl, heterocyclyl, and cycloalkyl; when an alkyl group is substituted, it is substituted with 1 to 4 substituents independently selected from oxo (=O), halogen, cyano, cycloalkyl, aryl, heteroaryl, heterocyclyl, —OR$^7$, —C(=O)OH, —C(=O)O(alkyl), —NR$^8$R$^{8A}$, —NR$^8$C(=O)R$^9$, and C(=O)NR$^8$R$^{8A}$; when the aryl group is substituted, it is substituted with 1 to 4 substituents independently selected from halogen, nitro, cyano, alkyl, perhaloalkyl, cycloalkyl, heterocyclyl, heteroaryl, —OR$^7$, —NR$^8$R$^{8A}$, —NR$^8$C(=O)R$^9$, C(=O)R$^9$, C(=O)NR$^8$R$^{8A}$, —SO$_2$-alkyl, —C(=O)OH, —C(=O)O-alkyl, and haloalkyl; when the heteroaryl group is substituted, it is substituted with 1 to 4 substituents independently selected from halogen, nitro, cyano, alkyl, haloalkyl, perhaloalkyl, cycloalkyl, heterocyclyl, aryl, heteroaryl, —OR$^7$, —NR$^8$R$^{8a}$, —NR$^7$C(=O)R$^9$, C(=O)R$^9$, C(=O)NR$^8$NR$^{8a}$, —SO$_2$alkyl, —C(=O)OH, and —C(=O)O-alkyl; when the heterocycle group is substituted, it is substituted either on a ring carbon atom or on a ring hetero atom, and when it is substituted on a ring carbon atom, it is substituted with 1 to 4 substituents independently selected from oxo (=O), halogen, cyano, alkyl, cycloalkyl, perhaloalkyl, —OR$^7$, C(=O)NR$^8$R$^{8a}$, —C(=O)OH, —C(=O)O-alkyl, —N(H)C(=O)(alkyl), —N(H)R$^8$, and —N(alkyl)$_2$; and when the heterocycle group is substituted on a ring nitrogen, it is substituted with substituents independently selected from alkyl, cycloalkyl, aryl, heteroaryl, —SO$_2$(alkyl), C(=O)R$^9$, and C(=O)O (alkyl); when the heterocycle group is substituted on a ring sulfur, it is substituted with 1 or 2 oxo (=O) group(s); $R^7$ is selected from hydrogen, alkyl, perhaloalkyl, and cycloalkyl; $R^8$ and $R^{8a}$ are each independently selected from hydrogen, alkyl, and cycloalkyl; and $R^9$ is selected from alkyl and cycloalkyl. In some cases, the compound is a compound numbered 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, or 240 at pages 17-37 of WO 2018/020474.

In some embodiments of any of the aspects, the agent that inhibits activity of a CBM signalosome complex is an inhibitory nucleic acid. Inhibitors of the expression of a given gene (e.g., CARMA1, Bcl10, and/or MALT1) can be, e.g., an inhibitory nucleic acid. In some embodiments of any of the aspects, the inhibitory nucleic acid is an inhibitory RNA (iRNA), e.g., a siRNA, or a shRNA. Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of mRNA transcripts, resulting in decreased expression and/or activity of the target.

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of the expression and/or activity of a target, e.g. a CBM signalosome complex or component (e.g., CARM1, Bcl10, and/or MALT1). In certain embodiments, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA (e.g., a CBM signalosome complex or component thereof) level found in the cell without the presence of the iRNA.

In some embodiments of any of the aspects, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target. The other strand (the sense strand) includes a region that is complementary to the antisense strand, such that the two strands hybridize and form a duplex structure when combined under suitable conditions.

In one embodiment, the agent that inhibits activity of a CBM signalosome complex is an antisense oligonucleotide. As used herein, an "antisense oligonucleotide" refers to a synthesized nucleic acid sequence that is complementary to a DNA or mRNA sequence, such as that of a microRNA. Antisense oligonucleotides are can be designed to block expression of a DNA or RNA target by binding to the target and halting expression at the level of transcription, translation, or splicing. Antisense oligonucleotides of the present invention are complementary nucleic acid sequences designed to hybridize under stringent conditions to a CBM signalosome complex or component thereof. For example, an antisense oligonucleotide that inhibits CARMA1 may comprise at least 5, at least 10, at least 15, at least 20, at least 25, at least 30, or more bases complementary to a portion of the coding sequence of the human CARMA1 gene (e.g., SEQ ID NO: 1); an antisense oligonucleotide that inhibits Bcl10 may comprise at least 5, at least 10, at least 15, at least 20, at least 25, at least 30, or more bases complementary to a portion of the coding sequence of the human Bcl10 gene (e.g., SEQ ID NO: 2); and an antisense oligonucleotide that inhibits MALT1 may comprise at least 5, at least 10, at least 15, at least 20, at least 25, at least 30, or more bases complementary to a portion of the coding sequence of the human MALT1 gene (e.g., SEQ ID NO: 3).

In yet another embodiment, the RNA of an iRNA, e.g., a dsRNA, is chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference.

Exemplary embodiments of inhibitory nucleic acids can include, e.g., siRNA, shRNA, miRNA, and/or a miRNA, which are well known in the art, and thus, not described herein.

In some embodiments of any of the aspects, the agent is siRNA that inhibits activity of a CBM signalosome complex. In some embodiments of any of the aspects, the agent is shRNA that inhibits activity of a CBM signalosome complex. In some embodiments of any of the aspects, the agent is miRNA that inhibits activity of a CBM signalosome complex. One skilled in the art can design siRNA, shRNA, or miRNA to target activity of a CBM signalosome complex, e.g., using publically available design tools, such as the siDESIGN Center found on the world wide web at www.dharmacon.gelifesciences.com/design-center/. siRNA, shRNA, or miRNA is commonly made using companies such as Dharmacon (Lafayette, Colo.) or Sigma Aldrich (St. Louis, Mo.). One skilled in the art will be able to readily assess whether the siRNA, shRNA, or miRNA effective target for downregulation of activity of a CBM signalosome complex, for example by transfecting the siRNA, shRNA, or miRNA into cells and detecting the activity of a CBM signalosome complex via Western-blotting (to detect expression levels of the CBM signalosome complex) of function assays (e.g., activation of downstream targets for the CBM signalosome complex, e.g., NF-κB signaling).

In one embodiment, the agent that inhibits activity of a CBM signalosome complex is an antibody or antigen-binding fragment thereof, or an antibody reagent. As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments of any of the aspects, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, CDRs, and domain antibody (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, or IgM (as well as subtypes and combinations thereof). Antibodies can be from any source, including mouse, rabbit, pig, rat, and primate (human and non-human primate) and primatized antibodies. Antibodies also include midibodies, nanobodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Rabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

In one embodiment, the antibody or antibody reagent binds to an amino acid sequence that corresponds to the amino acid sequence encoding CARMA1 (SEQ ID NO: 4).

In another embodiment, the anti-CARMA1 antibody or antibody reagent binds to an amino acid sequence that comprises the sequence of SEQ ID NO: 4; or binds to an amino acid sequence that comprises a sequence with at least 80%, at least 85%, at least 90%, at least 95%, at least 96%, at least 97%, at least 98%, at least 99% or greater sequence identity to the sequence of SEQ ID NO: 4. In one embodiment, the anti-CARMA1 antibody or antibody reagent binds to an amino acid sequence that comprises the entire sequence of SEQ ID NO: 4. In another embodiment, the antibody or antibody reagent binds to an amino acid sequence that comprises a fragment of the sequence of SEQ ID NO: 4, wherein the fragment is sufficient to bind its target, e.g., CARMA1, and for example, inhibit the function of CARMA1.

In one embodiment, the antibody or antibody reagent binds to an amino acid sequence that corresponds to the amino acid sequence encoding Bcl10 (SEQ ID NO: 5).

In another embodiment, the anti-Bcl10 antibody or antibody reagent binds to an amino acid sequence that comprises the sequence of SEQ ID NO: 5; or binds to an amino acid sequence that comprises a sequence with at least 80%, at least 85%, at least 90%, at least 95%, at least 96%, at least 97%, at least 98%, at least 99% or greater sequence identity to the sequence of SEQ ID NO: 5. In one embodiment, the anti-Bcl10 antibody or antibody reagent binds to an amino acid sequence that comprises the entire sequence of SEQ ID NO: 5. In another embodiment, the antibody or antibody reagent binds to an amino acid sequence that comprises a fragment of the sequence of SEQ ID NO: 5, wherein the fragment is sufficient to bind its target, e.g., Bcl10, and for example, inhibit the function of Bcl10.

In one embodiment, the antibody or antibody reagent binds to an amino acid sequence that corresponds to the amino acid sequence encoding MALT1 (SEQ ID NO: 6).

In another embodiment, the anti-MALT1 antibody or antibody reagent binds to an amino acid sequence that comprises the sequence of SEQ ID NO: 6; or binds to an amino acid sequence that comprises a sequence with at least 80%, at least 85%, at least 90%, at least 95%, at least 96%, at least 97%, at least 98%, at least 99% or greater sequence identity to the sequence of SEQ ID NO: 6. In one embodiment, the anti-MALT1 antibody or antibody reagent binds to an amino acid sequence that comprises the entire sequence of SEQ ID NO: 6. In another embodiment, the antibody or antibody reagent binds to an amino acid sequence that comprises a fragment of the sequence of SEQ ID NO: 6, wherein the fragment is sufficient to bind its target, e.g., MALT1, and for example, inhibit the function of MALT1.

In one embodiment, the agent that inhibits activity of a CBM signalosome complex is an inhibitory polypeptide. The term "polypeptide" as used herein refers to a polymer of amino acids. The terms "protein" and "polypeptide" are used interchangeably herein. A peptide is a relatively short polypeptide, typically between about 2 and 60 amino acids, 2 and 10 amino acids, 2 and 20 amino acids, 2 and 30 amino acids, 2 and 40 amino acids, 2 and 50 amino acids, 2 and 60 amino acids, 50 and 60 amino acids, 40 and 60 amino acids, 30 and 60 amino acids, 20 and 60 amino acids, 10 and 60 amino acids, 2 and 15, 10 and 30 amino acids, 20 and 50 amino acids, 30 and 60 amino acids, 30 and 40 amino acids, or 40 and 50 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a non-polypeptide moiety covalently or non-covalently associated therewith is still considered a "polypeptide." Exemplary modifications include glycosylation and palmitoylation. Polypeptides can be purified from natural sources, produced using recombinant DNA technology or synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

In some embodiments, a nucleic acid encoding a polypeptide as described herein (e.g. an inhibitory polypeptide) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, artificial chromosome, virus, virion, etc.

Engineered Cell

One aspect of the invention described herein provides a cell that has been engineered to have a reduced activity of the CBM signalosome complex that can be used to treat a subject having cancer. The cell can be an immune cell, such as a lymphocyte, a neutrophil, a monocyte, or a macrophage. In one embodiment, the cell is a T cell. Various types of T cells include, but are not limited to, effector T cells, helper T cells, cytotoxic (killer) T cells, memory T cells, regulatory T cells, natural killer T cells, mucosal associated invariant T cells, gamma delta T cells. In one embodiment, the cell is a regulatory T cell.

In one embodiment, the cell is an ex vivo cell.

In one embodiment, the engineered cells are allogenic. In another embodiment, the engineered cells are autologous.

T cells can be obtained from a subject using standard techniques known in the field, for example, T cells are isolated from peripheral blood taken from a patient. Regulatory T cells can be identified by analyzing cells for regulatory T cell-specific markers, e.g., using flow cytometry. Regulatory T cell-specific markers include, but are not limited to, CD4, FoxP3, CD45RA, and CD25. In one embodiment, low expression of CD127 (i.e., CD127$^{lo}$) can be used as an identifier of human Tregs, alone or in combination with other markers.

In one embodiment, the cell is engineered to inhibit the formation of the complex, e.g., via disruption, deletion, or alteration of the binding sites comprised within the complex needed for the higher order assembly (e.g., the binding site for MALT1 on Bcl10). In one embodiment, the cell is engineered to inhibit or slow the release of CARMA1 from its auto-inhibition confirmation. In one embodiment, the cell is engineered to have reduced levels of at least one component of the CBM signalosome complex by at least 10% compared to a reference level. In one embodiment, the cell is engineered to have reduced levels of at least one component of the CBM signalosome complex by at least 20%, at least 30%, at least 40%, at least 50%, at least 60%, at least 70%, at least 80%, at least 90%, at least 99% or more compared to a reference level. A reference level can be, e.g., the level of CBM signalosome complex in a non-engineered cell. In one embodiment, the cell is engineered to reduce or inhibit at least one upstream factor required for CBM signalosome complex formation (e.g., PKCθ/PKCβ phosphorylation).

In another embodiment, the cell is engineered to inhibit a CBM signalosome complex from activating its downstream targets (e.g., NF-κB nuclear translocation and activation). In one embodiment, the cell is engineered to inhibit the paracaspase activity of MALT1. In one embodiment, the cell is engineered to inhibit the interaction with or activation of MALT1 substrates. In one embodiment, the cell is engineered to inhibit the cleavage of MALT1 substrates. In another embodiment, the cell is engineered to inhibit mono-ubiquitination of MALT1.

In one embodiment, the cell is engineered to reduce the expression level of the CBM signalosome complex by 10% compared to a reference level. In one embodiment, the cell is engineered to reduce the expression level of the CBM signalosome complex by least 20%, at least 30%, at least 40%, at least 50%, at least 60%, at least 70%, at least 80%, at least 90%, at least 99% or more compared to a reference level. In one embodiment, the cell is engineered to reduce the expression level of at least one gene selected from: the CARMA1 gene, the Bcl10 gene, or the MALT1 gene by 10% compared to a reference level. In one embodiment, the cell is engineered to reduce the expression level of at least one gene selected from: the CARMA1 gene, the Bcl10 gene, or the MALT1 gene by least 20%, at least 30%, at least 40%, at least 50%, at least 60%, at least 70%, at least 80%, at least 90%, at least 99% or more compared to a reference level.

In one embodiment, the cell is engineered to reduce the expression level of at least one gene product selected from: the CARMA1 gene, the Bcl10 gene, or the MALT1 gene by 10% compared to a reference level. In one embodiment, the cell is engineered to reduce the expression level of at least one gene product selected from: the CARMA1 gene, the Bcl10 gene, or the MALT1 gene by least 20%, at least 30%, at least 40%, at least 50%, at least 60%, at least 70%, at least 80%, at least 90%, at least 99% or more compared to a reference level. A reference level can be, e.g., the level of CBM signalosome complex in anon-engineered cell.

In one embodiment, the engineered cell secretes the IFNγ cytokine. Methods for determining if a cell has been engineered in the manner described above can be found herein.

One skilled in the art can engineer a cell, e.g., to reduce the activity of a CBM signalosome complex using standard techniques. In one embodiment, the recently-discovered CRISPR-associated (Cas) system, such as CRISPR-Cas9, can be used for genome-editing. CRISPR-Cas technology for editing of genomes is fully described in Doudna, J A, and Charpentier, E. Science, 346: 6213, 2014, which is incorporated by reference herein in its entirety.

In alternative embodiments, mutations to a cell to reduce the activity of a CBM signalosome complex can be introduced by utilizing TALENs or ZEN technology, which are known in the art. Methods of engineering nucleases to achieve a desired sequence specificity are known in the art and are described, e.g., in Kim (2014); Kim (2012); Belhaj et al. (2013); Umov et al. (2010); Bogdanove et al. (2011); Jinek et al. (2012) Silva et al. (2011); Ran et al. (2013); Carlson et al. (2012); Guerts et al. (2009); Taksu et al. (2010); and Watanabe et al. (2012); each of which is incorporated by reference herein in its entirety.

In alternate embodiments, the activity of a CBM signalosome complex is reduced via other techniques known in the field. In some embodiments, the cell is exposed to an agent that reduces the activity of a CBM signalosome complex. The agent can be an inhibitory nucleic acid, inhibitory polypeptide, or antisense oligonucleotide. It is desired that the agent will induce a reduction in the activity of a CBM signalosome complex that is integrated into the genome (e.g., a stable reduction in the activity).

One can evaluate the lack of an expressible CBM signalosome complex or the gene expression of the CBM signalosome complex components, for example by RT-PCR, northern blotting, western blotting, ELISA, or immunohistochemistry. To evaluate the presence of a functional CBM signalosome complex, one can evaluate whether the CBM signalosome complex is capable of activating, for example, NFκB signaling, using standard techniques.

Treatment of Cancer

One aspect of the invention described herein provides a method for treating cancer comprising administering an agent that inhibits activity of a CARMA1-Bcl10-MATL1 signalosome complex to a subject in need thereof.

Another aspect of the invention described herein provides a method of treating cancer comprising administering any of the engineered cells described herein to a subject in need thereof.

In various embodiments, the method further comprises administering a checkpoint inhibitor to the subject. In various embodiments, the method further comprising administering an anti-cancer therapy to the subject.

One aspect of the invention described herein provides a method of treating cancer comprising administering MI-2 inhibitor and an inhibitor of PD-1 to a subject in need thereof.

Another aspect of the invention described herein provides a method of treating cancer comprising administering mepazine and an inhibitor of PD-1 to a subject in need thereof.

Yet another aspect of the invention described herein provides a method for treating cancer that is resistant to a checkpoint inhibitor therapy comprising administering an agent that inhibits activity of a CARMA1-Bcl10-MATL1 signalosome complex or any of the engineered cells described herein; and second therapeutic to a subject. The second therapeutic can be a checkpoint inhibitor or an anti-cancer therapy. The checkpoint inhibitor administered as a second therapeutic can be the same checkpoint inhibitor therapy that the cancer is resistant to (e.g., a cancer resistant to an anti-PD-1 therapy is treated with an agent that inhibits activity of a CARMA1-Bcl10-MATL1 signalosome complex or any of the engineered cells described herein, and an anti-PD-1 inhibitor). Alternatively, the checkpoint inhibitor administered as a second therapeutic can be different from the checkpoint inhibitor therapy that the cancer is resistant to (e.g., a cancer resistant to an anti-PD-1 therapy is treated with an agent that inhibits activity of a CARMA1-Bcl10-MATL1 signalosome complex or any of the engineered cells described herein, and an anti-PD-L1 inhibitor).

Non-limiting checkpoint inhibitor therapies include anti-PD-L1 therapy, anti-PD-L2 therapy, anti-PD-1 therapy, anti-CTLA-4 therapy, anti-TIM-3 therapy, anti-LAG-3 therapy, anti-VISTA therapy, or anti-TIGIT therapy. The cancer can have acquired a resistance to checkpoint inhibitor therapy (e.g., treatment with the checkpoint inhibitor therapy was previously effective in treating a cancer in a subject, but now fails to be effective). A skilled clinician can determine if a cancer is resistant to or has become resistant to a checkpoint inhibitor therapy using standard techniques for measuring the efficacy of a cancer treatment for a given cancer (e.g., measuring the growth rate of a tumor).

In one embodiment, the cancer is a carcinoma, a melanoma, a sarcoma, a myeloma, a leukemia, or a lymphoma.

A carcinoma is a cancer that originates in an epithelial tissue. Carcinomas account for approximately 80-90% of all cancers. Carcinomas can affect organs or glands capable of secretion (e.g., breasts, lung, prostate, colon, or bladder). There are two subtypes of carcinomas: adenocarcinoma, which develops in an organ or gland, and squamous cell carcinoma, which originates in the squamous epithelium. Adenocarcinomas generally occur in mucus membranes, and are observed as a thickened plaque-like white mucosa. They often spread easily through the soft tissue where they occur. Squamous cell carcinomas can originate from any region of the body. Examples of carcinomas include, but are not limited to, prostate cancer, colorectal cancer, microsatellite stable colon cancer, microsatellite instable colon cancer, hepatocellular carcinoma, breast cancer, lung cancer, small cell lung cancer, non-small cell lung cancer, lung adenocarcinoma, melanoma, basal cell carcinoma, squamous cell carcinoma, renal cell carcinoma, ductal carcinoma in situ, invasive ductal carcinoma.

Sarcomas are cancers that originate in supportive and connective tissues, for example bones, tendons, cartilage, muscle, and fat. Sarcoma tumors usually resemble the tissue in which they grow. Non-limiting examples of sarcomas include, Osteosarcoma or osteogenic sarcoma (originating from bone), Chondrosarcoma (originating from cartilage), Leiomyosarcoma (originating from smooth muscle), Rhabdomyosarcoma (originating from skeletal muscle), Mesothelial sarcoma or mesothelioma (originate from membranous lining of body cavities), Fibrosarcoma (originating from fibrous tissue), Angiosarcoma or hemangioendothelioma (originating from blood vessels), Liposarcoma (originating from adipose tissue), Glioma or astrocytoma (originating from neurogenic connective tissue found in the brain), Myxosarcoma (originating from primitive embryonic connective tissue), or Mesenchymous or mixed mesodermal tumor (originating from mixed connective tissue types).

Melanoma is a type of cancer forming from pigment-containing melanocytes. Melanoma typically develops in the skin, but can occur in the mouth, intestine, or eye.

Myelomas are cancers that originate in plasma cells of bone marrow. Non-limiting examples of myelomas include multiple myeloma, plasmacytoma and amyloidosis.

Leukemias (also known as "blood cancers") are cancers of the bone marrow, which is the site of blood cell production. Leukemia is often associated with the overproduction of immature white blood cells. Immature white blood cells do not function properly, rendering the patient prone to infection. Leukemia additionally affects red blood cells, and can cause poor blood clotting and fatigue due to anemia. Leukemia can be classified as being acute myeloid leukemia (AML), Chronic myeloid leukemia (CML), Acute lymphocytic leukemia (ALL), and Chronic lymphocytic leukemia (CLL). Examples of leukemia include, but are not limited to, Myelogenous or granulocytic leukemia (malignancy of the myeloid and granulocytic white blood cell series), Lymphatic, lymphocytic, or lymphoblastic leukemia (malignancy of the lymphoid and lymphocytic blood cell series), and Polycythemia vera or erythremia (malignancy of various blood cell products, but with red cells predominating).

Lymphomas develop in the glands or nodes of the lymphatic system (e.g., the spleen, tonsils, and thymus), which purifies bodily fluids and produces white blood cells, or lymphocytes. Unlike leukemia, lymphomas form solid tumors. Lymphoma can also occur in specific organs, for example the stomach, breast, or brain; this is referred to as extranodal lymphomas). Lymphomas are subclassified into two categories: Hodgkin lymphoma and Non-Hodgkin lymphoma. The presence of Reed-Sternberg cells in Hodgkin lymphoma diagnostically distinguishes Hodgkin lymphoma from Non-Hodgkin lymphoma.

Non-limiting examples of lymphoma include Diffuse large B-cell lymphoma (DLBCL), Follicular lymphoma, Chronic lymphocytic leukemia (CLL), Small lymphocytic lymphoma (SLL), Mantle cell lymphoma (MCL), Marginal zone lymphomas, Burkitt lymphoma, hairy cell leukemia (HCL). In one embodiment, the cancer is DLBCL or Follicular lymphoma.

In one embodiment, the cancer is a solid tumor. Non-limiting examples of solid tumors include Adrenocortical Tumor, Alveolar Soft Part Sarcoma, Chondrosarcoma, Colorectal Carcinoma, Desmoid Tumors, Desmoplastic Small Round Cell Tumor, Endocrine Tumors, Endodermal Sinus Tumor, Epithelioid Hemangioendothelioma, Ewing Sarcoma, Germ Cell Tumors (Solid Tumor), Giant Cell Tumor of Bone and Soft Tissue, Hepatoblastoma, Hepatocellular Carcinoma, Melanoma, Nephroma, Neuroblastoma, Non-Rhabdomyosarcoma Soft Tissue Sarcoma (NRSTS), Osteosarcoma, Paraspinal Sarcoma, Renal Cell Carcinoma, Retinoblastoma, Rhabdomyosarcoma, Synovial Sarcoma, and Wilms Tumor. Solid tumors can be found in bones, muscles, or organs, and can be sarcomas or carcinomas.

In one embodiment, the cancer is metastatic.

It is contemplated herein that an agent that inhibits activity of a CBM signalosome complex can be used to treat cancers of the same origin, e.g., all carcinomas can be treated with the agent given the agent's efficacy in treating colon cancer, or the agent can treat all solid tumors given the agent's efficacy in treating melanoma and colon cancer. It is further contemplated herein that an agent that inhibits activity of a CBM signalosome complex can be used to treat all cancers, and should not be limited to the cancer types listed in this present specification.

In various cases, the subject being treated using a method as disclosed herein suffers from a solid tumor or a soluble cancer with a microtumor environment. In various cases, the cancer is melanoma, head and neck cancer, lung cancer (e.g., non-small cell lung cancer), bladder cancer, kidney cancer, prostate cancer, a central nervous system (CNS) cancer, breast cancer, stomach cancer, thyroid cancer, ovarian cancer, or Non-Hodgkin's lymphoma. In some cases, the cancer is melanoma. In various cases, the cancer is bladder cancer. In various cases, the cancer is kidney cancer. In various cases, the cancer is non-small cell lung cancer. In various cases, the cancer is head and neck cancer.

Checkpoint Inhibitor

In one embodiment, the method further comprises administering a checkpoint inhibitor to the subject. In one embodiment, the checkpoint inhibitor is a small molecule, an inhibitory nucleic acid, an inhibitory polypeptide, antibody or antigen-binding domain thereof, or antibody reagent. In one embodiment, the checkpoint inhibitor is an antibody or antigen-binding domain thereof, or antibody reagent binds an immune checkpoint polypeptide and inhibits its activity. Common checkpoints that are targeted for therapeutics include, but are not limited to PD-L1, PD-L2, PD-1, CTLA-4, TIM-3, LAG-3, VISTA, or TIGIT. In one embodiment, the checkpoint inhibitor is an antibody or antigen-binding domain thereof, or antibody reagent binds a PD-1, PD-L1, or PD-L2 polypeptide and inhibits its activity.

Inhibitors of known checkpoint regulators (e.g., PD-L1, PD-L2, PD-1, CTLA-4, TIM-3, LAG-3, VISTA, or TIGIT) are known in the art. Non-limiting examples of checkpoint inhibitors (with checkpoint targets and manufacturers noted in parentheses) can include: MGA271 (B7-H3: MacroGenics); ipilimumab (CTLA-4; Bristol Meyers Squibb); pembrolizumab (PD-1; Merck); nivolumab (PD-1; Bristol Meyers Squibb); atezolizumab (PD-L1; Genentech); IMP321 (LAG3: Immuntep); BMS-986016 (LAG3; Bristol Meyers Squibb); IPH2101 (KIR; Innate Pharma); tremelimumab (CTLA-4; Medimmune); pidilizumab (PD-1; Medivation); MPDL3280A (PD-L1; Roche); MEDI4736 (PD-L1; AstraZeneca); MSB0010718C (PD-L1; EMD Serono); AUNP12 (PD-1; Aurigene); avelumab (PD-L1; Merck); durvalumab (PD-L1; Medimmune); or TSR-022 (TIM3; Tesaro).

In one embodiment, the checkpoint inhibitor inhibits PD-1. PD-1 inhibitors include, but are not limited to Pembrolizumab (Keytruda™), Nivolumab, AUNP-12, or Pidilizumab. In another embodiment, the checkpoint inhibitor inhibits PD-L1. PD-L1 inhibitors include, but are not limited to Atezolizumab, MPDL3280A, Avelumab, or Durvalumab.

Programmed death-ligand 1 (PD-L1; also known as cluster of differentiation 274 (CD274) or B7 homolog 1 (B7-H1)) is a transmembrane protein that functions to suppress the immune system in particular events such as pregnancy, tissue allografts, autoimmune disease, and hepatitis. Binding of PD-E1 to its receptor programmed death-1 (PD-1) transmits an inhibitory signal that reduces the proliferation of T cells and can induce apoptosis. Aberrant PD-L1 and/or PD-1 expression has been shown to promote cancer cell evasion in various tumors. PD-L1/PD-1 blockade can be accomplished by a variety of mechanisms including antibodies that bind PD-1 or its ligand, PD-L1. Examples of PD-1 and PD-L1 blockers are described in U.S. Pat. Nos. 7,488,802; 7,943,743; 8,008,449; 8,168,757; 8,217,149, and PCX Published Patent Application Nos: WO03042402, WO2008156712, WO2010089411, WO2010036959, WO2011066342, WO2011159877, WO2011082400, and WO2011161699; which are incorporated by reference herein in their entireties. In certain embodiments, the PD-1 inhibitors include anti-PD-L1 antibodies. PD-1 inhibitors include anti-PD-1 antibodies and similar binding proteins such as nivolumab (MDX 1106, BMS 936558, ONO 4538), a fully human IgG4 antibody that binds to and blocks the activation of PD-1 by its ligands PD-L1 and PD-L2; lambrolizumab (MK-3475 or SCH 900475), a humanized monoclonal IgG4 antibody against PD-1; CT-011 a humanized antibody that binds PD-1; AMP-224, a fusion protein of B7-DC; an antibody Fc portion; BMS-936559 (MDX-1105-01) for PD-L1 (B7-H1) blockade.

Anti-Cancer Therapy

In one embodiment, the agent is administered in combination with an anti-cancer therapy, e.g., a treatment for the intended use of treating a subject with cancer, in combination with the compositions described herein. An anti-cancer therapy can be, e.g., chemotherapy, radiation therapy, chemo-radiation therapy, immunotherapy, hormone therapy, surgery or stem cell therapy.

In accordance with one embodiment, the subject is administered a chemotherapeutic agent in combination with the compositions described herein. Exemplary chemotherapeutic agents include, but are not limited to, a platinum chemotherapeutic agent, an anthracyclin therapeutic agent, or an alkylating chemotherapeutic agent. Non-limiting examples of chemotherapeutic agents include an anthracycline (e.g., doxorubicin (e.g., liposomal doxorubicin)), a *vinca* alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, tositumomab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide). General chemotherapeutic agents considered for use in combination therapies include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®). Exemplary alkylating agents include, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®). Exemplary mTOR inhibitors include, e.g., temsirolimus; ridaforolimus (formally known as deferolimus, (1R,2R,45)-4-[(2R)-2 [(1R,9S,12S,15R,16E,18R,19R,21R,23S,24E,26E,28Z,30S, 32S,35R)-1,18-dihydroxy-19,30-dimethoxy-15,17,21,23, 29,35-hexamethyl-2,3,10,14,20-pentaoxo-11,36-dioxa-4-azatricyclo[30.3.1,04'9]hexatriaconta-16,24,26,28-tetraen-12-yl]propyl]-2-methoxycyclohexyl dimethylphosphinate, also known as AP23573 and MK8669, and described in PCX Publication No. WO 03/064383); everolimus (Afinitor® or RADOOl); rapamycin (AY22989, Sirolimus®); simapimod (CAS 164301-51-3); emsirolimus, (5-{2,4-Bis[(3S,)-3-methylmorpholin-4-yl]pyrido[2,3-(i]pyrimidin-7-yl}-2-methoxyphenyl)methanol (AZD8055); 2-Amino-8-[iraw5,-4-(2-hydroxyethoxy)cyclohexyl]-6-(6-methoxy-3-pyridinyl)-4-methyl-pyrido[2,3-J]pyrimidin-7(8H)-one (PF04691502, CAS 1013101-36-4); and N2-[1,4-dioxo-4-[[4-(4-oxo-8-phenyl-4H-1-benzopyran-2-yl)morpholinium-4-yl]methoxy]butyl]-L-arginylglycyl-L-a-aspartylL-serine-, inner salt (SF1126, CAS 936487-67-1), and XL765. Exemplary immunomodulators include, e.g., afutuzumab (available from Roche®); pegfdgrastim (Neulasta®); lenalidomide (CC-5013, Revlimid®); thalidomide (Thalomid®), actimid (CC4047); and IRX-2 (mixture of human cytokines including interleukin 1, interleukin 2, and interferon γ, CAS 951209-71-5, available from IRX Therapeutics). Exemplary anthracyclines include, e.g., doxorubicin (Adriamycin® and Rubex®); bleomycin (Lenoxane®); daunorubicin (dauorubicin hydrochloride, daunomycin, and rubidomycin hydrochloride, Cerubidine®); daunorubicin liposomal (daunorubicin citrate liposome, DaunoXome®); mitoxantrone (DHAD, Novantrone®); epirubicin (Ellence™); idarubicin (Idamycin®, Idamycin PFS®); mitomycin C (Mutamycin®); geldanamycin; herbimycin; ravidomycin; and desacetylravidomycin. Exemplary *vinca* alkaloids include, e.g., vinorelbine tartrate (Navelbine®), Vincristine (Oncovin®), and Vindesine (Eldisine®)); vinblastine (also known as vinblastine sulfate, vincaleukoblastine and VLB, Alkaban-AQ® and Velban®); and vinorelbine (Navelbine®). Exemplary proteosome inhibitors include bortezomib (Velcade®); carfilzomib (PX-171-007, (5)-4-Methyl-N-((5)-1-(((5)-4-methyl-1-((R)-2-methyloxiran-2-yl)-1-oxopentan-2-yl)amino)-1-oxo-3-phenylpropan-2-yl)-2-((5,)-2-(2-morpholinoacetamido)-4-phenylbutanamido)-pentanamide); marizomib (NPT0052); ixazomib citrate (MLN-9708); delanzomib (CEP-18770); and O-Methyl-N-[(2-methyl-5-thiazolyl)carbonyl]-L-seryl-O-methyl-N-[(llS')-2-[(2R)-2-methyl-2-oxiranyl]-2-oxo-1-(phenylmethyl)ethyl]-L-serinamide (ONX-0912).

One of skill in the art can readily identify a chemotherapeutic agent of use with methods and compositions describe herein (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff s Clinical Oncology, 2013 Elsevier; and Fischer D S (ed): The Cancer Chemotherapy Handbook, 4th ed. St. Louis, Mosby-Year Book, 2003).

In accordance with one embodiment, the subject is administered a radiation therapy in combination with the compositions described herein. Radiation therapy, according to the invention disclosed herein, encompasses both non-invasive (external) and invasive (internal) radiation therapies. In an external radiation therapy, treatment is affected by radiation sources outside the body, whereas in an invasive radiation therapy treatment is affected by radiation sources planted inside the body. The representative diseases treated by non-invasive or invasive radiation therapy include, for example, cancer, rheumatoid arthritis, angioplasty, or restenosis.

In accordance with one embodiment, the subject is administered a chemo-radiation therapy, e.g., a combination of a chemotherapy and radiation therapy, in combination with the compositions described herein.

In accordance with one embodiment, the subject is administered an immunotherapy in combination with the compositions described herein. As used herein, "immunotherapy" refers to a treatment designed, e.g., to increase the immune system of a subject to stop or slow the growth of cancer cells, stop the metastasis of cancer cells, and/or target the cancer cell for programmed cell death. Exemplary immunotherapies include a monoclonal antibody, a non-specific immunotherapy, an oncolytic virus therapy, adoptive T-cell therapy (e.g., adoptive $CD4^+$ or $CD8^+$ effector T cell therapy), adopted natural killer (NK) cell therapy, adopted NK T cell therapy and cancer (e.g., tumor) vaccines.

In accordance with one embodiment, the subject is administered a non-specific immunotherapy in combination with the compositions described herein. Two common non-specific immunotherapies include, e.g., interferons and interleukins. Interferons (such as Roferon-A [2α], Intron A [2β], Alferon [2α]) boost the immune system to target cancer cells for programmed cell death, and/or slow the growth of cancer cells. Interleukins (such as interleukin-2, IL-2, or aldesleukin (Proleukin)) boost the immune system to produce cells that target cancer cells for programmed cell death. Interleukins are used to treat, e.g., kidney cancer and skin cancer, including melanoma. Non-specific immunotherapies can be administered as a monotherapy, or administered after or at the same time as another anti-cancer therapy, such as chemotherapy or radiation therapy.

In accordance with one embodiment, the subject is administered an oncolytic virus in combination with the compositions described herein. Oncolytic virus therapy utilizes a genetically modified virus (e.g., a herpes simplex virus, or other virus) to target cancer cells for programmed cell death via an immune response. An oncolytic virus is administered locally, e.g., injected into a tumor, where the virus enters the cancer cells and replicates. The replication can result in lysis of the cancer cells, resulting in the release of antigens and activating an immune response that targets the cancer cells for programmed cell death. Administration of the virus can be repeated until the desired effect is obtained (e.g., the tumor is eradicated). Oncolytic virus therapy (e.g., talimogene laherparepvec (Imlygic), or T-VEC) has been approved for treatment of melanoma.

In one embodiment, a subject having cancer is administered an engineered T cell in combination with the compositions described herein. T cell therapy utilizes T cell that have been engineered express an exogenous chimeric antigen receptor (CAR). As used herein, "chimeric antigen receptor" or "CAR" refers to an artificially constructed hybrid polypeptide comprising an antigen-binding domain (e.g., an antigen-binding portion of an antibody (e.g., a scFV)), a transmembrane domain, and a T-cell signaling and/or T-cell activation domain (e.g., intracellular signaling domain). CARs have the ability to redirect T-cell specificity and reactivity toward a selected target in a non-MHC-restricted manner, exploiting the antigen-binding properties of monoclonal antibodies. Further discussion of CARs can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

In one embodiment, a subject having cancer is administered a CAR T cell that targets a tumor antigen on the cell surface of a tumor cell in combination with the compositions described herein. As used herein, the terms "tumor antigen" refers to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), and fusion proteins resulting from internal deletions or chromosomal translocations. Still other cancer antigens can be encoded by viral genes such as those carried on RNA and DNA tumor viruses. Many tumor antigens have been defined in terms of multiple solid tumors: MAGE 1, 2, & 3, defined by immunity; MART-1/Melan-A, gp100, carcinoembryonic antigen (CEA), HER2, mucins (i.e., MUC-1), prostate-specific antigen (PSA), and prostatic acid phosphatase (PAP). In addition, viral proteins such as some encoded by hepatitis B (HBV), Epstein-Barr (EBV), and human papilloma (HPV) have been shown to be important in the development of hepatocellular carcinoma, lymphoma, and cervical cancer, respectively.

In one embodiment, a subject having cancer is administered an CAR T cell that targets EGFR (Epidermal growth factor receptor) on non-small cell lung cancer, epithelial carcinoma, glioma; EGFRvIII (Variant III of the epidermal growth factor receptor) on glioblastoma; HER2 (Human epidermal growth factor receptor 2) on ovarian cancer, breast cancer, glioblastoma, colon cancer, osteosarcoma, medulloblastoma; MSLN (Mesothelin) on mesothelioma, ovarian cancer, pancreatic adenocarcinoma; PSMA (Prostate-specific membrane antigen) on prostate cancer; CEA (Carcinoembryonic antigen) on pancreatic adenocarcinoma, breast cancer, colorectal carcinoma; GD2 (Disialoganglioside 2) on neuroblastoma, melanoma; IL13Rα2 (Interleukin-13Ra2) on glioma; GPC3 (Glypican-3) on hepatocellular carcinoma; CAIX (Carbonic anhydrase IX) on renal cell carcinoma (RCC); L1-CAM (E1 cell adhesion molecule) on neuroblastoma, melanoma, ovarian adenocarcinoma; CA125 (Cancer antigen 125, also known as MUC16) on epithelial ovarian cancers; CD133 (Cluster of differentiation 133, also known as prominin-1) on glioblastoma, cholangiocarcinoma (CCA); FAP (Fibroblast activation protein) on malignant pleural mesothelioma (MPM); CTAG1B (Cancer/testis antigen 1B, also known as NY-ESO-1) on melanoma and ovarian cancer; MUC1 (Mucin 1) on seminal vesicle cancer; FR-α (Folate receptor-α) on ovarian cancer in combination with any of the compositions described herein.

In one embodiment, a subject having cancer is administered a CAR T cell that targets a checkpoint inhibitor in combination with the compositions described herein. In one embodiment, a subject having cancer is administered an anti-PD-1 CAR T cell. In one embodiment, a subject having cancer is administered an anti-PD-F1 CAR T cell in combination with the compositions described herein.

In one embodiment, a subject having cancer is administered a cancer vaccine in combination with the compositions described herein. Cancers that can be treated with and/or prevented by cancer vaccines include but are not limited to bladder cancer, brain tumors, breast cancer, cervical cancer, colorectal cancer, kidney cancer, leukemia, lung cancer, melanoma, myeloma, pancreatic cancer, and prostate cancer.

In one embodiment, the administered an adoptive T cell therapy in combination with the compositions described herein. Exemplary T cells that can be used in adoptive T cell therapy include $CD4^+$ or $CD8^+$ effector T cell, regulatory T cells, or cytolytic T cells.

In one embodiment, a subject having cancer is administered an adoptive NK cell therapy in combination with the compositions described herein. Natural killer (NK) cells are immune cells that function to target a cancer cell for programmed cell death without requiring prior sensitization to a tumor antigen. NK target cancer cells through a variety of mechanisms, e.g., through receptor-mediated cytotoxicity. NK cells express a germ-line encoded receptors, such as the c-type lectin homodimer, NKG2D, which binds to stress induced ligands (e.g., UFBP's, MICA/MICB) expressed on tumor cells. Upon ligation, NK cells degranulate, releasing perforin and granzymes to induce target cell apoptosis. NK cell degranulation can also be triggered though a process called antibody dependent cell-mediated cytotoxicity (ADCC). NK cells and T cells can be modified (e.g., with cytokines such as IL-2, IL-12, IL-15, or IL-18) to increase their cancer cell capabilities and specificity. NK cells administered to a subject can be autologous or allogeneic. NK cells administered to a subject can be expand in vivo or ex vivo. Cancers that can be treated with adoptive NK cell or T cell therapy include, but are not limited to advanced melanoma, renal cell carcinoma, acute myeloid leukemia, lymphoma, solid tumors, non-Hodgkin's lymphoma, chronic lymphocytic leukemia, non-B lineage hematologic malignancies, $Her2^+$ breast cancer, and $Her2^+$ gastric cancer. The use of adoptive NK cell and adoptive NK T cell therapies are further reviewed in, e.g., Davis, Z B, et al. Cancer J. 2015 November-December; 21(6): 486-491, which is incorporated by reference herein in its entirety.

In one embodiment, adoptive T cell therapy, e.g., $CD4^+$ or $CD8^+$ effector T cell therapy, or NK T cell therapy, is reactive with tumor antigens. T cells for adoptive T cell therapies can be are purified from, e.g., tumor tissue, blood, or other patient tissue. Purified T cells can be e.g., activated, expanded, and/or genetically modified, e.g., ex vivo in cell culture. Activated, expanded, and/or genetically modified T cells can be e.g., administered into the patient, for example, by intravenous injection or other acceptable routes, in combination with compositions described herein. It is envisioned that the agent that inhibits activity of CBM signalosome would to enhance recruitment of the administered cells to the site of the tumor.

In accordance with one embodiment, the subject is administered a hormone therapy in combination with the compositions described herein. Hormone therapy is designed to add, block, or remove hormones from the body to, e.g., halt or slow the growth of cancer cells. Hormone therapy can include administration of, e.g., progesterone, oophorectomy, tamoxifen, gonadotropin-releasing hormone (GnRH) agonists or analogues and androgen therapy. Hormone therapy can also refer to removing glands, e.g., thyroid, pancreas, and ovary, to reduce the levels of hormones in the body. Hormone therapies are known in the art and can be administered by a skilled person.

In accordance with one embodiment, the subject is administered a stem cell therapy in combination with the compositions described herein. Stem cell therapy can comprise removing a subjects stem cells prior to receiving treatment to destroy all stem cells (e.g., chemotherapy, radiotherapy, or a combination thereof). Stems cells can be re-administered to the patient following such treatment (e.g., a stem cell transplant). A stem cell transplant can be autologous, or allogenic. A stem cell transplant can be a tandem transplant (e.g., two or more transplants in a row), a mini-transplant (e.g., a subject's immune system is suppressed less than a typical transplant), or a syngeneic stem cell transplant (e.g., allogenic stem cells received from an identical twin). Cancers that can be treated with stem cell therapy include but are not limited to leukemias, lymphomas, multiple myeloma, testicular cancer, neuroblastoma, and certain childhood cancers.

Administration

In some embodiments, the methods described herein relate to treating a subject having or diagnosed as having cancer comprising administering an agent that inhibits activity of a CBM signalosome complex as described herein, or administering any of the engineered cells described herein.

It is contemplated herein that the subject comprises a cancer that is, or was previously, resistant to a checkpoint inhibitor therapy. Subjects having a cancer can be identified by a physician using current methods of diagnosing a cancer (e.g., melanoma, or other cancer). Symptoms and/or complications of the cancer, which characterize this disease and aid in diagnosis are well known in the art and include but are not limited to, fatigue, weight loss, bone pain, swollen or painful lymph nodes, and headaches. Tests that may aid in a diagnosis of, e.g. the cancer, include but are not limited to, punch or excision biopsy, and non-invasive imaging (e.g., Magnetic Resonance Imaging, or Computerized Tomography scan), and are known in the art for a given condition. A family history for a condition, or exposure to risk factors for a cancer can also aid in determining if a subject is likely to have the condition or in making a diagnosis of the cancer.

The agents or engineered cells described herein can be administered to a subject having or diagnosed as having a cancer (e.g., melanoma or colon cancer). In some embodiments, the methods described herein comprise administering an effective amount of an agent or engineered cells that inhibits activity of a CBM signalosome complex to a subject in order to alleviate a symptom of the cancer. As used herein, "alleviating a symptom of the cancer" is ameliorating any condition or symptom associated with cancer. As compared with an equivalent untreated control, such reduction is by at least 5%, 10%, 20%, 40%, 50%, 60%, 80%, 90%, 95%, 99% or more as measured by any standard technique known to those skilled in the art. A variety of means for administering the agent or engineered cells described herein to subjects are known to those of skill in the art.

In one embodiment, the agent or engineered cells are administered systemically or locally. In one embodiment, the agent or engineered cells are administered intravenously. In another embodiment, the agent or engineered cells are administered locally, e.g., at the site of the tumor. The route of administration of an agent that inhibits activity of a CBM signalosome complex will be optimized for the type of agent being delivered (e.g., inhibitory nucleic acid, or small molecule), and can be determined by a skilled person. In one embodiment, the agent or engineered cells described herein are administered enterally/gastrointestinally (orally), parenterally, or topically.

The term "effective amount" as used herein refers to the amount of an agent or engineered cells needed to alleviate at least one symptom of the cancer (e.g., headaches). The term "therapeutically effective amount" therefore refers to an amount of an agent or engineered cells that is sufficient to provide a particular anti-cancer effect when administered to a typical subject. An effective amount as used herein, in various contexts, would also include an amount of an agent or engineered cells sufficient to delay the development of a symptom of the cancer, alter the course of a symptom cancer (for example but not limited to, slowing the progression of a cancer), or reverse a symptom of the cancer. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be evaluated by standard pharmaceutical procedures in cell cultures or experimental animals. The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the agent, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., noninvasive imaging, among others. The dosage can be determined by a physician and adjusted, as necessary, to suit observed effects of the treatment.

Combination Treatment

While it is contemplated herein that the agent that inhibits activity of a CBM signalosome complex, or any of the engineered cells described herein can be administered as a monotherapy to a subject, combination therapy can be used to treat cancer in a subject. In various embodiments, the subject is further administered a checkpoint inhibitor or an anti-cancer therapy. In one aspect, the agent or engineered cells are administered with a second therapeutic (e.g., a checkpoint inhibitor or anti-cancer therapy).

Administered "in combination," as used herein, means that two (or more) different treatments are delivered to the subject during the course of the subject's affliction with the disorder, e.g., the two or more treatments are delivered after the subject has been diagnosed with the disorder or disease (for example, cancer) and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The agents described herein and the at least one additional therapy can be administered simultaneously, in the same or in separate compositions, or sequentially. For sequential administration, the agent described herein can be administered first, and the additional agent can be administered second, or the order of administration can be reversed. The agent and/or other therapeutic agents, procedures or modalities can be administered during periods of active disorder, or during a period of remission or less active disease. The agent can be administered before another treatment, concurrently with the treatment, post-treatment, or during remission of the disorder.

In one embodiment, an agent or engineered cell can be administered prior to a check point inhibitor or anti-cancer therapy. In one embodiment, an agent or engineered cell can be administered following to a check point inhibitor or anti-cancer therapy. In one embodiment, an agent or engineered cell can be administered at substantially the same time as a check point inhibitor or anti-cancer therapy.

In one embodiment, an agent or engineered cell can be administered locally. In one embodiment, an agent or engineered cell can be administered systemically. In one embodiment, a check point inhibitor or anti-cancer therapy can be administered locally. In one embodiment, a check point inhibitor or anti-cancer therapy can be administered systemically. When a subject is administered 1) an agent or engineered cell and 2) a checkpoint inhibitor or anti-cancer therapy, the target of action (e.g., local or systemic administration) can be the same (e.g., the agent and checkpoint inhibitor are administered locally) or different (e.g., the agent is administered locally and the checkpoint inhibitor is administered systemically). In one embodiment, the agent or engineered cells and second therapeutic are administered locally. In one embodiment, the agent or engineered cells and second therapeutic are administered systemically. In one embodiment, the agent or engineered cells is administered locally and second therapeutic is administered systemically. In one embodiment, the agent or engineered cells is administered systemically and second therapeutic is administered locally. The route and mode of administration for a given anti-cancer therapy is known in the art, and can be determined by a skilled clinician. An agent or engineered cell can be comprised in a composition with a checkpoint inhibitor or anti-cancer therapy (e.g., a chemotherapeutic).

Dosage

"Unit dosage form" as the term is used herein refers to a dosage for suitable one administration. By way of example a unit dosage form can be an amount of therapeutic disposed in a delivery device, e.g., a syringe or intravenous drip bag. In one embodiment, a unit dosage form is administered in a single administration. In another, embodiment more than one unit dosage form can be administered simultaneously.

The dosage of the agent as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further cells, discontinue treatment, resume treatment, or make other alterations to the treatment regimen. The dosage should not be so large as to cause adverse side effects, such as cytotoxic effects. The dosage can also be adjusted by the individual physician in the event of any complication.

The dosage range depends upon the potency, and includes amounts large enough to produce the desired effect, e.g., a decrease in tumor size. Generally, the dosage will vary with the type of agent (e.g., an inhibitory antibody, a small molecule inhibitor of MATL1, or an inhibitory nucleic acid), checkpoint inhibitor, or anti-cancer treatment (e.g., chemotherapeutic), and with the age, sex, and condition of the patient. Typically, the dosage will range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In some embodiments of any of the aspects, the dose range is from 1 µg/kg body weight to 20 µg/kg body weight. Alternatively, the dose range will be titrated to maintain serum levels between 1 µg/mL and 20 µg/mL. In some embodiments, the dosage range is from 1 µg/mL to 15 µg/mL, from 1 µg/mL to 10 µg/mL, from 1 µg/mL to 5 µg/mL, from 1 µg/mL to 2.5 µg/mL, from 2.5 µg/mL to 20 µg/mL, from 5 µg/mL to 20 µg/mL, from 10 µg/mL to 20 µg/mL, from 15 µg/mL to 20 µg/mL, from 10 µg/mL to 5 µg/mL, from 5 µg/mL to 15 µg/mL, from 5 µg/mL to 10 µg/mL, from 2.5 µg/mL to 10 µg/mL, or from 2.5 µg/mL to 15 µg/mL, A pharmaceutical composition comprising the engineered cells described herein (e.g., engineered cells) can generally be administered at a dosage of $10^4$ to $10^5$ cells/kg body weight, $10^4$ to $10^6$ cells/kg body weight, $10^4$ to $10^7$ cells/kg body weight, $10^4$ to $10^8$ cells/kg body weight, $10^4$ to $10^9$ cells/kg body weight, $10^8$ to $10^9$ cells/kg body weight, $10^7$ to $10^9$ cells/kg body weight, $10^6$ to $10^9$ cells/kg body weight, $10^5$ to $10^9$ cells/kg body weight, $10^4$ to $10^9$ cells/kg body weight, $10^4$ to $10^6$ cells/kg body weight, $10^5$ to $10^7$ cells/kg body weight, $10^7$ to $10^9$ cells/kg body weight, $10^5$ to $10^8$ cells/kg body weight, or $10^6$ to $10^7$ cells/kg body weight, including all integer values within those ranges. If necessary, engineered cell compositions can also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated engineered regulatory T cells to a subject and then subsequently redraw blood (or have an apheresis performed), activate T cells therefrom as described herein, and reinfuse the patient with these activated and expanded T cells. This process can be carried out multiple times every few weeks if desired.

Modes of administration can include, for example intravenous (i.v.) injection or infusion. The compositions described herein can be administered to a patient transarterially, intratumorally, intranodally, or intramedullary. In some embodiments, the compositions of T cells may be injected directly into a tumor, or lymph node. In one embodiment, the compositions described herein are administered into a body cavity or body fluid (e.g., ascites, pleural fluid, peritoneal fluid, or cerebrospinal fluid).

Parenteral Dosage Forms

Parenteral dosage forms of an agent or engineered cells described herein can be administered to a subject by various routes, including, but not limited to, epidural, intracerebral, intracerebroventricular, epicutaneous, nasal administration, intraarterial, intraarticular, intracardiac, intracavernous injection, intradermal, intralesional, intramuscular, intraocular, intraosseous infusion, intraperitoneal, intrathecal, intrauterine, intravaginal administration, intravenous, intravesical, intravitreal, subcutaneous, transdermal, perivascular administration, or transmucosal. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Efficacy

The efficacy of an agent that inhibits activity of a CBM signalosome complex or of the engineered cells described herein in, e.g. the treatment of a condition described herein (e.g., melanoma), or to induce a response as described herein (e.g. a reduction in tumor size) can be determined by the skilled clinician. However, a treatment is considered "effective treatment," as the term is used herein, if one or more of the signs or symptoms of a condition described herein is altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom (e.g., headaches, or bone pain), and/or the incidence of a condition treated according to the methods described herein or any other measurable parameter appropriate. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

Efficacy can also be measured by a failure of an individual to worsen as assessed by hospitalization, or need for medical interventions (i.e., progression of the disease is halted). Methods of measuring these indicators are known to those of skill in the art and/or are described herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

The present invention can be defined in any of the following numbered paragraphs.

1) A method of treating cancer, the method comprising; administering an agent that inhibits activity of a CARMA1-Bcl10-MALT1 signalosome complex to a subject in need thereof.

2) The method of paragraph 1, wherein the cancer is selected from the group consisting of a carcinoma, a melanoma, a sarcoma, a myeloma, a leukemia, or a lymphoma.

3) The method of paragraph 1, wherein the cancer is a melanoma or colon cancer.

4) The method of any of paragraphs 1-3, wherein cancer is a solid tumor.

5) The method of paragraph 4, wherein the solid tumor is selected from the group consisting of an Adrenocortical Tumor, an Alveolar Soft Part Sarcoma, a Chondrosarcoma, a Colorectal Carcinoma, a Desmoid Tumors, a Desmoplastic Small Round Cell Tumor, an Endocrine Tumors, an Endodermal Sinus Tumor, an Epithelioid Hemangioendothelioma, a Ewing Sarcoma, a Germ Cell Tumors (Solid Tumor), a Giant Cell Tumor of Bone and Soft Tissue, a Hepatoblastoma, a Hepatocellular Carcinoma, a Melanoma, a Nephroma, a Neuroblastoma, a Non-Rhabdomyosarcoma Soft Tissue Sarcoma (NRSTS), an Osteosarcoma, a Paraspinal Sarcoma, a Renal Cell Carcinoma, a Retinoblastoma, a Rhabdomyosarcoma, a Synovial Sarcoma, or a Wilms Tumor.

6) The method of any of paragraphs 1-5, wherein the cancer is metastatic.

7) The method of paragraph 1, further comprising administering a checkpoint inhibitor to the subject.

8) The method of paragraph 7, wherein the checkpoint inhibitor is a small molecule, an inhibitory nucleic acid, an inhibitory polypeptide, antibody or antigen-binding domain thereof, or antibody reagent.

9) The method of paragraph 8, wherein the antibody or antigen-binding domain thereof, or antibody reagent binds an immune checkpoint polypeptide and inhibits its activity.

10) The method of paragraph 9, wherein the immune checkpoint polypeptide is selected from the group consisting of PD-L1, PD-L2, PD-1, CTLA-4, TIM-3, LAG-3, VISTA, or TIGIT.

11) The method of paragraph 9, wherein the immune checkpoint polypeptide is PD-1, PD-L1, or PD-L2.

12) The method of any of paragraphs 7-11, wherein the checkpoint inhibitor inhibits PD-1, PD-L1, or PD-L2.

13) The method of paragraph 12, wherein the checkpoint inhibitor that inhibits PD-1 is selected from the group consisting of Pembrolizumab (Keytruda), Nivolumab, AUNP-12, or Pidilizumab.

14) The method of paragraph 12, wherein the checkpoint inhibitor that inhibits PD-L1 is selected from the group consisting of Atezolizumab, MPDL3280A, Avelumab, or Durvalumab.

15) The method of paragraph 1, wherein the activity inhibited by the agent is the CARMA1-Bcl10-MALT1 signalosome complex function.

16) The method of paragraph 1, wherein the activity inhibited by the agent is the formation of the CARMA1-Bcl10-MALT1 signalosome complex.

17) The method of paragraph 1, wherein the activity inhibited by the agent is function of at least one component of the CARMA1-Bcl10-MALT1 signalosome complex.

18) The method of paragraph 1, wherein the activity inhibited by the agent is the expression level of at least one component of the CARMA1-Bcl10-MALT1 signalosome complex.

19) The method of paragraph 1, wherein the activity of a CARMA1-Bcl10-MALT1 signalosome complex is inhibited in a regulatory T cell.

20) The method of paragraph 1, wherein the regulatory T cell is a tumor-infiltrating regulatory T cell.

21) The method of paragraph 1, wherein the agent is selected from the group consisting of a small molecule, an inhibitory nucleic acid, an antibody or antigen-binding fragment thereof or antibody reagent, or an inhibitory polypeptide.

22) The method of paragraph 21, wherein the small molecule is a small molecule inhibitor of MALT1 paracaspase activity.

23) The method of paragraph 22, wherein the small molecule inhibitor of MALT1 paracaspase activity is selected from the group consisting of MI-2 or analogs thereof, or a pyrazolo pyrimidine derivative, a phenothiazine derivative, or tetrapeptide Z-VRPR-FMK (SEQ ID NO: 7).

24) The method of paragraph 23, wherein the phenothiazine derivative is mepazine, thioridazine, or promazine.

25) The method of paragraph 1, wherein administration is systemic.

26) The method of paragraph 1, wherein administration local.

27) The method of paragraph 1, further comprising administering at least one anti-cancer therapy to the subject.

28) The method of paragraphs 27, wherein the anti-cancer therapy is selected from the group consisting of chemotherapy, radiation therapy, chemo-radiation therapy, immunotherapy, hormone therapy, or stem cell therapy.

29) The method of paragraph 28, wherein the immunotherapy is a tumor vaccine, a chimeric antigen receptor T cell (CAR T cell), an adoptive T cell therapy, an adoptive natural killer (NK) cell therapy, or an adoptive NK T cell therapy.

30) A method of treating cancer, the method comprising: administering an MI-2 inhibitor and an inhibitor of PD-1 to a subject in need thereof.

31) A method of treating cancer, the method comprising: administering mepazine and an inhibitor of PD-1 to a subject in need thereof.

32) A cell engineered to have reduced CARMA1-Bcl10-MALT1 signalosome activity.

33) The cell of paragraph 32, wherein the cell has been engineered to inhibit the function of at least one gene selected from the group consisting of CARMA1, Bcl10, or MALT1.

34) The cell of paragraph 32, wherein the cell has been engineered to inhibit the function of at least one gene product selected from the group consisting of CARMA1, Bcl10, or MALT1.

35) The cell of paragraph 32, wherein the cell has been engineered to reduce the expression level of at least one gene selected from the group consisting of CARMA1, Bcl10, or MALT1.

36) The cell of paragraph 32, wherein the cell has been engineered to reduce the expression level of at least one gene product selected from the group consisting of CARMA1, Bcl10, or MALT1.

37) The cell of paragraph 32, wherein the cell is an immune cell.

38) The cell of paragraph 37, wherein immune cell is a T cell.

39) The cell of paragraph 38, wherein the T cell is a T regulatory cell.

40) A method of treating cancer, the method comprising; administering any of the cells of paragraphs 32-39 to a subject in need thereof.

41) The method of paragraph 40, further comprising administering a checkpoint inhibitor to the subject.

42) The method of paragraph 40, further comprising administering an anti-cancer therapy to the subject.

43) A method of treating cancer that is resistant to a checkpoint inhibitor therapy, the method comprising;
   a. administering an agent that inhibits activity of a CARMA1-Bcl10-MALT1 signalosome complex, or any of the cells of paragraphs 32-39; and
   b. a second therapeutic to a subject in need thereof.

44) The method of paragraph 43, wherein the checkpoint inhibitor therapy is selected from the group consisting of an anti-PD-L1 therapy, an anti-PD-L2 therapy, an anti-PD-1 therapy, an anti-CTLA-4 therapy, an anti-TIM-3 therapy, an anti-LAG-3 therapy, an anti-VISTA therapy, or an anti-TIGIT therapy.

45) The method of paragraph 43, wherein the checkpoint inhibitor therapy is an anti-PD-1 therapy.

46) The method of paragraph 43, wherein the second therapeutic is a checkpoint inhibitor or an anti-cancer therapy.

EXAMPLES

Example 1

Prior studies showed that local exposure of tumor-infiltrating Treg to their cognate antigens is required to sustain their tumor-promoting immunosuppressive functions[4]. Thus, whether T cell receptor (TCR)-dependent signaling pathways could be therapeutically targeted to disable the functions of tumor-reactive Treg was investigated. The scaffold protein CARMA1/Card11 is part of the CARMA1/Bcl10/MALT1 (CBM) multiprotein complex, which in T cells is assembled in response to TCR-dependent PKCθ activity and serves as a signaling platform promoting several functions, including activation of the AP-1, mTOR, and classical NF-κB pathways, as well as mRNA stabilization[5]. Constitutive genetic deletion of either CARMA1, Bcl10, or MALT1 abrogates thymic Treg development[6-9], but their role in the function of mature Treg is unknown.

Conditionally deleted CARMA1 in mature Treg resulting from crossing Foxp3YFP-Cre to CARMA1fl/fl mice (hereafter called 'FCrexC1$^{fl/fl}$'), caused CARMA1 protein in Foxp3+CD4+ Treg from lymph nodes (LNs) to be proportionally reduced in FCrexC1fl/+ that lacked one and FCrex C1fl/f mice that lacked both alleles of the CARMA1 gene (FIG. 1A). FCrexC1fl/fl, but not FCrexC1fl/+ mice, failed to thrive starting between days 17 and 19 after birth and the majority died before 4 weeks of age (FIGS. 1B and 1C). While FCrexC1fl/fl animals developed a TH1-dominated multiorgan lymphoproliferative disease characterized by splenomegaly, lymphadenopathy and expansion of effector memory T cells that produced inflammatory cytokines, FCrexC1fl/+ mice resembled control mice (FIGS. 1D-1G and FIG. 5A) and remained healthy up to at least 9 months of age (data not shown). Hence, CARMA1 is essential for Treg to maintain immune homeostasis, but its reduced expression is well tolerated.

Figure 7A:
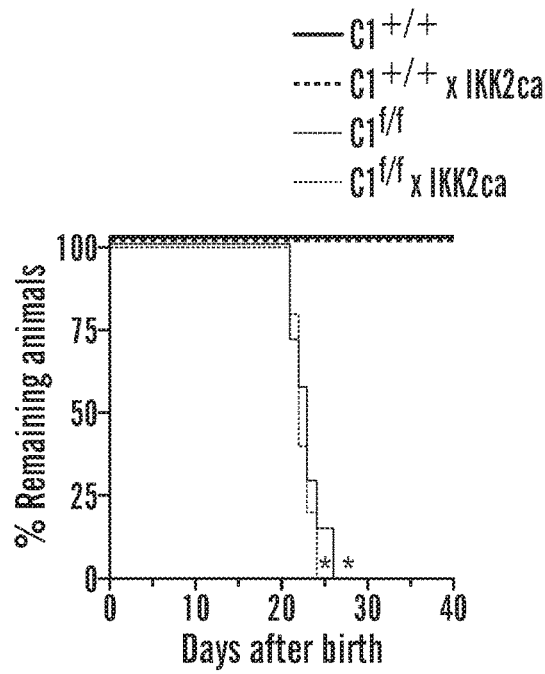
FIGS. 7A-7F.
Figure 7B:
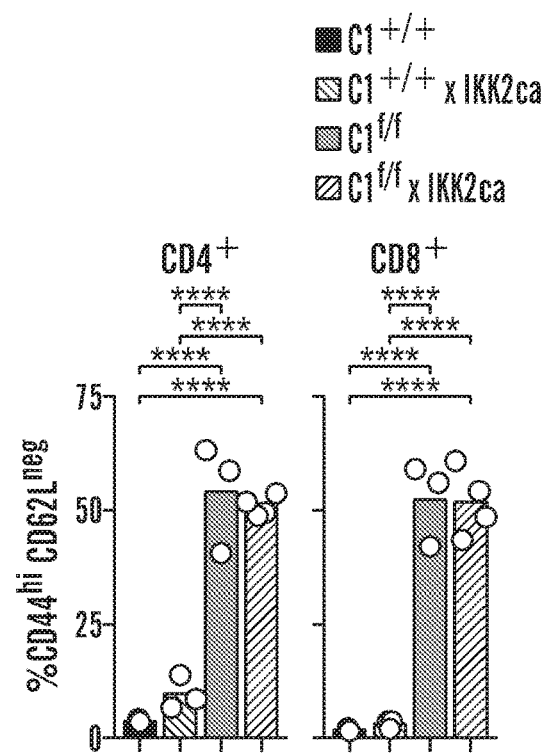

Failed thymic Treg development in absence of CARMA1 primarily results from disabled activation of the canonical NF-κB pathway and can be restored through expression of IKK2ca, a constitutively active form of the NF-κB activator IKK2/β.[11] More recently, important roles for the NF-κB proteins c-Rel and p65/RelA in peripheral Treg function have been established,[12-14] suggesting that failed NF-κB may primarily account for the effects of CARMA1-deletion in Treg. However, expression of IKK2ca in Treg did no prolong the lifespan of F$^{Cre}$×C1$^{fl/fl}$ mice or reduce Teff cytokine expression (FIGS. 7A-7B), suggesting that, although activation of c-Rel and RelA is evidently essential,[14-15] additional CBM complex effector functions are similarly critical to maintaining peripheral Treg function.

Figure 1G:
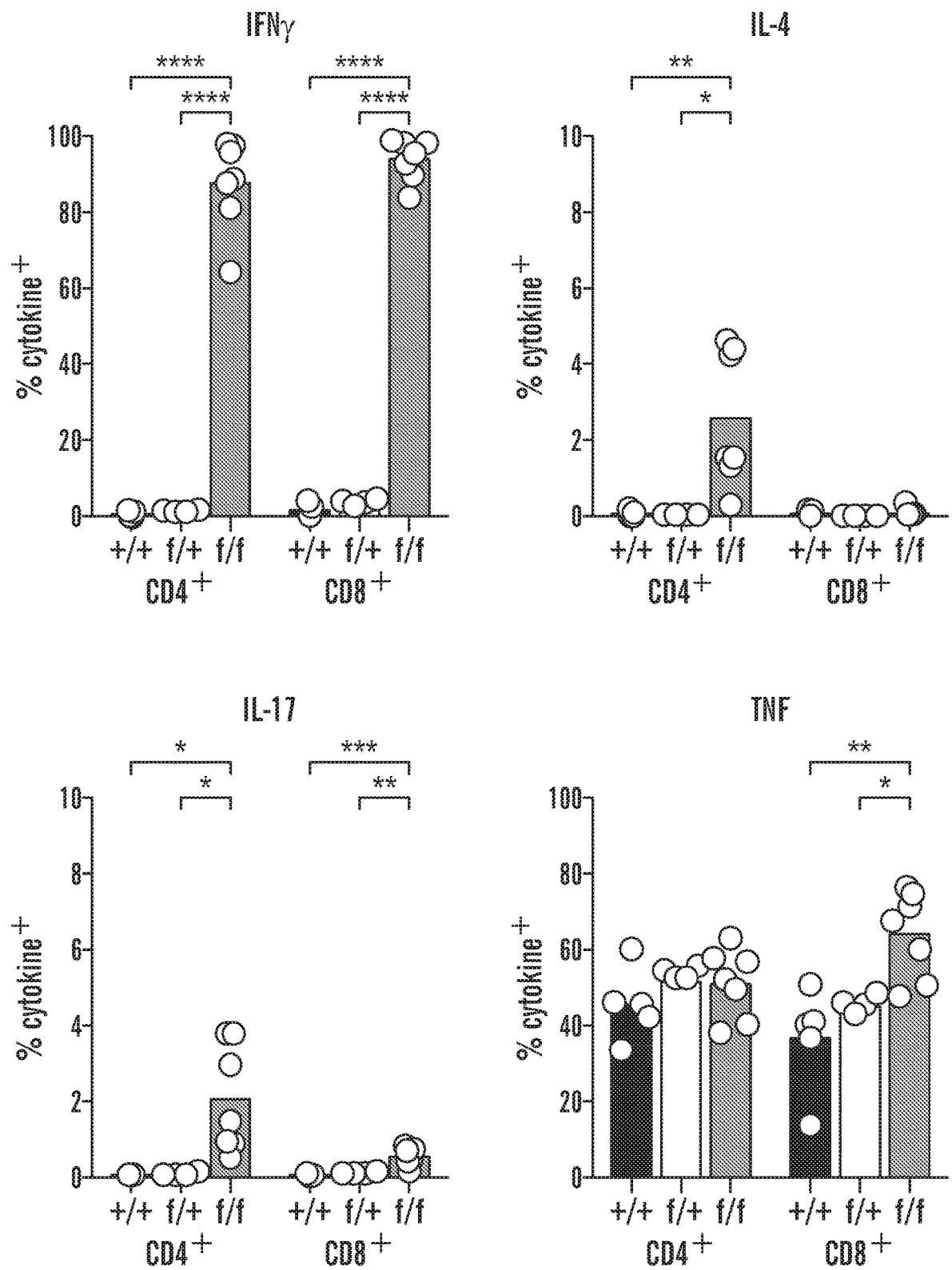
(FIG. 1G) Effector cytokine expression of CD4$^+$ and CD8$^+$ conventional T cells from LNs indicated mice upon ex vivo activation on αCD3 and αCD28 antibody-coated plates.
Figure 1H:
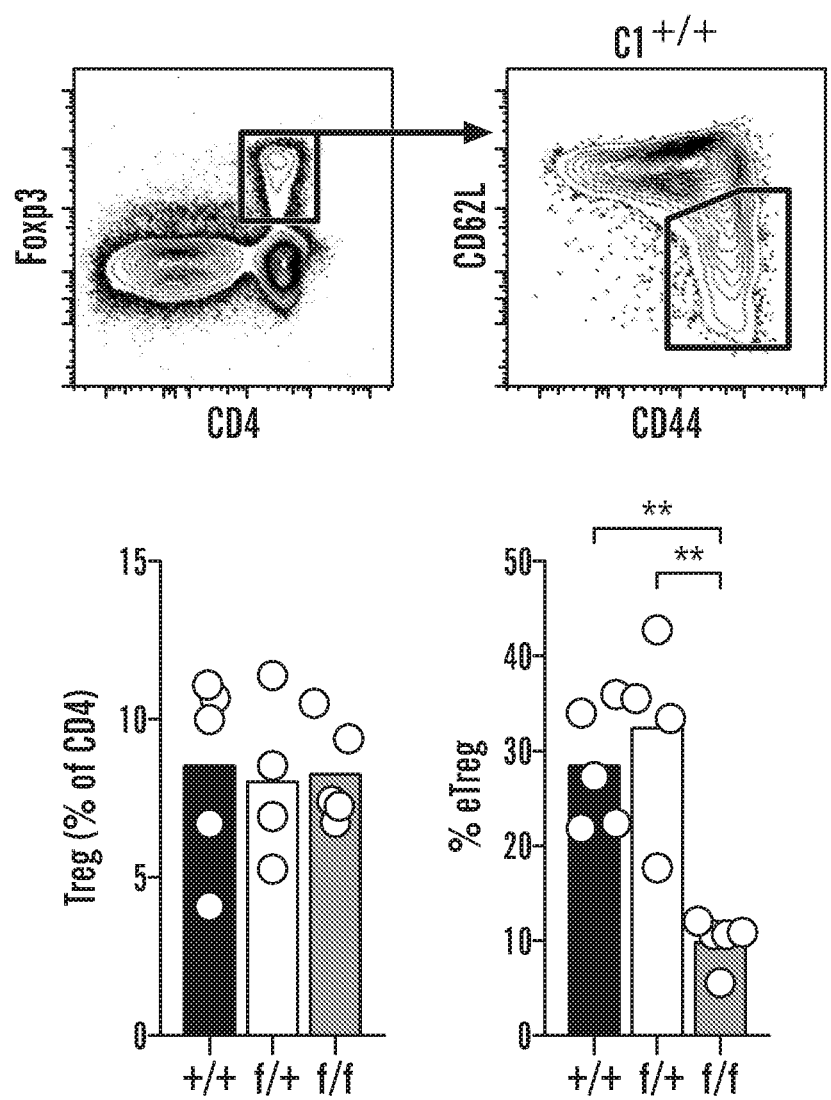
(FIG. 1H), Frequency of Treg among total CD4$^+$ T cells and of CD44$^{hi}$ CD62L$^{low}$ eTreg among total Treg in LNs of indicated mice. i, Effector cytokine expression of Treg from LNs of indicated mice upon ex vivo activation on αCD3 and αCD28 antibody-coated plates.
Figure 1I:
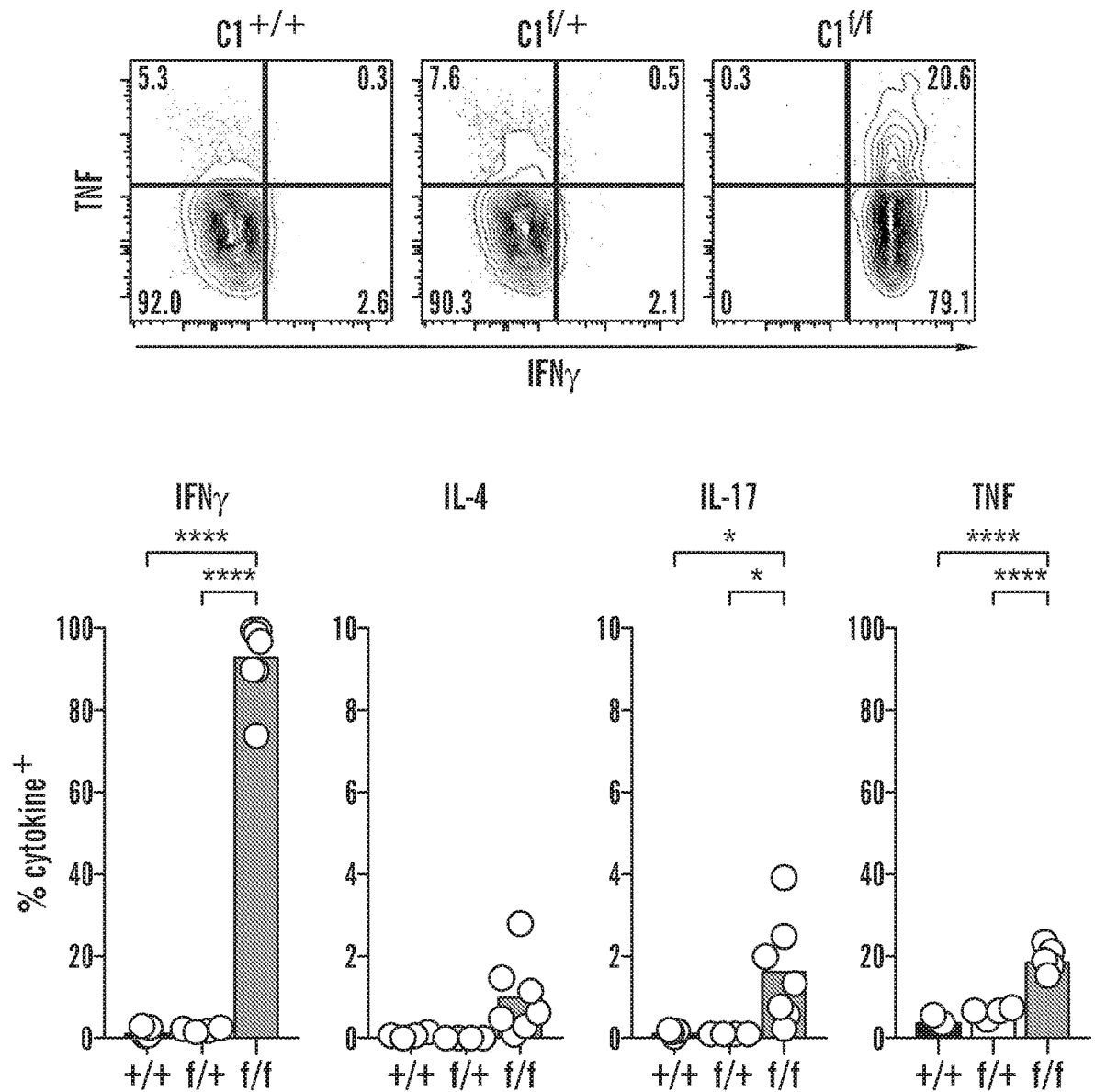
FIGS. 1A-1O present exemplary experimental data showing that loss of CARMA1 in mature Treg is fatal, but reduced expression is sufficient to maintain immune tolerance.
(FIG. 1J) Frequency of conventional T cells with a CD44$^{hi}$ CD62L$^{lo}$ effector memory phenotype in peripheral blood of aging F$^{YFP-Cre/+}$×C1$^{+/+}$, ×C1$^{f/+}$, and ×C1$^{f/f}$ mice (n=4/group).
(FIG. 1K) Appearance of spleens and LNs of indicated mice at 1 year of age.
(FIG. 1L) Effector cytokine expression of YFP$^+$ Treg from LNs indicated mice at 9 weeks of age upon ex vivo activation on αCD3 and αCD28 antibody-coated plates.
(FIG. 1M) Frequency of YFP$^+$ Treg among total CD4$^+$ T cells and of CD44$^{hi}$ CD62L$^{low}$ eTreg among total YFP$^+$ Treg in LNs of indicated mice.
(FIG. 1N) Expression of indicated proteins in YFP$^+$ eTreg from indicated 9 week-old mice. Data in 1G, 1H, 1I, 1L, 1M, and N represent 2 independent experiments with similar results.
Figure 1J:
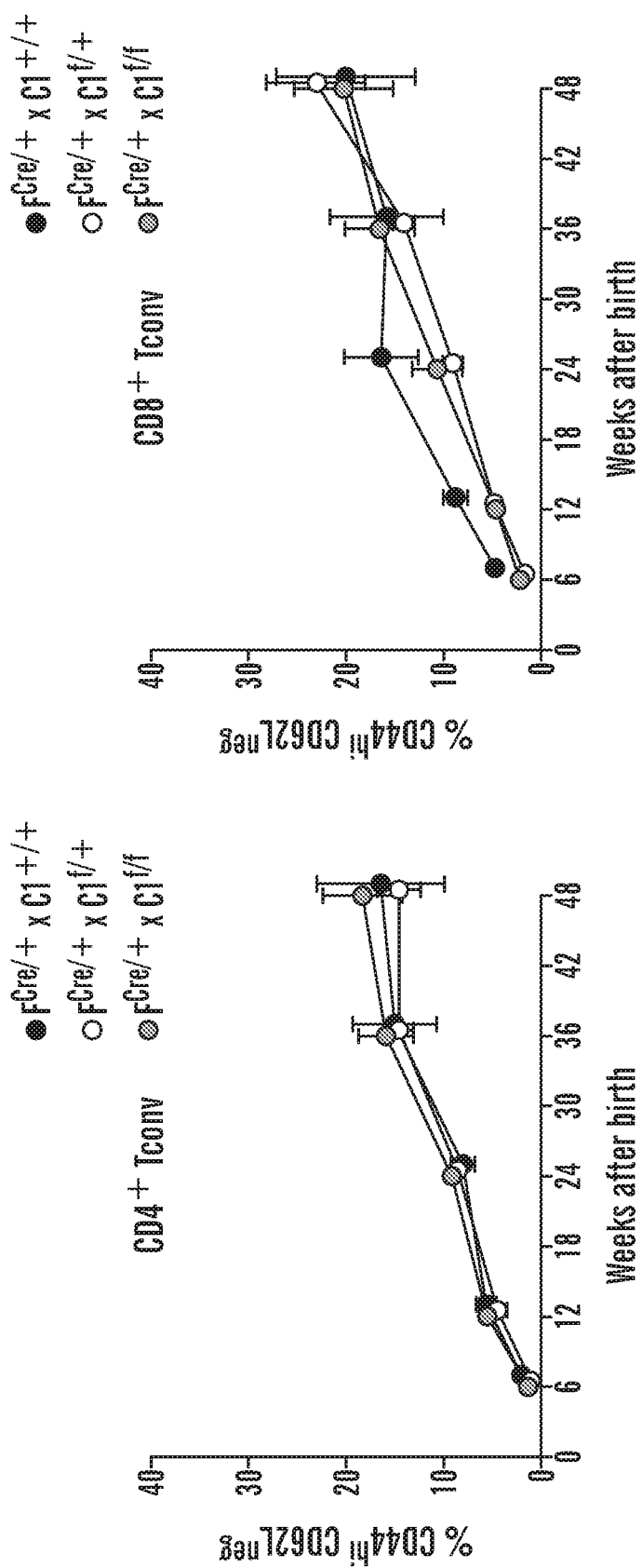
Figures 1K, 1L:
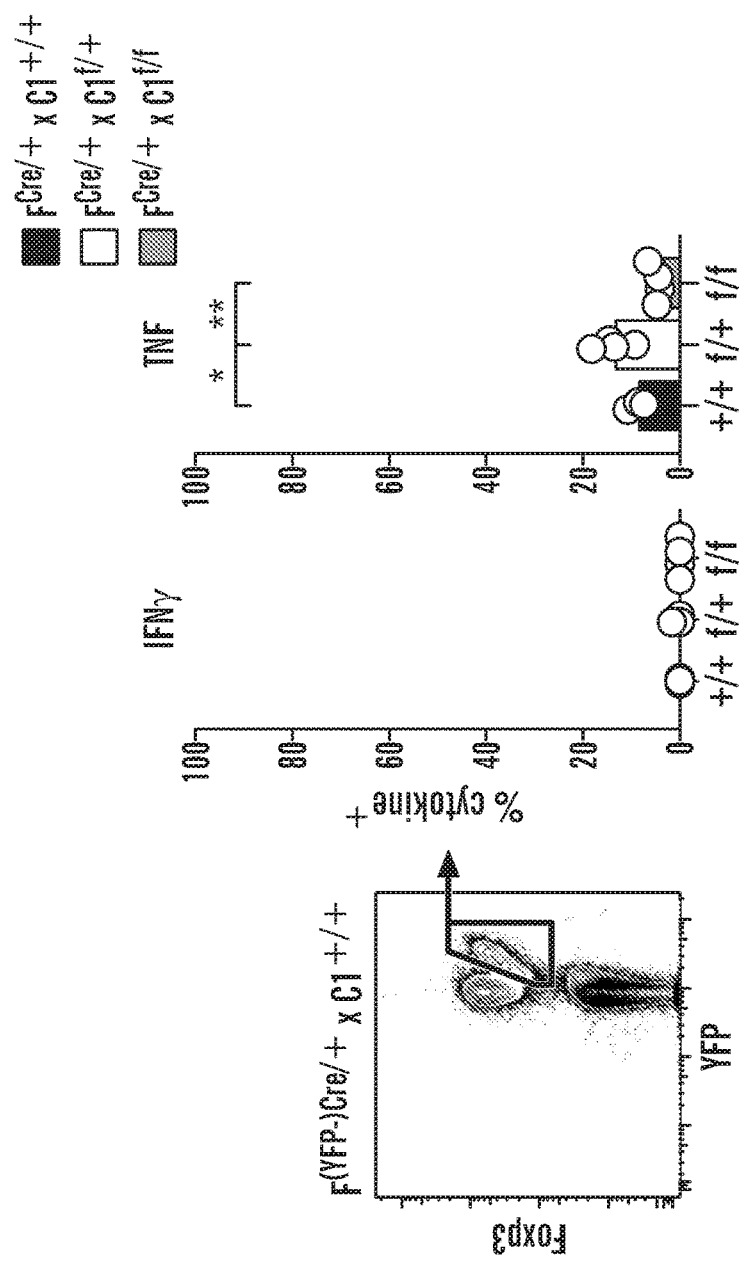
Figure 7C:
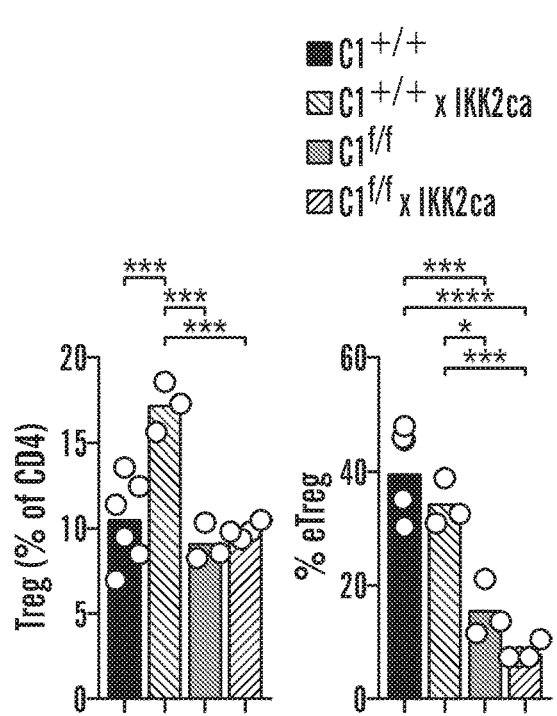
Figure 7D:
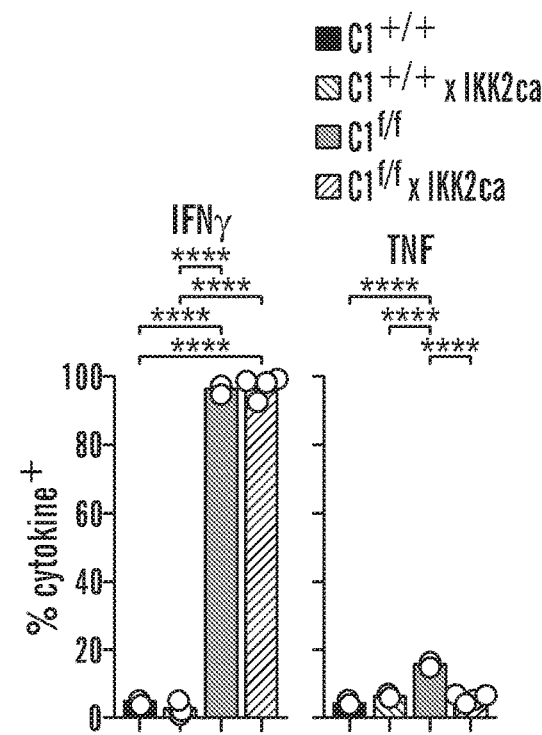
Figure 7E:
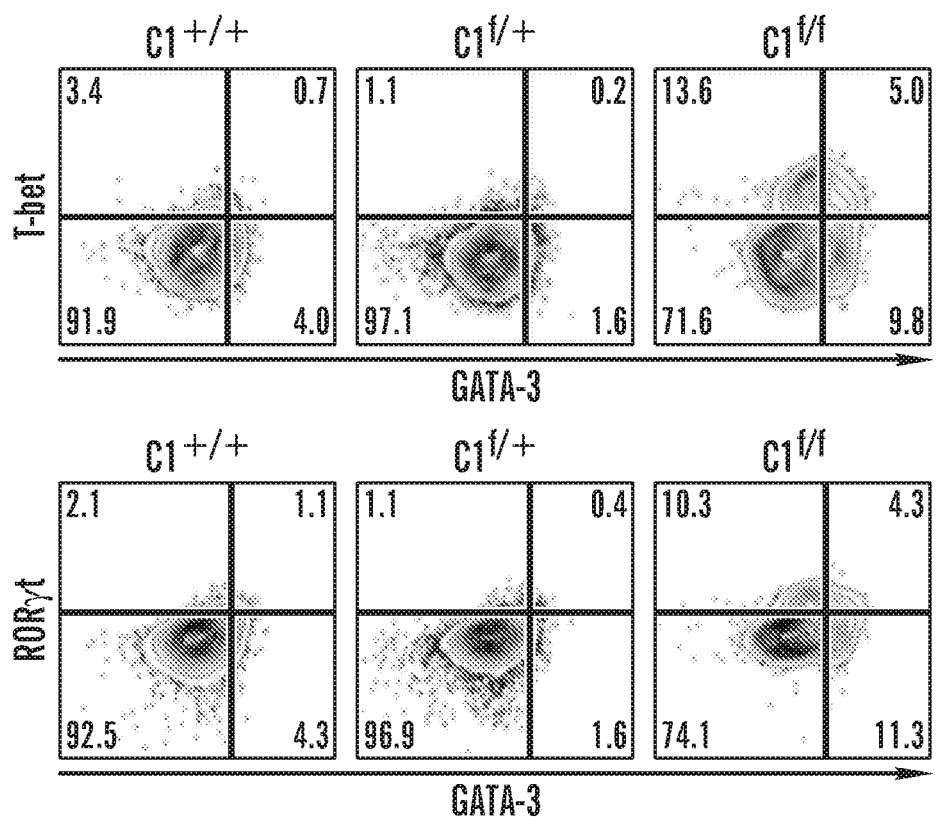
Figure 7F:
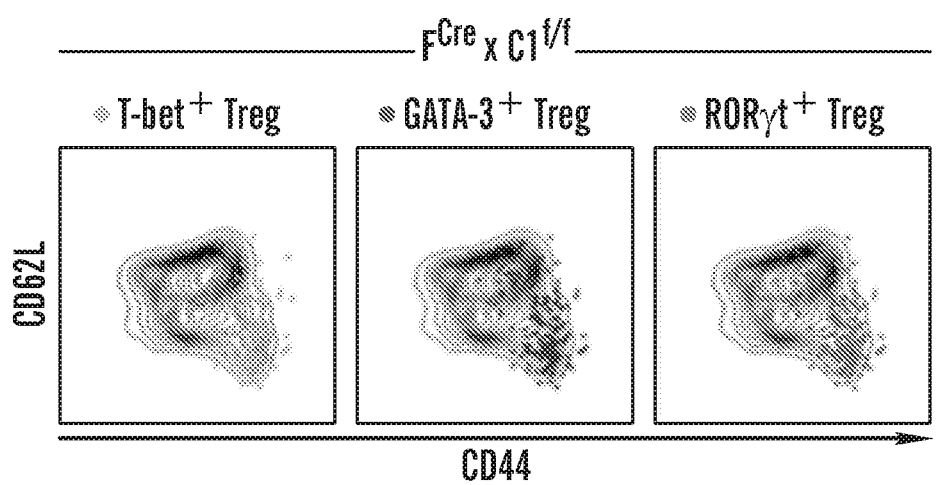
Figure 14A:
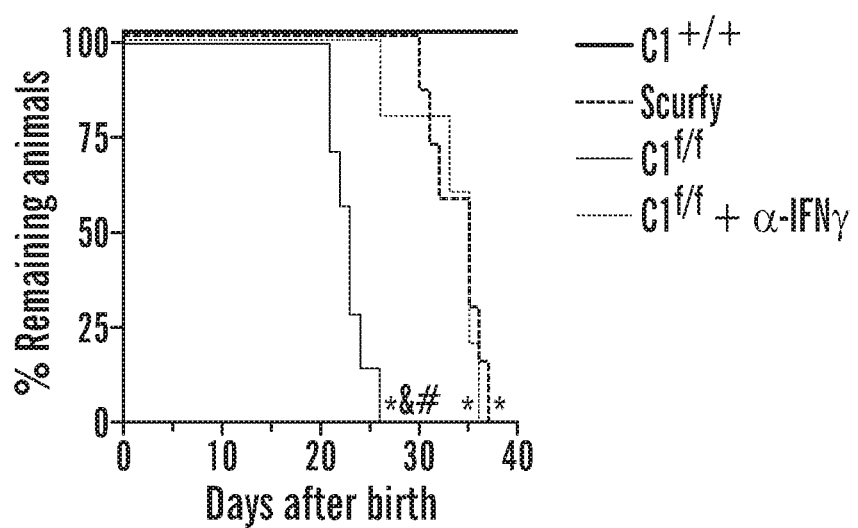
FIGS. 14A-14N.
Figure 14B:
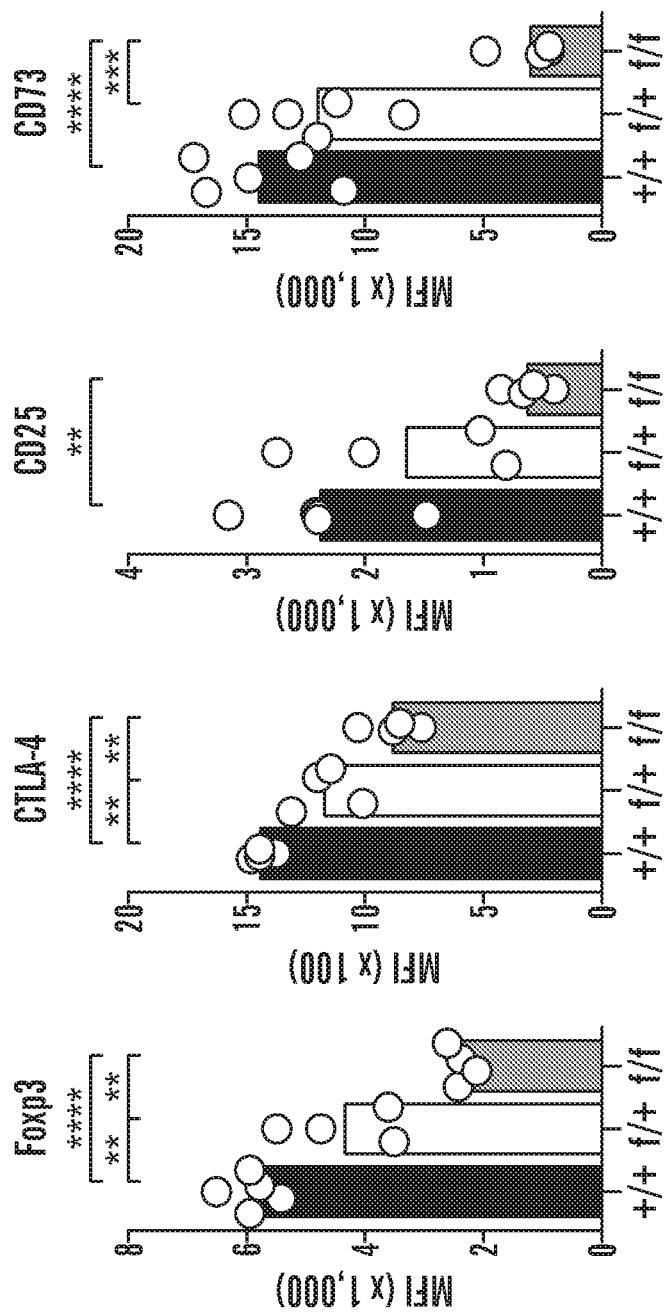
(FIG. 14B), Expression of indicated proteins in YFP$^+$ eTreg from indicated 9 week-old mice. Data represent 2 independent experiments with similar results. All graphs show means and either individual replicates or ±SEM. *, &, #=any p<0.05 vs WT, scurfy, and αIFNγ, respectively.
Figure 14B:
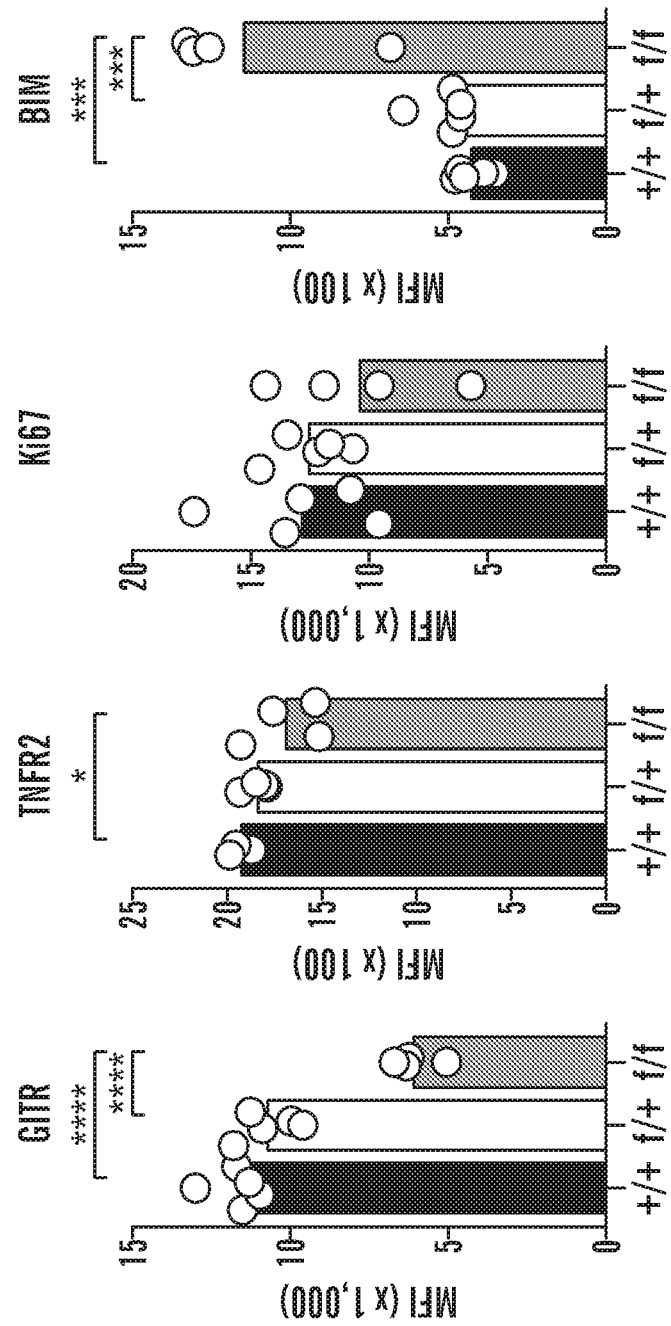

While the overall frequency of Treg among CD4+ T cells did not vary with CARMA1 expression, the proportion of CD44$^{hi}$ CD62L$^{neg}$ activated, or effector Treg ('eTreg') was strongly reduced in its absence (FIG. 1H). At the same time, CARMA1-deficient Treg, while retaining Foxp3 expression, almost uniformly secreted IFNγ and, at lower frequencies, IL-4, IL-17, and TNF upon ex vivo activation (FIG. 1H). At the same time, CARMA1-deficient Treg, while retaining Foxp3 expression, almost uniformly secreted IFNγ and, at lower frequencies, IL-4, IL-17, and TNF upon ex vivo stimulation (FIG. 1I). Restoration of NF-κB activation did not reduce expression of IFNγ, but only prevented excessive secretion of TNF by CARMA1-deficient Treg (FIGS. 7C-7D). Unexpectedly, although nearly all Treg secreted the TH1 cytokine IFNγ, much fewer, and mostly eTreg expressed the TH1 lineage-defining transcription factor T-bet in FCrexC1fl/fl mice. Many of these co-expressed RORγt, while few co-expressed GATA-3 (FIG. 1G and FIGS. 7E-7F). Hence, complete, but not partial deletion of CARMA causes profound dysregulation of cytokine expression in Treg that in the case of IFNγ is dissociated from expression of its regulator T-bet, and can contribute to inflammatory disease pathogenesis in these animals. Indeed, it was noticed that FCrexC1fl/fl mice died more rapidly than scurfy mice, which lack functional Treg, but their lifespan was similar when IFNγ was neutralized (FIG. 14A). Thus, at least under inflammatory conditions, CARMA1-deficient Treg can be induced to secrete IFNγ and thereby convert from an immunoregulatory into a pathogenic cell type in inflammatory disease.

Figure 1M:
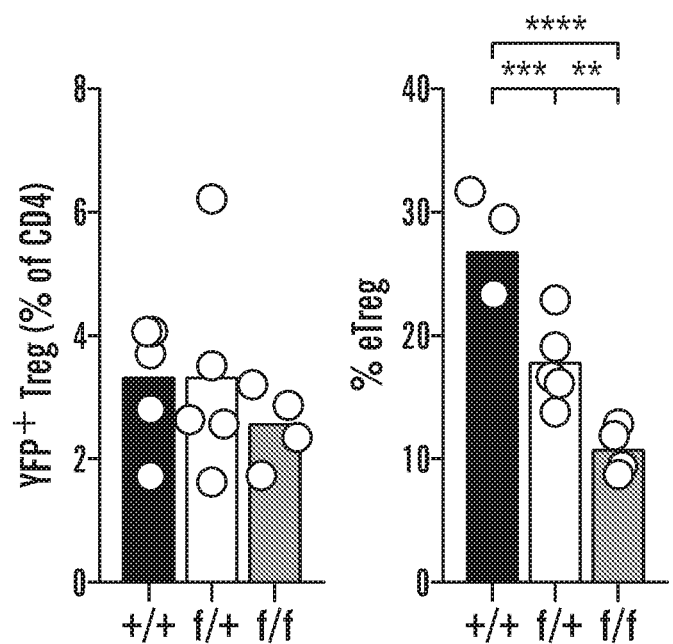
Figure 1N:
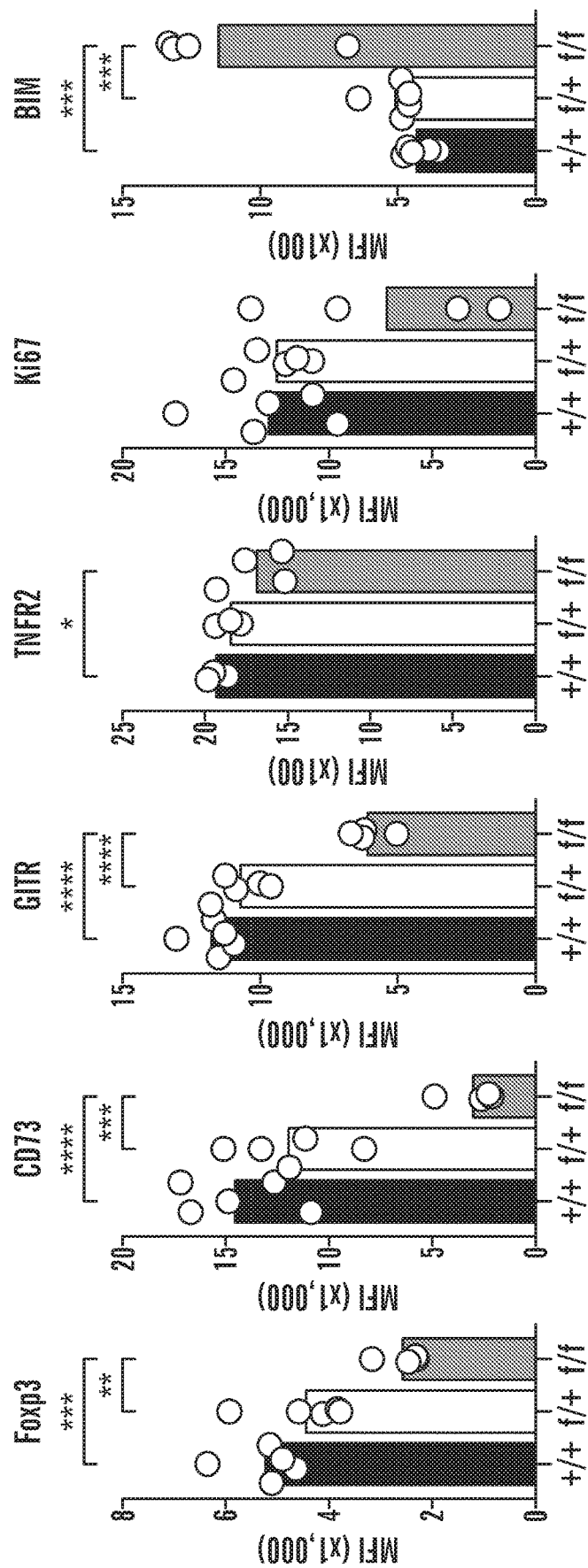
Figure 5A:
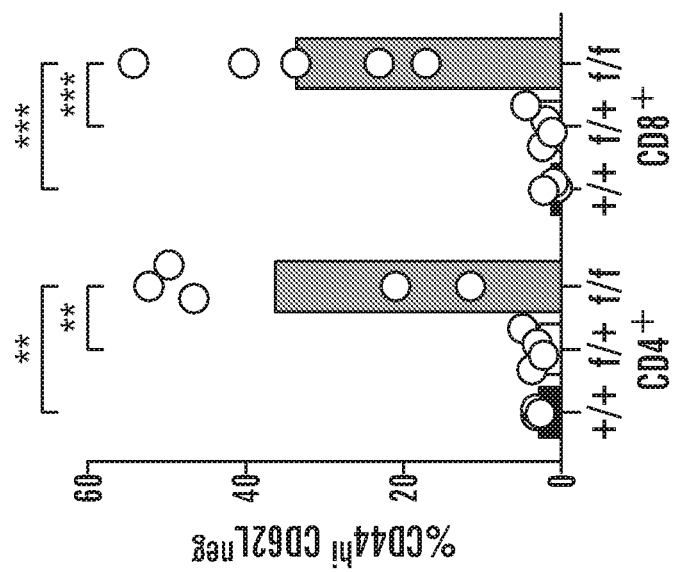
FIGS. 5A and 5B present exemplary experimental data showing that frequency of $CD4^+$ $Foxp3^{neg}$ and $CD8^+$ conventional T cells with a $CD44^M$ $CD62L^{neg}$ effector memory phenotype in LNs of $Foxp3^{YFP-Cre/+}\times$ $CARMA1^{+/+}$, $\times CARMA1^{fl/+}$, and $\times CARMA1^{fl/fl}$ mice.
Figure 5A:
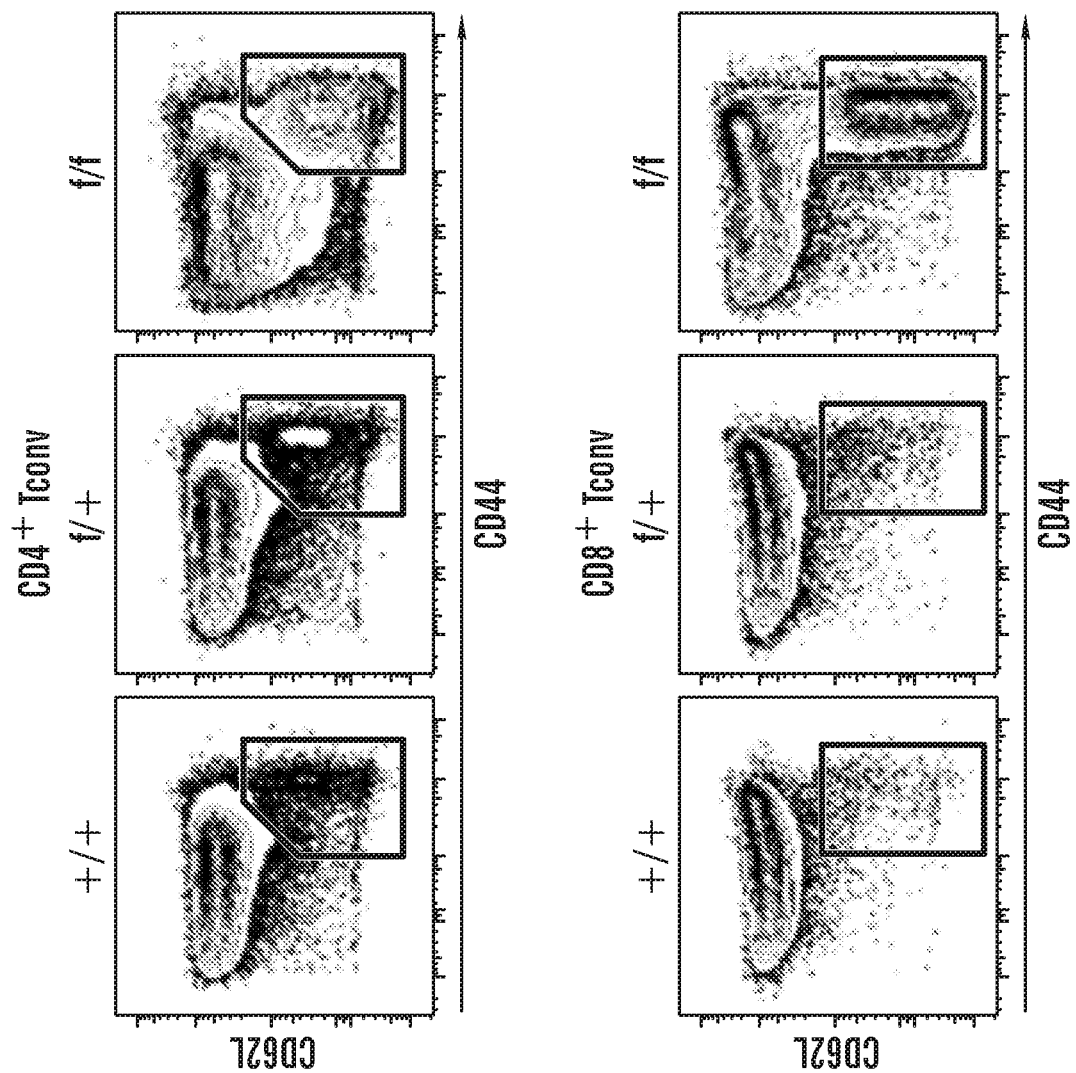
Figure 5B:
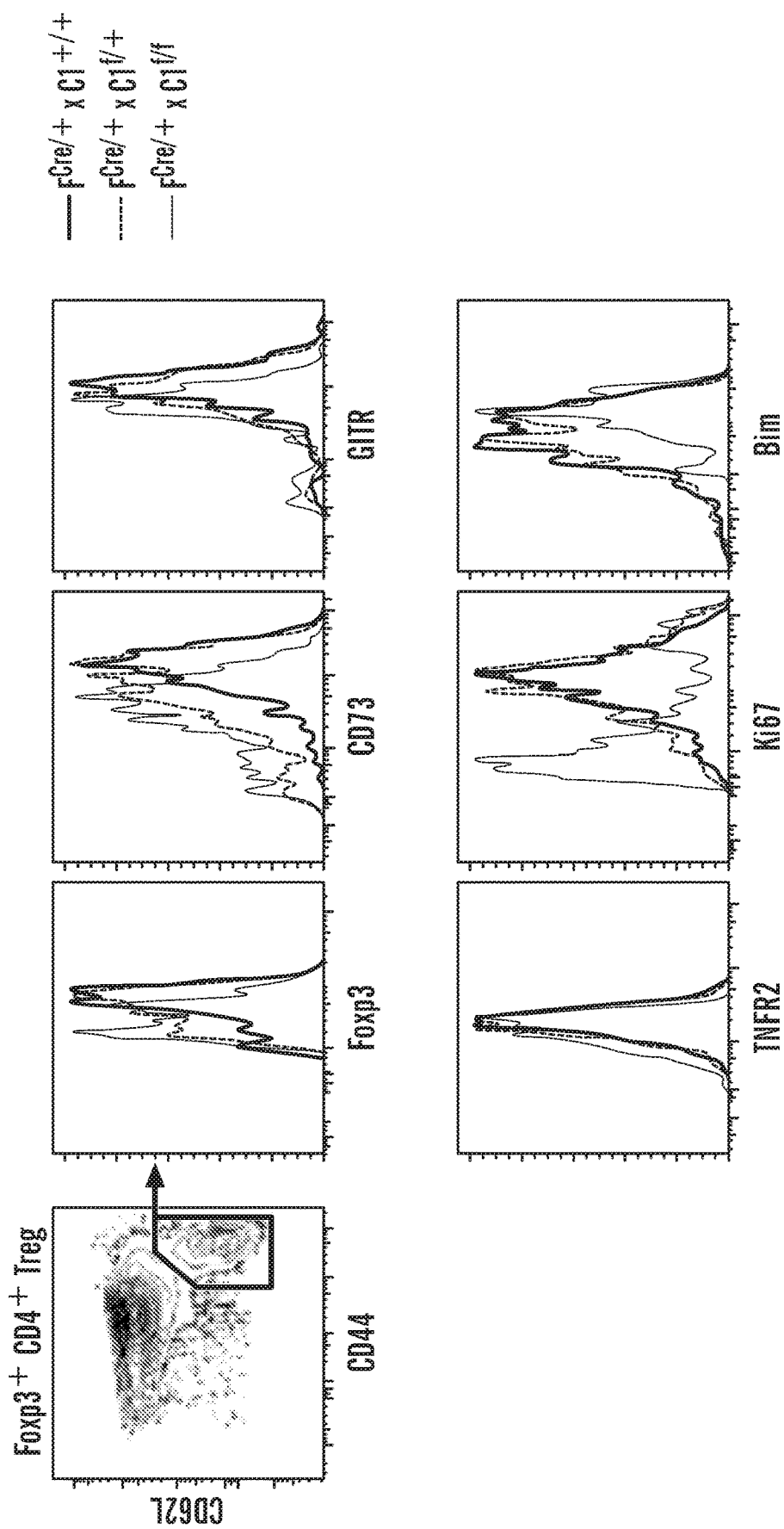
Figure 6A:
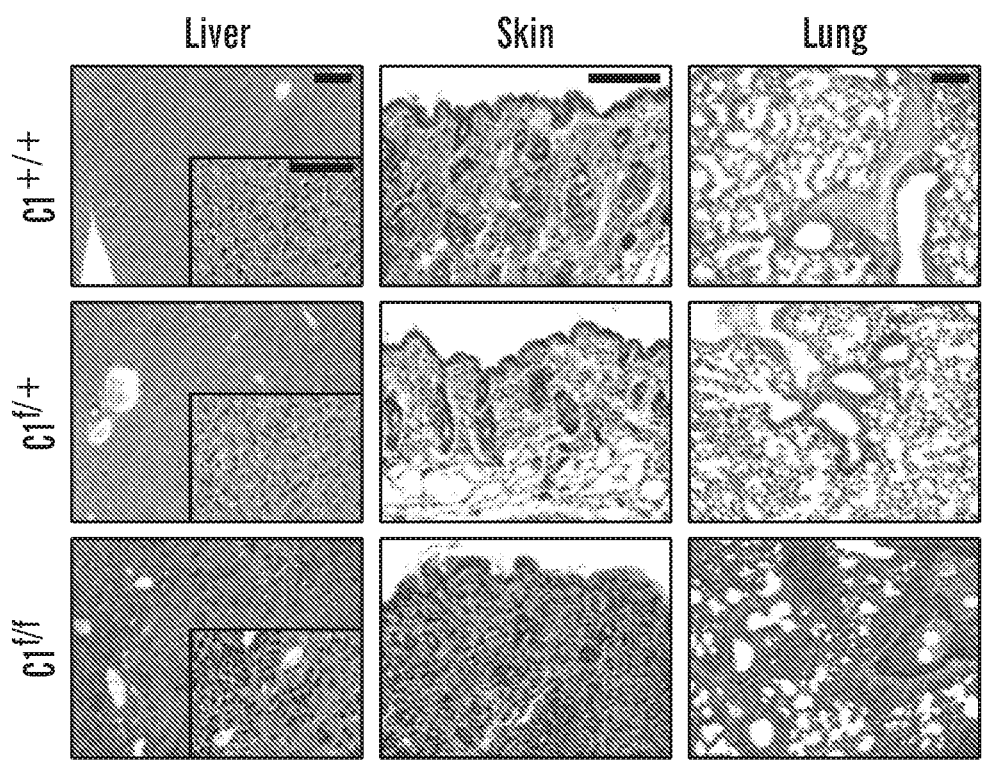
FIGS. 6A-6H.
Figure 6B:
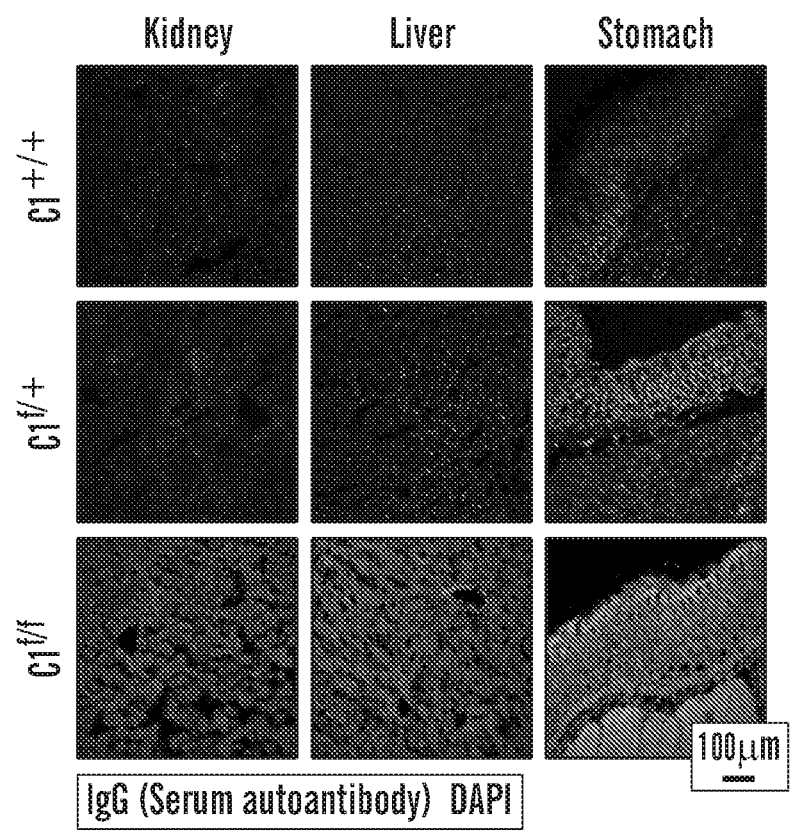
Figure 6C:
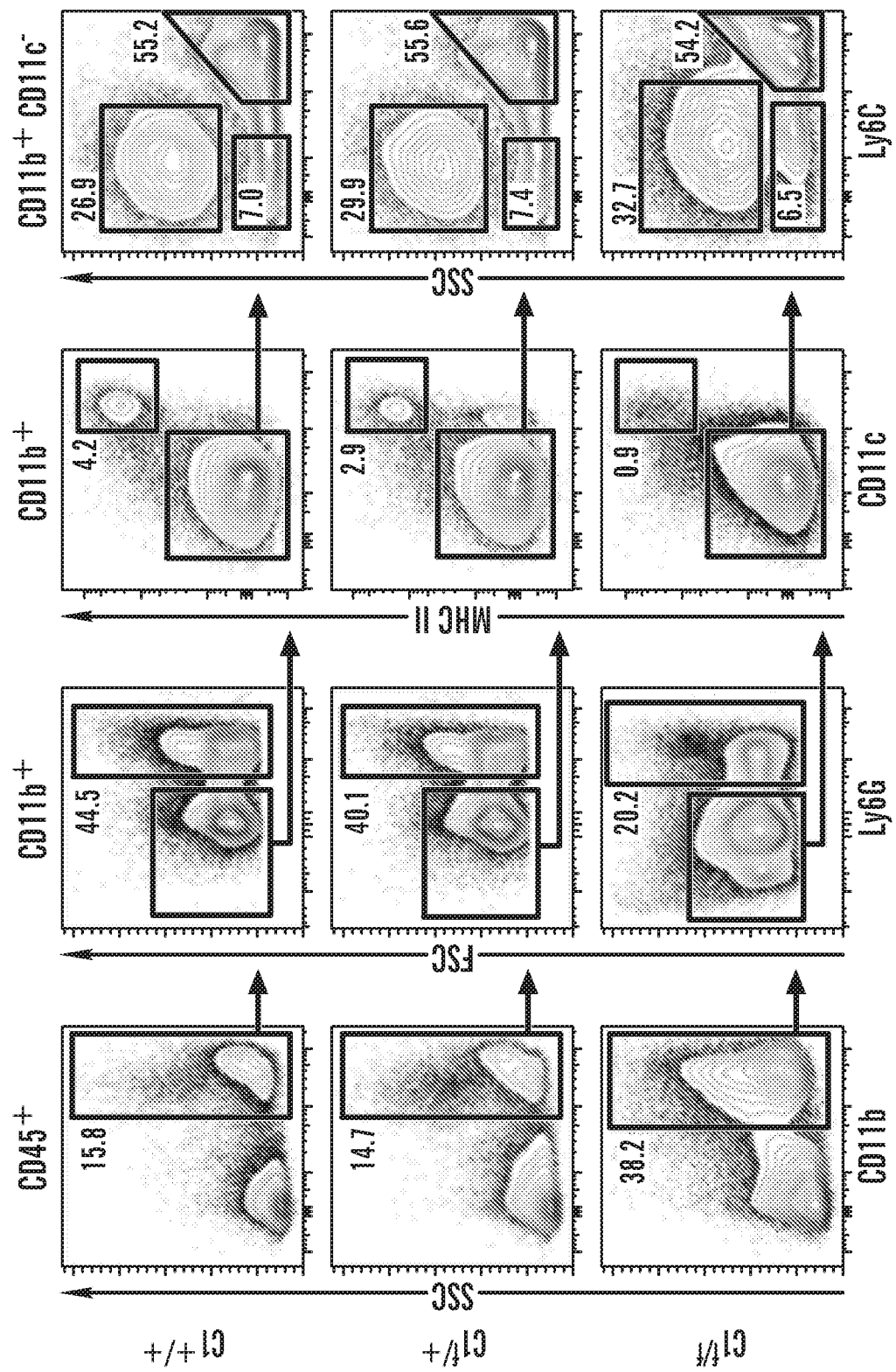
Figure 6D:
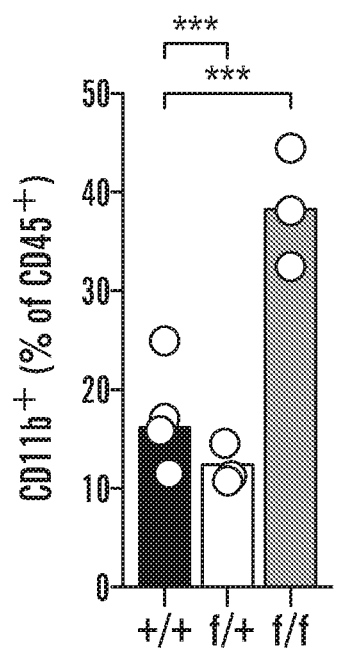
Figure 6E:
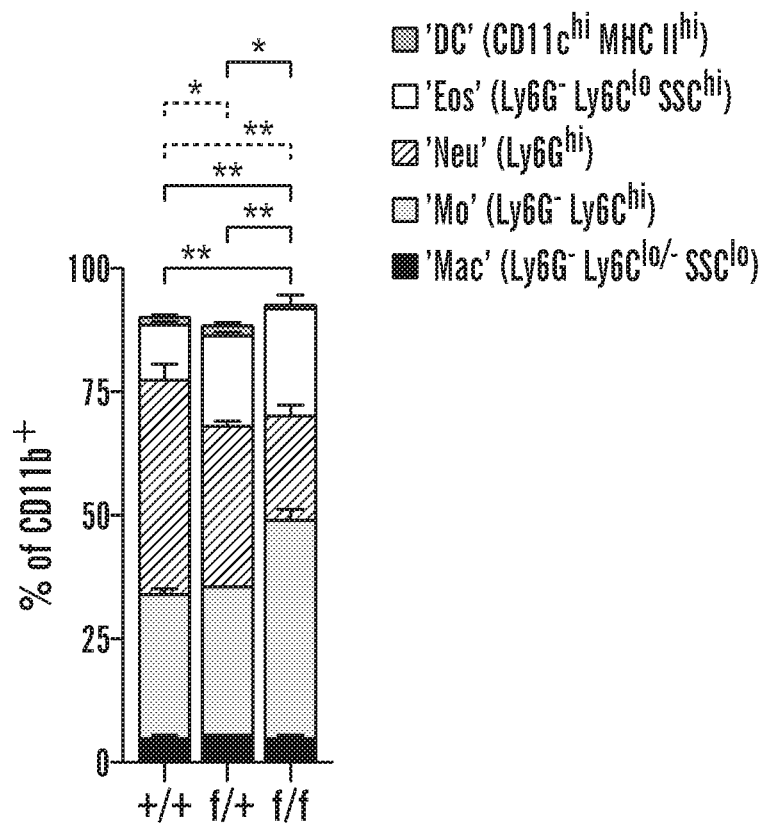
Figure 6F:
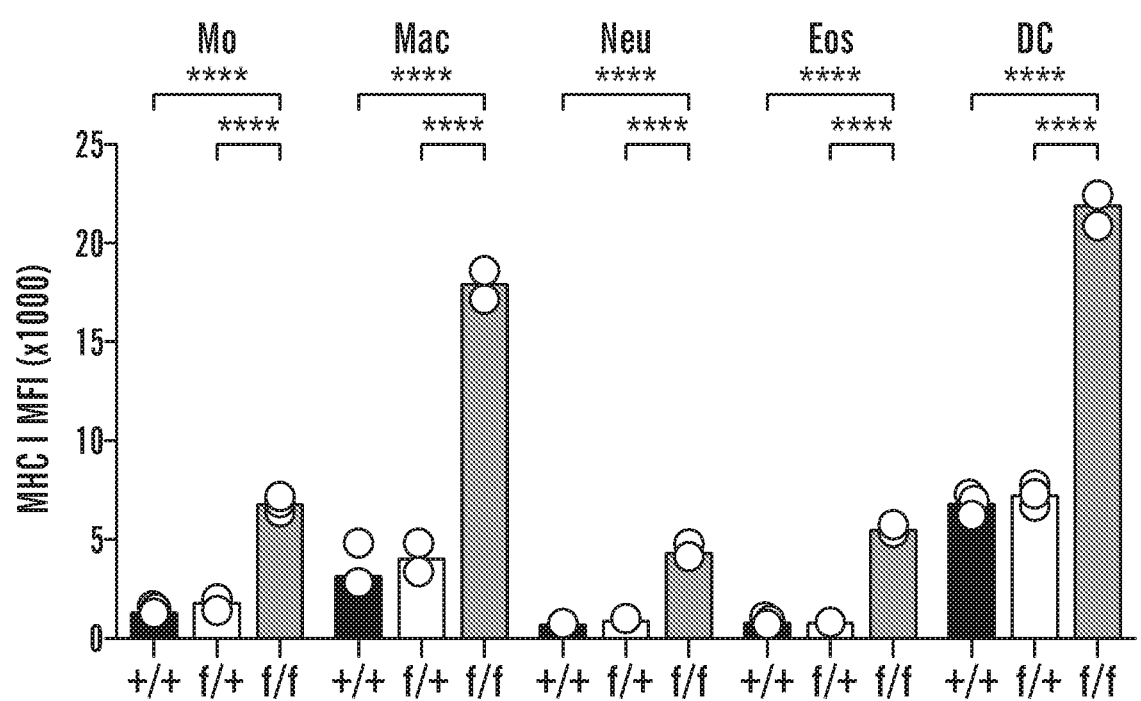
Figure 6F:
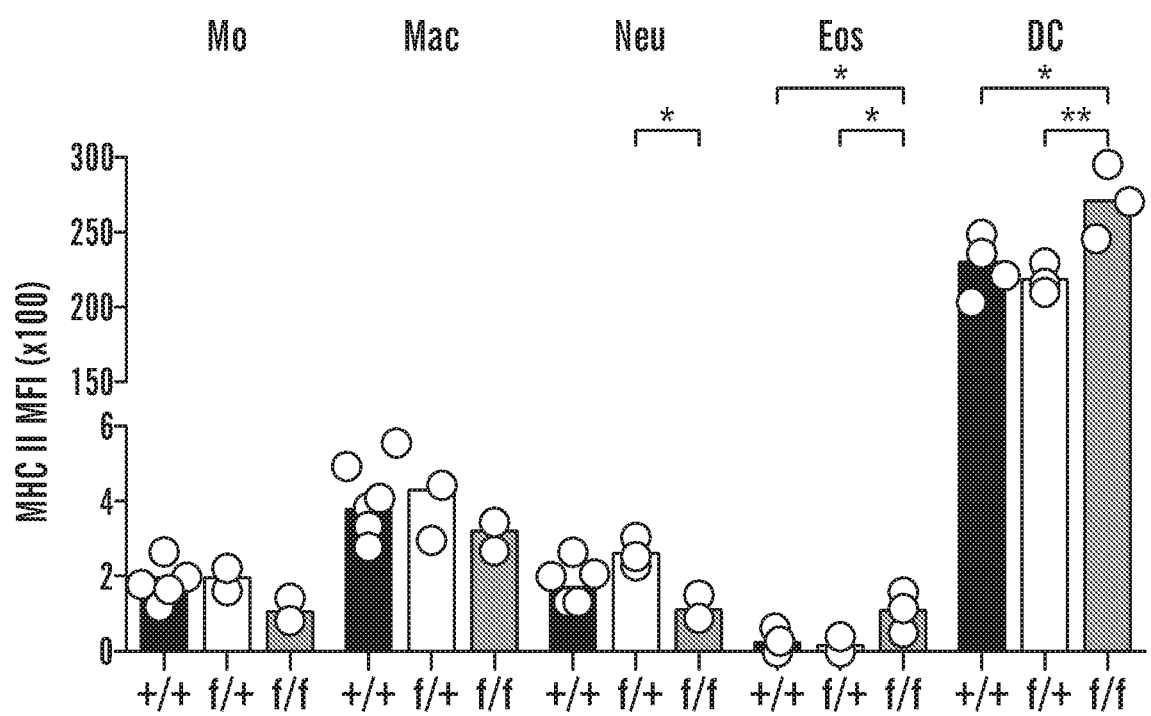
Figure 6F:
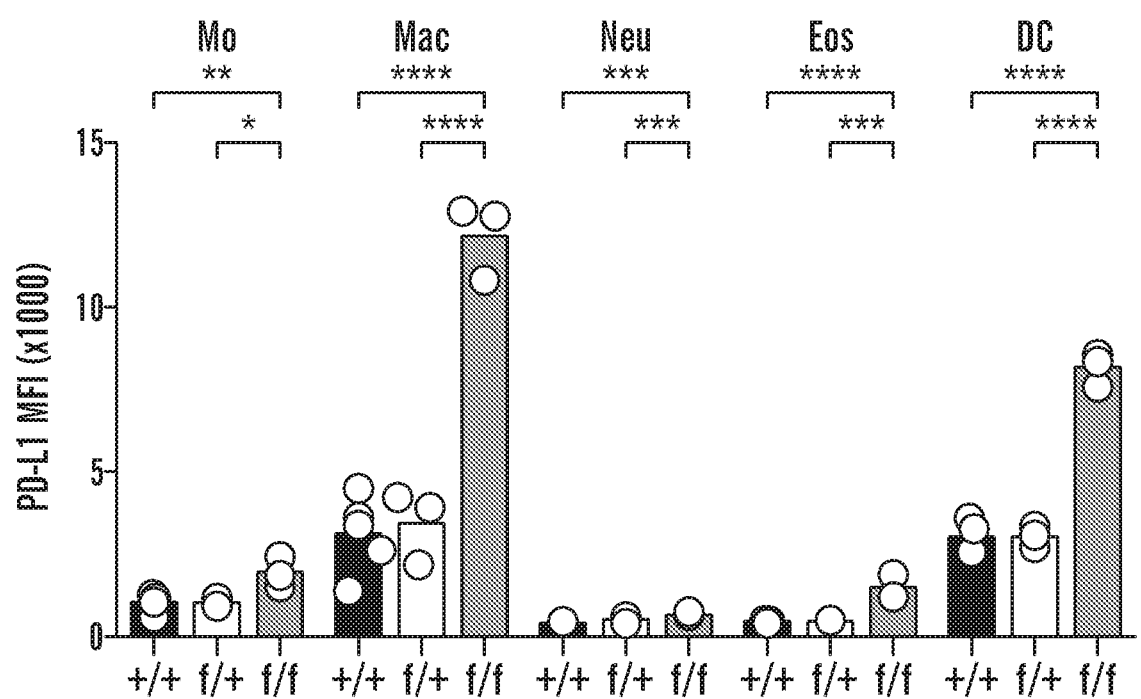
Figure 6G:
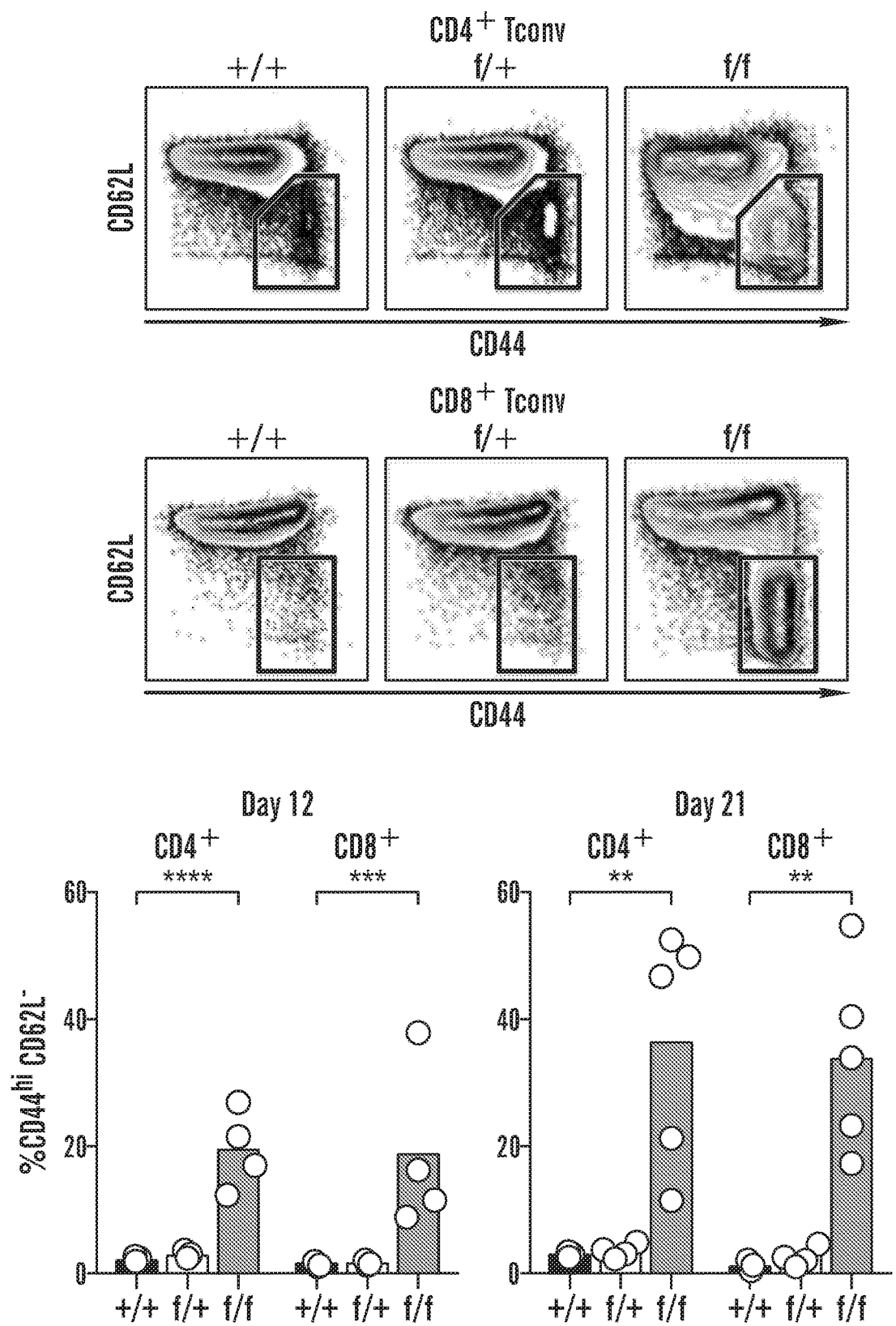
Figure 6H:
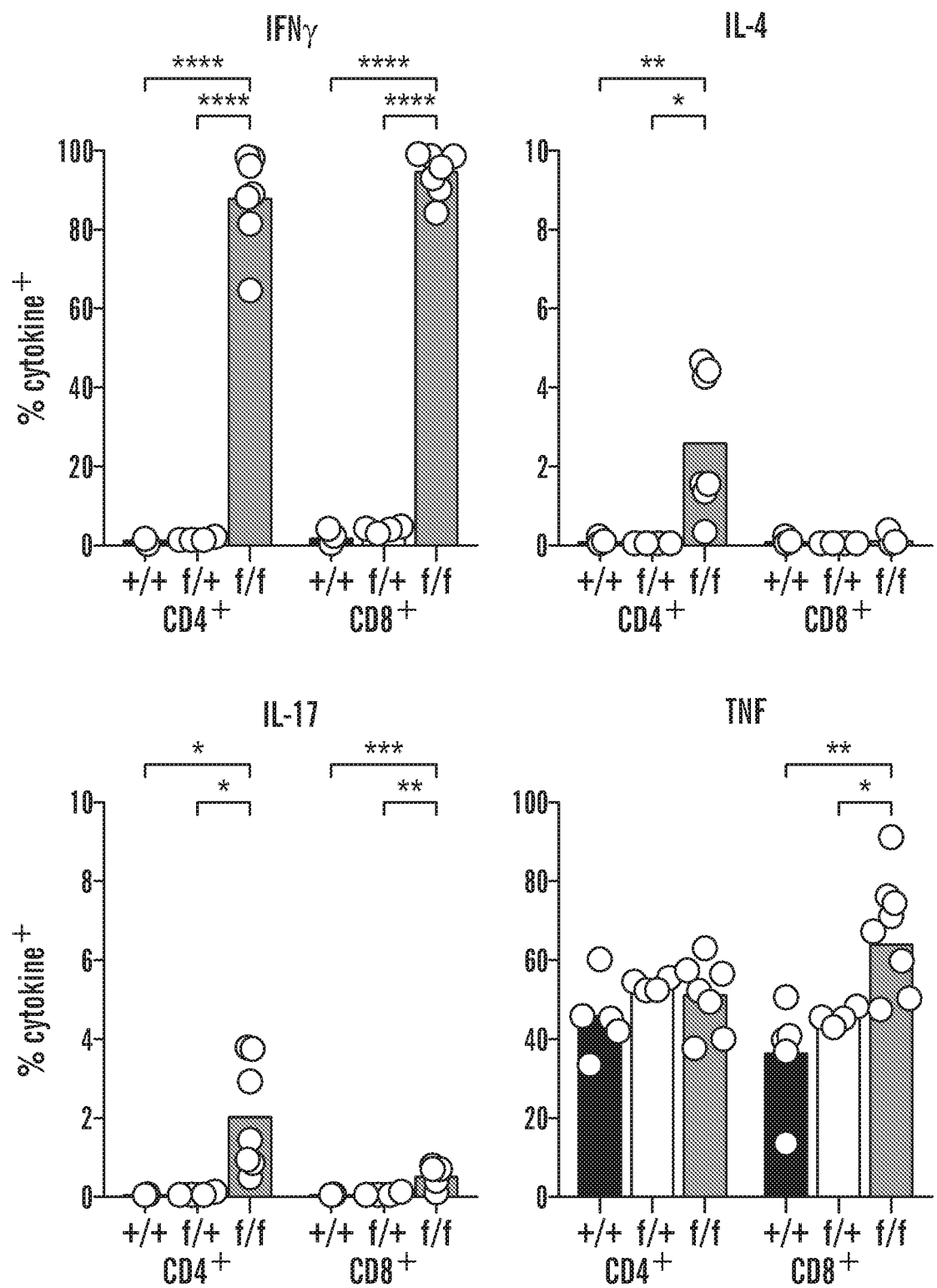
Figure 8A:
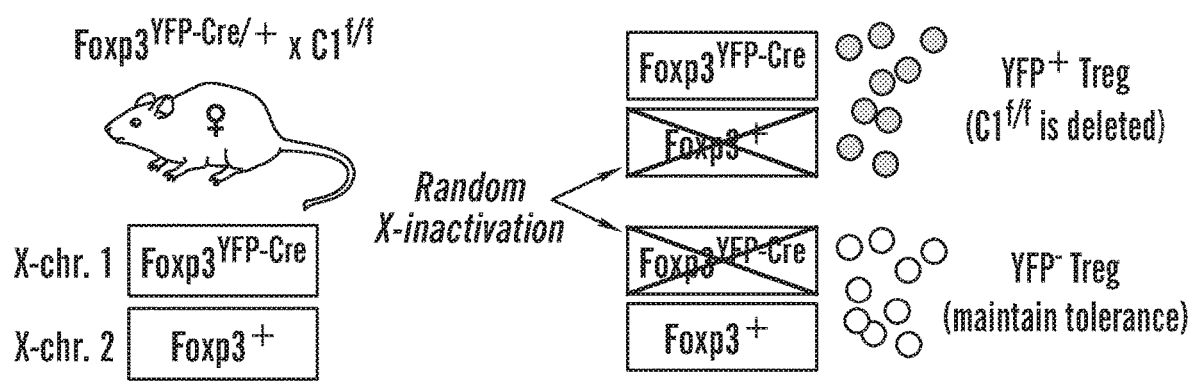
FIGS. 8A-8H.
Figure 8B:
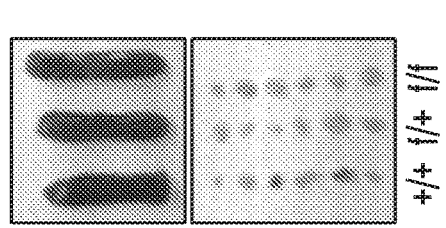
Figure 8C:
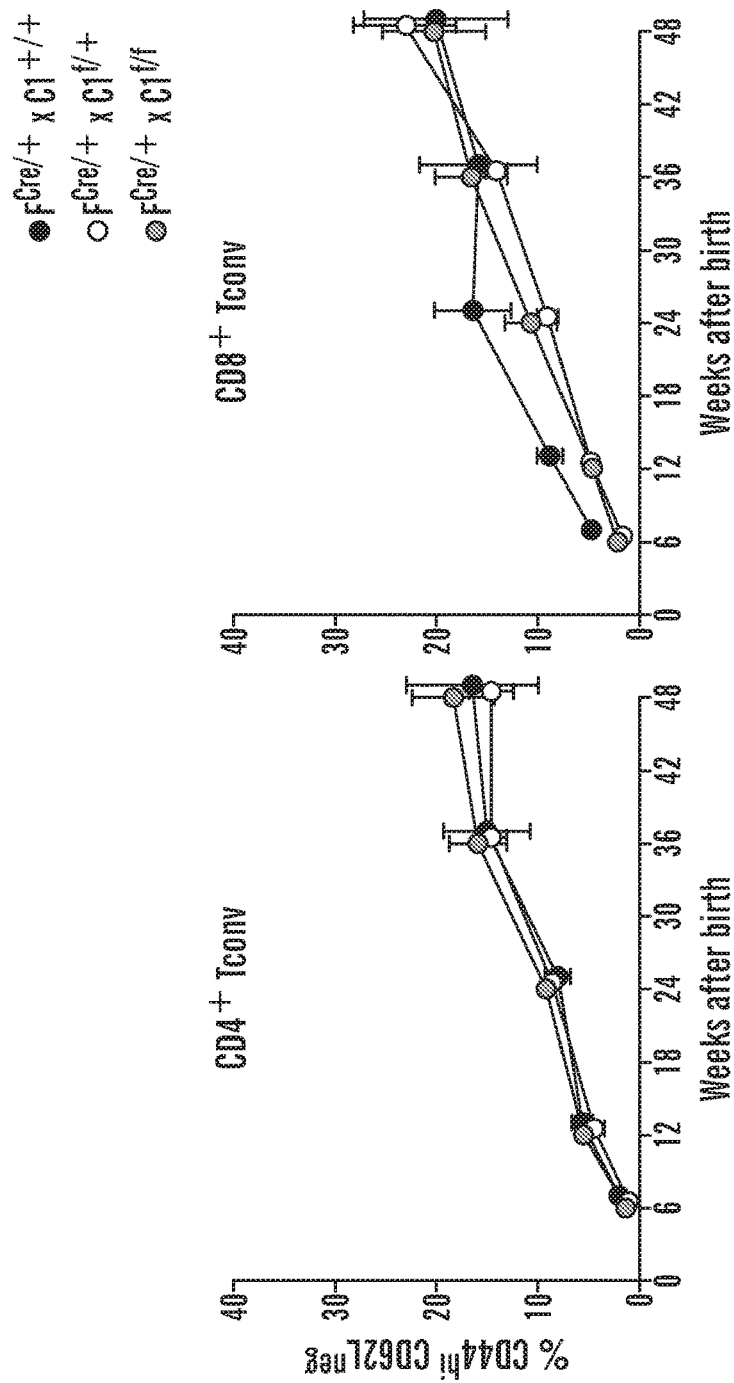
Figure 8D:
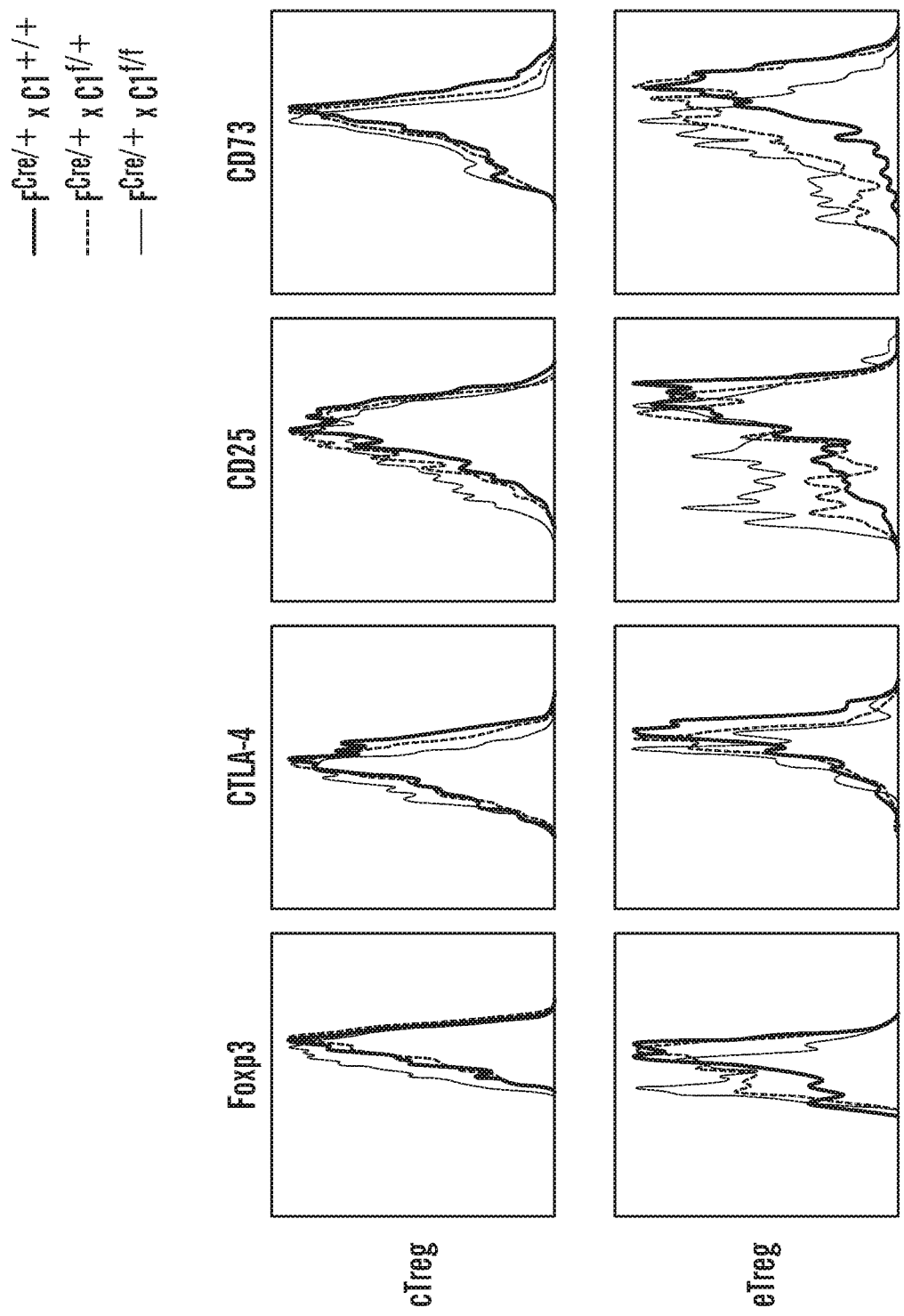
Figure 8D:
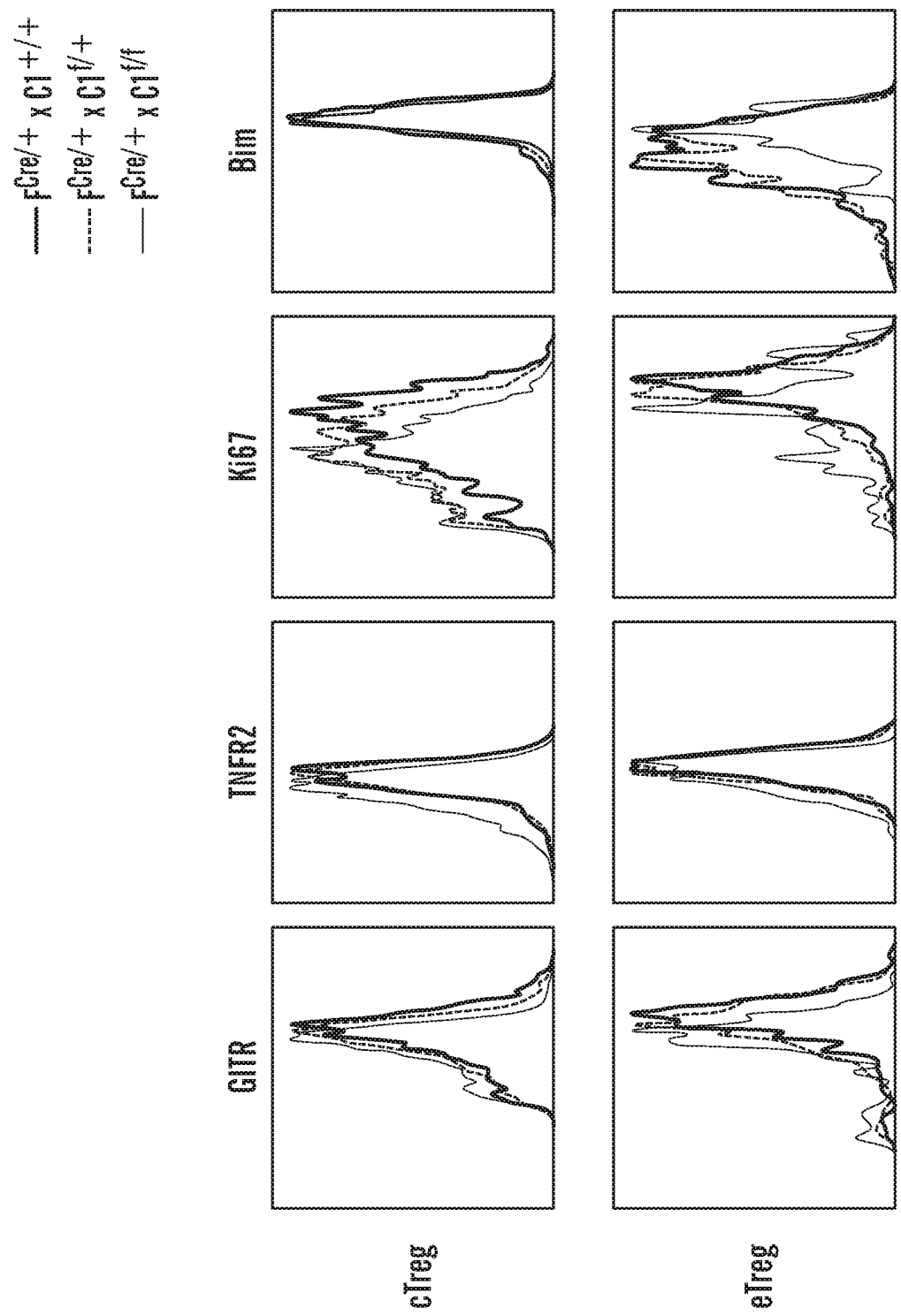
Figure 8E:
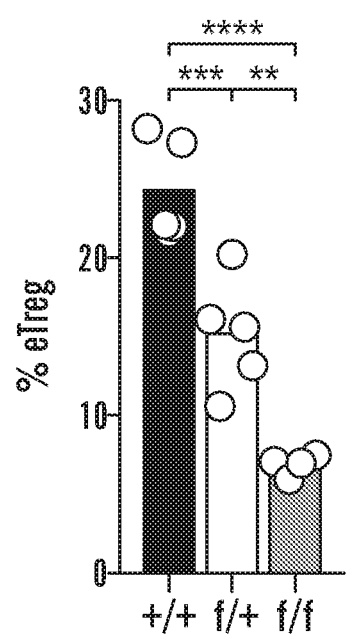
Figure 8F:
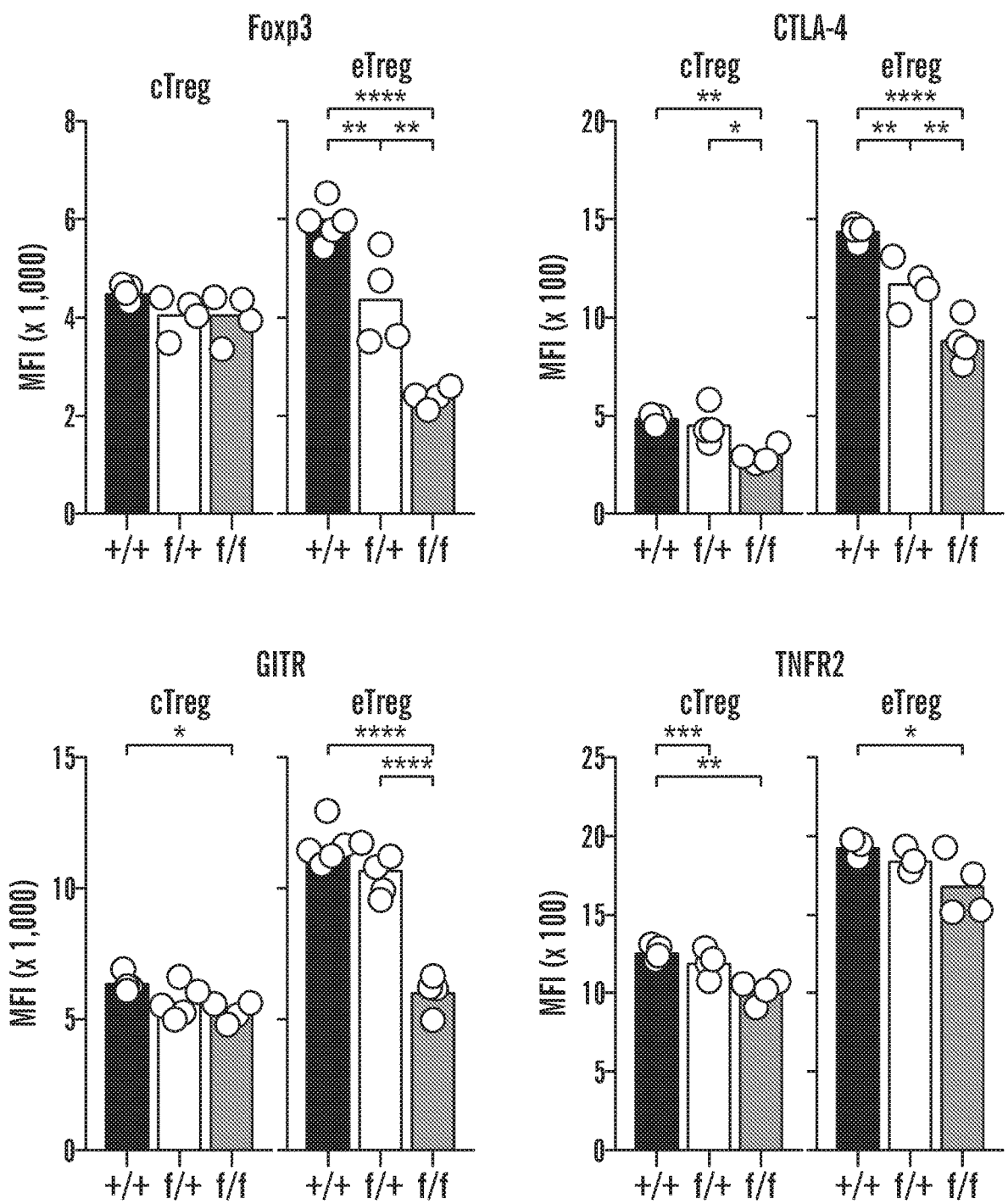
Figure 8F:
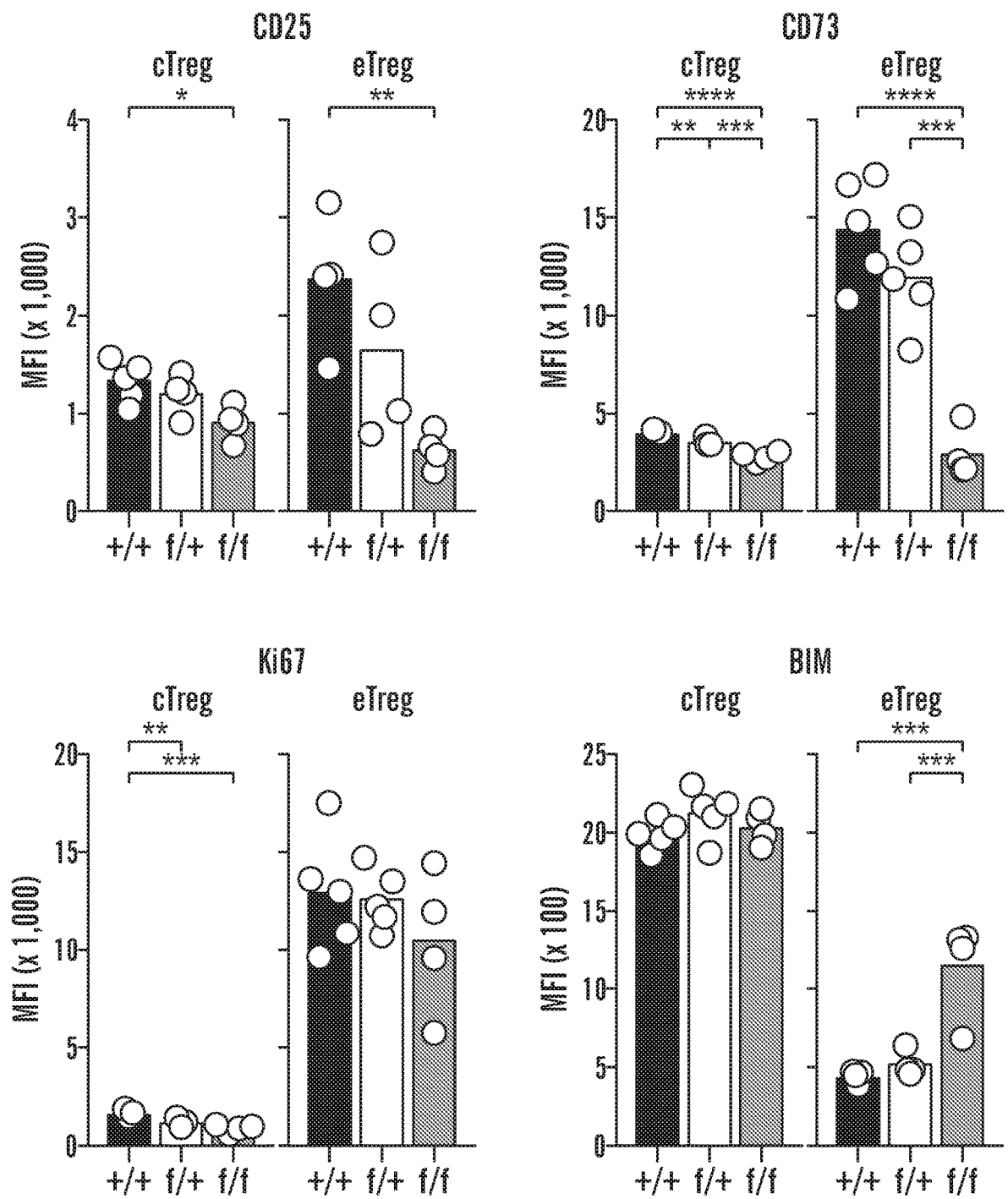
Figure 8G:
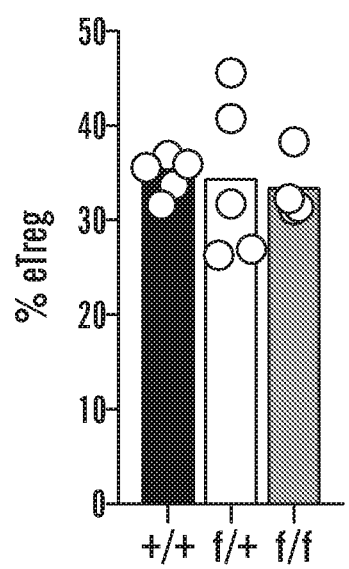
Figure 8H:
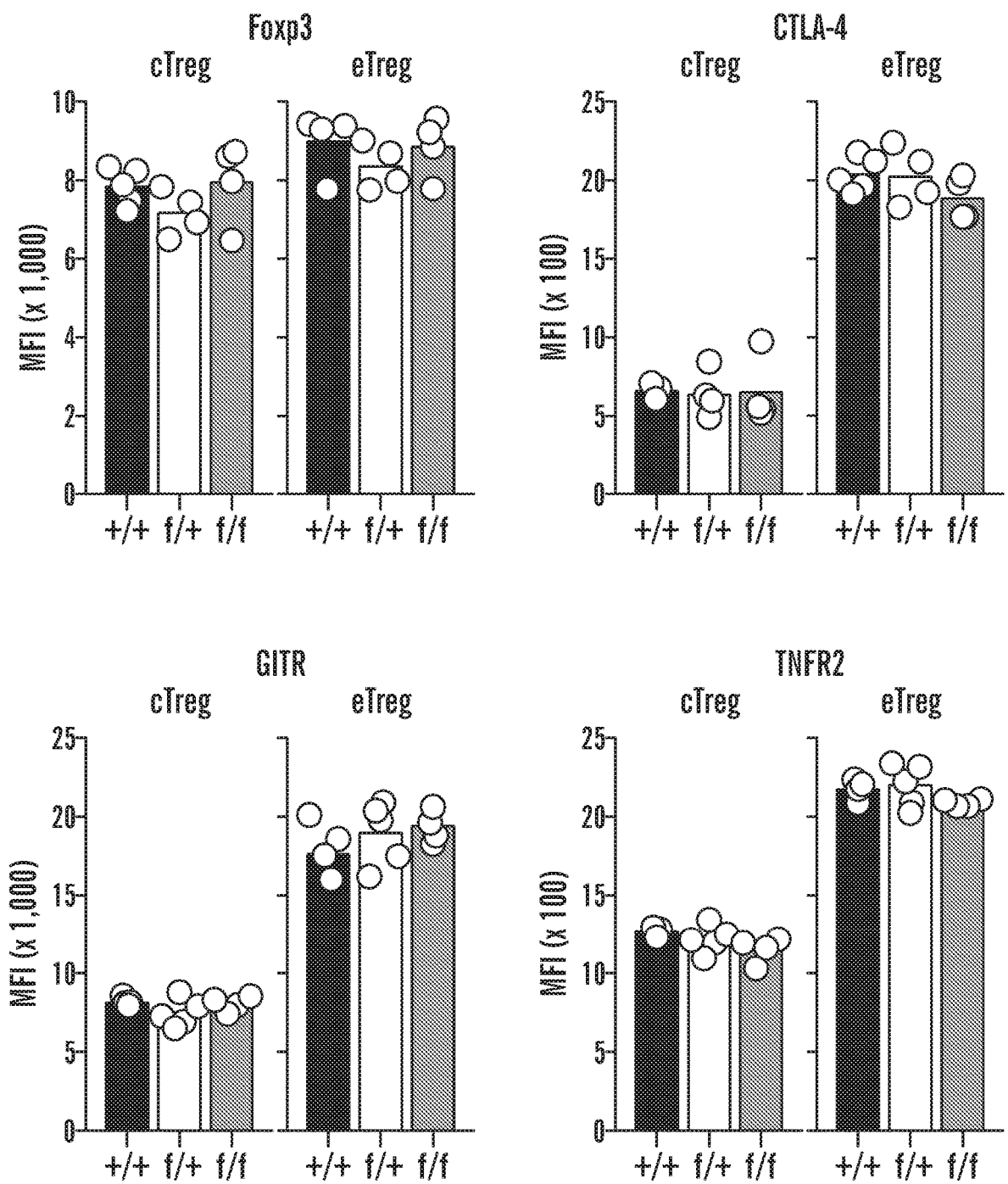
Figure 8H:
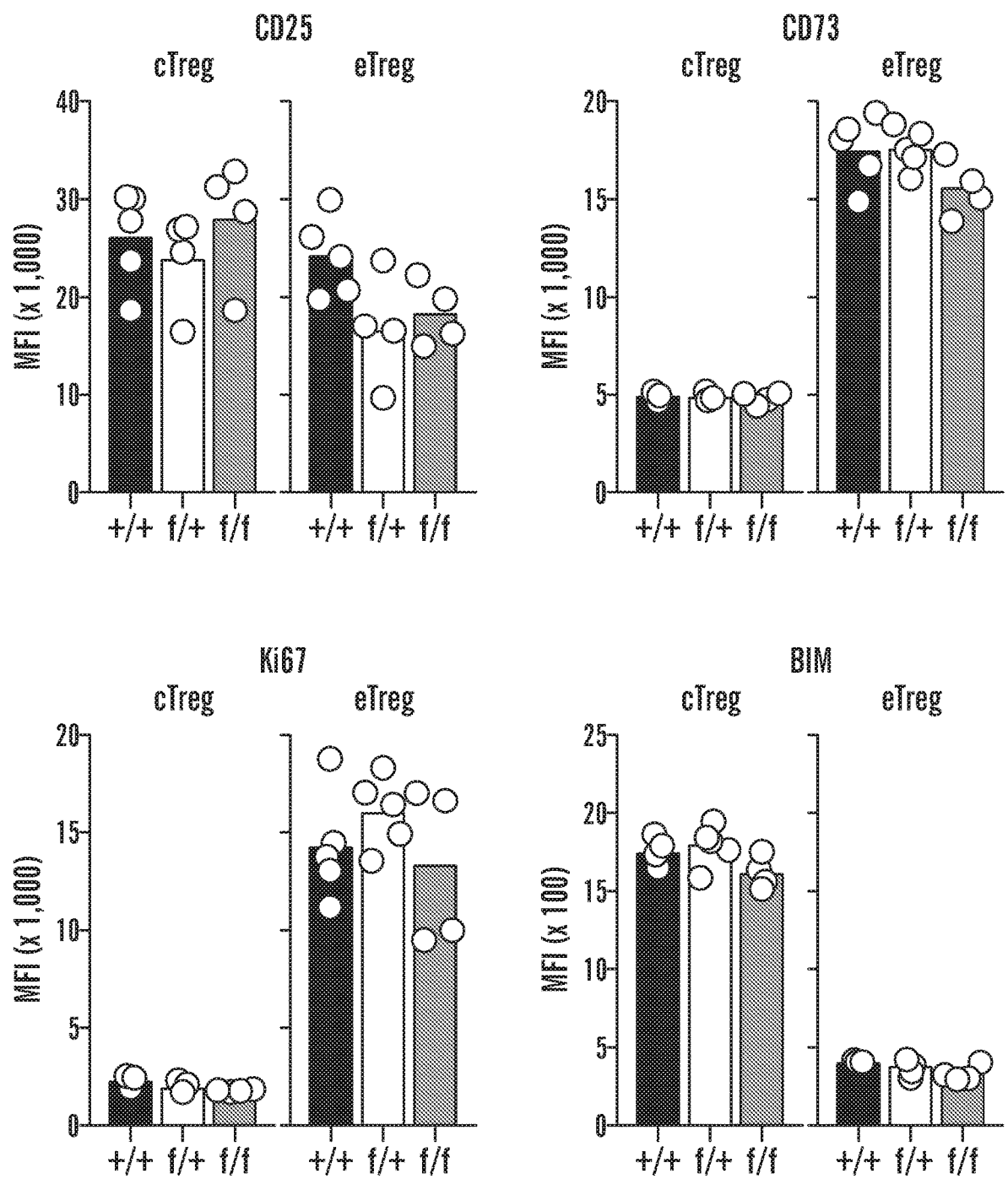
Figure 9A:
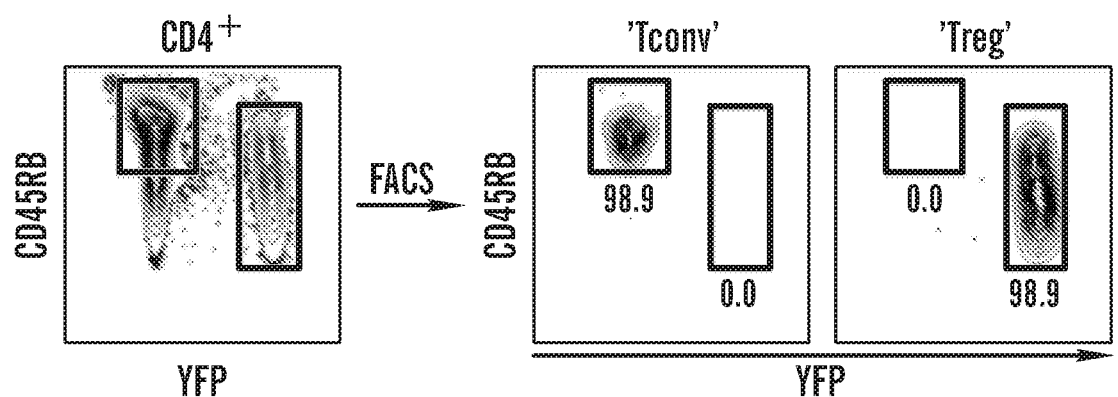
FIGS. 9A-9D.
Figure 9B:
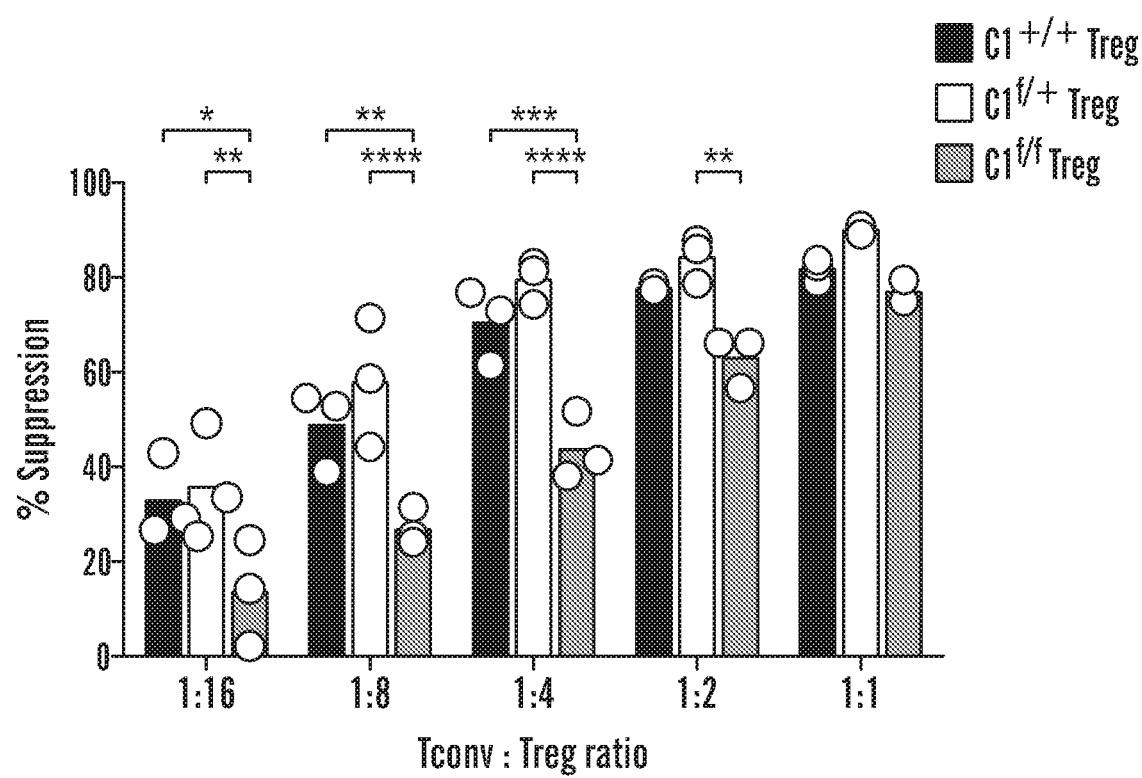
Figure 9C:
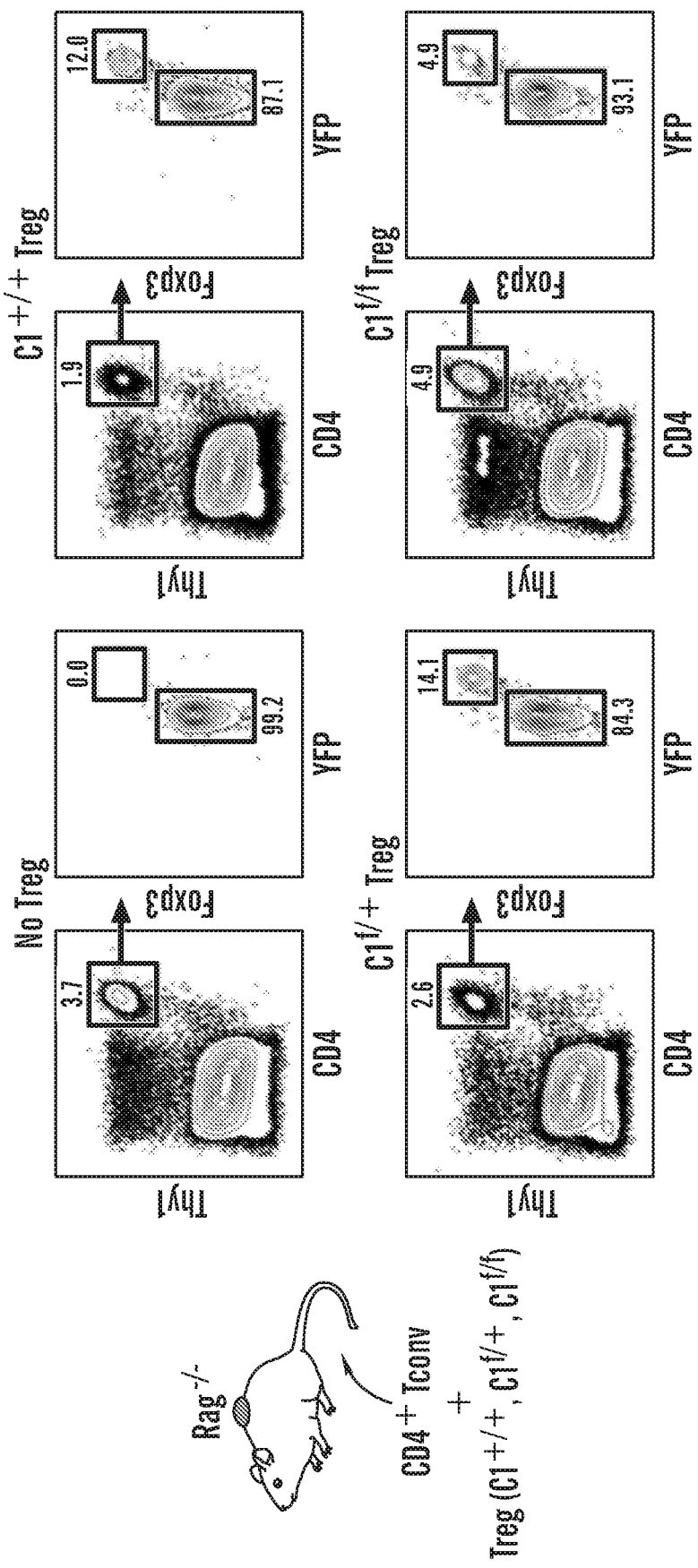
Figure 9C:
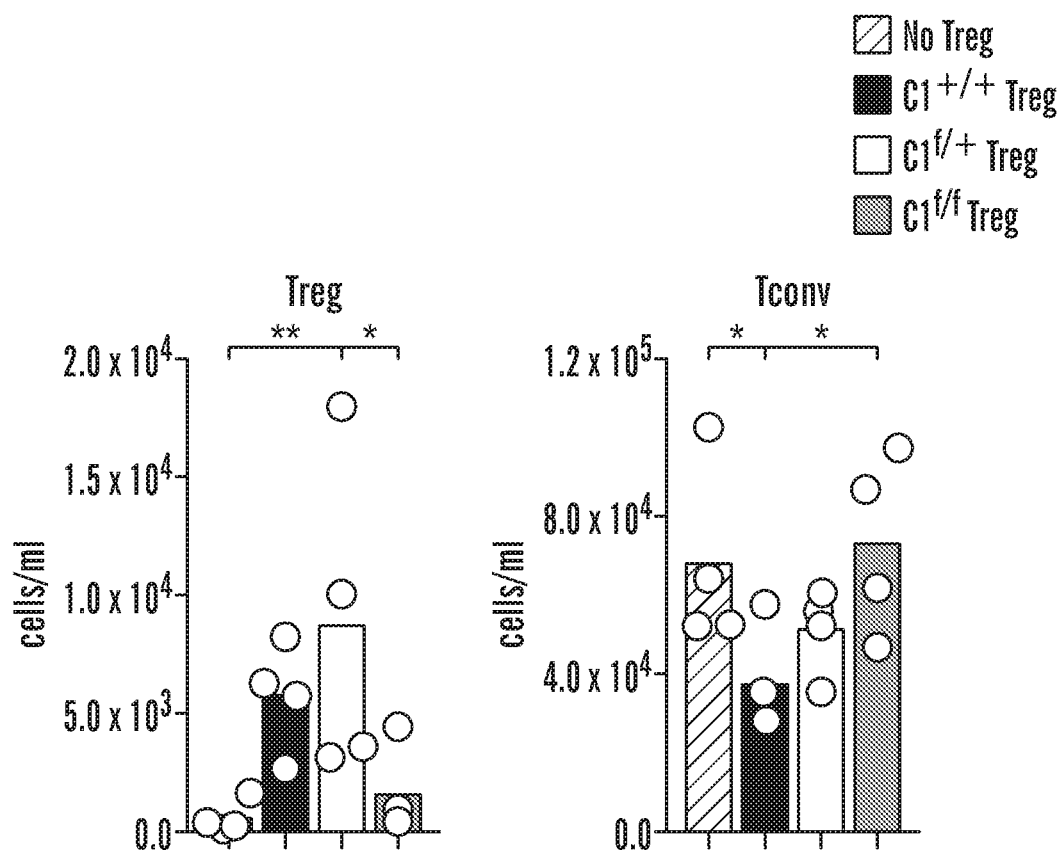
Figure 9D:
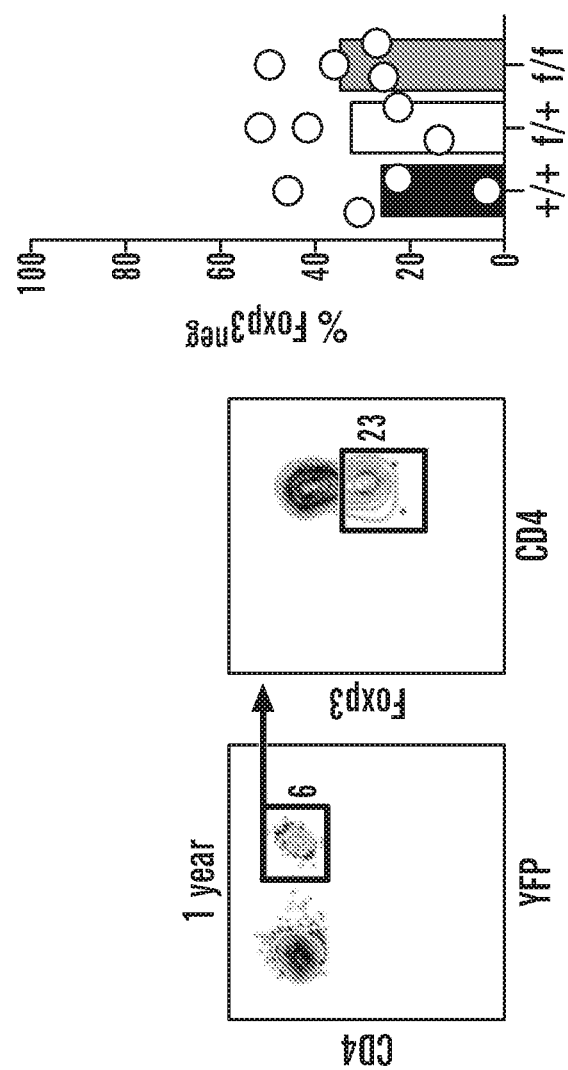

In heterozygous female F$^{Cre/+}$×C1$^{fl/fl}$ mice, random X-inactivation causes Cre to be expressed and CARMA1 to be deleted in only half of Treg, which can be identified, e.g., based on expression of the yellow fluorescent protein (YFP) fused to the Cre recombinase (FIG. 8A). No lymphoproliferative disease was observed in these animals, indicating that the remaining CARMA1-sufficient (YFP$^-$) Treg maintained immune homeostasis and that in healthy mice, even fully CARMA1-deficient Treg do not initiate inflammation (FIGS. 1I and 1M; FIGS. 8B-8C); accordingly, these cells did not secrete IFNγ upon ex vivo activation (FIG. 1I). In this setting, however, where CARMA1-deficient Treg likely compete with CARMA1-sufficient Treg for niche space it was observed that a proportional decline occurred specifically in the frequency of CD44$^{hi}$ eTreg that lacked either one or both alleles of CARMA1 (FIG. 1M). The remaining YFP+CD44$^{hi}$ eTreg also expressed less Foxp3 as well as markers of Treg effector differentiation and proliferated less, but expressed larger quantities of the proapoptotic protein BIM (FIGS. 1n and 5b (FIG. 14A; FIGS. 8D-8H). In vitro suppressive function of CARMA-1 deficient Treg was reduced, but not abrogated (FIGS. 9A-9D), while upon adoptive transfer into Rag-deficient hosts, they failed to persist and did not suppress lymphopenia-driven expansion of co-adoptively transferred Teff (FIG. 8C). Lack of CARMA1 did not, however, lead to an increase in the formation of Foxp3$^{neg}$ exTreg, as detectable in R26$^{YFP}$ mice, in which prior expression of Foxp3 is recorded by irreversible high level expression of YFP (FIG. 14E; FIG. 9D).

Figure 10:
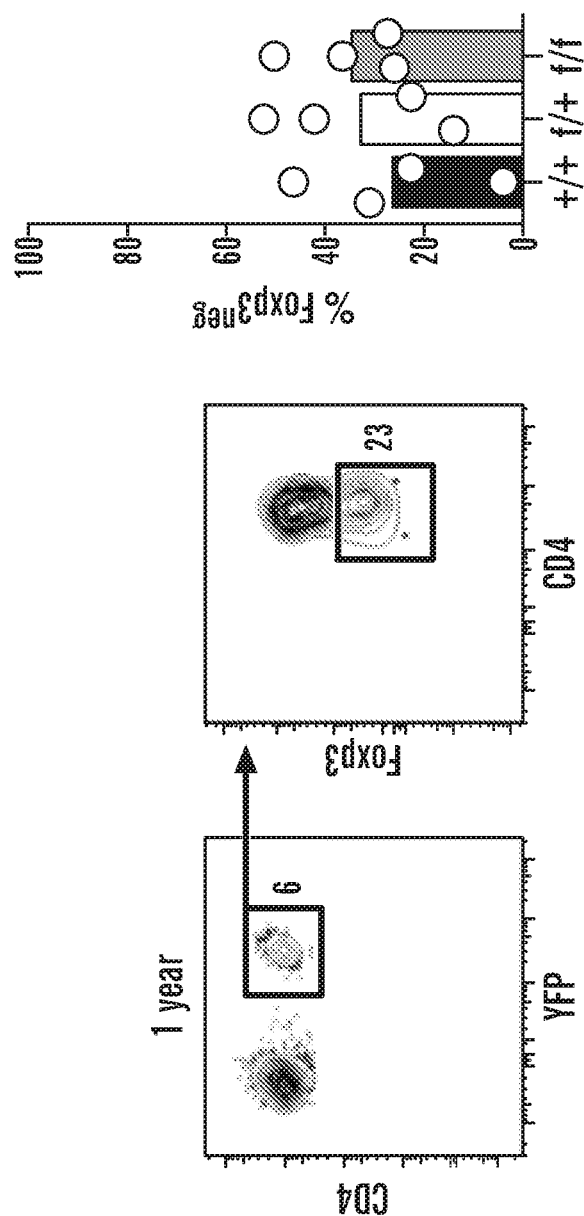
FIGS. 10A-10B.
Figure 10A:
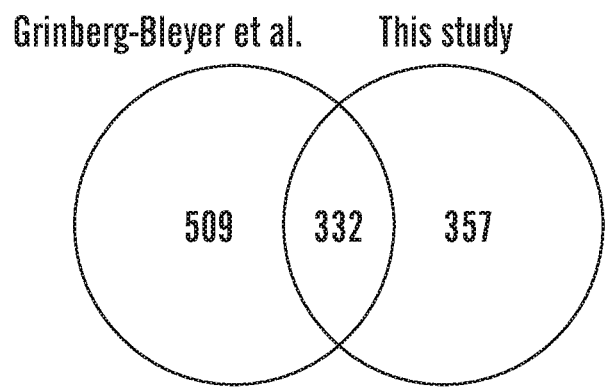
Figure 10B:
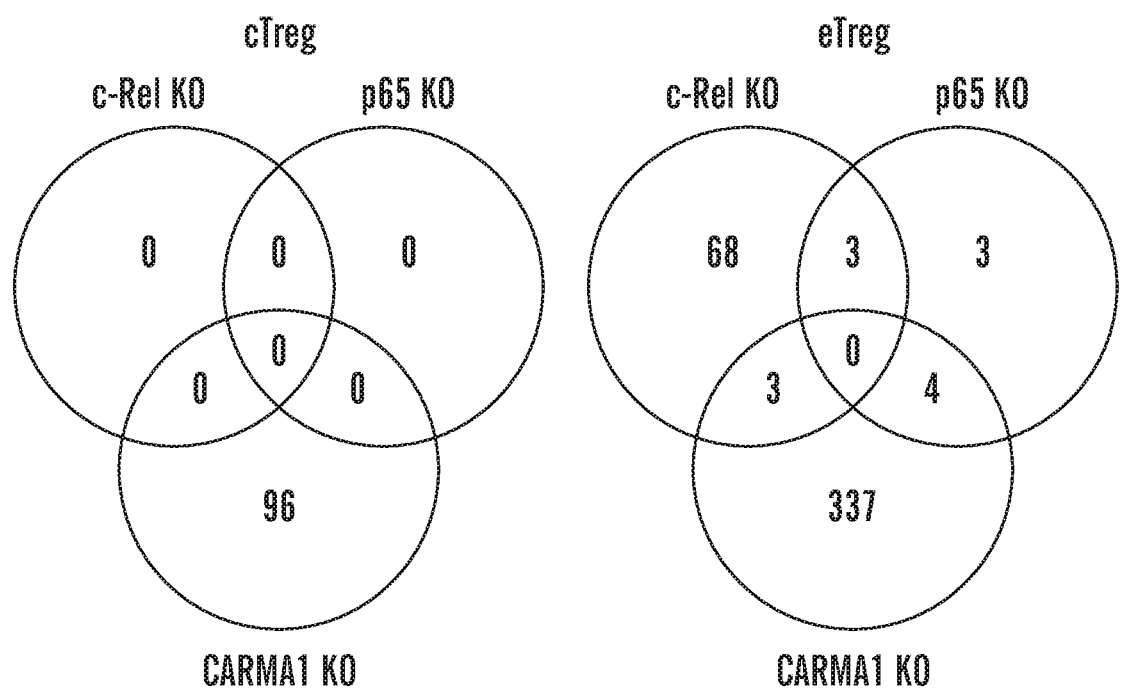
Figure 11C:
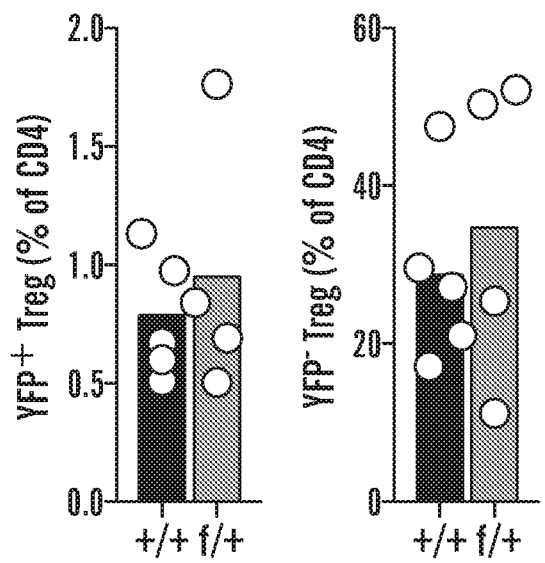
Figure 11D:
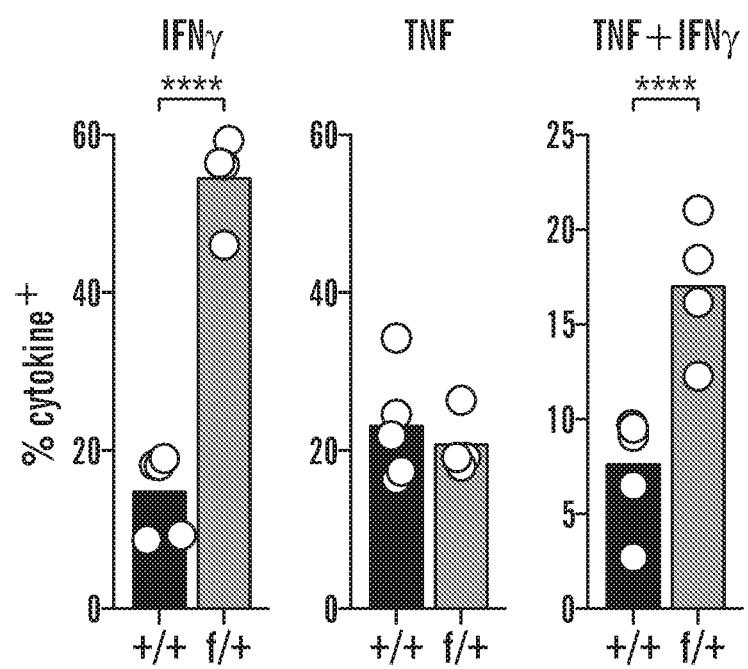
Figure 11E:
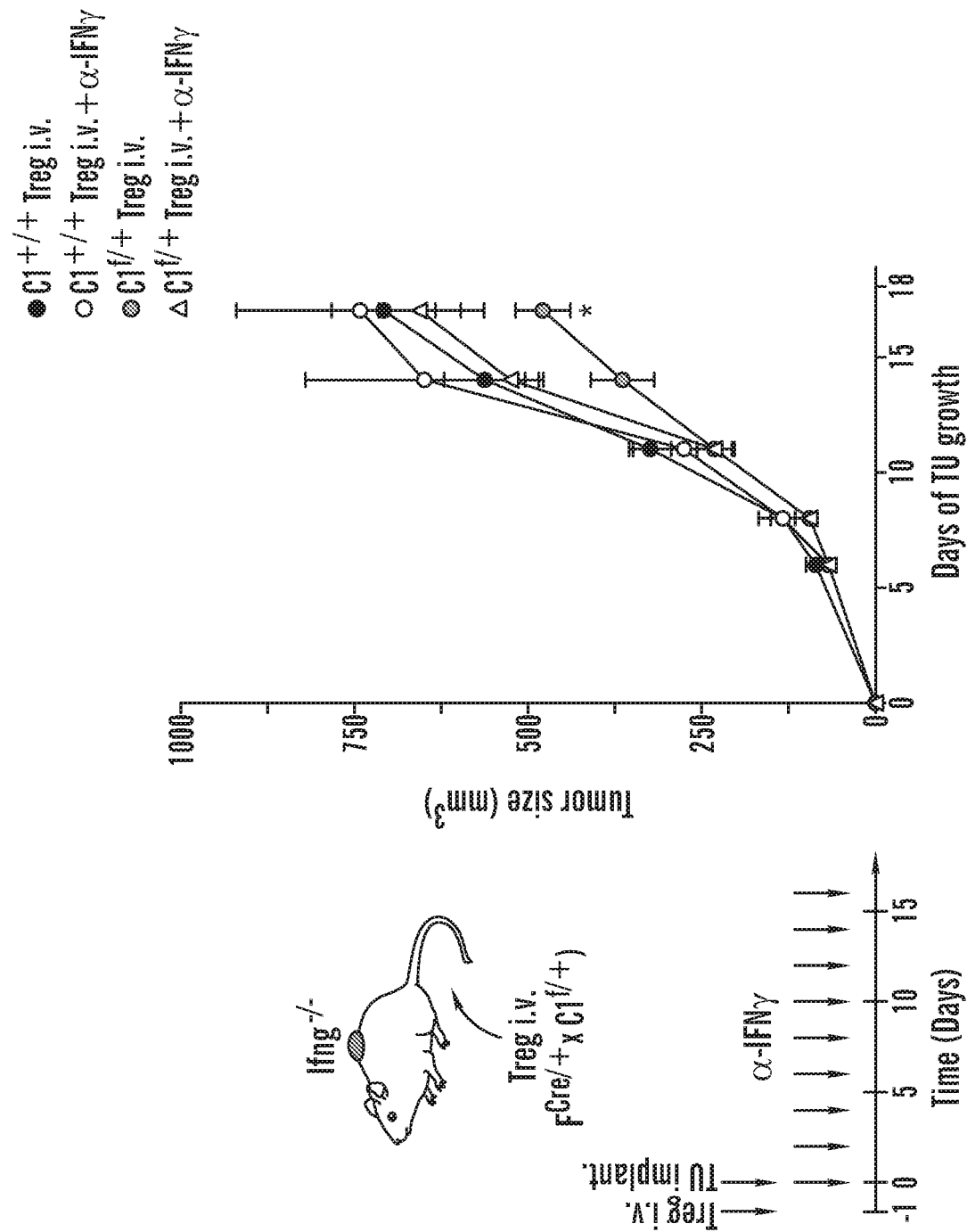
Figure 14D:
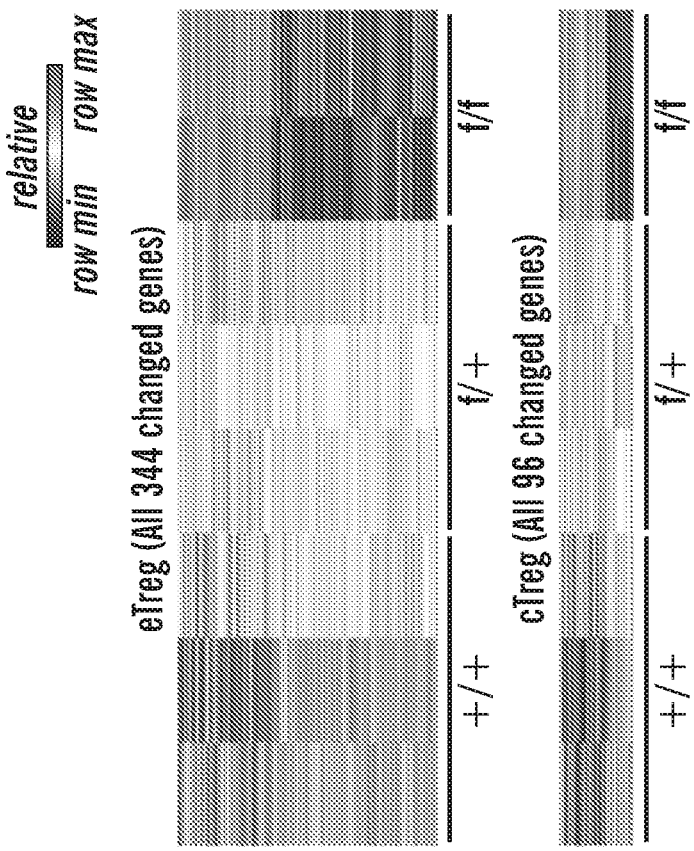
(FIGS. 14C-14D), Bulk RNA sequencing analysis of YFP$^+$ eTreg and eTreg sorted from LNs of F$^{Cre/+}$×C1$^{+/+}$, ×C1$^{fl/+}$, and ×C1$^{fl/fl}$ mice. Principal component analysis of transcriptomes (FIG. 14C) and heatmap display of scaled expression in eTreg (top) and eTreg (bottom) of genes differentially expressed (fold change >2 and $p_{adj}$<0.05) between C1$^{+/+}$ and C1$^{f/f}$ (FIG. 14D).
Figure 14C:
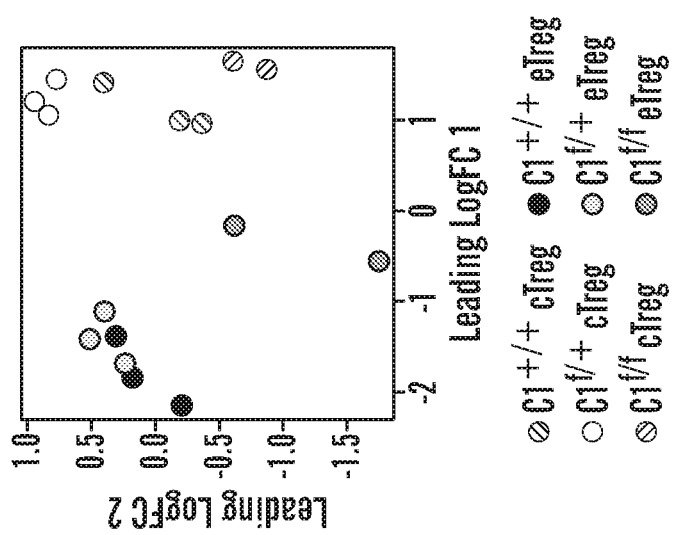
Figure 14E:
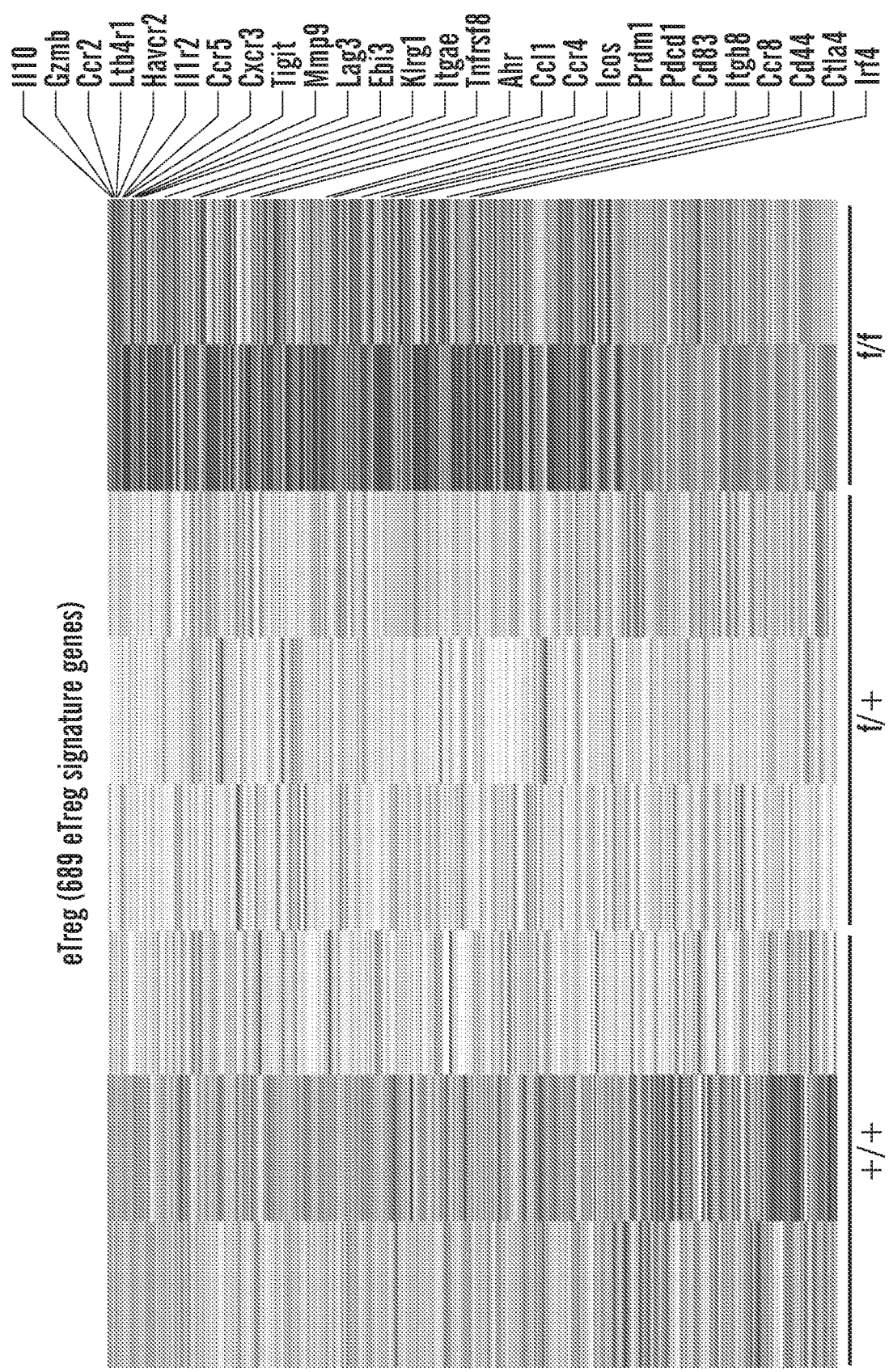
(FIG. 14E), heatmap display of scaled expression of 'eTreg signature' genes (fold change >2 and $p_{adj}$<0.01 between C1$^{+/+}$ eTreg and C1$^{+/+}$ eTreg) by eTreg of indicated genotypes. Selected eTreg genes are annotated.

Based on global gene expression analyses, CARMA1-deficient eTreg were equally dissimilar to WT eTreg as they were to WT tTreg, whereas CARMA1-deficient eTreg were only moderately dissimilar to WT eTreg (FIG. 14C). In the latter, 96 genes were differentially expressed, compared to 344 genes that were either up- or down-regulated in CARMA1-deficient compared to WT eTreg (FIG. 14D; FIG. 10A). Based on differences between WT eTreg and tTreg we defined an 'eTreg signature', which to a large extent overlapped with previously reported differences between these cell types (FIG. 5B).[12,15] Based on these 689 genes, hemizygous CARMA1-deletion had only moderate impact, while homozygous deletion induced major changes specifically in the eTreg gene expression program (FIG. 14E and FIG. 10C). Surprisingly, these changes showed only partial overlap with changes induced in eTreg by Treg-specific deletion of the NF-κB proteins c-Rel or RelA/p65 (FIG. 10D),[15] emphasizing the importance of the other CBM complex effector pathways for Treg homeostasis. Thus, loss and already a decrease in CARMA1 expression impairs Treg effector differentiation and survival, but does not induce them to become pathogenic or convert to exTreg under non-inflammatory conditions. However, in the context of incipient inflammation trigged by global loss of Treg suppressive function in FCre×C1fl/fl mice, CARMA1-deficient Treg secrete IFNγ, which further accelerates inflammatory disease.

Figure 2A:
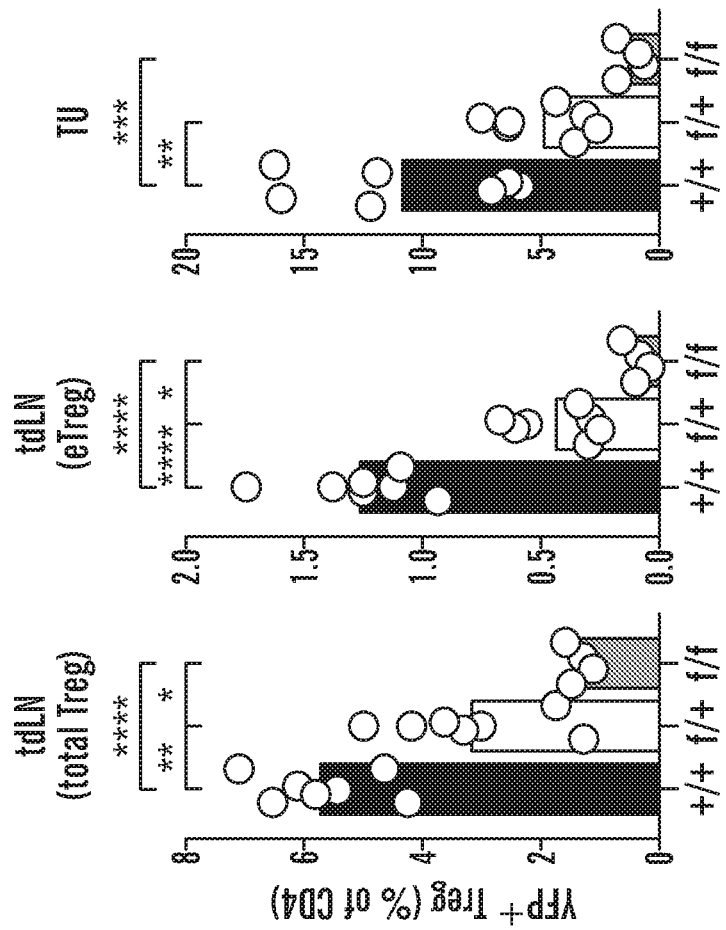
Figure 2A:
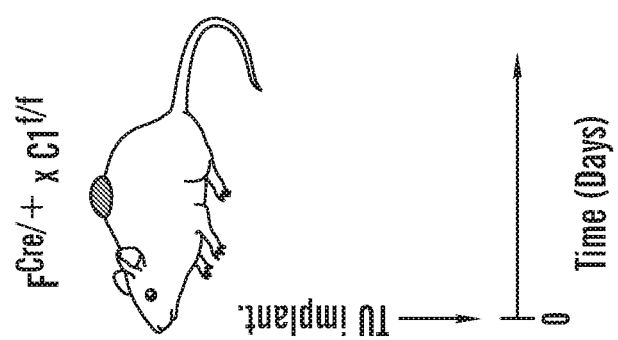
Figure 2D:
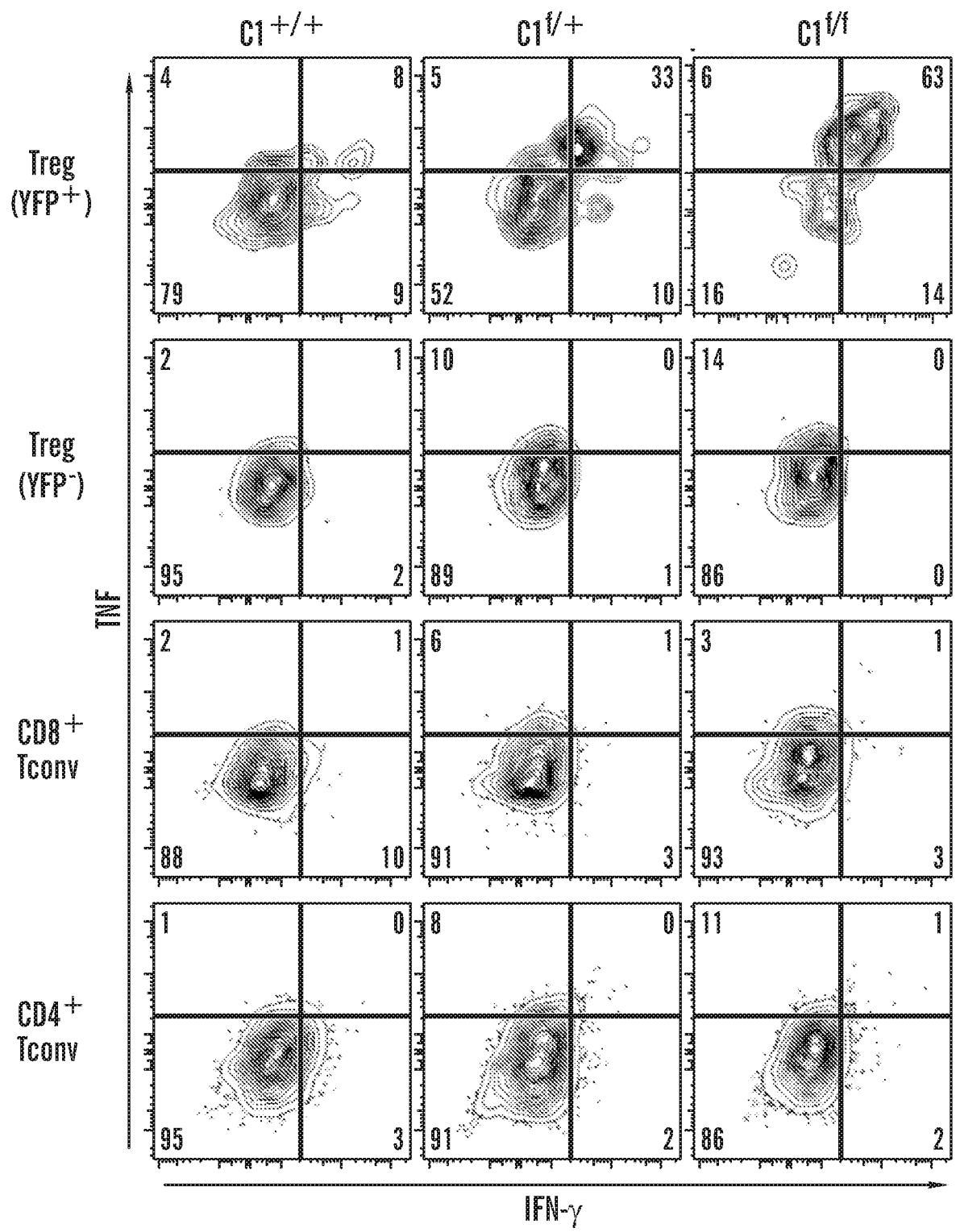
Figure 2E:
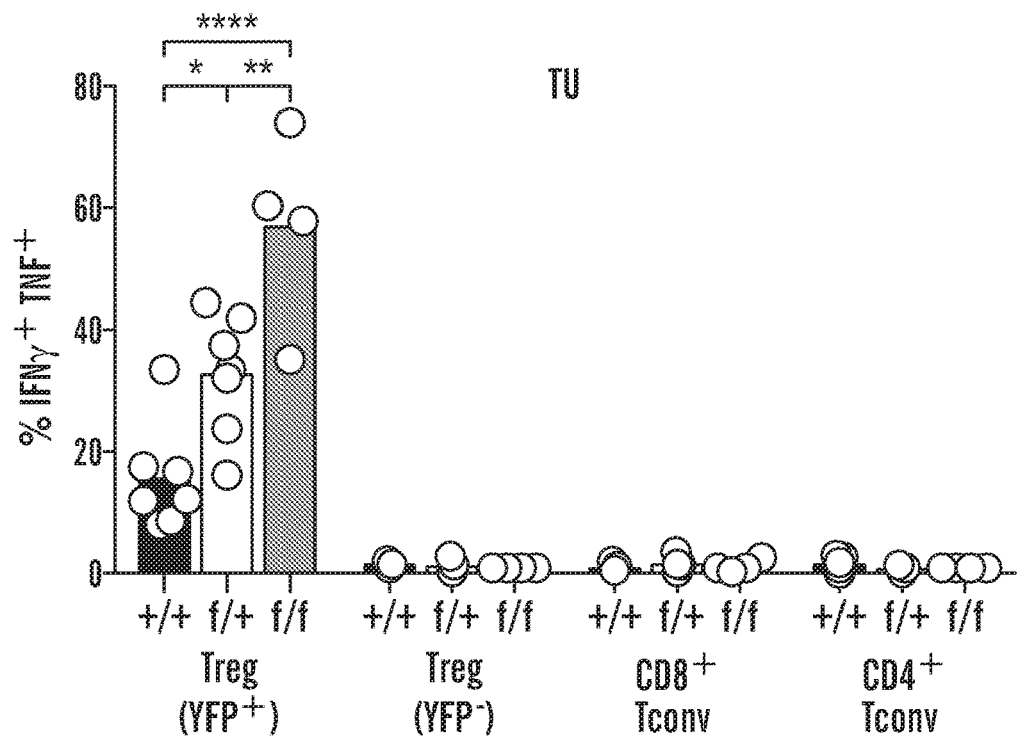
Figure 2F:
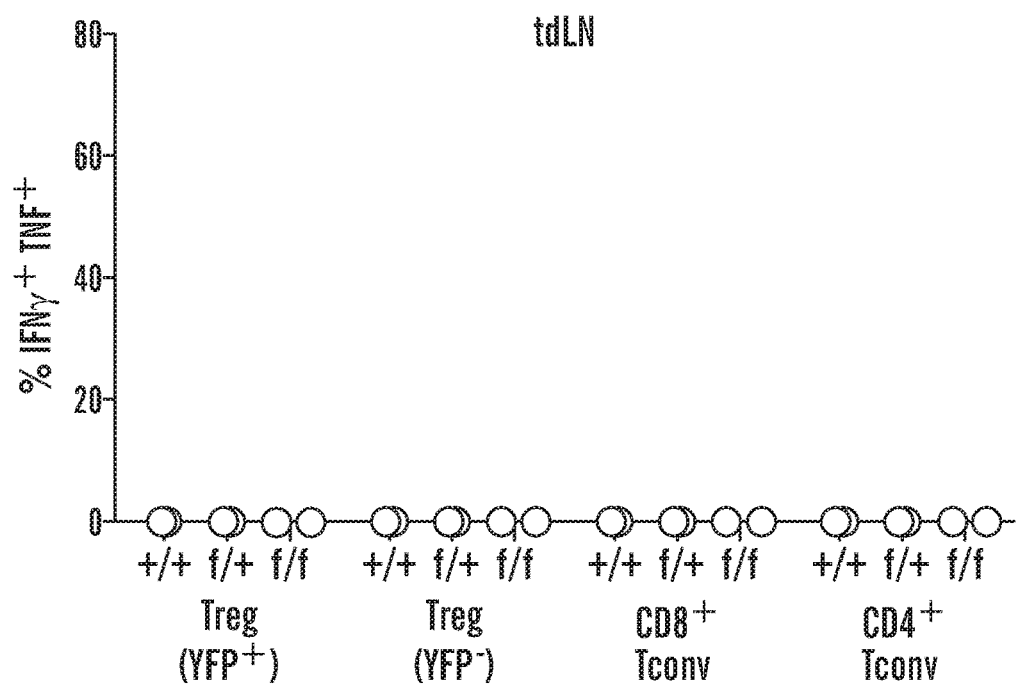
Figure 2G:
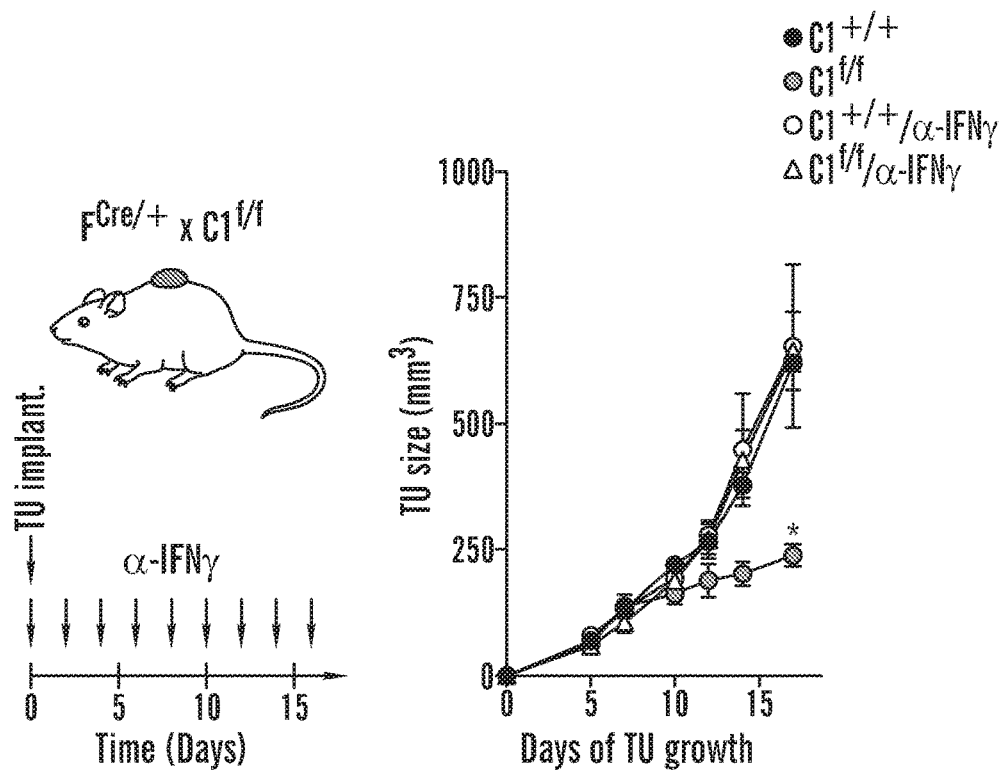
Figure 2H:
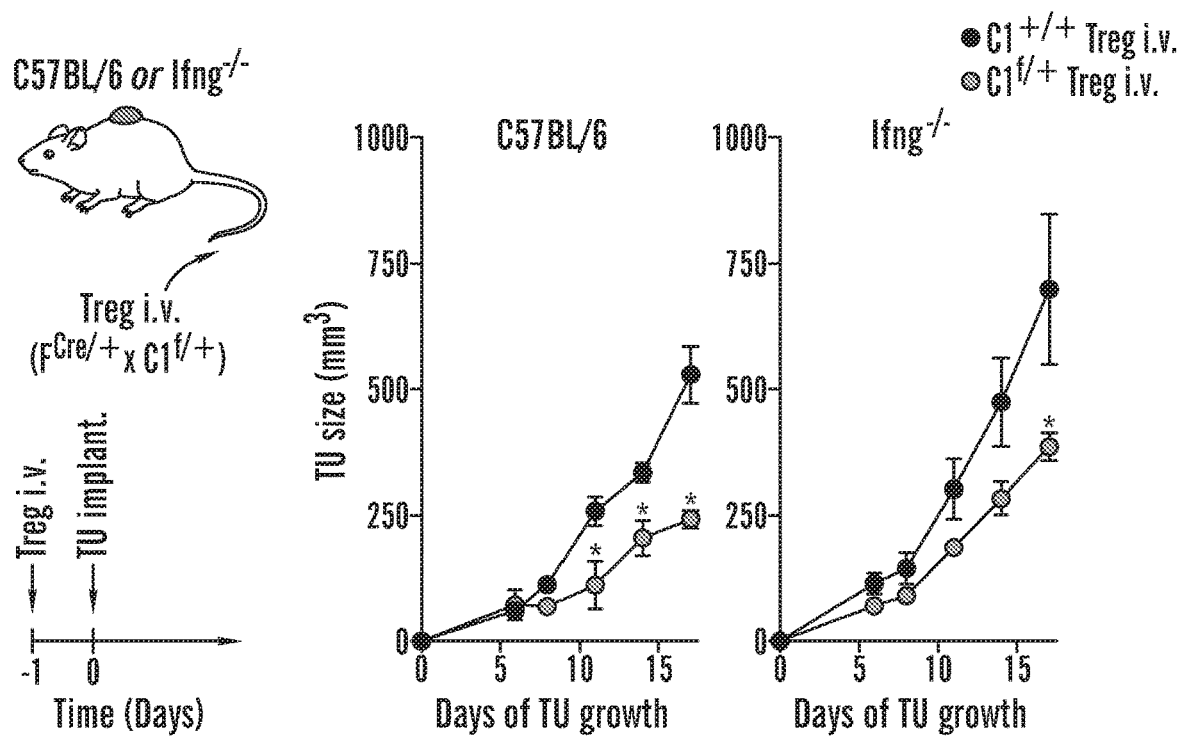
Figure 14F:
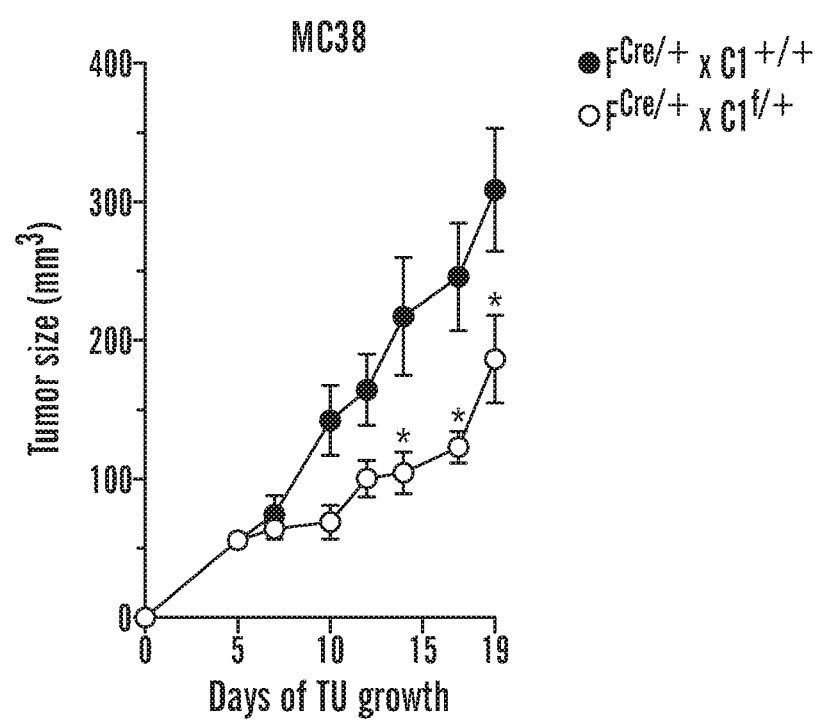
(FIG. 14F), MC38 tumor growth in indicated mice, where either one or both alleles of CARMA1 were deleted in half of Treg.
Figure 14G:
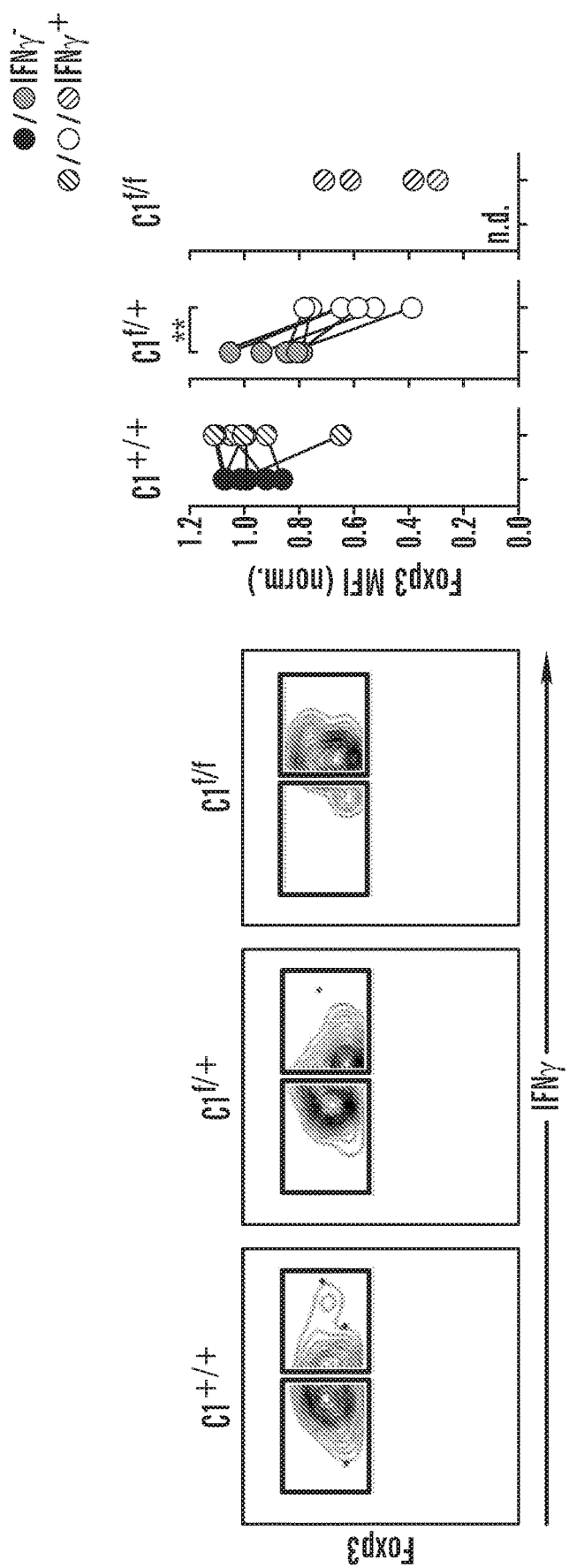
(FIG. 14G), Normalized Foxp3 expression in IFNγ$^+$ and IFNγ$^-$ Treg from tumor tissue, n.d.=not detectable (FIG. 14H), Foxp3$^{GFP-CreERT2}$×CARMA1$^{+/+}$ and ×CARMA1+/+ mice ('F$^{CreERT2}$×C1$^{+/+, \, f/f}$) were implanted with D4M.3A melanoma and treated with 5 daily doses of tamoxifen starting on day 8 as well as with FTY720 daily starting the same day until the end of the experiment. YFP$^+$ Treg were sorted from tdLN and tumor after 5 days of treatment and analyzed for CARMA1 expression by RT-qPCR. n.d.=not detectable.
Figure 14H:
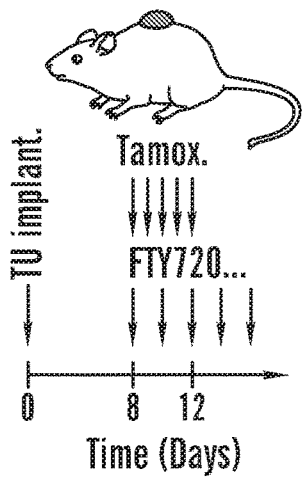

Without wishing to be bound by a particular theory, it was hypothesized that CARMA1-deletion may preferentially reduce intratumoral Treg numbers since lack of CARMA1 impairs maintenance of eTreg more than that of tTreg, and given that tumors are populated by eTreg. Considering poor eTreg formation by CARMA1-deficient Treg and IFNγ-secretion in an inflammatory context (FIGS. 1H-1I), the response to malignant tumor growth of such mice were examined. Indeed, the conditions produced by subcutaneous implantation of D4M.3A tumors, a poorly immunogenic BRAF$^{V600E}$×PTEN$^{null}$ melanoma,[16] into young female heterozygous F$^{Cre/+}$×C1$^{fl/fl}$ mice amplified the effects of CARMA1-deficiency on Treg maintenance, since not only the frequency of eTreg, but also of total YFP+ Treg were reduced in tdLNs as a function of decreasing CARMA1-expression, accompanied by an even more pronounced reduction in Foxp3 expression (FIGS. 2A-2B). Interestingly, a deceleration of the growth of D4M.3A melanoma, and also of MC38 colon carcinoma, was observed in mice where half of Treg lacked either one or both alleles of the CARMA1 gene (FIGS. 2C and 14F). This was unexpected, since a mere loss of function of only half of Treg is not predicted to cause loss of tumor tolerance,[11] and suggested active Treg-mediated anti-tumor activity. Indeed, even without ex vivo re-stimulation, a large fraction of either completely or even just partially CARMA1-deficient Treg secreted both TNF and IFNγ, while these effector cytokines were undetectable in tumor-infiltrating CD4+ and CD8+ conventional T cells under these conditions (FIGS. 2D-2E). Importantly, no cytokine secretion was observed in tdLNs (FIG. 2F), indicating that while formation of CARMA1-deficient eTreg is more strongly impaired here than in LNs of tumor-free mice (FIG. 1M), their secretion of effector cytokines is restricted to the tumor environment. IFNγ-expression in tumor tissue correlated with down-regulation, but not loss of Foxp3 in both partially and fully CARMA1-deficient Treg (FIG. 14G). Notably, destabilization of WT Treg by IFNγ-producing Treg, as recently described for mice with heterozygous loss of Nrp-1 in Treg,[18] did not occur in this case, since no increase in expression was detectable in YFP-Cre$^{neg}$ CARMA1-sufficient Treg in the same tumors (not shown). In agreement with an important role for IFNγ in Treg-mediated anti-tumor immunity, neutralization of IFNγ fully restored tumor growth in FCre/+×C1fl/fl mice (FIG. 2G). However, the anti-tumor effect could also have resulted from IFNγ produced by other cellular sources, including NK cells, following Treg destabilization. To specifically test the role of Treg-produced IFNγ, Treg with reduced CARMA1 expression obtained from F$^{Cre/+}$×C1$^{f/+}$ mice were adoptively transferred into tumor-bearing C57BL/6 or Ifng−/− mice. In both types of hosts tumor growth was similarly stunted, but not when IFNγ was neutralized, indicating that Treg-derived IFNγ is both necessary and sufficient to mediate observed anti-tumor effects (FIG. 2H; FIGS. 11A-11E). Therefore, while partially or fully CARMA1-deficient Treg do not cause inflammatory disease in healthy mice, they are destabilized in tumor tissue and secrete IFNγ, which decelerates tumor growth.

Figure 12A:
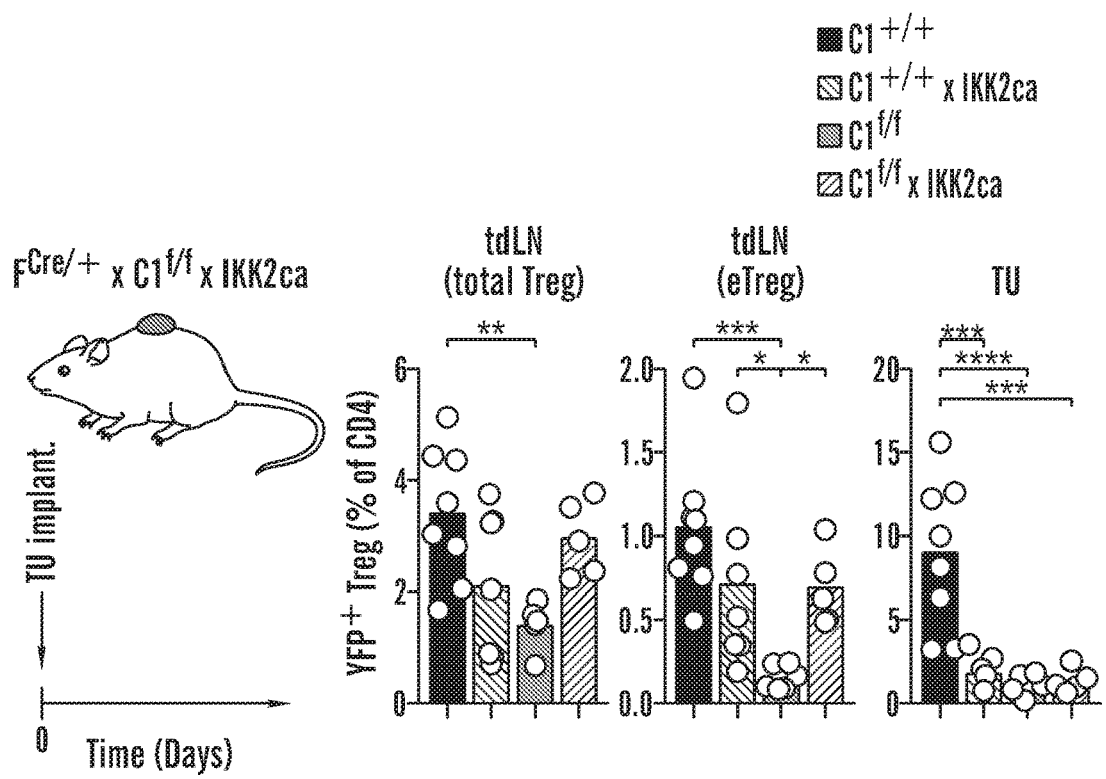
FIGS. 12A-12D. D4M.3A melanoma were implanted into $F^{Cre/+}\times C1^{+/+\ or\ f/f}\times Rosa26^{STOP\ f/f-IKK2ca}$ mice to record (FIGS. 12A-12B), Frequency of Treg among $CD4^+$ T cells and of $CD44^{hi}$ eTreg (FIG. 12A) and normalized Foxp3 expression of Treg (FIG. 12B) in tdLN and tumor tissue.
Figures 12B, 12C:
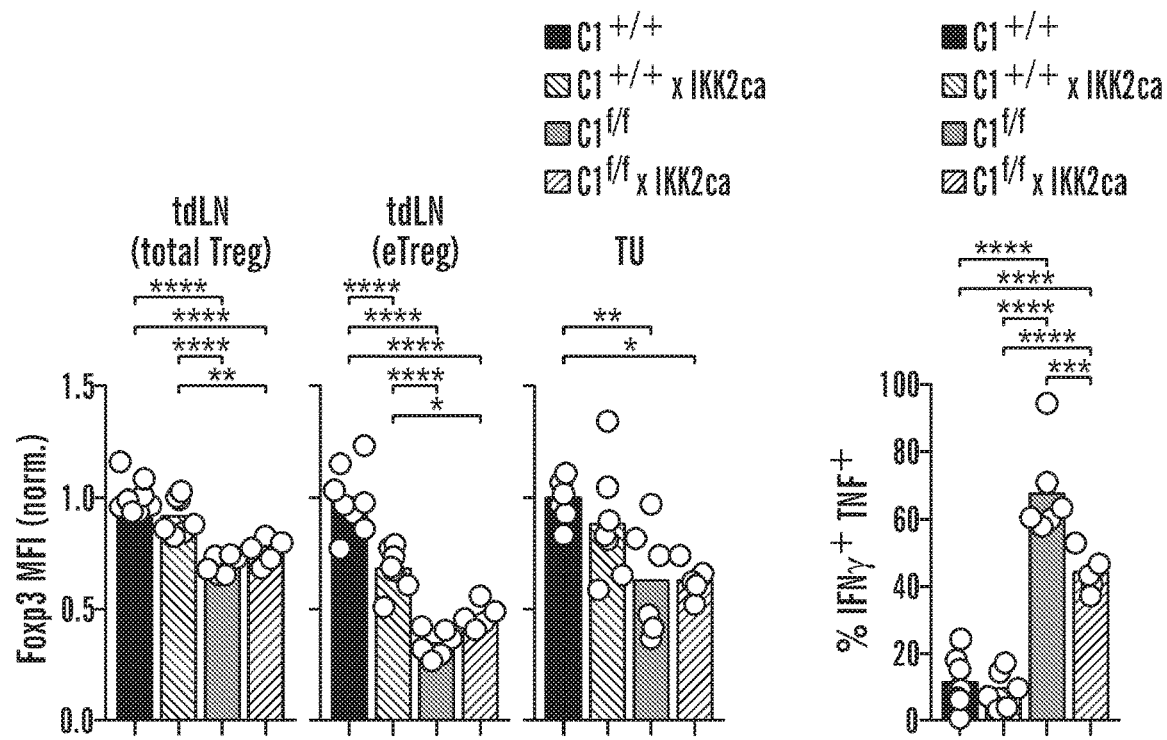
Figure 12D:
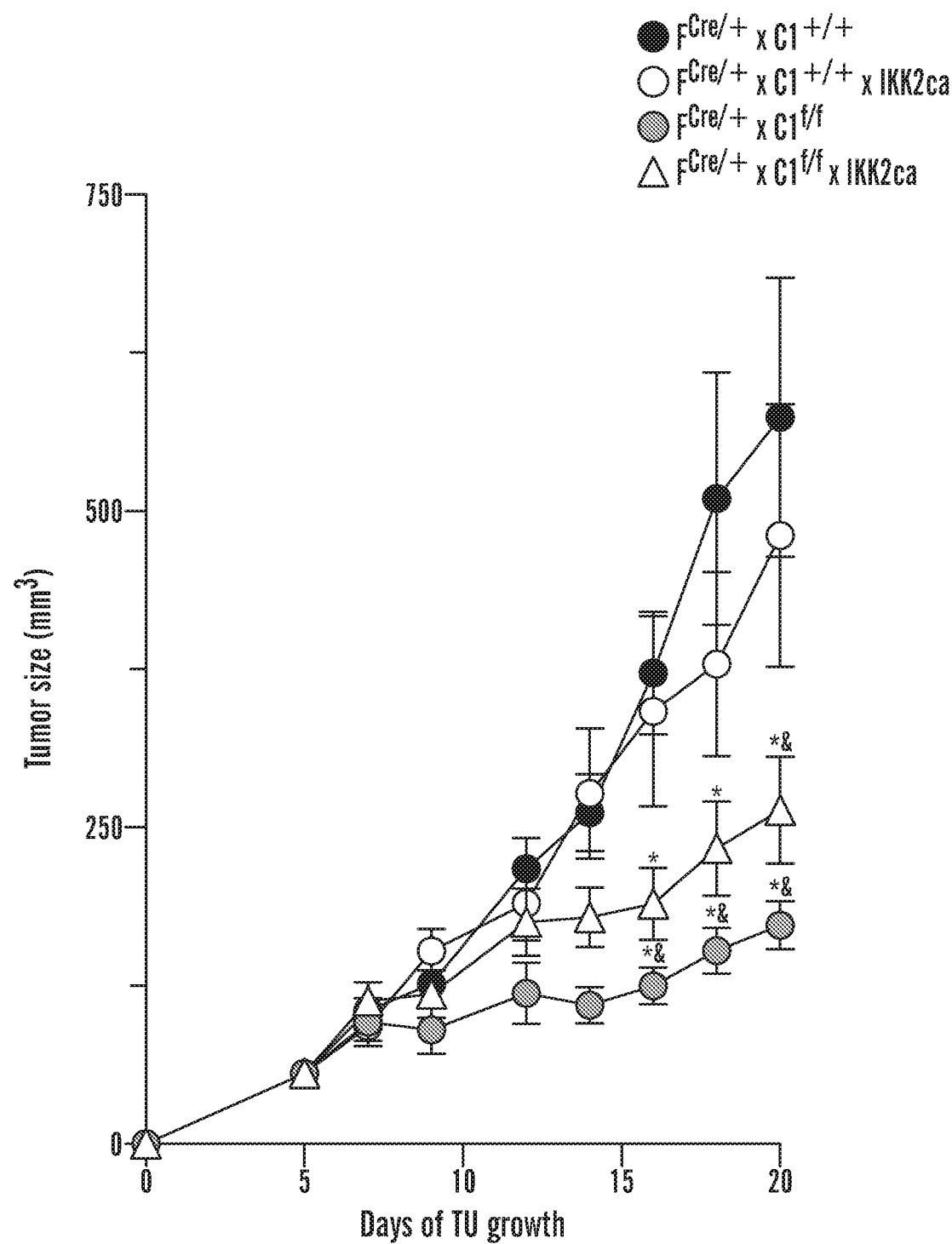

Expression of IKK2ca restored total Treg and eTreg frequencies in tdLNs, but not in tumor tissue (FIG. 12A). It also did not restore Foxp3 expression, and only partially reduced co-expression of TNF and IFNγ by tumor-infiltrating CARMA1-deficient Treg and, accordingly, did not prevent their anti-tumor activity (FIGS. 12B-12D), again emphasizing the importance of one or several CBM complex effector functions in addition to activation of NF-kB proteins[15] in stabilizing tumor-reactive Treg.

Figure 3E:
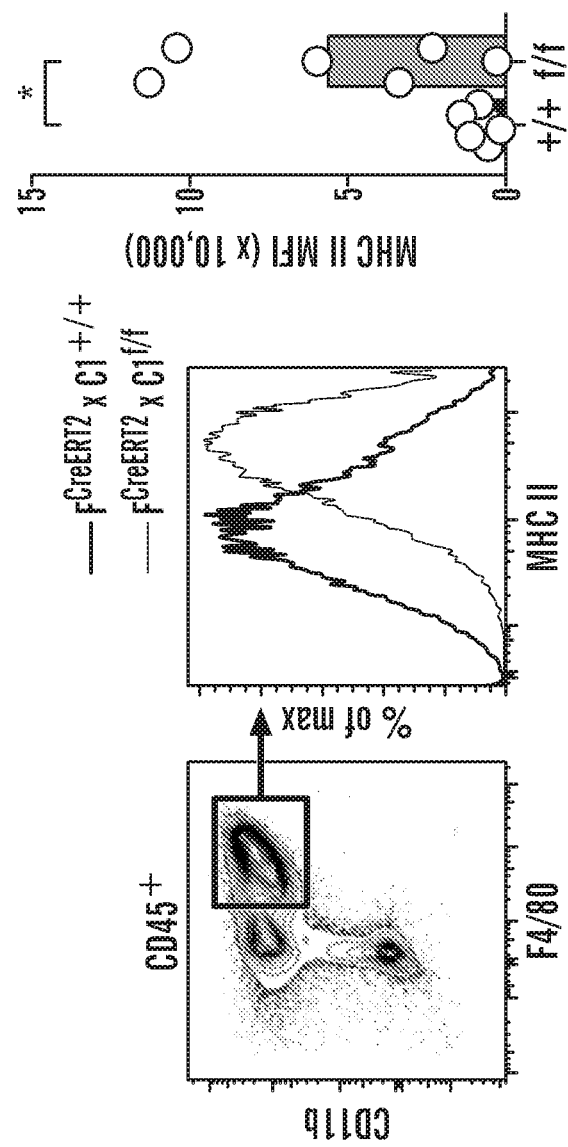
Figure 3F:
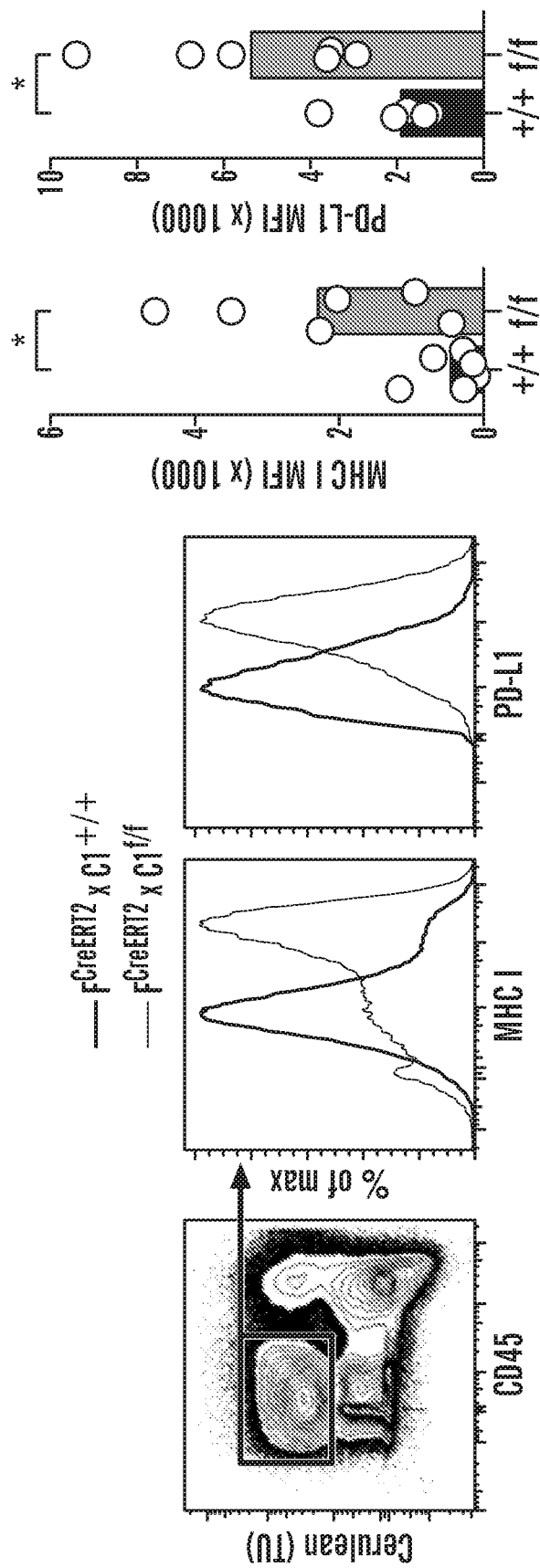
Figure 13A:
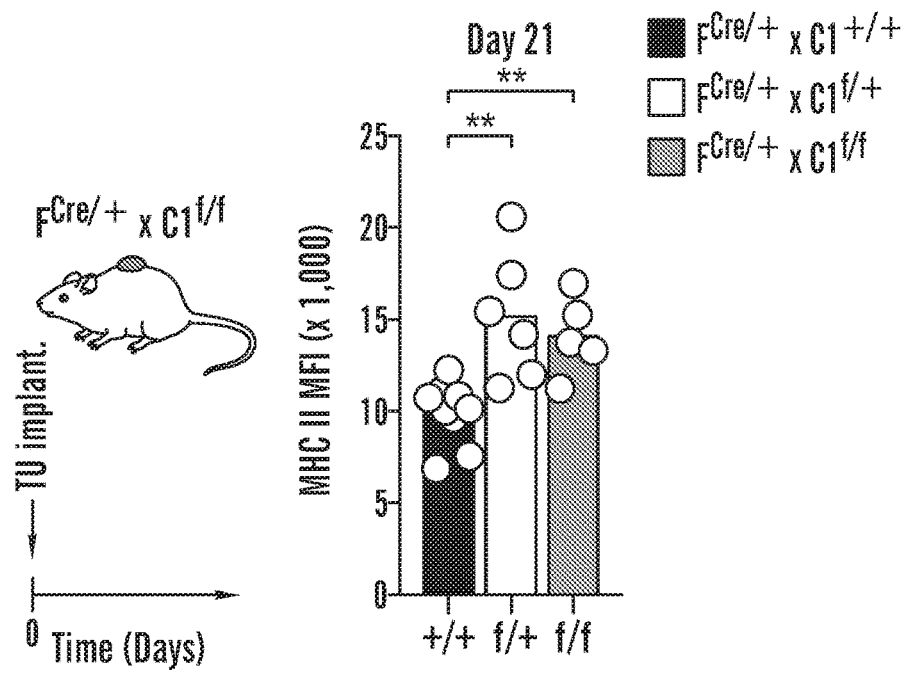
Figure 14I:
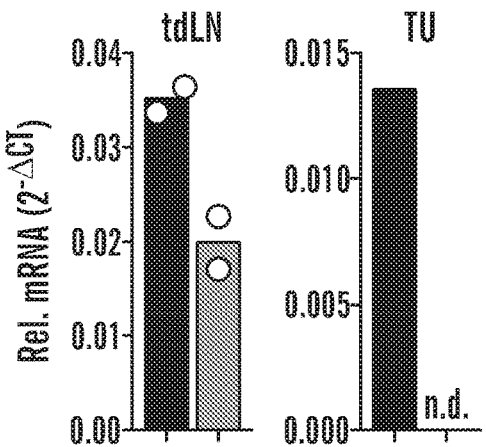
(FIG. 14I), In situ expression of effector cytokines in YFP$^+$ Treg 5 days following deletion of CARMA1 in half or in all Treg in tumor tissue from F$^{CreERT2}$×C1$^{f/f}$ or F$^{CreERT2/+}$× C1$^{+/+ \, or \, f/f}$ mice.
Figure 14J:
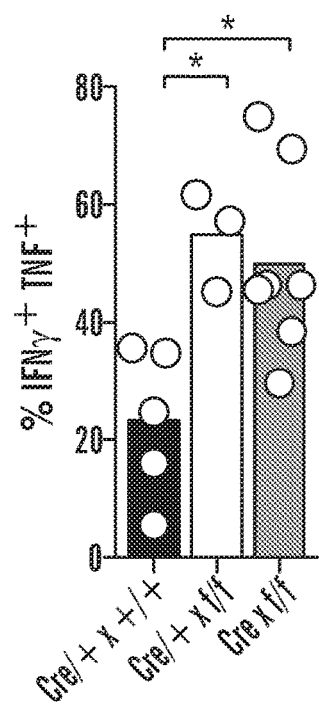
(FIG. 14J), CBM complex effector pathways and effects of MALT1 protease inhibitor mepazine and MI-2.

In order to examine if CARMA1-deletion could destabilize Treg that had already infiltrated tumor tissue, Foxp3$^{GFP-CreERT2}$×CARMA1$^{fl/fl}$ ('FCreERT2×C1fl/fl') mice were generated and treated with tamoxifen to activate nuclear recombinase activity of the GFP-CreERT2 fusion protein when implanted tumors were already established (FIG. 3A). To prevent the subsequent recruitment of additional Treg from tdLNs, lymphocyte egress from lymphoid tissues was concurrently blocked through treatment with the S1P-1 functional antagonist FTY720, as described.[4] Within 2 days of treatment, tumor growth deceleration was apparent (FIG. 3C). A similarly rapid, but slightly less pronounced effect as well as increased TNF and IFNγ secretion by CARMA1-deficient Treg resulted from deletion in only half of Treg in female heterozygous F$^{CreERT2/+}$×C1$^{fl/fl}$ mice (FIG. 3D; FIG. 14I). Yet, no inflammatory processes were observed in healthy tissues 10 days after tamoxifen treatment, indicating that systemic immune tolerance was preserved over this time frame (data not shown). Tumor growth deceleration and intratumoral Treg destabilization were accompanied by rapid and pronounced induction of macrophage cell surface expression of MHC class II protein, as was also observed upon constitutive deletion of either one or both alleles of CARMA1 in Treg (FIG. 3E; FIG. 13A). The inventors also observed MHC class I expression in tumor cells, predicted to sensitize them to CTL-mediated lysis (FIG. 3F). While these changes indicated that IFNγ-secreting Treg caused widespread tumor inflammation, up-regulation of the IFNγ-regulated T cell co-inhibitory ligand PD-L1 on tumor cells suggested concurrent induction of adaptive immune tolerance,[3] which likely limited the improved tumor growth control that tumor inflammation facilitated through recruitment of additional anti-tumor immune effector functions (FIG. 3F).

Figures 4A, 4B:
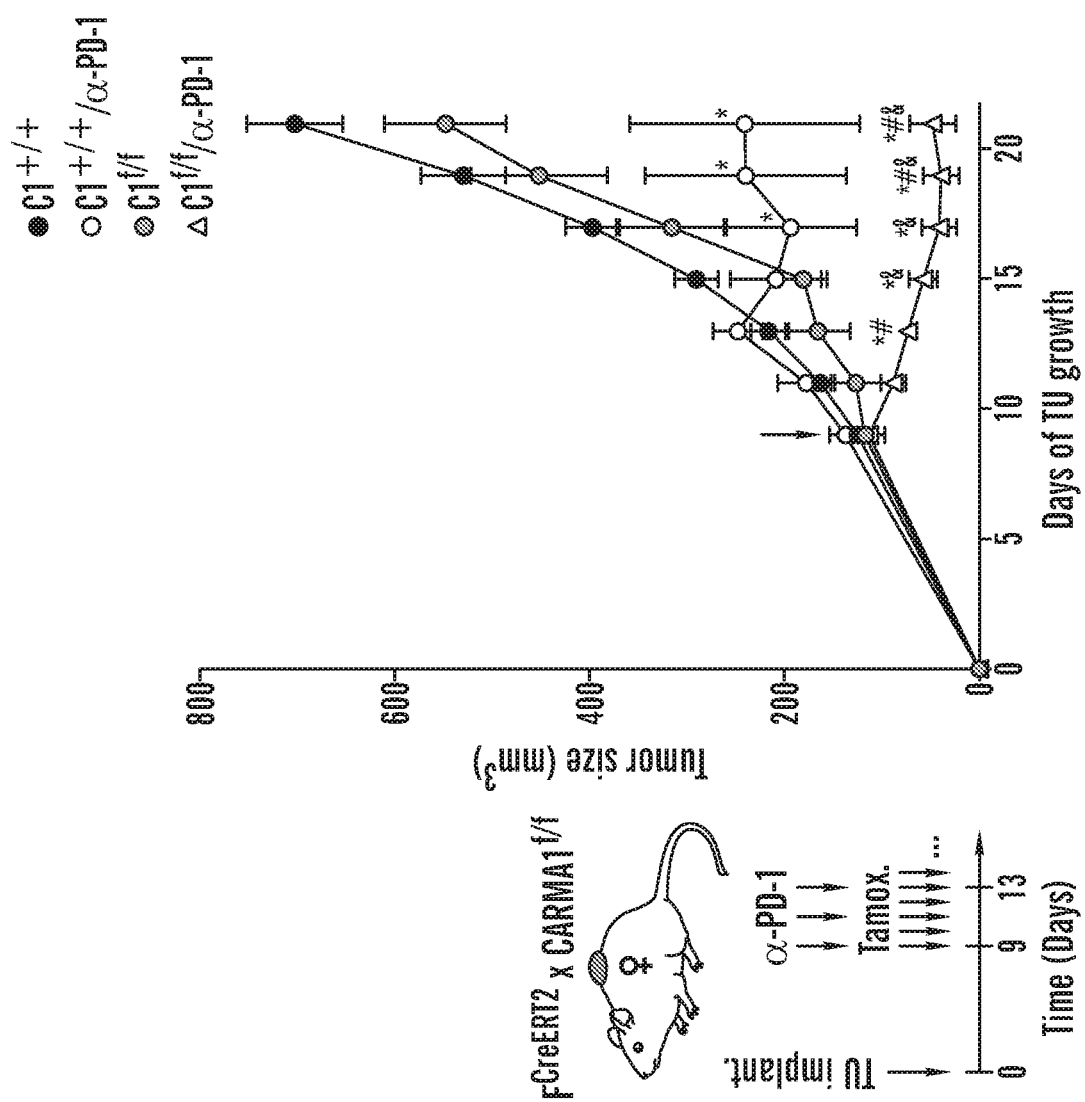
FIGS. 4A-4J present exemplary experimental data showing that CARMA1 deletion in Treg and pharmacologic MALT1 protease inhibition synergize with PD-1 checkpoint blockade therapy.

Considering the elevated expression of PD-L1 by tumor cells, it was hypothesized that antibody-mediated blockade of the PD-1 pathway may synergize with the anti-tumor effects of Treg that secrete IFNγ. Indeed, when αPD-1 therapy was initiated at the time of CARMA1-deletion in Treg, a much more rapid and consistent control of D4M.3A melanoma was observed than with either treatment alone (FIG. 4A). This indicates that targeting the CBM signalosome in Treg can be a highly effective approach to enhance the potency of checkpoint blockade therapy in cancer patients.

Figure 4D:
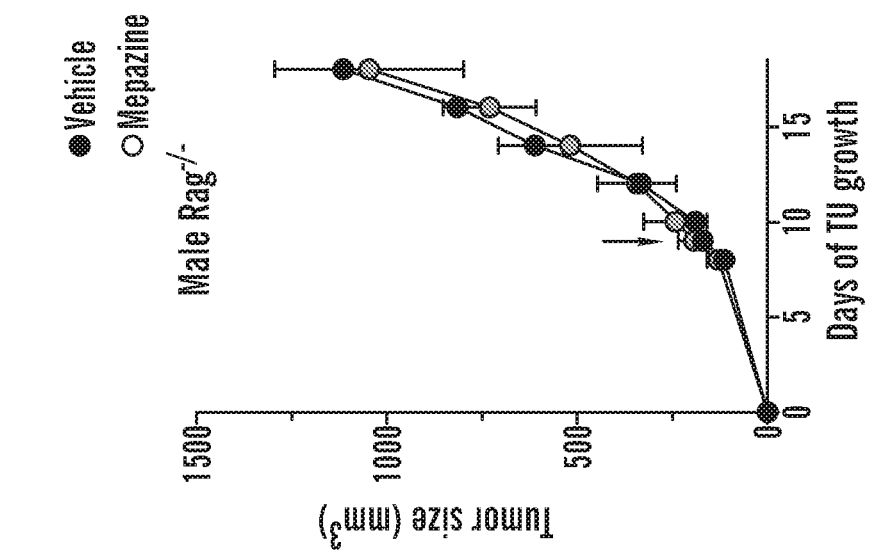
Figure 4C:
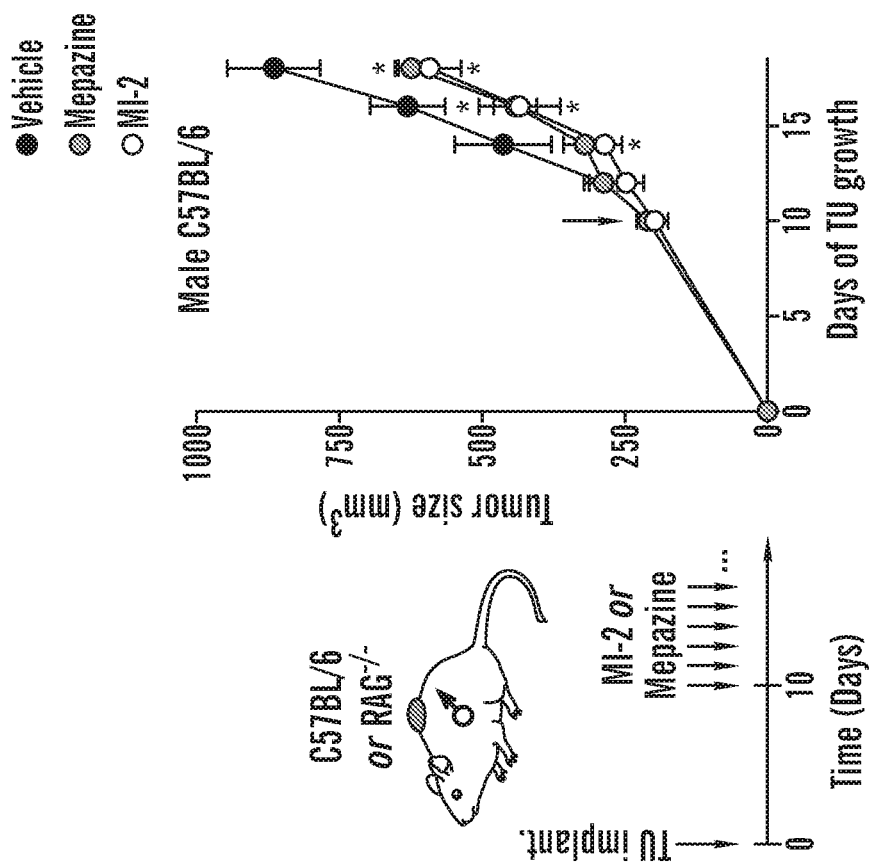
Figure 13B:
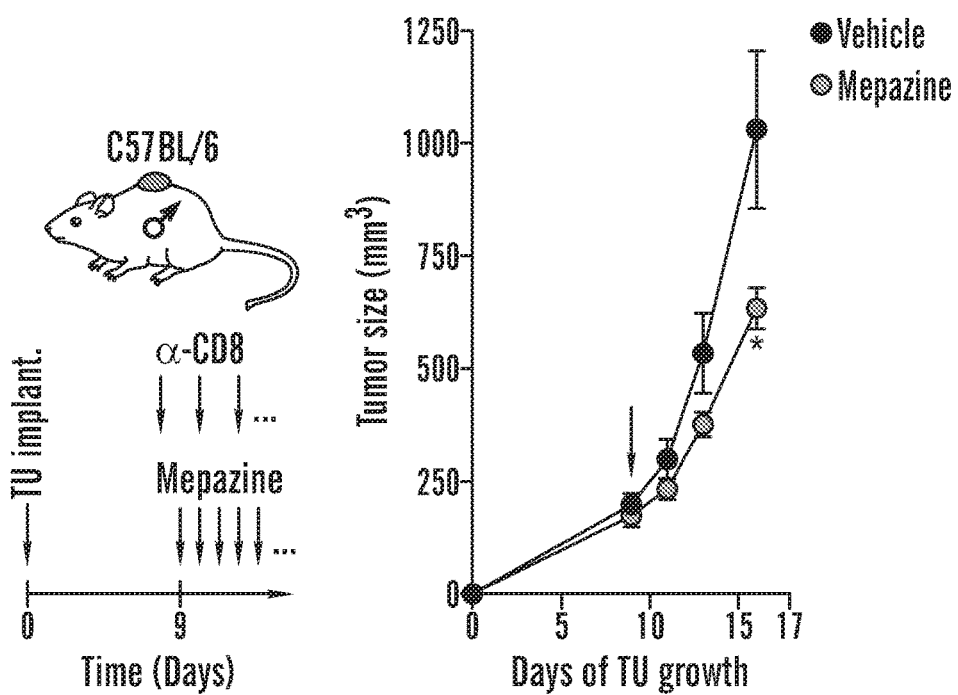
Figure 13C:
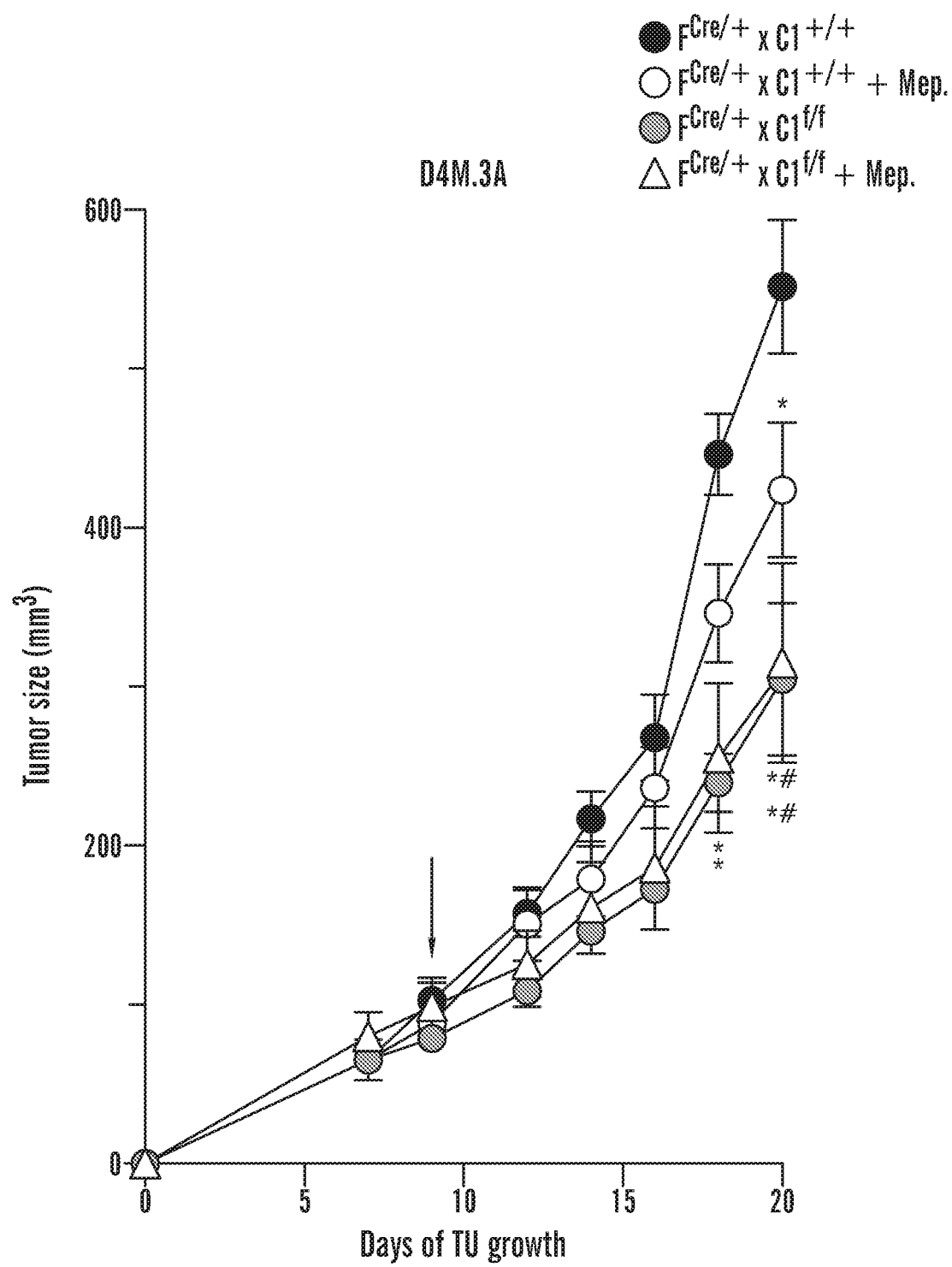

While pharmacological inhibitors of the scaffold protein CARMA1 are currently not available, inhibitors of the paracaspase activity of MALT1 are predicted to attenuate the majority of CBM complex-dependent effector pathways (FIG. 4B). Indeed, similar to CARMA1-deficient mice that lack Treg, mice expressing mutant MALT1 proteins lacking paracaspase activity (replicating complete pharmacological inhibition) show impaired regulatory T cell development.[19-21]. Therefore, the allosteric MALT1 inhibitor mepazine[22] and the catalytic site binder MI-2,[23] were tested for possible activity against solid tumors, and it was found that both produced a similar deceleration of melanoma growth as observed following CARMA1-deletion in Treg (FIG. 4C), even when CD8+ T cell were depleted (FIG. 13B). Since systemic MALT1 inhibition will also target cells other than Treg, and may have direct effects on melanoma cells,[24] treatment of Rag1-deficient mice that lack lymphocytes was tested, but no effect on tumor growth was observed in these animals (FIG. 4D). MALT1 inhibition also did not add to the anti-tumor effect of CARMA1-deletion in Treg, indicating that its anti-tumor activity does not result from effects other than disruption of CBM complex function in Treg (FIG. 13C). Considering these results and the fact that MALT1 inhibition is predicted to, if at all, attenuate, but not enhance the effector functions of conventional CD4+ and CD8+ effector T cells,[25] it is concluded that the impact of MALT1 inhibition on tumor growth is most likely mediated through effects on Treg.

Figure 4E:
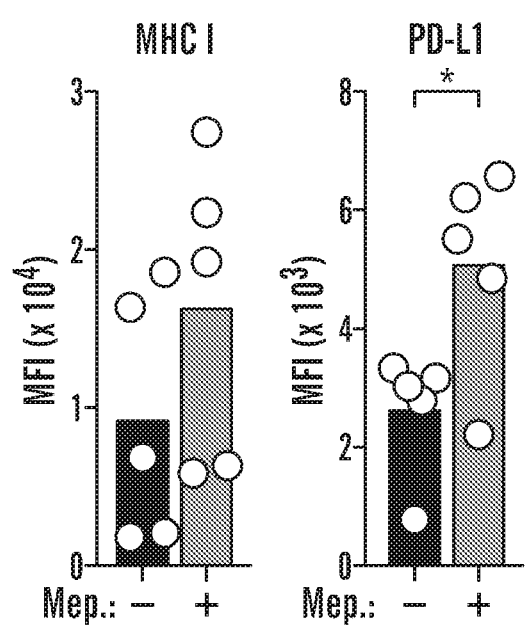
Figure 4F:
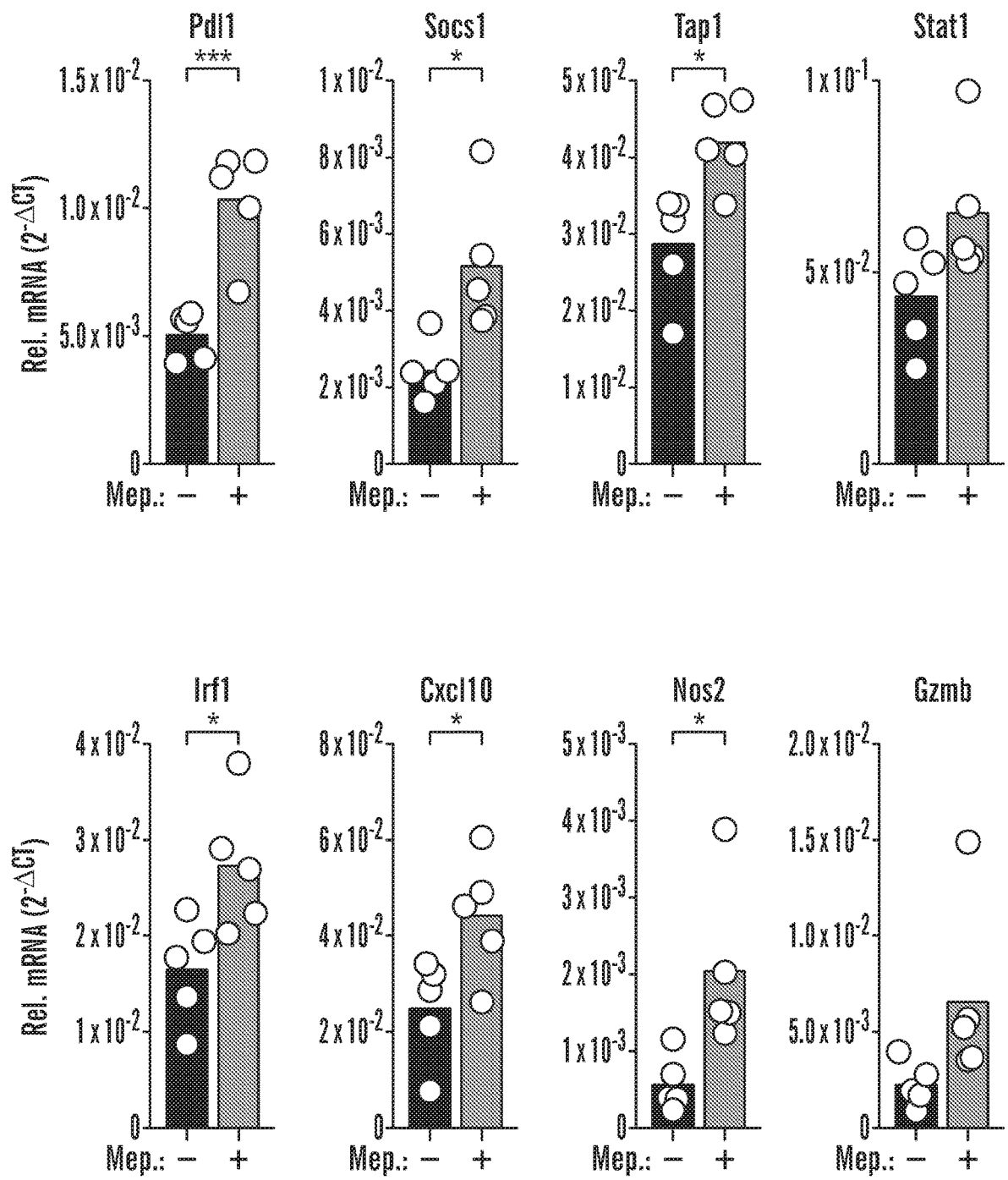
Figure 4G:
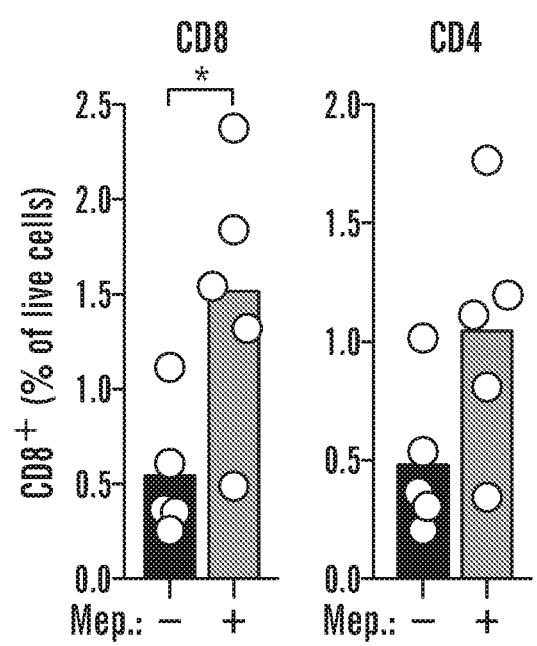
Figure 13D:
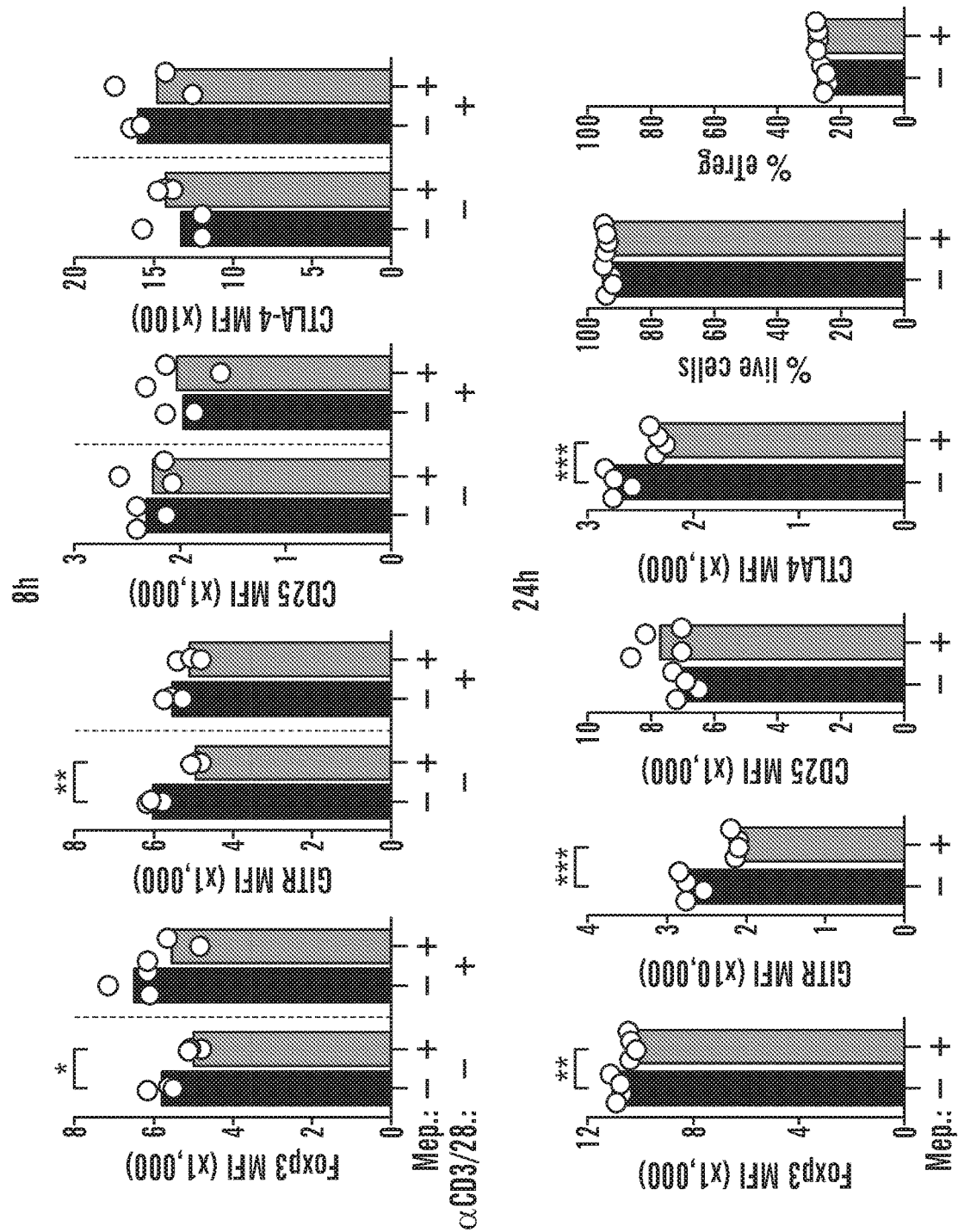
Figure 13E:
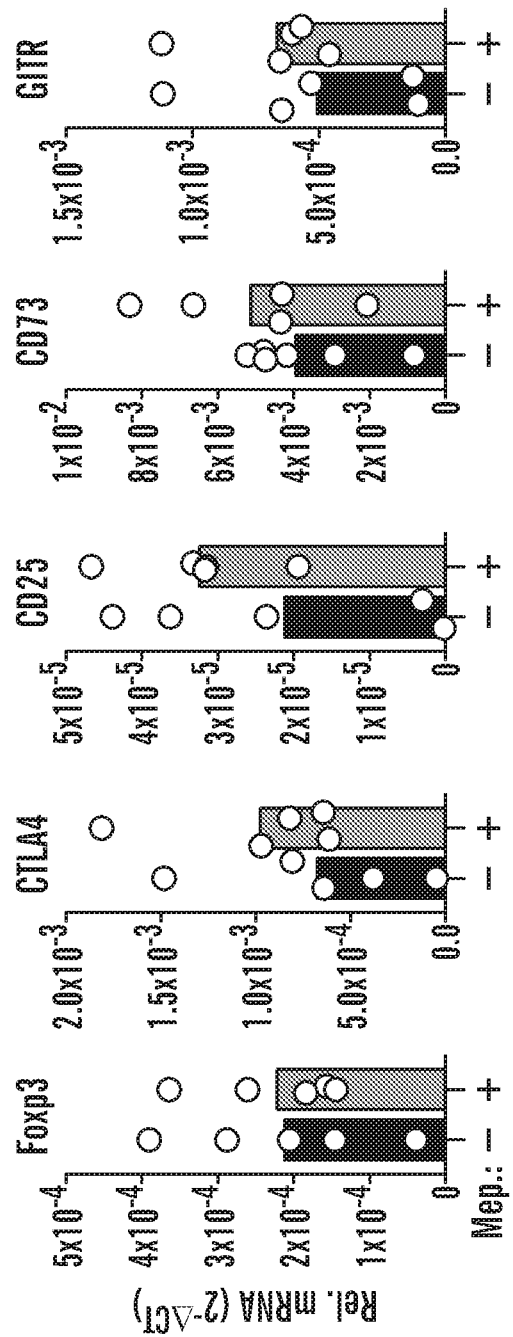
Figure 13F:
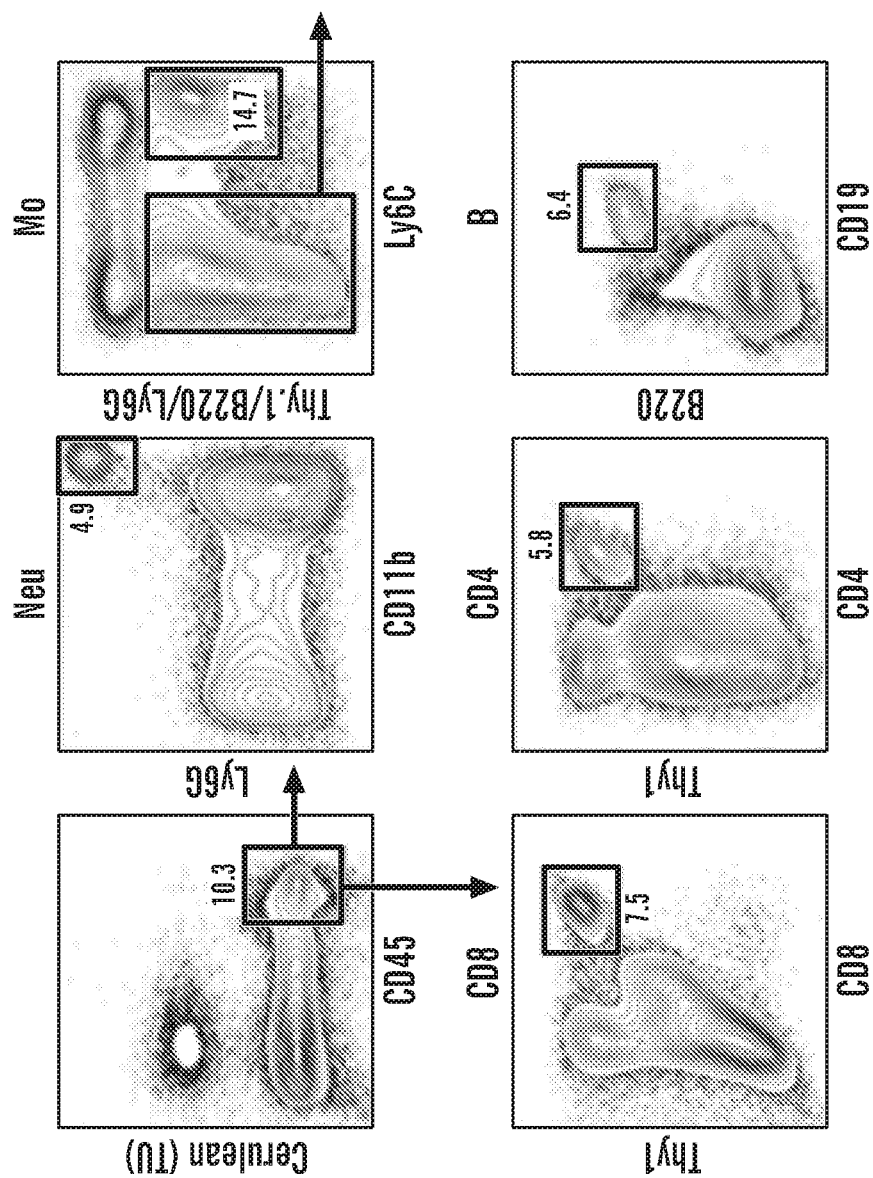
Figure 13F:
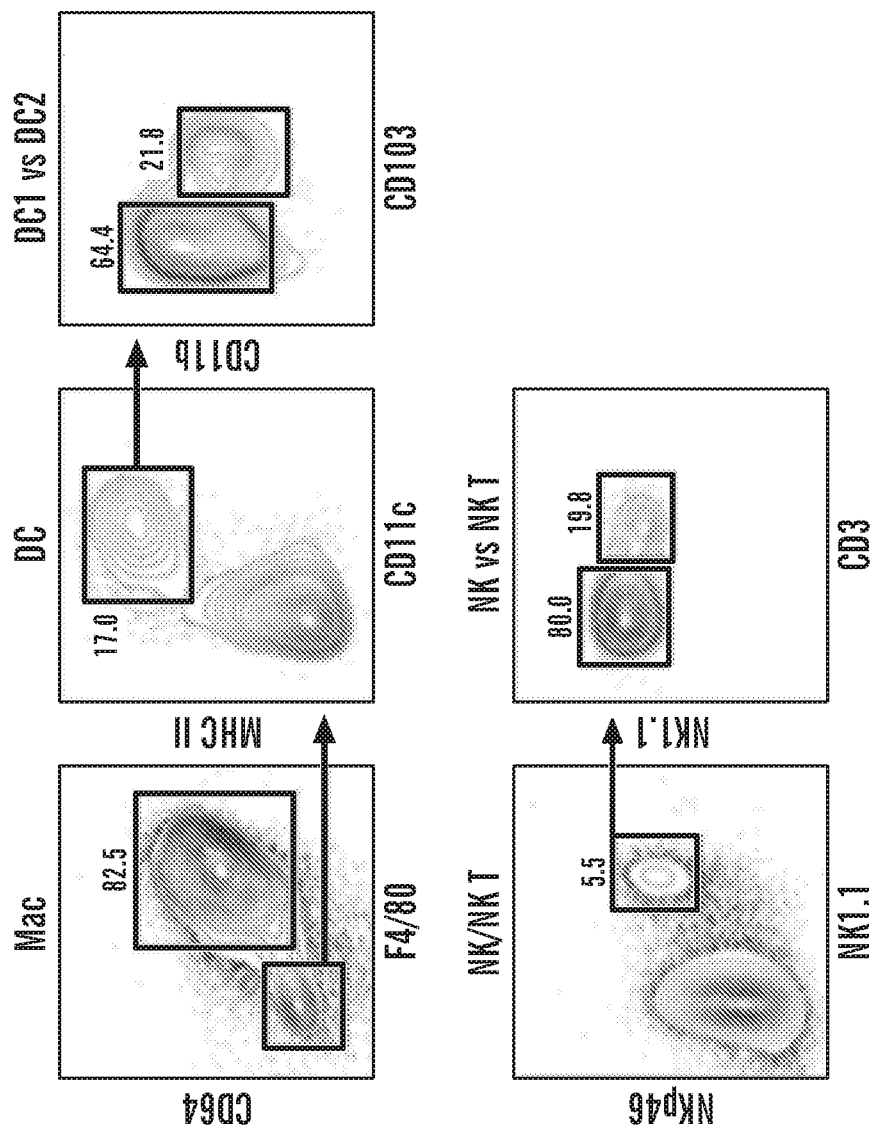
Figure 14K:
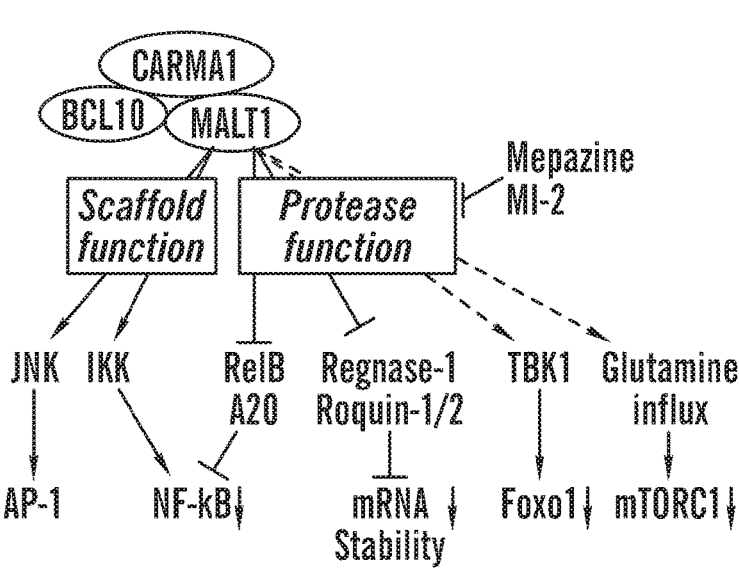
(FIG. 14K-14L), Mepazine effects within 3 days on intratumoral Treg numbers and their in situ effector cytokine expression (FIG. 14K), MHC I, and expression of Ifng, genes of adaptive immune resistance (Pdl1, Socs1), MHC I antigen presentation (Tap1), IFNγ-signaling (Stat1, Irf1), T cell recruitment (CXCL10), M1 macrophage activation (Nos2) (FIG. 14L).
Figure 14L:
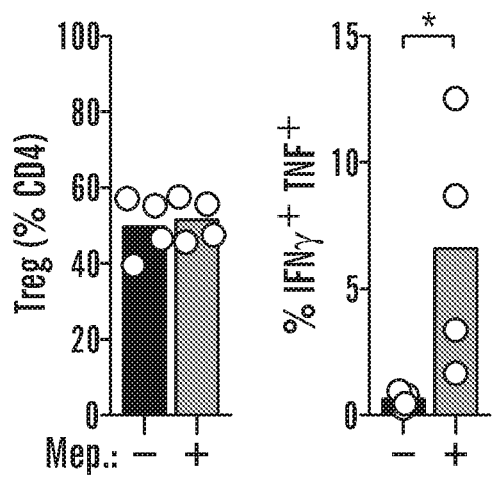
Figure 14M:
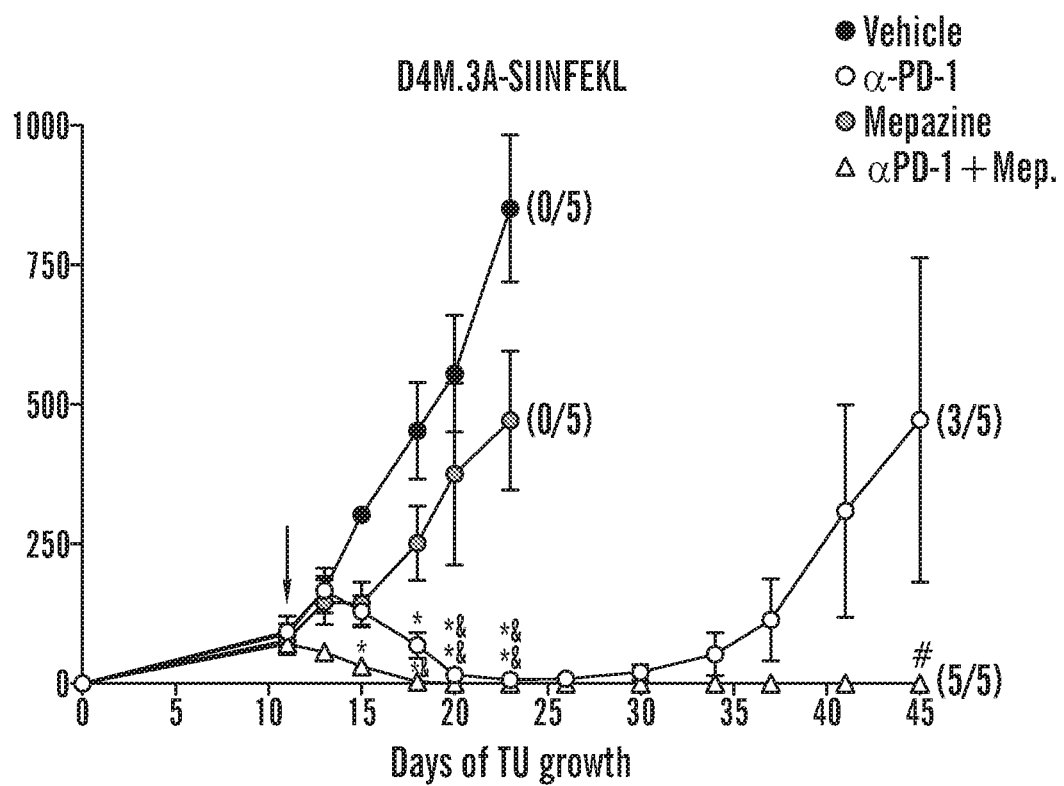
Figure 14N:
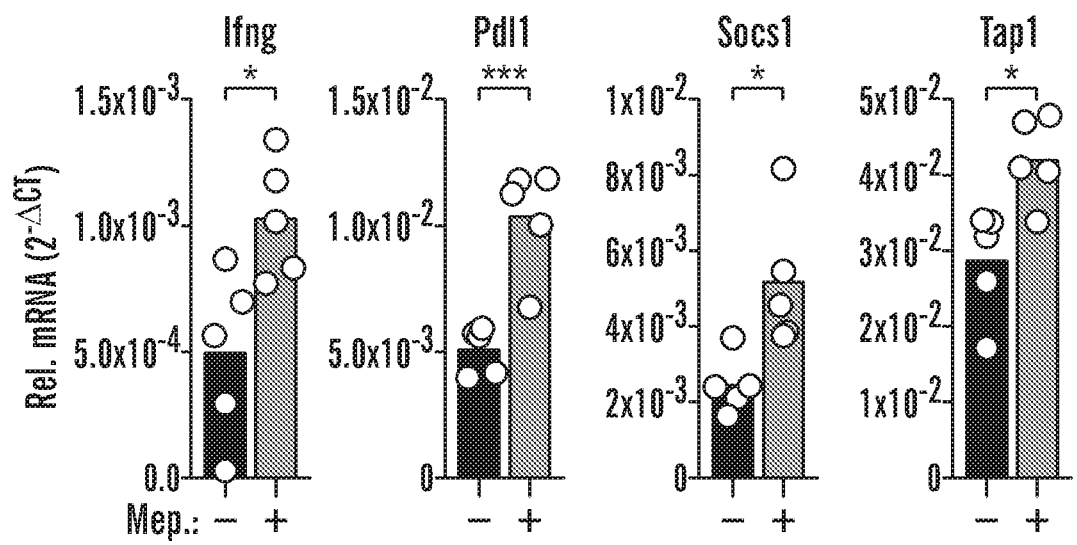
Figure 14N:
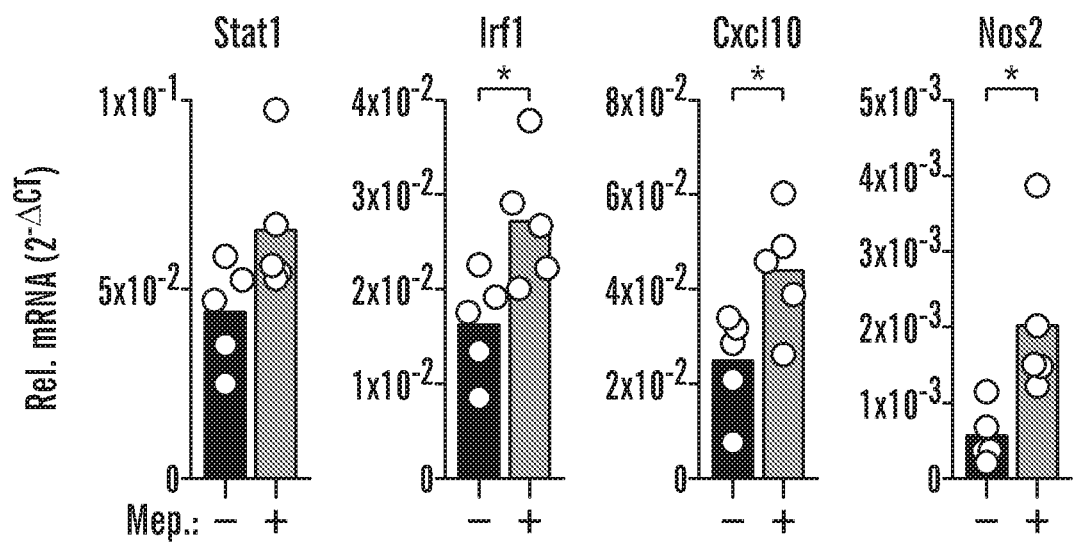

Indeed, similar to what was observed upon CARMA1-deletion in Treg, mepazine caused rapid induction of TNF- and IFNγ-expression by tumor-infiltrating Treg (FIG. 14K), while in vitro treatment of Treg triggered only a minor reduction of Foxp3 and GITR and no effector cytokine expression (FIG. 13D and not shown). Mepazine also caused up-regulation of MHC I and PD-L1-expression on tumor cells (FIG. 4E). In addition, whole tumor tissue transcriptome analysis revealed induction of a wide range of IFN-γ-regulated genes indicative of both enhanced inflammation and adaptive immune resistance in tumor tissue (FIG. 4G). In contrast to CARMA1-deletion, however, MALT1-inhibition did not reduce Treg frequency, and the expression of Treg-associated genes in tumor tissue was not altered (FIG. 14K; FIG. 13E). Nevertheless, in addition to generally enhanced immune cell infiltration, mepazine treatment increased the frequencies of CTL and NK cells in tumor tissue (FIGS. 13F-13J).

Figure 4H:
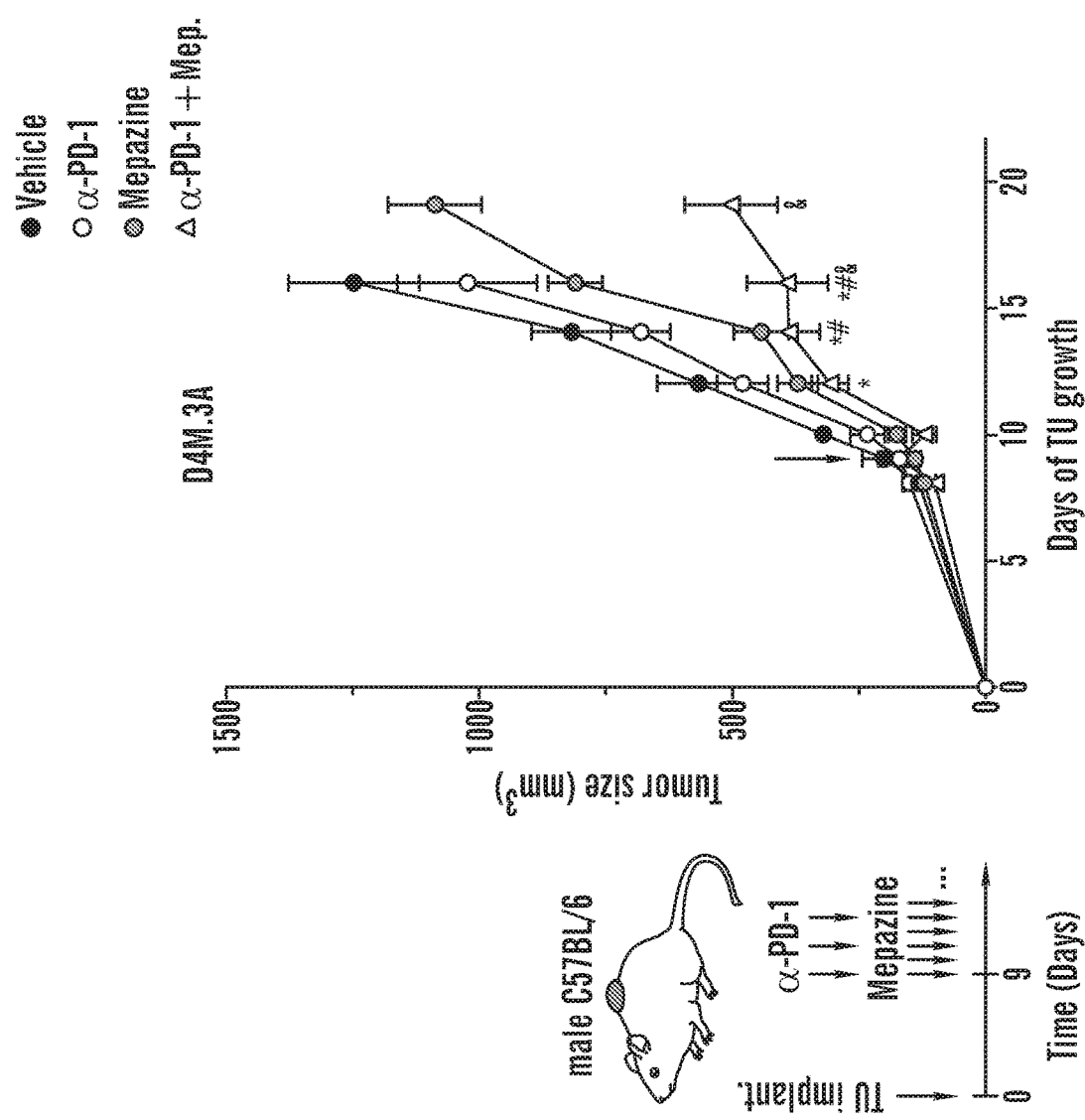
Figures 4I, 4J:
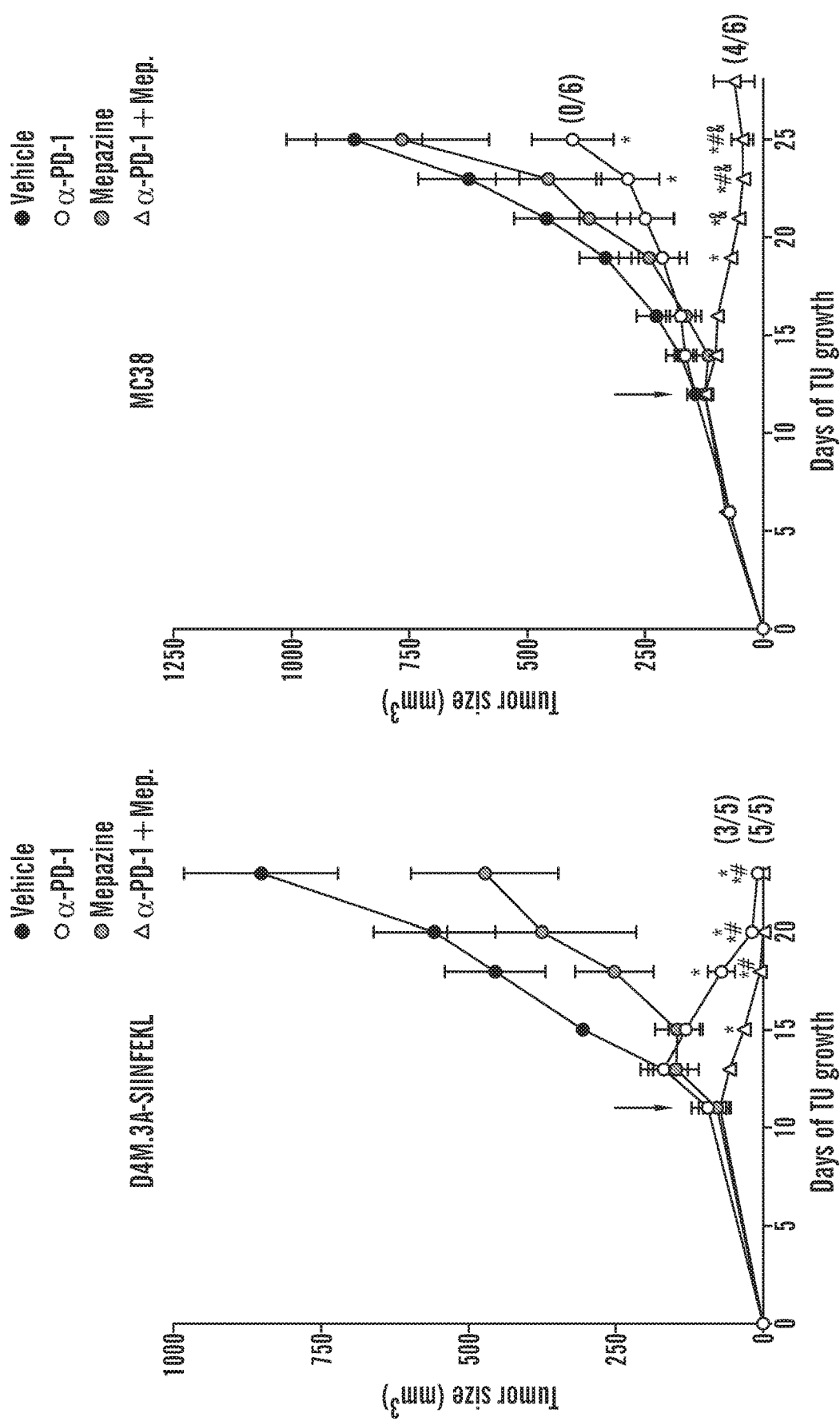

Tumor mutational load predicts the response to checkpoint blockade in cancer patients,[26,27] and tumors with low mutational burden remain a major challenge that restricts the success of this form of immunotherapy to some cancer types and to subgroups of patients. Accordingly, D4M.3A melanoma, which based on exome sequencing carries a very small mutational load relative to the C57BL/6J reference exome, is completely resistant to αPD-1 monotherapy in male hosts (FIG. 4H), in contrast to female hosts in which male D4M.3A tumors, likely based on Y antigen expression, showed a partial response (FIG. 4A). Concurrent MALT1 inhibition, however, synergized with αPD-1 treatment, and even in male hosts arrested tumor growth (FIG. 4H). αPD-1 treatment did not further increase Treg-expression of IFNγ, indicating that Treg expression of PD-1 did not restrict their proinflammatory function and that PD-1 blockade primarily acted on PD-1-expressing effector cells (FIG. 13K). Furthermore, when a defined degree of immunogenicity to D4M.3A tumors was introduced by expressing the chicken ovalbumin-derived SIINFEKL (SEQ ID NO: 8) epitope as a surrogate mutational neoantigen, a pronounced initial response to αPD-1 monotherapy was observed, but 40% of tumors relapsed. Combination of αPD-1 Abs with mepazine, however, produced even more rapid rejection of tumors, and reduced the frequency of relapse (FIG. 4I). Finally, to explore whether the effects of MALT1 inhibition on the anti-tumor response also extend to other cancer types, animals implanted with colon carcinoma-derived epithelial MC38 tumors were treated. While αPD-1 monotherapy had only a moderate impact on late-stage tumors, combination with mepazine enabled profound tumor control and rejection without relapse in 4 out of 6 animals (FIG. 4J). Hence, systemic MALT1 inhibition inflames the tumor environment, renders poorly immunogenic tumors responsive to αPD-1 therapy while strongly enhancing the responses of immunogenic tumors and minimizing the frequency of relapse, which has emerged as a common problem in clinical checkpoint blockade therapy.[28]

Without wishing to be bound by theory, it is proposed that disruption of CBM complex function through pharmacological inhibition of MALT1 or by other means could be a useful therapeutic strategy to provoke an intratumoral Th1 autoimmune-reaction mediated by locally destabilized, self-reactive Treg and thus increase the fraction of cancer patients that respond to concurrent PD-1-targeted immune checkpoint blockade or other forms of immunotherapy without inducing systemic autoimmune toxicity.

Example 2

Methods and Materials

Mice. Foxp3YFP-Cre (Ref. 1), Foxp3GFP-Cre-ERT2 (Ref 2), Rosa26YFP (Ref. 4), Ifng KO (Ref.5) and C57BL/6/J mice were purchased from Jackson laboratories. Ramnik J. Xavier and James J. Moon (MGH) provided CARMA1fl/fl (Ref.6) and Rag1 KO mice, respectively. Animals were housed in specific pathogen-free facilities at the Massachusetts General Hospital (MGH) and all experimental studies were approved and performed in accordance with guidelines and regulations implemented by the MGH Institutional Animal Care and Use Committee (IACUC). For survival studies the age of mice at euthanasia mandated by a moribund state of health was recorded in Kaplan Meyer plots.

Tumor cell lines. The BRAFV600E×PTEN$^{null}$ melanoma cell line D4M.3A7 was provided by David. E. Fisher. For some experiments D4M.3A were lentivirally transduced to express a blue fluorescent histone H2B-Cerulean fusion protein (D4M.3A-H2B-Cerulean), as described[8], e.g., to facilitate visualization by flow cytometry. To generate D4M.3A-SIINFEKL ("SIINFEKL" disclosed as SEQ ID NO: 8) expressing the chicken ovalbumin-derived H-2Kb-restricted SIINFEKL peptide (SEQ ID NO: 8) D4M.3A cells were transduced with a VSV-G pseudotyped pHAGE-EF1α lentiviral vector engineered to express a fusion of histone H2B and Cerulean separated by two copies of the SIINFEKL (SEQ ID NO: 8) minigene and its native flanking sequences in the ovalbumin protein to facilitate processing for antigen presentation. The colon adenocarcinoma cell line MC389 was obtained from Andrew D. Luster. All tumor lines were grown in DMEM with 10% FCS and used for experiments when in exponential growth phase.

Tumor growth studies and treatments. $10^6$ D4M.3A, D4M.3A-H2B-Cerulean, D4M.3A-SIINFEKL or MC38 tumor cells were s.c. injected in 100 μL HESS without $Ca^{2+}$ into the flanks of mice. Wherever possible, animals were randomized into treatment groups. Tumor volumes were measured every second to third day after start of treatments and calculated as V=(length×width²)/2.

1 mg/mouse of tamoxifen in 100 μl of a 9:1 mixture of olive oil and ethanol was i.p. injected daily as indicated. 1 mg/kg bodyweight of FTY720 in 150 μl $H_2O$ was i.p. injected every other day until the end of the experiment. 500 μg/mouse of αIFNγ antibody (clone XMG1.2) per mouse was i.p. injected on day 14 after birth or on the day of tumor implantation and then every other day thereafter until the end of the experiment. 200 μg of aPD1 (clone 29F.1A12) or of rat IgG2a isotype control (clone 2A3) were i.p. injected three times in 100 μl PBS every other day at the indicated time-points. 150 μg of αCD8α (clone YTS 169.4) were i.p. injected in 100 μl PBS every other day from the indicated time-point until the end of the experiment. 16 mg/kg bodyweight of Mepazine in 5% DMSO or 20 mg/kg of MI-2 in 5% DMSO in purified $H_2O$ were i.p injected daily starting at the indicated time-points until the end of the experiment, unless indicated otherwise. For adoptive Treg cell transfer studies, CD4+ YFP+ Treg were purified to >95% purity through magnetic-activated cell sorting (Miltenyi) from LNs and spleen of Foxp3YFP-Cre×CARMA1fl/+ of CARMA1+/+ mice and $10^6$ cells/mouse i.v. injected into the tail vein the day before tumor implantation.

Preparation of single cell suspensions, antibody staining and flow cytometry. Heparinized peripheral blood collected through sub-mandibular vein puncture was treated with ACK red blood cell lysis buffer. LNs and spleens were passed through 40 μm cell strainers, followed by red blood cell lysis (spleens only). Tumors were minced into small fragments and treated with 1.5 mg/ml collagenase IV and 50 U/ml DNAse I for 30 min. at 37° C. under agitation.

Cell surface proteins were stained for 20 minutes at 4° C. with the following antibodies from Biolegend: α-CD11b (M1/70), -CD120b/TNFR2 (polyclonal Armenian hamster IgG), -CD274/PD-L1 (10F.9G2), -CD357/GITR (DTA-1), -CD4 (GK1.5), -CD45 (30-F11), -CD62L (MEL-14), -CD73 (TY/11.8), -CD8a (53-6.7), -CD90.2 (30-H12), -F4/80 (BM8), —H-$2K^b$ (AF6-88.5), -I-A/I-E (M5/114.15.2), and -CD44 (IM7).

Intracellular and nuclear proteins were stained for 60 minutes at room temperature after permeabilization and fixation (Mouse regulatory T cell staining Kit; eBioscience) using antibodies against: CD152/CTLA-4-(UC10-4B9), TNF (MP6-XT22), IL-4 (11B11), IL-17A (TC11-18H10.1), IFNγ (XMG1.2), and Ki67 (16A8) (BD Biosciences), BIM (C34C5), CARD11/CARMA1 (1D12) (Cell Signaling), Foxp3 (FJK-16s, eBioscience), GFP (rabbit polyclonal, Invitrogen). Polyclonal goat α-rabbit Ig (H+L) secondary antibody (Life Technologies) was used to reveal primary α-CARMA1 staining.

Preceding antibody staining, Fc receptors were blocked with TruStain fcX (Biolegend) for 20 minutes at 4° C., followed by dead cells staining using the fixable viability violet dye Zombie Red (Biolegend) for 15 minutes at room temperature. Cells were analyzed on LSRII, LSRFortessa or LSRFortessa X-20 flow cytometers (BD Biosciences), and data were analyzed with FlowJo software version 9.9.5.

Analysis of in situ and ex vivo stimulated cytokine secretion. To detect in situ cytokine secretion, mice were slowly i.v. injected with 500 μg of fully dissolved Brefeldin A in 250 μl PBS 6 h before sacrifice and intracellular cytokine staining.

To detect cytokine secretion in T cells upon ex vivo re-stimulation, single cell suspensions from tumors and lymph nodes were resuspended in RPMI 1640 with 10% FCS and added to α-CD3 (clone 145-2C11)/α-CD28 (clone 37.51) antibody-coated (overnight at 10 μg/ml antibody) tissue culture plates for 8 hours at 37° C. in the presence of 1 μg/mL Golgiplug and monensin (both from Biolegend) and cells processed for intracellular cytokine staining.

Analysis of exTreg. CD4+ $YFP^{bright}$ cells were first purified by FACS from LNs and spleens of Foxp3$^{YFP-Cre/+}$×CARMA1$^{fl/fl\ (or\ fl/+\ or\ +/+)}$×Rosa26$^{YFP}$ mice and stained for Foxp3 expression for flow cytometry analysis, as described above.

In vivo and in vitro suppression. For in vivo suppression studies, $3\times10^5$ Miltenyi (negative selection) enriched CD4+ and FACS sorted (>98% purity) CD45RB$^{high}$ YFP− cells from LNs and spleens of Foxp3YFP-Cre/Cre mice were i.v. injected into the tail vein of Rag1 KO mice with or without $1\times10^5$ Miltenyi (negative selection) enriched CD4+ and FACS sorted (>98% purity) $YFP^{bright}$ Treg cells from LNs and spleens of Foxp3$^{YFP-Cre/+}$×CARMA1$^{fl/fl\ (or\ fl/+\ or\ +/+)}$×Rosa26$^{YFP}$ mice.

For in vitro suppression studies, $1\times10^4$ FACS sorted (>98% purity) CD4+ YFP− conventional T cells from LNs and spleens of Foxp3YFP-Cre/Cre mice were labeled with 5 μM CellTrace Violet and stimulated with 250 ng/ml of αCD3 mAb (145-2c11, Biolegend) in presence of $2.5\times10^4$ T-cell depleted splenocytes and different concentrations (from 1:1 to 1:16) of Miltenyi (negative selection) enriched CD4+ and FACS sorted (>98% purity) $YFP^{bright}$ Treg cells from LNs and spleens of Foxp3$^{YFP-Cre/+}$×CARMA1$^{fl/fl\ (or\ fl/+\ or\ +/+)}$×Rosa26$^{STOP\ fl/-YFP}$ mice. CD4+ YFP− conventional T cell proliferation was read out after 72 h, as previously described.[11] Briefly, percentage of suppression was scaled from 0 (proliferation of conventional T cell in absence of Treg) to 100 (complete absence of proliferation).

RNA-Sequencing studies. Sample collection. CD4+ T cells from LNs and spleens of F$^{Cre/+}$×C1$^{+/+,\ fl/+,\ or\ f/f}$ mice were pre-enriched by immunomagnetic cell sorting (Miltenyi negative selection) and then $5\times10^3$ YFP+ CD4+CD44$^{lo}$ CD62L+cTreg/animal and the same number of YFP+CD4+ CD44$^{hi}$ CD62L$^{neg}$ eTreg sorted to >99% purity directly into 10 μL lysis buffer consisting of TCL buffer (Qiagen) and 1% of beta-mercaptoethanol. Samples were the flash frozen and kept at −80° C. prior to further processing following a modified version of the Smart-Seq2 protocol,[11-13] as described below. A total of 18 samples were collected, but 2 samples were discarded for technical reasons.

Reverse transcription. Samples were thawed on ice for 2 minutes, then centrifuged at 2,500 rpm at 4° C. for 1 minute and the RNA concentration normalized. 1.9 μL of RNA per sample were moved to a full-skirt 96-well plate (Eppendorf). Each sample was then mixed with 1 μL 10 μM RT primer (SEQ ID NO: 13), 1 μL 10 mM dNTP (Life Technologies/Thermo Fisher Scientific), and 0.1 μL SUPERase•In RNase-Inhibitor (20 U/μL, Life Technologies/Thermo Fisher Scientific). Samples were denatured at 72° C. for 3 minutes using an Eppendorf Mastercycler and placed immediately on ice afterwards. 7 μL of the Reverse Transcription Mix was subsequently added to every well, consisting of: 2 μL 5×RT buffer (Thermo Fisher Scientific), 2 μL 5 M Betaine (Sigma-Aldrich), 0.9 μL 100 mM $MgCl_2$ (Sigma-Aldrich), 1 μL 10 μM TSO (5'-AAGCAGTGGTATCAACGCAGAGTACATr-GrG+G-3'(SEQ ID NO: 14), Exiqon), 0.25 μL SUPERase•In RNase-Inhibitor (20 U/μL, Life Technologies/Thermo Fisher Scientific), 0.1 μL Maxima H Minus Reverse Transcriptase (200 U/μL, Thermo Fisher Scientific), and 0.75 μL nuclease-free water. Reverse transcription was carried out by incubating the plate at 50° C. for 90 minutes, followed by heat inactivation at 85° C. for 5 minutes.

PCR pre-amplification and cDNA purification. 14 μL of PCR Mix, consisting of 0.5 μL 10 μM PCR primer 5'-AAGCAGTGGTATCAACGCAGAGT-3' (SEQ ID NO: 15) (IDT), 12.5 μL 2×KAPA HiFi HotStart Ready Mix (KAPA Biosystems), and 1 μL nuclease-free water, was added to each well for a final PCR reaction volume of 25 μL. The reaction was carried out with an initial incubation at 98° C. for 3 minutes, followed by 16 cycles at (98° C. for 15 seconds, 67° C. for 20 seconds, and 72° C. for 6 minutes) and a final extension at 72° C. for 5 minutes. PCR products were purified by mixing them with 20 μL (0.8×) of Agencourt AMPureXP SPRI beads (Beckman-Coulter), followed by a 6 minute incubation period at room temperature. The plate was then placed onto a magnet for 6 minutes prior to removing the supernatant. SPRI beads were washed twice with 100 μL of freshly prepared 70% ethanol, with care being taken to avoid loss of beads during the washes. Upon removing all residual ethanol traces, SPRI beads were left to dry at room temperature for 10 minutes. The beads were then resuspended in 20 μL of TE buffer (Teknova) and incubated at room temperature for 5 minutes. The plate was placed on the magnet for 5 minutes prior to transferring the supernatant containing the amplified cDNA to a new 96-well plate. This cDNA SPRI clean-up procedure was repeated a second time to remove all residual primer dimers. The concentration of amplified cDNA was measured on the Synergy H1 Hybrid Microplate Reader (BioTek) using the Qubit dsDNA High Sensitivity Assay Kit (Life Technologics/Thermo Fisher Scientific). The cDNA size distribution of few selected wells was assessed on a High-Sensitivity Bioanalyzer Chip (Agilent), and the expected size distribution sharply peaked around 2 kb.

Sequencing library preparation. Library preparation was carried out using the Nextera XT DNA Sample Kit (Illumina) with custom indexing adapters, allowing the 18 libraries to be simultaneously generated in a 384-well PCR plate (Eppendorf). For each library, the amplified cDNA was normalized to a 0.15-0.20 ng/μL concentration range. The tagmentation reaction consisted of mixing 0.625 μL of normalized cDNA with 1.25 μL of Tagmentation DNA (TD) Buffer and 0.625 μL of Amplicon Tagment enzyme Mix (ATM). The 2.5 μL reaction was incubated at 55° C. for 10 minutes and then immediately placed on ice upon completing this incubation step. The reaction was quenched with 0.625 μL of Neutralize Tagment (NT) Buffer and incubated at room temperature for 10 minutes. The libraries were amplified by adding 1.875 μL of Nexstera PCR Master (NPM) Mix, 0.625 μL of 10 μM i5 adapter 5'-AATGA-TACGGCGACCACCGAGATCTACAC[i5] TCGTCGGCAGCGTC-3' (SEQ ID NO: 16) (IDT), where [i5] signifies the 8 bp i5 barcode sequence (see below for sequences), and 0.625 μL of 10 μM i7 adapter 5'CAAGCAGAAGACGGCATACGAGAT[i7]GTGACTG-GAGTTCAGACGTGTGCTCTTCCGATCT GGG-3' (SEQ ID NO: 17) (IDT), where [i7] represents the reverse-complement of the 8 bp i7 barcode sequence (see below for sequences used). The PCR was carried out at an initial incubation at 72° C. for 3 minutes, 95° C. for 30 seconds, followed by 12 cycles of (95° C. for 10 seconds, 55° C. for 30 seconds, 72° C. for 1 minute), and a final extension at 72° C. for 5 minutes. Following PCR amplification, 2.5 μL of each library were pooled together in a 1.5 mL Eppendorf tube. The pool was mixed with 67.5 μL (0.9× ratio for 2.5 ul of 30 samples pooled together) of Agencourt AMPureXP SPRI beads (Beckman-Coulter) and incubated at room temperature for 5 minutes. The pool was then placed on a magnet (DynaMag-2, Life Technologies) and incubated for 5 minutes. The supernatant was removed and the SPRI beads were washed twice with 1 mL of freshly prepared 70% ethanol. Upon removing all residual ethanol traces, the SPRI beads were left to dry at room temperature for 10 minutes. The beads were resuspended in 100 μL of nuclease-free water and incubated at room temperature for 5 minutes. The tube was then placed back on the magnet for 3 minutes prior to transferring the supernatant to a new 1.5 mL Eppendorf tube. This SPRI clean-up procedure of the library was repeated a second time to remove all residual primer dimers, using the same approach. The concentration of the pooled libraries was measured using the Qubit dsDNA High Sensitivity Assay Kit (Life Technologies/Thermo Fisher Scientific), and the library size distribution measured on a High-Sensitivity Bioanalyzer Chip (Agilent), showing the expected size distribution of 300-500 bp. The 18-pooled samples were sequenced as paired-end on an Illumina NextSeq 500 instrument using the NextSeq 500/550 High Output v2 kit (75 cycles).

i5 barcodes: AAGTAGAG, ACACGATC, TGTTCCGA i7 barcodes: GAATTGCT, GTCAAGTT, ATCCGACA, CAAGGCGA, AGTGTCTT, GACCGAGA Data sources. Publicly available GSE82008 gene expression matrix data was downloaded from the GEO NCBI repository.

RNA Sequencing Analysis. Raw sequencing reads were demultiplexed and converted to FASTQ files using Illumina bcl2fastq2 Illumina software (version 2.17.1.14). FASTQ sequencing reads were then aligned to $mm^{10}$ reference genome using the STAR aligner with default parameters. 12 RSEM (version 1.2.8) was used to quantify gene expression level from aligned reads and generate count expression matrices for each experimental condition.[13] Lowly expressed genes with a count per million (CPM)<0.5 in more than 2 conditions were filtered out, leaving a total of 14168 genes for further analysis. Distribution of $log_2$ normalized CPM data was visualized to assess for coverage, and all conditions had similar distributions.

Gene Expression Analysis. Gene expression matrices were analyzed using the limma package in $R._{14}$ The global topology of quantile normalized data was visualized using the multidimensional scaling (plotMDS) function in limma after removing batch effects using the removebatchEffect function in limma with default parameters taking into account design and batch matrices. Differential gene expression was performed using empirical Bayesian statistics (eBayes) function in limma simultaneously correcting for batch using blocking terms for batch covariates. Differentially expressed genes with log fold change greater than 1 and a p-value below cut-off were visualized using the heatmap.2 function in gplots. All p values were corrected for multiple hypothesis testing using Benjamini-Hochberg correction. For R scripts used to perform the gene expression analyses see Supplementary Material and Methods. The same differential expression steps were used to re-analyze the gene expression data from GSE82008 in order to obtain the list of differentially expressed genes between c-Rel KO and p65 KO vs WT resting and activated Tregs. A list of 831 'eTreg signature' genes from Grinberg-Bleyer et al. was obtained through direct correspondence with the authors. Overlap between differentially expressed genes, including the list of eTreg signatures from the current study and Grinberg-Bleyer et al., was visualized using the vennDiagram function in limma.

Quantitative RT-PCR. For analysis of gene expression, RNA was isolated (AllPrep, DNA/RNA Mini kit; Qiagen) from CD4+ GFP+ Treg sorted to >99% purity from tdFNs and tumors, or from homogenized tumor tissue, and reverse transcribed using iScript cDNA Synthesis Kit (Bio-RAD). Quantitative RT-PCR was performed using iQ SYBR green supermix (Bio-RAD) and primers:

CARMA1-Fwd
(SEQ ID NO: 18)
5'-ACATGCTGAGCCGTTACATCA-3',

CARMA1-Rev
(SEQ ID NO: 19)
5'-CCACATAGCCCCTTTGTCCC-3',

Ifng-Fwd
(SEQ ID NO: 20)
5'-CGGCACAGTCATTGAAAGCCTA-3',

Ifng-Rev
(SEQ ID NO: 21)
5'-GTTG CTGATGGCCTGATTGTC-3',

CTLA4-Fwd
(SEQ ID NO: 22)
5'-GCTTCCTAGATTACCCCTTCTGC-3',

CTLA4-Rev
(SEQ ID NO: 23)
5'-CGGGCATGGTTCTGGATCA-3',

CD25-Fwd
(SEQ ID NO: 24)
5'-CCACATTCAAAGCC CTCTCCTA-3',

CD25-Rev
(SEQ ID NO: 25)
5'-GTTTTCCCACACTTCATCTTGC-3',

Foxp3-Fwd
(SEQ ID NO: 26)
5'-TTGG CCAGCGCCA TCTT-3',

Foxp3-Rev
(SEQ ID NO: 27)
5'-TGCCTCCTCCAGAGAGAAGTG-3',

GITR-Fwd
(SEQ ID NO: 28)
5'-AAGGTTCA GAACGGAAGTG-3',

GITR-Rev
(SEQ ID NO: 29)
5'-GGGTCTCCACAGTGGTACT-3',

CD73-Fwd
(SEQ ID NO: 30)
5'-CAA ATCCCACACAACCACTG-3',

CD73-Rev
(SEQ ID NO: 31)
5'-TGCTCACTTGGTCACA GGAC-3',

Gzmb-Fwd
(SEQ ID NO: 32)
5'-CATGTAGGGTCGAGAGTGGG-3',

Gzmb-Rev
(SEQ ID NO: 33)
5'-CCTCCTGC TACTGCTGACCT-3',

Pdl1-Fwd
(SEQ ID NO: 34)
5'-TGCTGCATAATCAGCTACGG-3',

Pdl1-Rev
(SEQ ID NO: 35)
5'-GCTGGTCACATT GAGAAGCA-3',

Socs1-Fwd
(SEQ ID NO: 36)
5'-ACAAGCTGCTACAACCAGG G-3',

Socs1-Rev
(SEQ ID NO: 37)
5'-ACTTCTGGCTGGAGACCTCA-3',

Tap1-Fwd
(SEQ ID NO: 38)
5'-GTGGCCGCAGTGGGA CAAGAG-3',

Tap1-Rev
(SEQ ID NO: 39)
5'-AGGGCACTGGTGGCATCATC-3',

Stat1-Fwd
(SEQ ID NO: 40)
5'-TGGTGAAATTGCAAG AGCTG-3',

Stat1-Rev
(SEQ ID NO: 41)
5'-CAGACTTCCGTTGGTGGATT-3',

Irf1-Fwd
(SEQ ID NO: 42)
5'-CAG AGGAAAG AGAGAAAGTCC-3',

Irf1-Rev
(SEQ ID NO: 43)
5'-CACACGGTGACAGTGCTGG,

Cxcl10-Fwd
(SEQ ID NO: 44)
5'-CATCCTGCTGGGTCTGAGTG-3',

Cxcl10-Rev
(SEQ ID NO: 45)
5'-ATTCTCACTGGCCCGTCATC,

Nos2-Fwd
(SEQ ID NO: 46)
5'-CAAGAGAGTGCTGTTCCAGGT-3'
and

Nos2-Rev
(SEQ ID NO: 47)
5'-GAGCACGCTGAGTACC TCATT-3',

GAPDH-Fwd
(SEQ ID NO: 48)
5'-TGGTGAAGGTCGGTGAAC-3'
and

GAPDH-Rev
(SEQ ID NO: 49)
5'-CCATGTAGTTGAGGTCAATGAAGG-3'.

Results were expressed as 2-ΔCT relative to the house keeping gene GAPDH.

Histology: Tissue samples obtained from all organs were fixed in 10% buffered formalin for 48 h, trimmed and placed into microcassettes, and embedded in paraffin wax. Sections of 5 μm were stained with haematoxylin and eosin according to standard procedures.

Immunofluorescence. Kidney, liver, and stomach from a RAG1 KO mouse were embedded in OCT and flash frozen in cold methylbutane equilibrated on dry ice. Sections of 10 μm were permeabilized with pre-cooled 90% methanol for 10 minutes at −20° C., blocked in TruStain FcX (93, Biolegend) with 1% goat serum and 0.25% BSA in PBS for 60 minutes, incubated with sera (1:100 dilution) from Foxp3$^{YFP\text{-}Cre/Y}$×CARMA1$^{fl/fl\ (or\ fl/+\ or\ +/+)}$ mice for 120 minutes and stained with anti-mouse IgG (H+L)-Alexa Fluor647 (1:500) (A-21235, Thermo Fisher) and DAPI (Sigma) for 120 minutes. Sections were mounted on coverslips in Prolong (Thermo Fisher) and imaged with FSM 780 AxioObserver confocal microscope (Carl Zeiss) using a 20× lens (Apochromat, 0.8 W).

Statistical analysis. Two-tailed student's t-test was used for comparisons between two groups while two-way ANOVA with Bonferroni post-test (multiple time-points) or one-way ANOVA with Tukey post-test (single time-points) were used for comparisons across multiple groups, unless otherwise indicated. A log-rank (Mantel-Cox) test was used to compare survival curves. All statistical tests were performed with GraphPad Prism software, and $p<0.05$ was considered statistically significant. No statistical methods were used to predetermine sample size. Investigators were not blinded to allocation during experiments and outcome assessment.

Data availability. The data sets generated during the current study are available from the corresponding authors on reasonable request. RNA sequencing data will be deposited in the GEO NCBI repository.

REFERENCES

1. Savage, P. A., Feventhal, D. S. & Malchow, S. Shaping the repertoire of tumor-infiltrating effector and regulatory T cells. Immunol. Rev. 259, 245-258 (2014).
2. Mellman, I., Coukos, G. & Dranoff, G. Cancer immunotherapy comes of age. Nature 480, 480-489 (2011).
3. Spranger, S. et al. Up-regulation of PD-F1, IDO, and T(regs) in the melanoma tumor microenvironment is driven by CD8(+) T cells. Sci Transl Med 5, 200ra116 (2013).
4. Bauer, C. A. et al. Dynamic Treg interactions with intratumoral APCs promote local CTL dysfunction. J. Clin. Invest. 124, 2425-2440 (2014).
5. Meininger, I. & Krappmann, D. Lymphocyte signaling and activation by the CARMA1-BCL10-MALT1 signalosome. Biol. Chem. 397, 1315-1333 (2016).
6. Medoff, B. D. et al. Differential requirement for CARMA1 in agonist-selected T-cell development. Eur. J. Immunol. 39, 78-84 (2009).
7. Molinero, L. L. et al. CARMA1 Controls an Early Checkpoint in the Thymic Development of FoxP3+ Regulatory T Cells. The Journal of Immunology 182, 6736-6743 (2009).
8. Bames, M. J. et al. Commitment to the regulatory T cell lineage requires CARMA1 in the thymus but not in the periphery. Plos Biol 7, e51 (2009).
9. Brüstle, A. et al. MALT1 is an intrinsic regulator of regulatory T cells. Cell Death Differ. (2015). doi:10.1038/cdd.2015.104
10. Schmidt-Supprian, M. et al. Differential dependence of CD4+CD25+ regulatory and natural killer-like T cells on signals leading to NF-kappaB activation. Proc. Natl. Acad. Sci. U.S.A. 101, 4566-4571 (2004).
11. Long, M., Park, S.-G., Strickland, I., Hayden, M. S. & Ghosh, S. Nuclear factor-kappaB modulates regulatory T cell development by directly regulating expression of Foxp3 transcription factor. Immunity 31, 921-931 (2009).
12. Vasanthakumar, A. et al. The TNF Receptor Superfamily-NF-κB Axis Is Critical to Maintain Effector Regulatory T Cells in Lymphoid and Non-lymphoid Tissues. Cell Reports 20, 2906-2920 (2017).
13. Messina, N. et al. The NF-κB transcription factor RelA is required for the tolerogenic function of Foxp3(+) regulatory T cells. J. Autoimmun. (2016). doi: 10.1016/j.jaut.2016.03.017
14. Oh, H. et al. An NF-κB Transcription-Factor-Dependent Lineage-Specific Transcriptional Program Promotes Regulatory T Cell Identity and Function. Immunity (2017). doi: 10.1016/j.immuni.2017.08.010
15. Grinberg-Bleyer, Y. et al. NF-κB c-Rel Is Crucial for the Regulatory T Cell Immune Checkpoint in Cancer. Cell 170, 1096-1108.e13 (2017).
16. Jenkins, M. H. et al. Multiple murine BRaf(V600E) melanoma cell lines with sensitivity to PLX4032. Pigment Cell Melanoma Res 27, 495-501 (2014).
17. Pierson, W. et al. Antiapoptotic Mcl-1 is critical for the survival and niche-filling capacity of Foxp3$^+$ regulatory T cells. Nat. Immunol. 14, 959-965 (2013).
18. Overacre-Delgoffe, A. E. et al. Interferon-gamma Drives Treg Fragility to Promote Anti-tumor Immunity. Cell (2017). doi: 10.1016/j.cell.2017.05.005
19. Gewies, A. et al. Uncoupling Malt1 threshold function from paracaspase activity results in destructive autoimmune inflammation. Cell Reports 9, 1292-1305 (2014).
20. Jaworski, M. et al. Malt1 protease inactivation efficiently dampens immune responses but causes spontaneous autoimmunity. EMBO J. 33, 2765-2781 (2014).
21. Bomancin, F. et al. Deficiency of MALT1 paracaspase activity results in unbalanced regulatory and effector T and B cell responses leading to multiorgan inflammation. The Journal of Immunology 194, 3723-3734 (2015).
22. Nagel, D. et al. Pharmacologic inhibition of MALT1 protease by phenothiazines as a therapeutic approach for the treatment of aggressive ABC-DLBCL. Cancer Cell 22, 825-837 (2012).
23. Fontan, F. et al. MAFT1 small molecule inhibitors specifically suppress ABC-DFBCF in vitro and in vivo. Cancer Cell 22, 812-824 (2012).
24. Wang, Y. et al. MAFT1 promotes melanoma progression through JNK/c-Jun signaling. Oncogenesis 6, e365 (2017).
25. Thome, M., Charton, J. E., Pelzer, C. & Hailfinger, S. Antigen Receptor Signaling to NF-B via CARMA1, BCF10, and MAFT1. Cold Spring Harbor Perspectives in Biology 2, a003004-a003004 (2010).
26. Fe, D. T. et al. PD-1 Blockade in Tumors with Mismatch-Repair Deficiency. N Engl J Med 372, 2509-2520 (2015).
27. Rizvi, N. A. et al. Cancer immunology. Mutational landscape determines sensitivity to PD-1 blockade in non-small cell lung cancer. Science (New York, N.Y.) 348, 124-128 (2015).
28. Zaretsky, J. M. et al. Mutations Associated with Acquired Resistance to PD-1 Blockade in Melanoma. N Engl J Med 375, 819-829 (2016).

The invention claimed is:

1. A method of treating a solid tumor, the method comprising: administering (S)-mepazine and an inhibitor of PD-1 or PDL-1 to a subject in need thereof, wherein the solid tumor is not a lymphoma.

2. The method of claim 1, wherein the solid tumor is selected from the group consisting of a carcinoma, a melanoma, and a sarcoma.

3. The method of claim 1, wherein the solid tumor is selected from the group consisting of an adrenocortical tumor, an alveolar soft part sarcoma, a chondrosarcoma, a colorectal carcinoma, a desmoid tumor, a desmoplastic small round cell tumor, an endocrine tumor, an endodermal sinus tumor, an epithelioid hemangioendothelioma, an Ewing sarcoma, a germ cell tumor (solid tumor), a giant cell tumor of bone and soft tissue, a hepatoblastoma, a hepatocellular carcinoma, a melanoma, a nephroma, a neuroblastoma, a non-rhabdomyosarcoma soft tissue sarcoma (NRSTS), an osteosarcoma, a paraspinal sarcoma, a renal cell carcinoma, a retinoblastoma, a rhabdomyosarcoma, a synovial sarcoma, or a Wilms tumor.

4. The method of claim 1, wherein the solid tumor is metastatic.

5. The method of claim 1, wherein the inhibitor of PD-1 or PDL-1 is selected from the group consisting of pembrolizumab, nivolumab, AUNP-12, and pidilizumab.

6. The method of claim 1, wherein the checkpoint inhibitor of PD-1 or PDL-1 is selected from the group consisting of atezolizumab, avelumab, and durvalumab.

7. A method of treating a solid tumor that is resistant to a checkpoint inhibitor therapy, the method comprising;
   a. administering (S)-mepazine or a salt thereof; and
   b. an anti-PD-1 or anti-PD-L1 therapy to a subject in need thereof.

8. The method of claim 7, wherein anti-PD-1 or anti-PD-L1 therapy is pembrolizumab, nivolumab, AUNP-12, and pidilizumab.

9. The method of claim 7, wherein the anti-PD-1 or anti-PD-L1 therapy is atezolizumab, avelumab, and durvalumab.

* * * * *